United States Patent
Burgess

(10) Patent No.: US 9,562,023 B2
(45) Date of Patent: Feb. 7, 2017

(54) DIPEPTIDE MIMICS, LIBRARIES COMBINING TWO DIPEPTIDE MIMICS WITH A THIRD GROUP, AND METHODS FOR PRODUCTION THEREOF

(75) Inventor: Kevin Burgess, College Station, TX (US)

(73) Assignee: Kevin Burgess, College Station, TX (US)

( * ) Notice: Subject to any disclaimer, the term of this patent is extended or adjusted under 35 U.S.C. 154(b) by 0 days.

(21) Appl. No.: 13/418,917

(22) Filed: Mar. 13, 2012

(65) Prior Publication Data

US 2012/0232268 A1  Sep. 13, 2012

Related U.S. Application Data

(63) Continuation of application No. 12/181,168, filed on Jul. 28, 2008.

(60) Provisional application No. 60/952,149, filed on Jul. 26, 2007.

(51) Int. Cl.
| | | |
|---|---|---|
| C07D 403/14 | (2006.01) | |
| C07D 249/04 | (2006.01) | |
| C07D 241/08 | (2006.01) | |
| C07D 271/10 | (2006.01) | |
| C07D 273/00 | (2006.01) | |
| C07D 401/04 | (2006.01) | |
| C07D 401/12 | (2006.01) | |
| C07D 401/14 | (2006.01) | |
| C07D 403/12 | (2006.01) | |
| C07D 405/14 | (2006.01) | |
| C07D 413/12 | (2006.01) | |
| C40B 40/04 | (2006.01) | |
| C40B 50/08 | (2006.01) | |

(52) U.S. Cl.
CPC ........... *C07D 249/04* (2013.01); *C07D 241/08* (2013.01); *C07D 271/10* (2013.01); *C07D 273/00* (2013.01); *C07D 401/04* (2013.01); *C07D 401/12* (2013.01); *C07D 401/14* (2013.01); *C07D 403/12* (2013.01); *C07D 403/14* (2013.01); *C07D 405/14* (2013.01); *C07D 413/12* (2013.01); *C40B 40/04* (2013.01); *C40B 50/08* (2013.01)

(58) Field of Classification Search
None
See application file for complete search history.

(56) References Cited

U.S. PATENT DOCUMENTS

2009/0264315 A1  10/2009  Burgess

FOREIGN PATENT DOCUMENTS

| WO | 2006078576 A2 | 7/2006 |
| WO | 2006078577 A1 | 7/2006 |
| WO | 2007079312 A2 | 7/2007 |

OTHER PUBLICATIONS

Angell et al. J. Am. Chem. Soc. 2008, 130, pp. 556-565.*
Angell, Yu, et al., "A Combinatorial Method for Solution-Phase Synthesis of Labeled Bivalent B-Turn Mimics", 2008, American Chemical Society, 130:556-565.
Angelo, N.G., et al., "Solution- and Solid-Phase Synthesis of Triazole Oligomers That Display Protein-Like Functionality", 2007, J. Org. Chem, 72:7963-7967.
Angelo, N.G., et al., "Nonpeptidic Foldamers from Amino Acids: Synthesis and Characterization of 1,3-Substituted Triazole Oligomers", J. Am. Chem. Soc. 2005, 127:17134-17135.
Biron, E., et al., "Solid-Phase Synthesis of 1,3-Azole-Based Peptides and Peptidomimetics", Organic Letters, 2006, 8: 11:2417-2420.
Borg, S., et al., "Design, Synthesis, and Evaluation of Phe-Gly Mimetics: Heterocyclic Building Blocks for Pseudopeptides", 1999, J. Med. Chem., 42:4331-4342.
Borg, S., et al., "Synthesis of 1,2,4=Oxadiazole-, 1,3,4-Oxadiazole-, and 1,2,4-Triazole-Derived Dipeptidomimetics", 1995, J. Org. Chem., 60:3112-3120.
Burgess, K., Solid-Phase Syntheses of B-Turn Analogues to Mimic or Disrupt Protein—Protein Interactions, Accounts of Chemical Research, 2001, 34:826-835.
Gong, Xi, et al., "A New Route for the Synthesis of N-Substituted Diketopiperazine Derivatives" 2006, Chinese Chemical Letters, 17:4:469-472.
Liu, Jing, et al., "Bivalent Diketopiperazine-Based Tropomysin Receptor Kinase C (TrkC) Antagonists" 2010, J. Med. Chem., 53:5044-5048.
Mann, Enrique, et al., "New Oxazole-Based Peptidomimetics: Useful Building Blocks for the Synthesis of Orthogonally Protected Macrocyclic Scaffolds", 2003, Organic Letters, 5:24:4567-4570.
Pattarawarapan, M., et al., "Selective Formation of Homo- and Heterobivalent Peptidomimetics" 2003, J. Med. Chem, 46:3565-3567.
Bai, Y., et al., "In Glaucoma the Upregulated Truncated TrkC.T1 Receptor Isoform in Glia Causes Increased TNF-Production, Leading to Retinal Ganglion Cell Death" Dec. 2010, Investigative Ophthalmology & Visual Science, 51:12:6639-6651.

\* cited by examiner

*Primary Examiner* — Alicia L Otton
(74) *Attorney, Agent, or Firm* — Parker Highlander PLLC

(57) ABSTRACT

Monovalent compounds having moieties comprising at least one amino acid side chain are bound to a core molecule, which also comprises a nucleophilic moiety bound to said core molecule. Monovalent compounds also comprise a macrocyclic ring, a nucleophilic moiety, and a spacer group. Monovalent compounds may be combined into bivalent and trivalent compounds, some of which may have a labeling tag. Methods of production of bivalent compounds and contemplated uses thereof are disclosed.

7 Claims, No Drawings

DIPEPTIDE MIMICS, LIBRARIES COMBINING TWO DIPEPTIDE MIMICS WITH A THIRD GROUP, AND METHODS FOR PRODUCTION THEREOF

CROSS-REFERENCE TO RELATED APPLICATIONS

This application is a Continuation of U.S. application Ser. No. 12/181,168, filed Jul. 28, 2008, which claims priority to U.S. Application Provisional Ser. No. 60/952,149 filed Jul. 26, 2007, the contents of each of which are incorporated by reference herein in their entirety.

STATEMENT REGARDING FEDERALLY SPONSORED RESEARCH

This work was funded, in part, through support from the National Institutes of Health, Grant Nos. MH070040 and GM076261.

BACKGROUND

Many proteins interact via two or more contact points that account for the majority of the binding energy between the two. Such a point of interaction may be termed a 'hot-spot.' Molecules may be designed having pharmacophores positioned with known separation to interact with these hot-spots. A molecule positioning two pharmacophores for interaction with hot spots may be termed a bivalent molecule. Bivalent compounds may have increased binding energy over similar monovalent compounds, since more than one pharmacophore may interact with the protein. Such compounds may be useful for studying protein-protein interactions, comprise a pharmaceutical lead compounds, or comprise pharmaceuticals.

For protein-protein interactions, studies have shown that amino acid side chain groups or side chains based on amino acid side chain groups contribute a majority of the binding energy, whereas main-chain carbonyl groups contribute relatively little toward the binding energy. Thus, pharmacophores bearing amino acid side chain groups or groups based on amino acid side chain groups are likely to have enhanced binding properties over compounds not having amino acid side chains. Drug leads utilizing unprotected amino acids as pharmacophores are undesirable from both a synthetic and pharmacological standpoint. In response to this need, peptidomimetics have been developed as a means to improve pharmacological properties and lessen synthetic burden. A number of different peptidomimetics have been prepared.

The ability to rapidly prepare libraries of compounds is advantageous for screening of new pharmacophores. Preparation of compound libraries is often achieved by combinatorial methods utilizing solid-phase syntheses. Solution-phase syntheses offer considerable handling advantages over solid-phase methods, but they are usually much slower than solid phase methods for production of compound libraries.

In view of the foregoing, it would be highly beneficial to design peptidomimetics having amino acid side chains or groups based on amino acid side chains, whose structures are amenable to rapid bivalent compound library syntheses by solution phase synthesis methods.

SUMMARY

In some aspects, the disclosure describes a compound whose structure is selected from the group consisting of

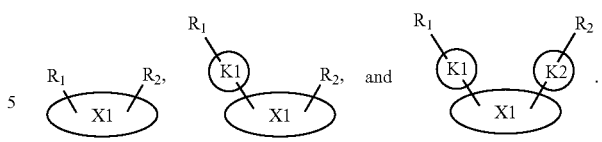

$R_1$ and $R_2$ are comprised by at least one moiety comprising an amino acid side chain. $R_1$ and $R_2$ further comprise non-peptidic bonds. X1 comprises a core molecule selected from the group consisting of heteroarylenes, arylenes and heterocyclenes and a nucleophilic moiety bound to said core molecule. K1 and K2 comprise at least one spacer atom between said core molecule and said at least one moiety comprising an amino acid side chain In other aspects, the disclosure describes a compound having the structure

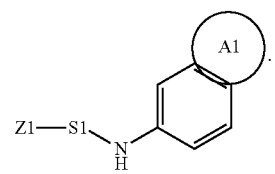

A1 comprises a macrocyclic ring comprising at least two amino acids, wherein said at least two amino acids are bound to each other in a ring comprising at least one peptide bond. Z1 comprises a nucleophilic moiety selected from the group consisting of piperidine, piperazine, pyrrolidine, azetidine, and any derivative or analog thereof. S1 comprises a spacer group having at least one carbonyl moiety, wherein S1 does not comprise glycine.

In another aspect, the disclosure describes a compound having the structure

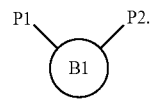

B1 is a core molecule selected from the group consisting of heteroarylenes, arylenes, and heterocyclenes. P1 and P2 comprise an organic moiety comprising removal of a hydrogen atom from compounds disclosed herein. P1 and P2 are independently selected.

In still another aspect, the disclosure describes a compound having the structure

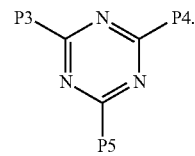

P3 and P4 comprise an organic moiety comprising removal of a hydrogen atom from the nitrogen atom of the piperidine or piperazine ring of compounds disclosed herein. P3 and P4 are independently selected. P5 comprises a moiety selected from the group consisting of an organic moiety comprising removal of a hydrogen atom from the nitrogen atom of the piperidine or piperazine ring of compounds disclosed herein and a labeling tag T1. P5 is selected independently of P3 and P4.

In still another aspect, the disclosure provides a method of producing a library of compounds, comprising the following steps:
1) providing

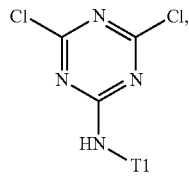

wherein T1 comprises a labeling tag;
2) reacting a first equivalent of a piperazine or piperidine compound disclosed herein or morpholine in the presence of a base and a solvent; 3) removing the solvent; and 4) reacting a second equivalent of a piperazine or piperidine compound disclosed herein or morpholine in the presence of a base and a solvent. Selection of said first equivalent and said second equivalent is conducted with the proviso that said first equivalent and said second equivalent are not both morpholine.

The disclosure also provides pharmaceutical compounds, pharmaceutical lead compounds, and pharmacological probes selected from the compounds described herein. The disclosure also provides compounds selected from the compounds described herein which demonstrate protein-protein interactions.

The foregoing has outlined rather broadly the features of the present disclosure in order that the detailed description that follows may be better understood. Additional features and advantages of the disclosure will be described hereinafter, which form the subject of the claims.

DETAILED DESCRIPTION

In the following description, certain details are set forth such as specific quantities, sizes, etc. so as to provide a thorough understanding of the present embodiments disclosed herein. However, it will be obvious to those skilled in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

While most of the terms used herein will be recognizable to those of skill in the art, the following definitions are nevertheless put forth to aid in the understanding of the present disclosure. It should be understood, however, that when not explicitly defined, terms should be interpreted as adopting a meaning presently accepted by those of skill in the art.

"Alkyl," as defined herein refers to groups comprising straight, branched, and cyclic substituents containing about 1 to about 20 carbons, or about 1 to about 10 carbons in some embodiments. Alkyl groups may have carbon-carbon double bonds and contain about 2 to about 20 carbons, or about 2 to about 10 carbons in some embodiments. Alkyl groups may also have carbon-carbon triple bonds and contain about 2 to about 20 carbons, or about 2 to about 10 carbons in some embodiments. In an embodiment, an alkyl group is a methyl group. Representative alkyl groups include, but are not limited to, methyl, ethyl, propyl, isopropyl, isobutyl, n-butyl, sec-butyl, tert-butyl, isopentyl, neopentyl, tert-pentyl, isohexyl, ethenyl, propenyl, butenyl, pentenyl, acetylenely, propynyl, butynyl, pentynyl, hexynyl, cyclopropyl, cyclobutyl, cyclopentyl, and cyclohexyl. Alkyl groups may be substituted with heteroatoms in the carbon chain comprising the alkyl group, wherein heteroatoms include, but are not limited to oxygen, nitrogen, and sulfur. Alkyl groups may be substituted with one or more substituents, in certain embodiments one substituent, and in other embodiments three or four substituents.

"Amino acid side chain moieties," as defined herein includes groups of atoms linked to the α-carbon of naturally-occurring amino acids and their derivatives, homologues, and analogues.

"Arylene," as defined herein, is a monocyclic or polycyclic aromatic group having from about 5 to about 20 carbon atoms, at least one aromatic ring, and at least two substituents. In some embodiments, the arylene group has about 5 to about 12 carbon atoms. In an embodiment, the arylene is monocyclic and has 5 or 6 carbon atoms. Arylene groups may include, but are not limited to 1,2-, 1,3- and 1,4-disubstituted phenylene.

"Heteroarylene," as defined herein, is a monocyclic or polycyclic aromatic ring having about 5 to about 15 atoms in the ring, wherein about 1 to about 5 of the atoms in the ring are heteroatoms, and said ring has at least two substituents. "Heteroatom," as defined herein, is an atom other than carbon, including but not limited to nitrogen, oxygen, and sulfur. In an embodiment, a heteroarylene is monocyclic and has 5 or 6 atoms, wherein 1 to 3 of the atoms are heteroatoms.

"Heterocyclene," as defined herein, is a monocyclic or polycyclic non-aromatic ring having about 5 to about 11 atoms in the ring, wherein about 1 to about 4 of the atoms in the ring are heteroatoms, and said ring has at least two substituents. Heteroatoms are atoms other than carbon that may include, but are not limited to, nitrogen, oxygen, and sulfur. In an embodiment, a heterocyclene is monocyclic and has 5 or 6 atoms, wherein 1 to 3 of the atoms are heteroatoms. In another embodiment, a heterocyclene is monocyclic and has 6 or 7 atoms, wherein 1 to 3 of the atoms are heteroatoms. In an embodiment, a heterocyclene is monocyclic, has 6 atoms, and 2 heteroatoms.

"Macrocyclic ring," as defined herein, is a ring having more than about 12 atoms. In an embodiment, a macrocyclic ring has more than about 14 atoms. In an embodiment, a macrocyclic ring has 14 atoms. Macrocyclic rings may contain heteroatoms.

"Non-peptidic bond," as defined herein, is a chemical bond not comprising a peptide bond. A non-peptidic bond may be an amide bond, provided the amide bond is not between two amino acids, wherein said amide bond between two amino acids is between the backbone amino and carboxylic acid groups of said amino acids. A non-peptidic bond may be a bond between two amino acids, if said bond comprises any one other atom than the backbone amino and carboxylic acid groups.

"Peptide bond," as defined herein, is an amide bond formed between the backbone amino and carboxylic acid groups of amino acids, peptides, proteins, and any of their derivatives or analogs.

It is to be understood that compounds provided herein may contain chiral centers. Such chiral centers may be of either the (R) or (S) configuration, or a mixture thereof.

Compounds containing more than one chiral center may be enantiomerically pure, or be a mixture of stereoisomeric and diastereomeric forms.

Compounds disclosed herein are substantially pure. "Substantially pure," as disclosed herein comprises a purity assay of >85% as determined by reversed-phase HPLC and identification of a molecular ion peak or fragment thereof by mass spectrometry (MS). A substantially pure compound may be a mixture of stereoisomers, which may be further separable if desired.

In a general aspect of the disclosure, a compound having the structure selected from the group consisting of

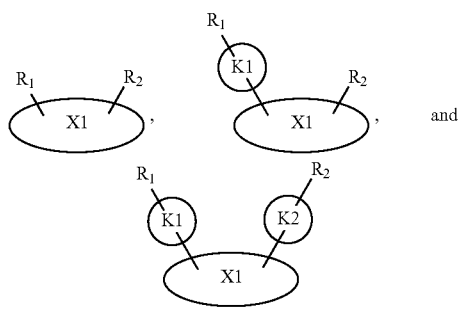

is described. $R_1$ and $R_2$ are comprised by at least one moiety comprising an amino acid side chain, and $R_1$ and $R_2$ further comprise non-peptidic bonds. X1 comprises a core molecule selected from the group consisting of heteroarylenes, arylenes, and heterocyclenes. A nucleophilic moiety also comprises X1 with the nucleophilic moiety bound to the core molecule in some manner. X1 may be further comprised by at least one 1,2,3-triazine moiety bound to the core molecule. In an embodiment, two 1,2,3-triazine moieties are bound to the core molecule. K1 and K2 comprise at least one spacer atom between the core molecule and the at least one moiety comprising an amino acid side chain. Spacer atoms may comprise chains or rings of atoms and may contain single bonds, double bonds, triple bonds, and combinations thereof. Compounds comprising this aspect of the disclosure may be considered diamino acid peptidomimetics, since the compounds mimic two amino acids present in protein structures.

Amino acid side chain moieties, which comprise $R_1$ and $R_2$, may include a structural fragment including, but not limited to:

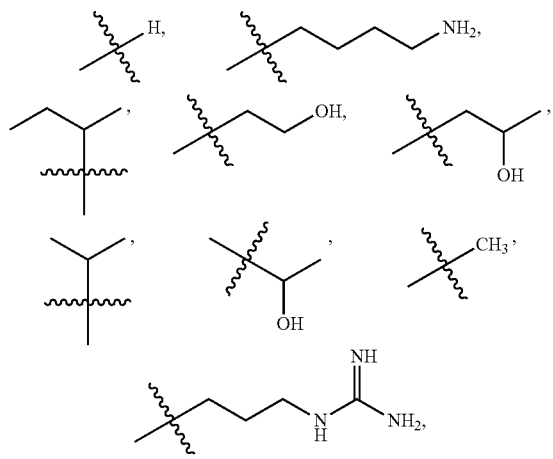

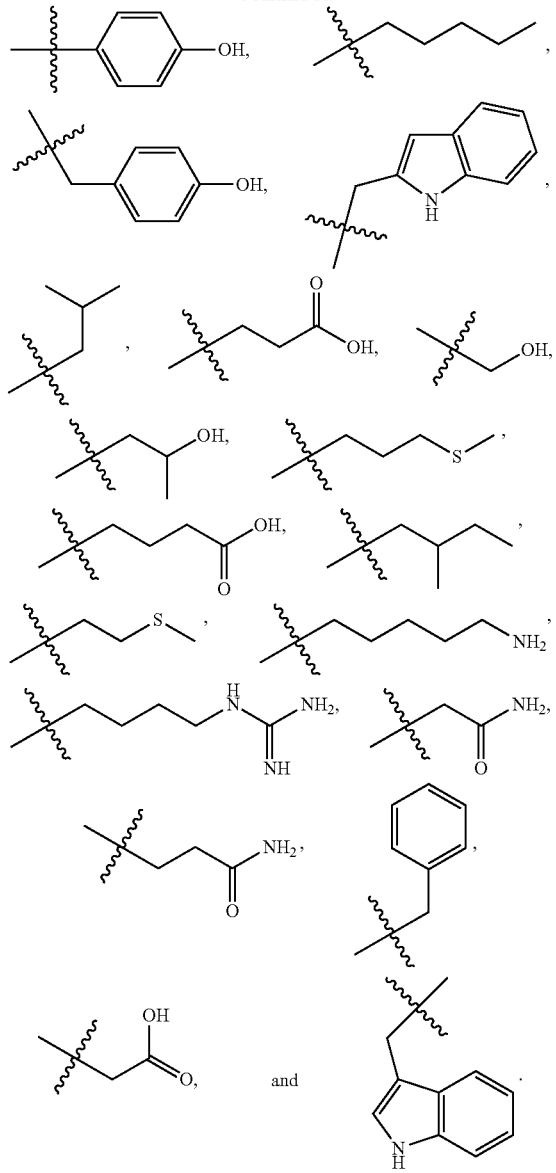

Structural fragment, as used hereinabove, refers to a grouping of atoms comprising the amino acid side chain moieties listed hereinabove. $R_1$ and $R_2$ may be comprised solely by the amino acid side chain moieties comprising a structural fragment, or the structural fragment may be part of a larger grouping of atoms comprising $R_1$ and $R_2$. The point of attachment to the amino acid side chain moieties is indicated by the bond disconnection shown in the listing of moieties hereinabove. $R_1$ and $R_2$ may be independently selected and comprise any of the amino acid side chain moieties listed hereinabove.

The nucleophilic moiety comprising X1 comprises a moiety selected from piperidine, piperazine, pyrrolidine, azetidine, and any derivative or analog thereof. In an embodiment of the disclosure, the nucleophilic moiety is piperidine. In another embodiment of the disclosure, the nucleophilic moiety is piperazine. The nucleophilic moiety may be bound directly to X1 in an embodiment. In another embodiment, the nucleophilic moiety may be bound to X1 through at least one spacer atom. The at least one spacer atom may comprise $R_1$ or $R_2$ or comprise additional atoms bound to X1. The nucleophilic moiety may provide a synthetic handle for further synthetic manipulation of the compounds.

The core molecule comprising X1 may be an aromatic ring in some embodiments, a heteroaromatic ring in other embodiments, or a heterocyclic ring in still other embodiments. Aromatic rings may include, but are not limited to, a 1,2-substituted phenyl ring, a 1,3-substituted phenyl ring, and a 1,4-substituted phenyl ring. An aromatic ring may be trisubstituted, such as a 1,2,4-substituted phenyl ring, a 1,2,5-substituted phenyl ring, a 1,2,3-substituted phenyl ring, and a 1,3,5-substituted phenyl ring. An aromatic ring may be tetrasubstituted, such as a 1,2,3,4-substituted phenyl ring, a 1,2,3,5-substituted phenyl ring, and a 1,2,4,5-substituted phenyl ring. An aromatic ring may be pentasubstituted, such as a 1,2,3,4,5-substituted phenyl ring. An aromatic ring may be hexasubstituted, such as a 1,2,3,4,5,6-substituted phenyl ring. A heteroaromatic ring may include, but is not limited to, a 1,2,3-triazole ring, a 1,3,4-oxadiazole ring, and a pyridine ring. A heterocyclic ring may include, but is not limited to a diketopiperazine ring. In embodiments of the disclosure, derivatives and analogs of any of these rings are contemplated.

In one aspect of the disclosure, a compound having the structure

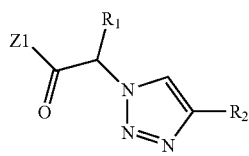

is described, wherein Z1 comprises a nucleophilic moiety selected from the group consisting of piperidine, piperazine, pyrrolidine, azetidine, and any derivative or analog thereof, and wherein $R_1$ and $R_2$ are defined as detailed hereinabove.

In one aspect of the disclosure, a compound having the structure

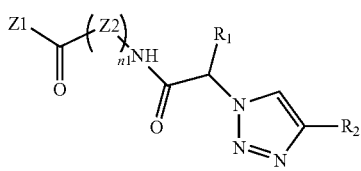

is described, wherein Z1, $R_1$ and $R_2$ are defined as detailed hereinabove. Z2 is a moiety that may include, but is not limited to —$CH_2$—, —$CH_2CH_2$— and —$CH_2CH_2O$—, and n1 is an integer from 1-20. In an embodiment of the disclosure, a compound having the structure

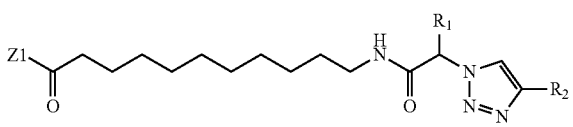

is described, wherein Z1, $R_1$ and $R_2$ are defined as detailed hereinabove.

In another aspect of the disclosure, a compound having the structure

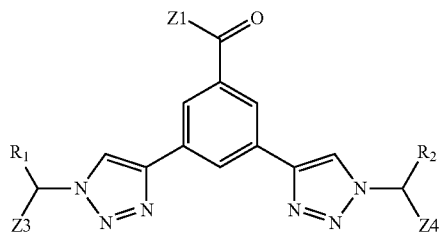

is described wherein Z1 comprises a nucleophilic moiety selected from the group consisting of piperidine, piperazine, pyrrolidine, azetidine, and any derivative or analog thereof, and wherein $R_1$ and $R_2$ are defined as detailed hereinabove. Z3 and Z4 comprise moieties independently selected from the group consisting of $CO_2R_3$, $CONR_4R_5$, and $CH_2OH$, wherein $R_3$ is H or alkyl, $R_4$ is H or alkyl, and $R_5$ is H or alkyl. $R_4$ and $R_5$ are selected independently from one another. In an embodiment, the compound has the structure

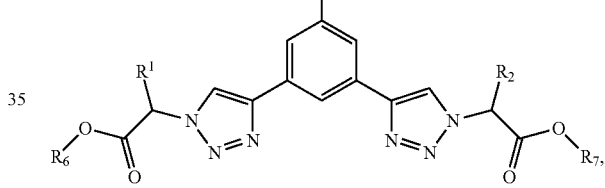

wherein Z1, $R_1$, and $R_2$ are defined as detailed hereinabove. $R_6$ and $R_7$ are independently selected from the group consisting of hydrogen and alkyl. In certain embodiments of the disclosure, $R_6$ is methyl and $R_7$ is H. In other embodiments of the disclosure, $R_6$ is H and $R_7$ is methyl. In still other embodiments of the disclosure, both $R_6$ and $R_7$ are methyl.

In another aspect of the disclosure, a compound having a structure

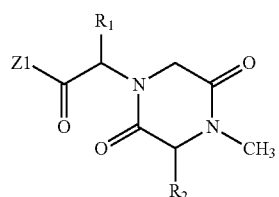

is described, wherein Z1 comprises a nucleophilic moiety selected from the group consisting of piperidine, piperazine, pyrrolidine, azetidine, and any derivative or analog thereof, and wherein $R_1$ and $R_2$ are defined as detailed hereinabove. In an embodiment, a compound having the structure

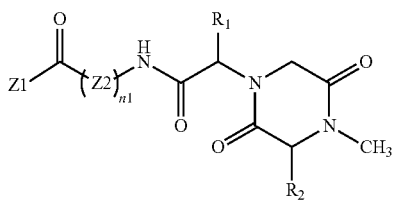

is described, wherein Z1, $R_1$ and $R_2$ are defined as detailed hereinabove. Z2 is a moiety that may include, but is not limited to, —$CH_2$—, —$CH_2CH_2$— and —$CH_2CH_2O$—, and n1 is an integer from 1-20. In an embodiment of the disclosure, a compound having the structure

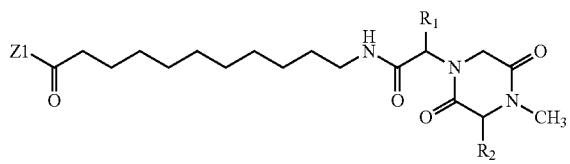

is described, wherein Z1, $R_1$ and $R_2$ are defined as detailed hereinabove

In another aspect of the disclosure, a compound having the structure

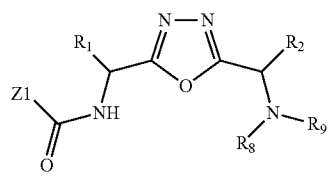

is described, wherein Z1 comprises a nucleophilic moiety selected from the group consisting of piperidine, piperazine, pyrrolidine, azetidine, and any derivative or analog thereof, and wherein $R_1$ and $R_2$ are defined as detailed hereinabove. $R_8$, and $R_9$ are independently selected from the group consisting of hydrogen and alkyl. In an embodiment, both $R_8$ and $R_9$ are hydrogen. In another embodiment, both $R_8$ and $R_9$ are methyl groups.

In another aspect of the disclosure, a compound having the structure

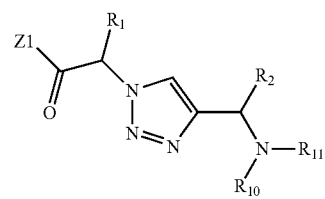

is described, wherein Z1 comprises a nucleophilic moiety selected from the group consisting of piperidine, piperazine, pyrrolidine, azetidine, and any derivative or analog thereof, and wherein $R_1$ and $R_2$ are defined as detailed hereinabove. $R_{10}$ and $R_{11}$ are independently selected from the group consisting of hydrogen and alkyl. In an embodiment, both $R_{10}$ and $R_{11}$ are hydrogen.

In another aspect of the disclosure, a compound having the structure

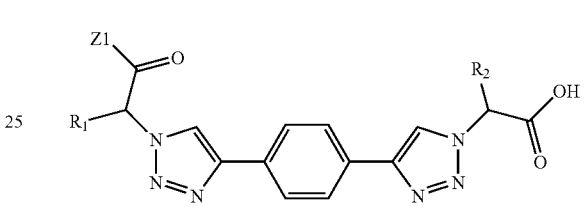

is described, wherein Z1 comprises a nucleophilic moiety selected from the group consisting of piperidine, piperazine, pyrrolidine, azetidine, and any derivative or analog thereof, and wherein $R_1$ and $R_2$ are defined as detailed hereinabove.

In still another aspect of the disclosure a compound having the structure

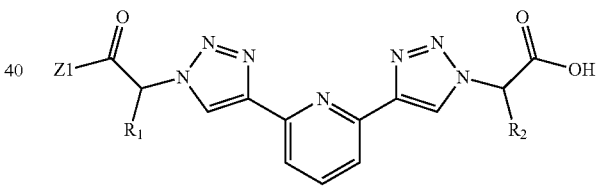

is described, wherein Z1 comprises a nucleophilic moiety selected from the group consisting of piperidine, piperazine, pyrrolidine, azetidine, and any derivative or analog thereof, and wherein $R_1$ and $R_2$ are defined as detailed hereinabove.

In the embodiments described hereinabove, the compounds may have the structure selected from the group, including but not limited to:

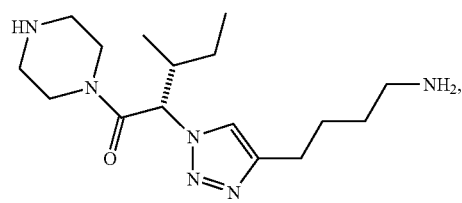

a

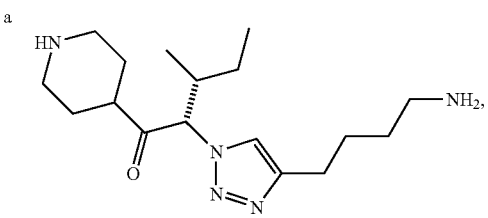

A

-continued
| 11 | | 12 | |
|---|---|---|---|
| b | 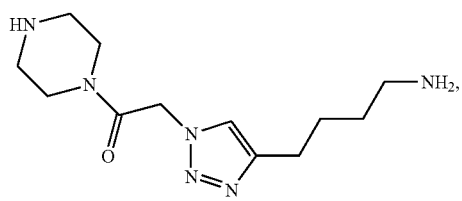 | B | 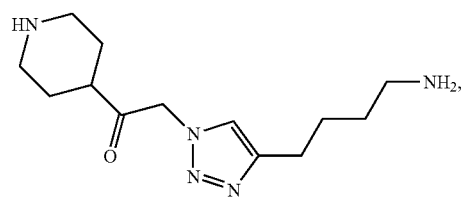 |
| c | 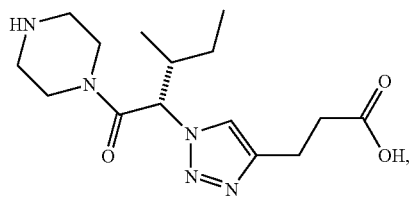 | C | 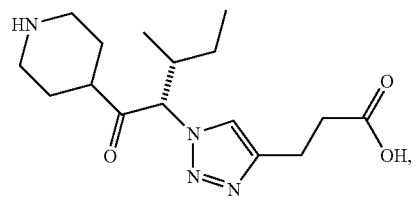 |
| d | 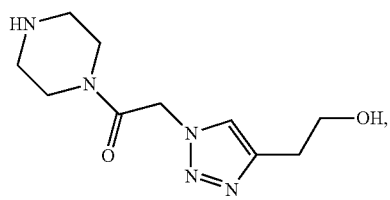 | D | 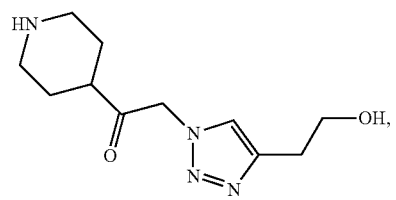 |
| e | 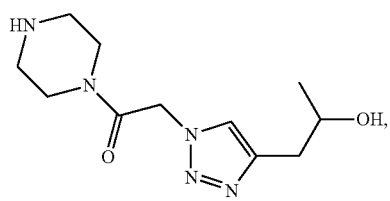 | E | 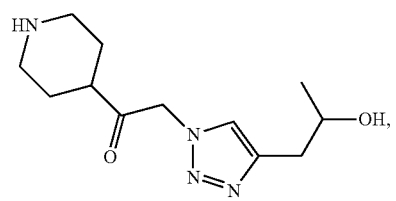 |
| f | 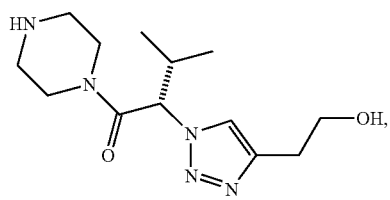 | F | 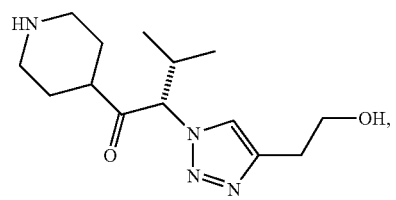 |
| g | 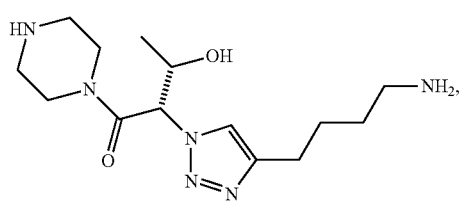 | G | 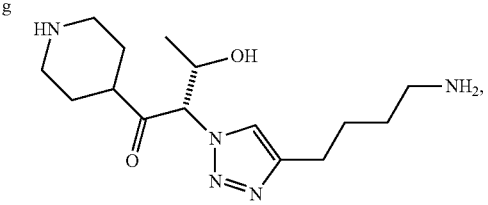 |
| h | 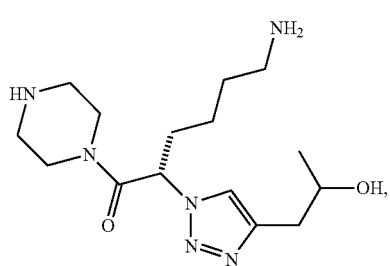 | H | 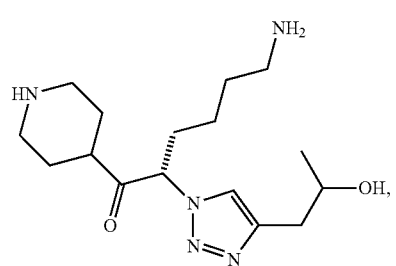 |

-continued
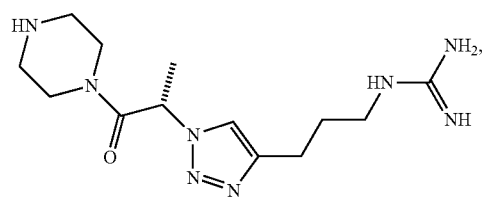
i
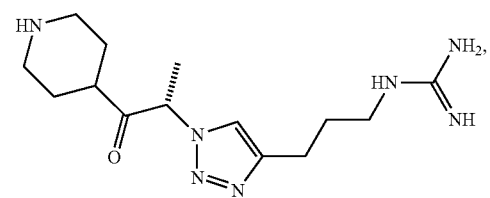
I
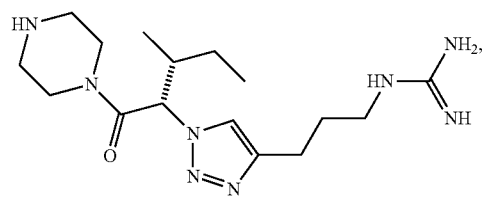
j
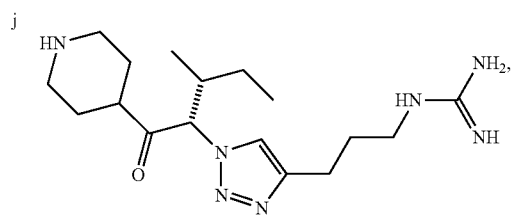
J
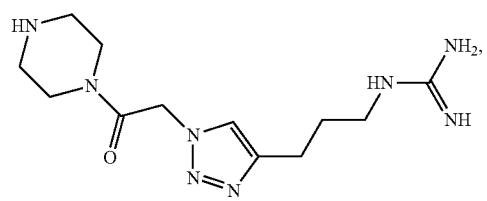
k
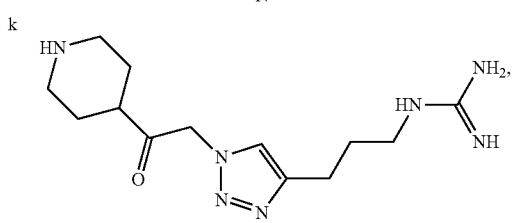
K
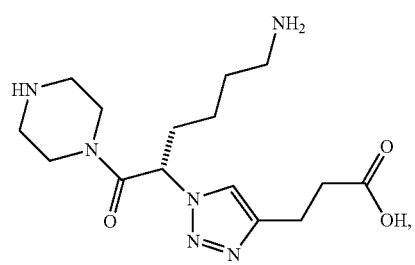
l
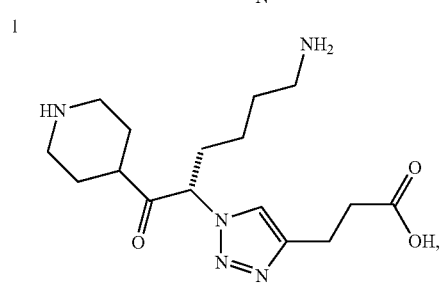
L
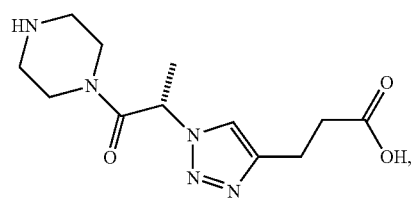
m
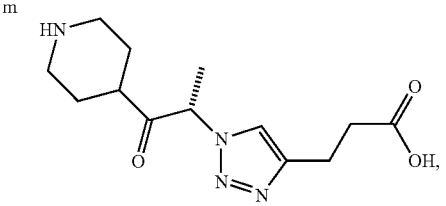
M
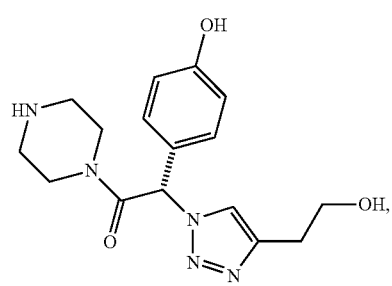
n
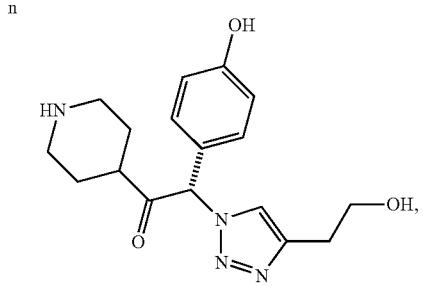
N
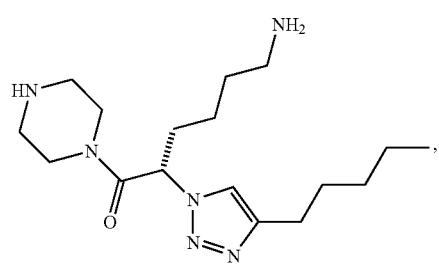
o
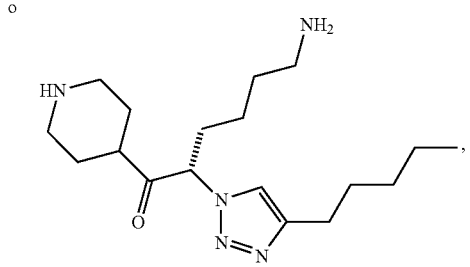
O -continued
q
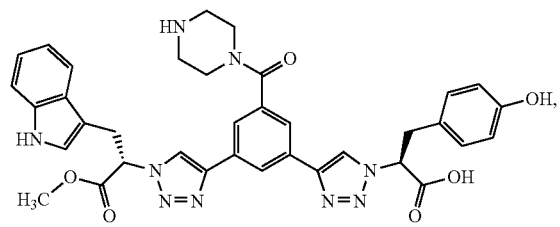
Q
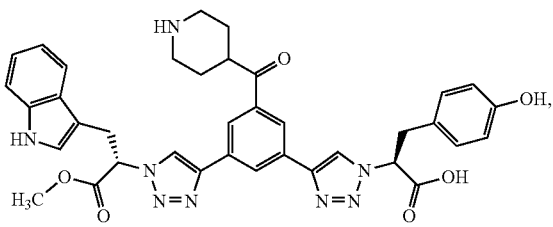
r
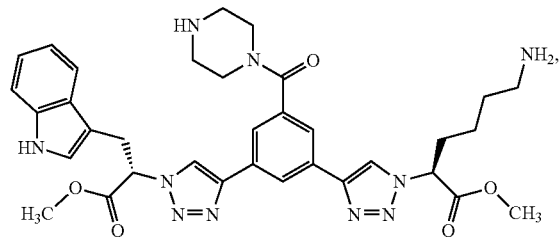
R
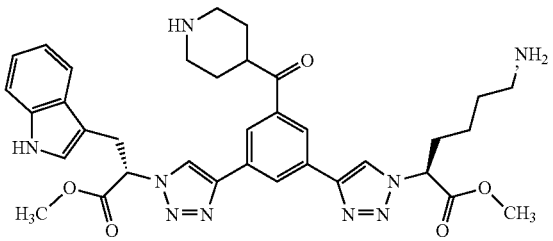
s
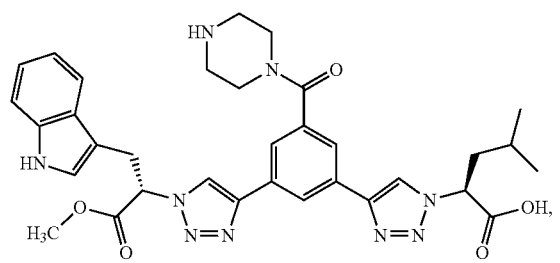
S
t
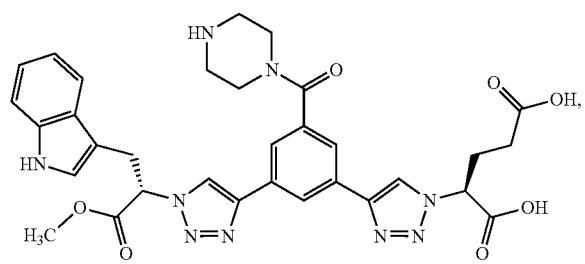
T
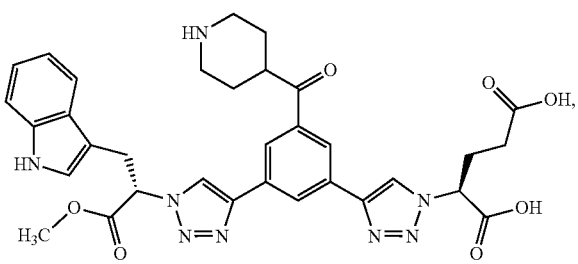
u
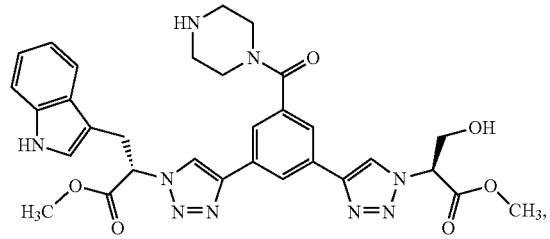
U
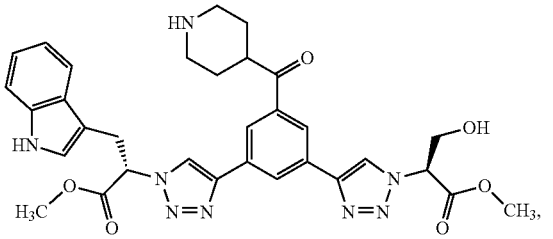
v
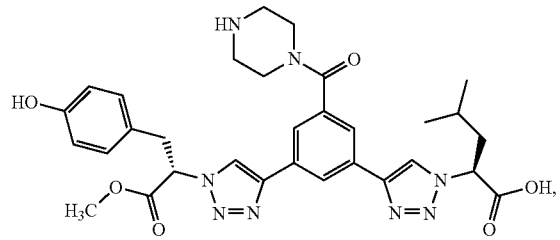
V
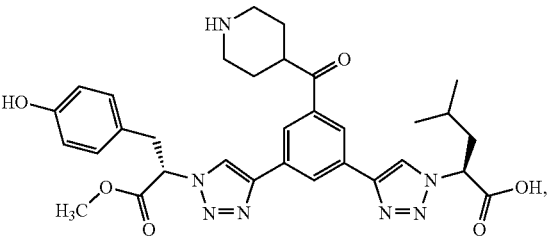

-continued
w
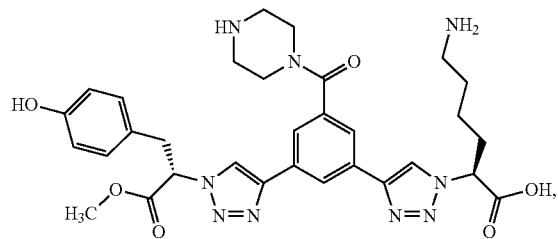
W
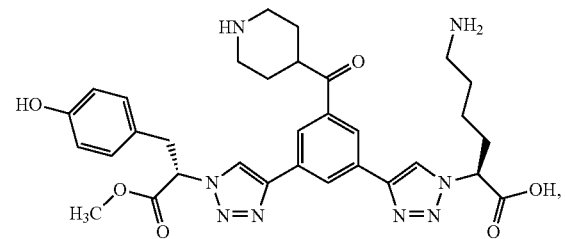
x
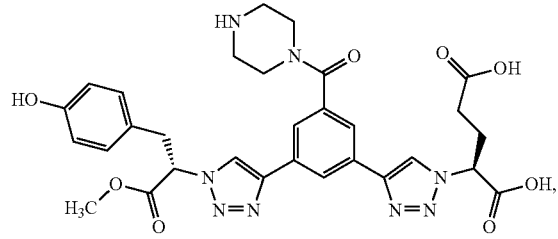
X
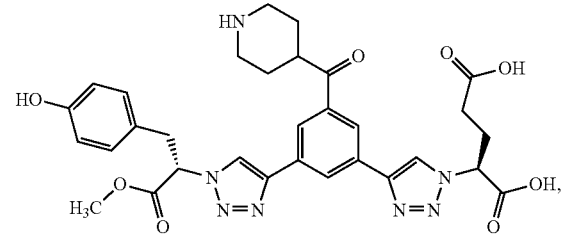
y
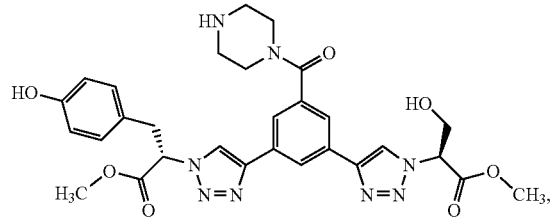
Y
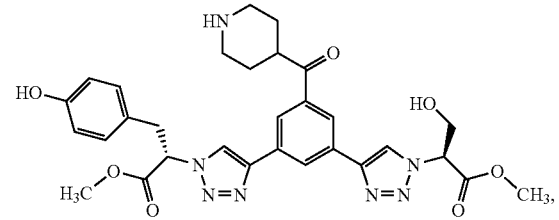
z
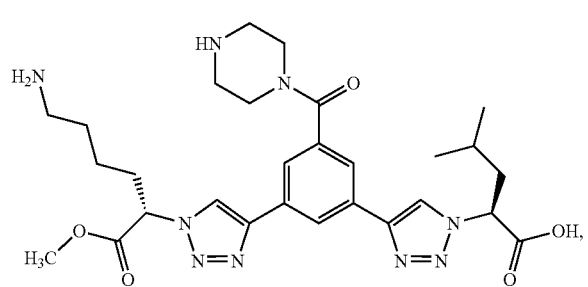
Z
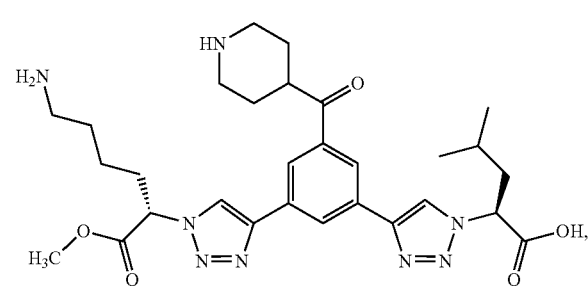
a'
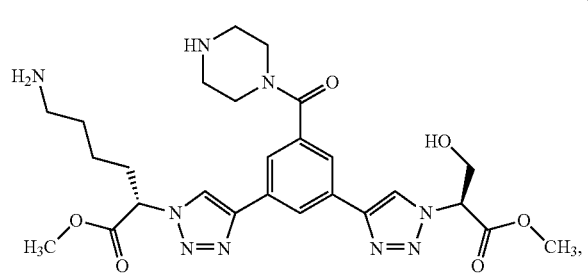
A'
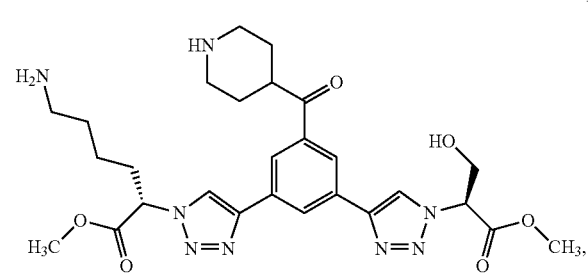
b'
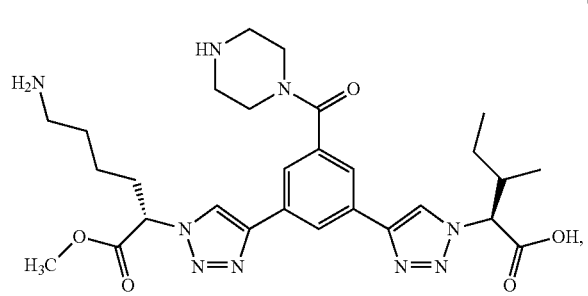
B'
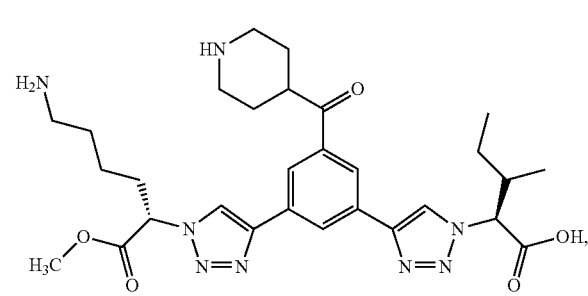

-continued
c'
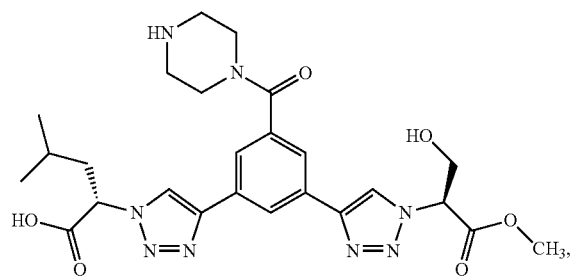
C'
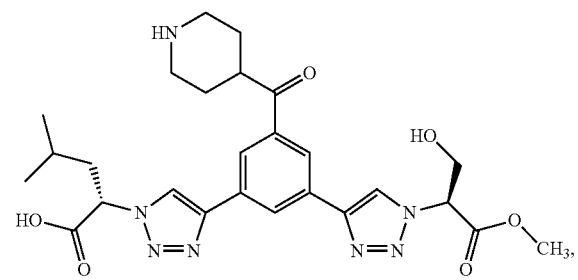
d'
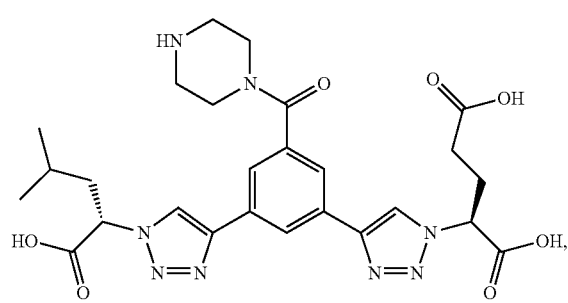
D'
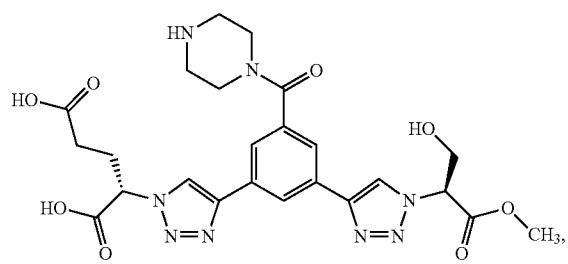
e'
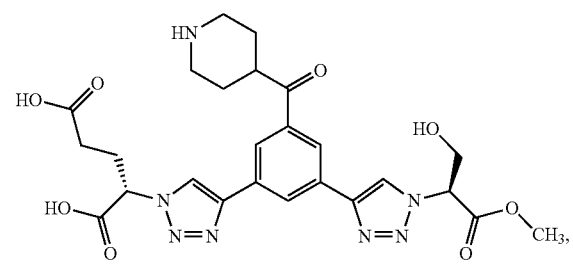
E'
f'
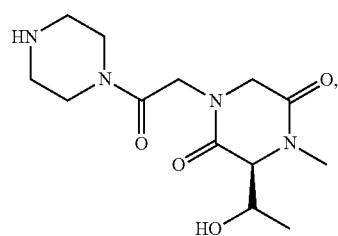
F'
g'
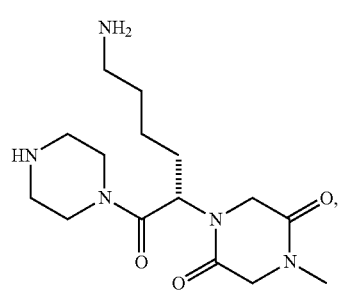
G'

-continued
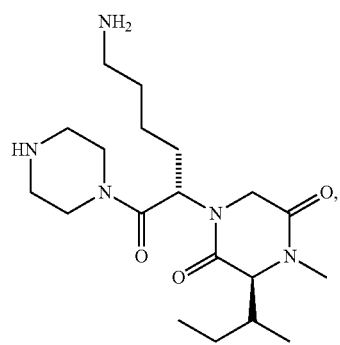
h'
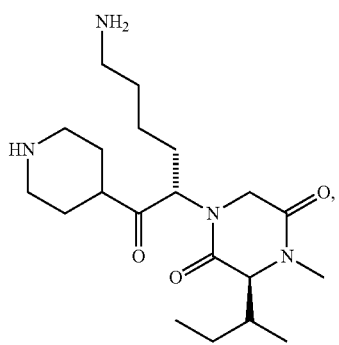
H'
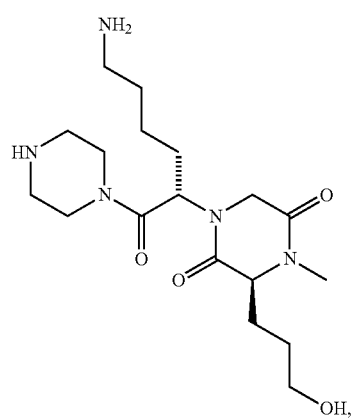
i'
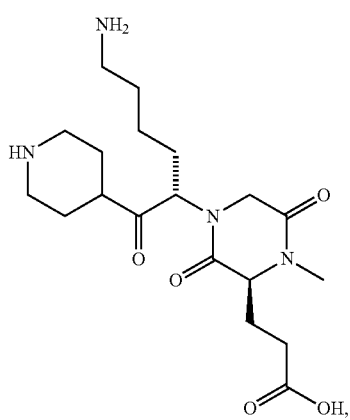
I'
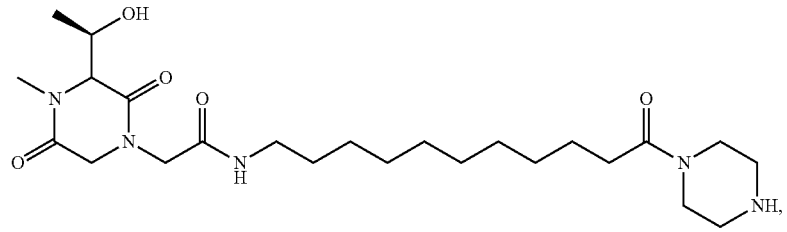
j'
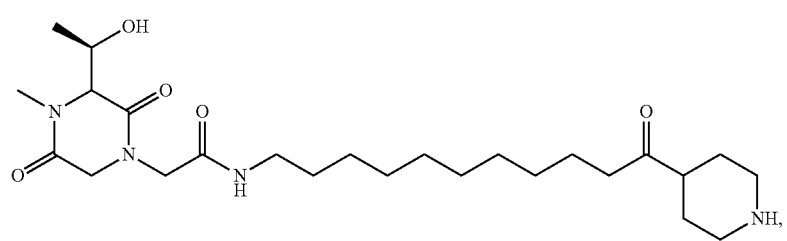
J'
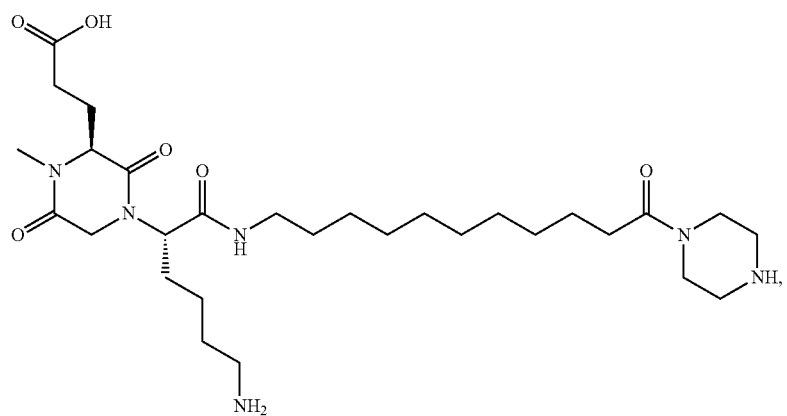
k'

-continued
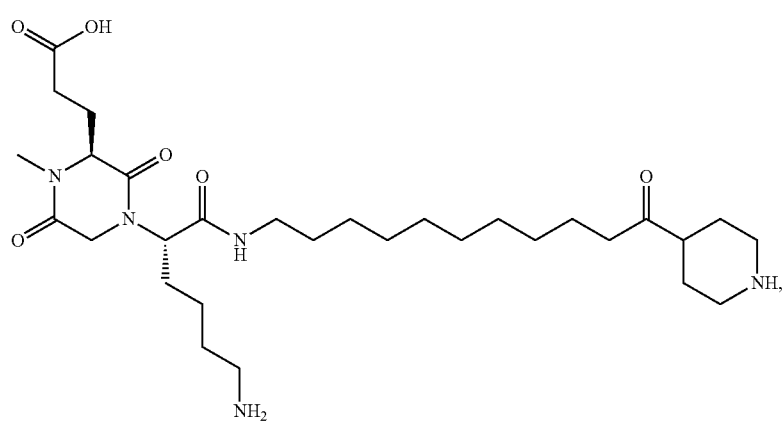
K'
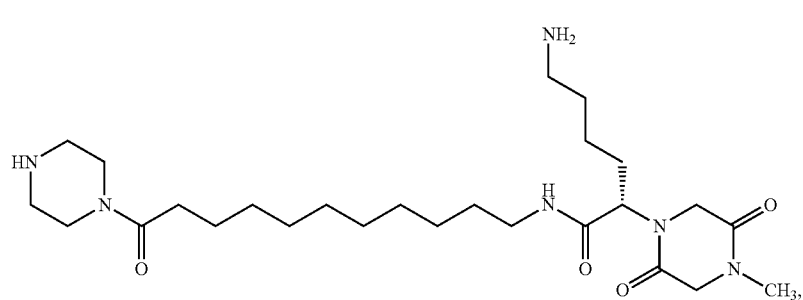
I'
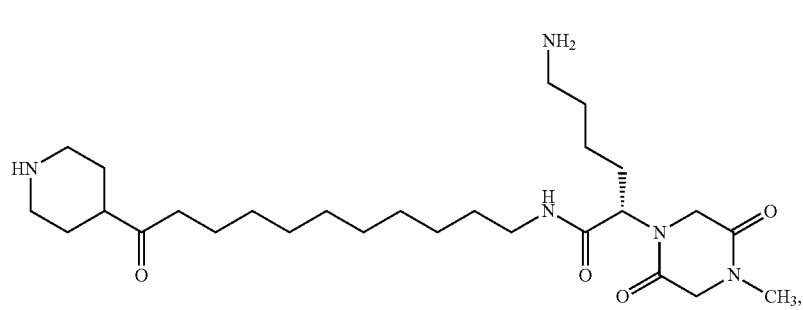
L'
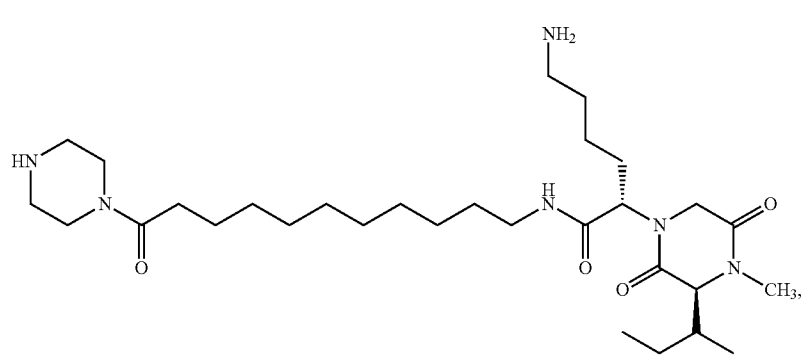
m'

-continued
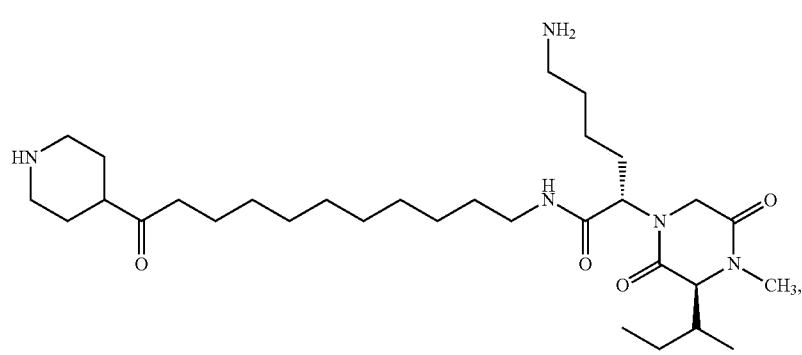
M'
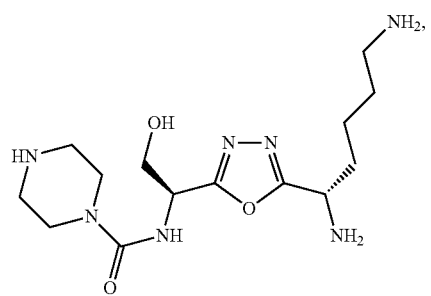
N'
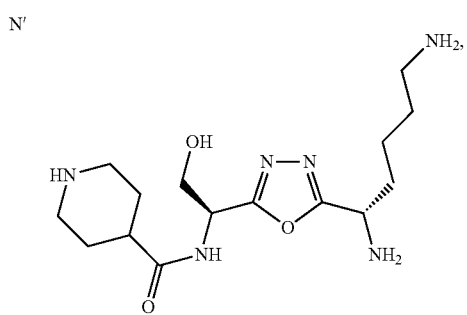
n'
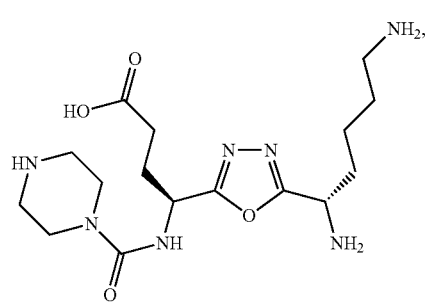
O'
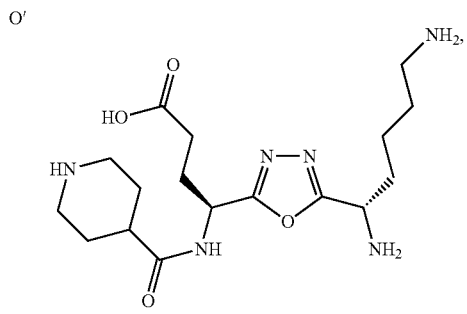
o'
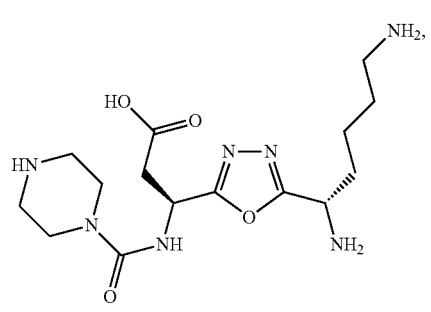
P'
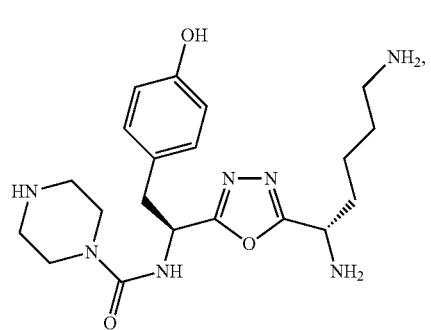
Q'
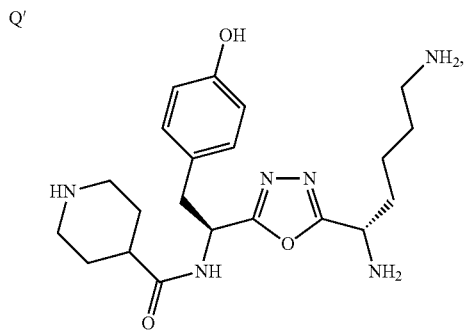
q'

-continued
R' 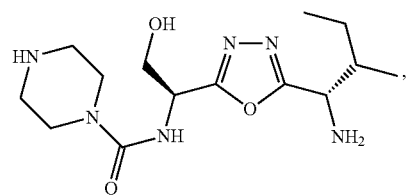 r'
S' 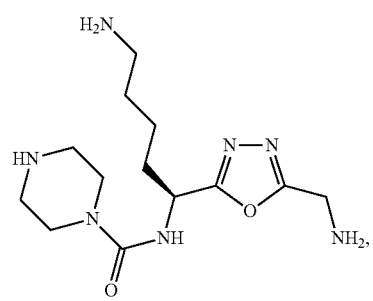 s'
T' 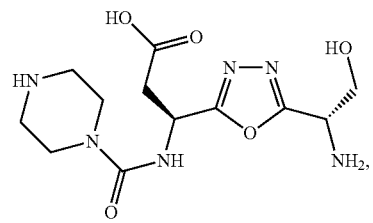 t'
U' 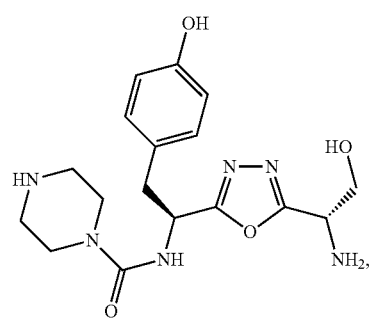 u'
V' 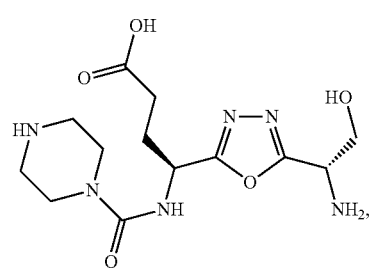 v'
W' 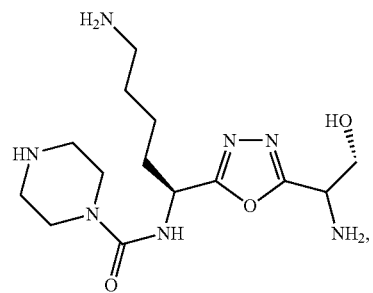 w'

-continued
| | |
|---|---|
| X' 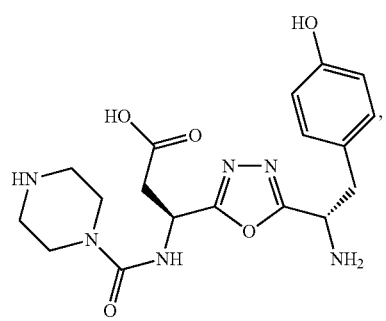 | x' 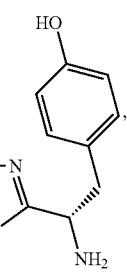 |
| Y' 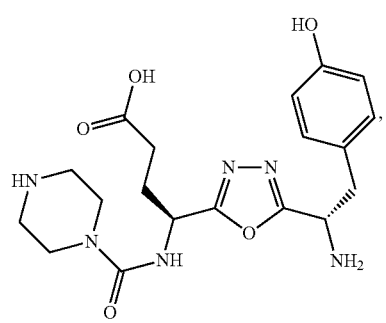 | y' 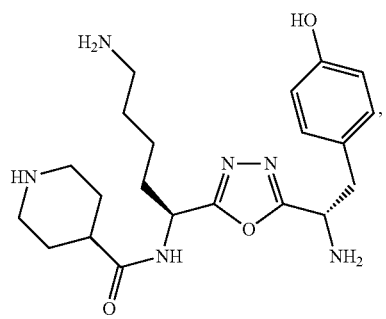 |
| Z' | z' 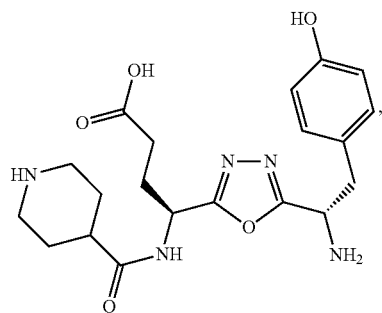 |
| A" 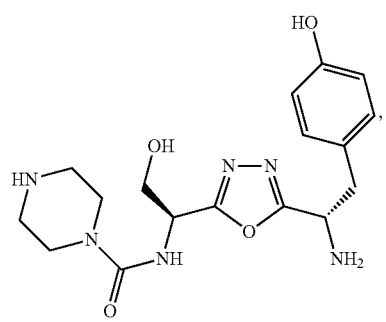 | a" 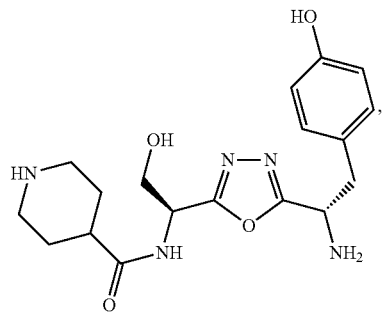 |
| B" | b" 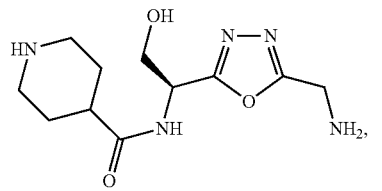 |

-continued
| | |
|---|---|
| C″ 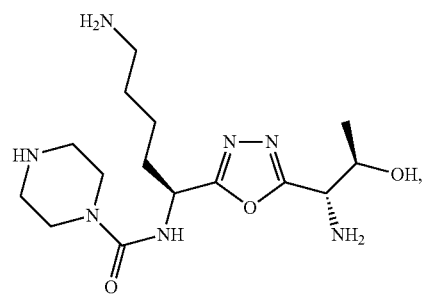 | c″ 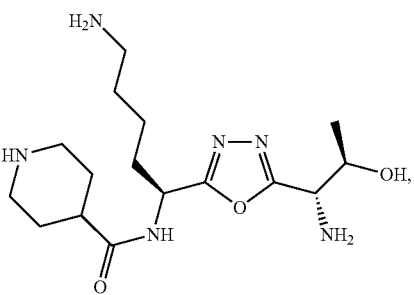 |
| D″ 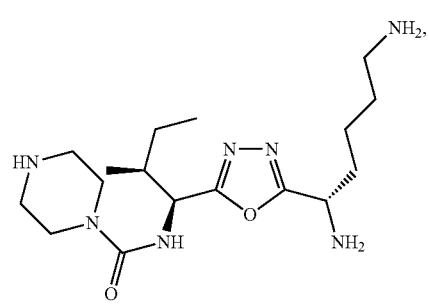 | d″ 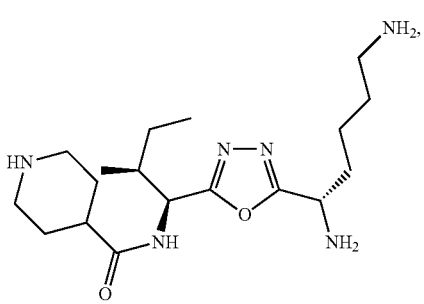 |
| E″ 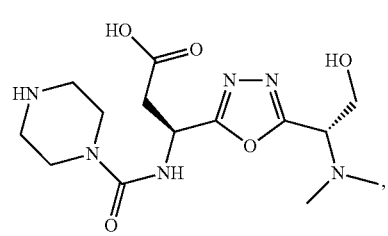 | e″ 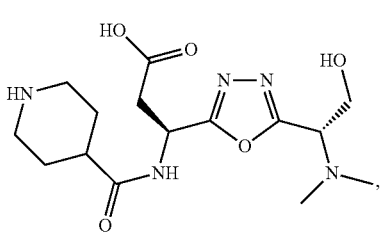 |
| F″ 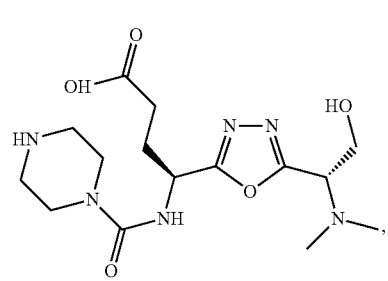 | f″ 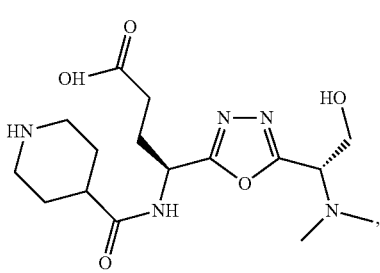 |
| G″ 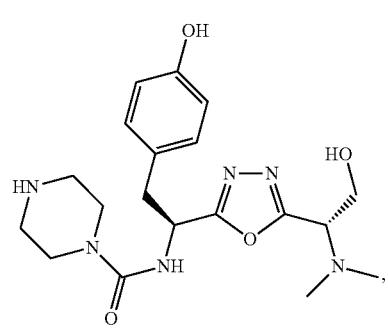 | g″ 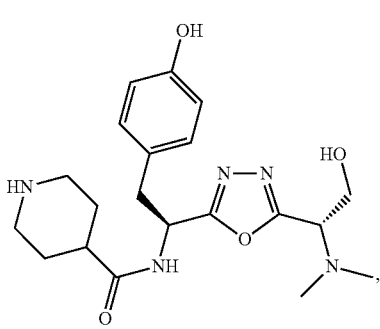 |
| H″ 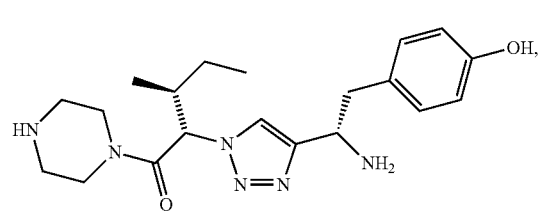 | H″ 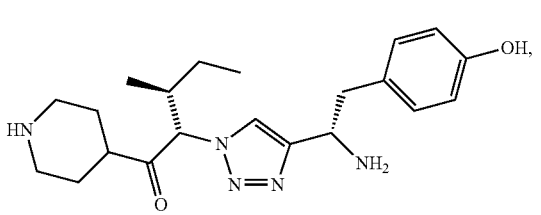 |

-continued
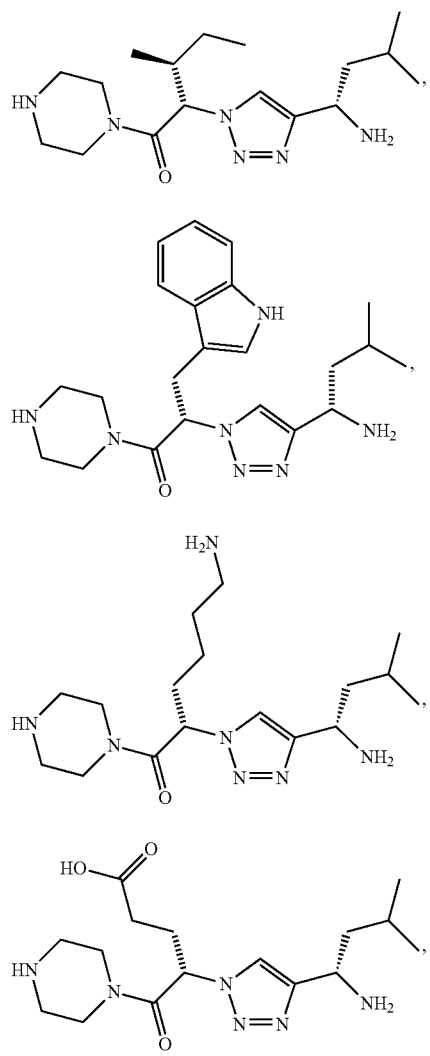
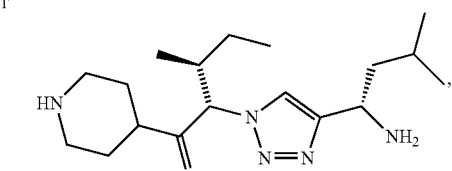
i″
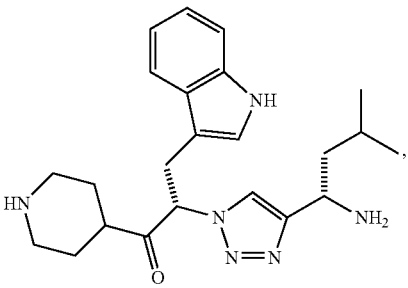
j″
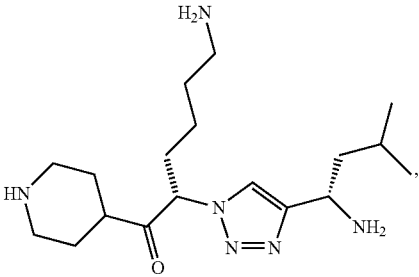
k″
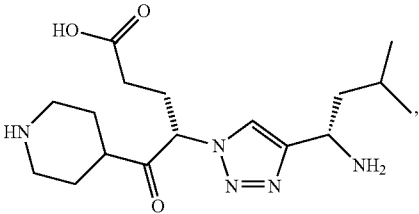
l″
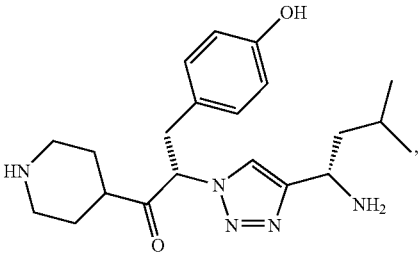
m″
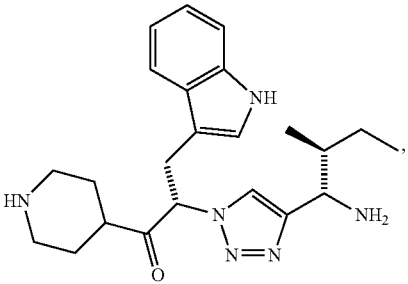
n″

-continued
o″
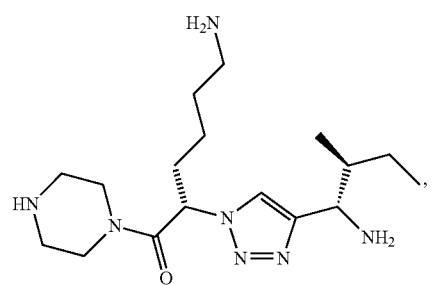
O″
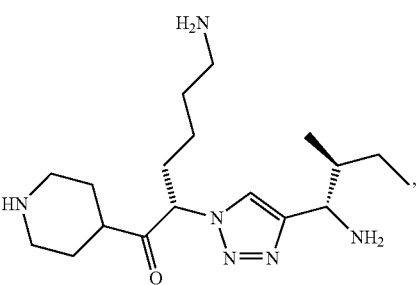
p″
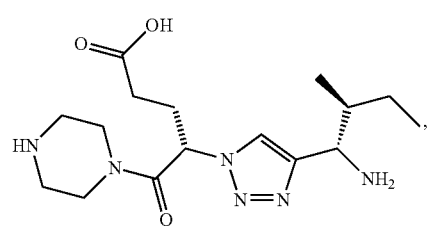
P″
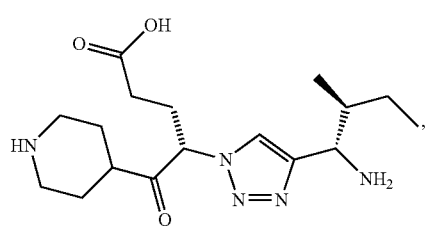
q″
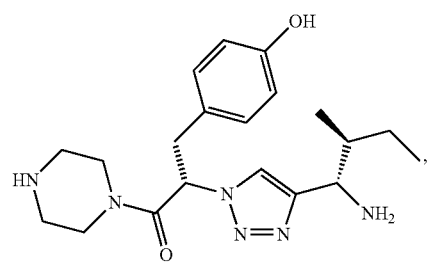
Q″
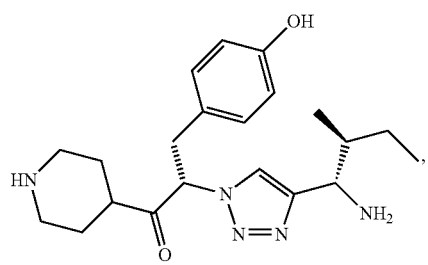
r″
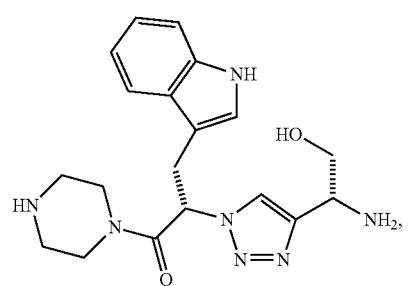
R″
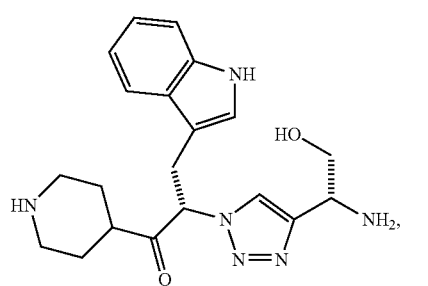
s″
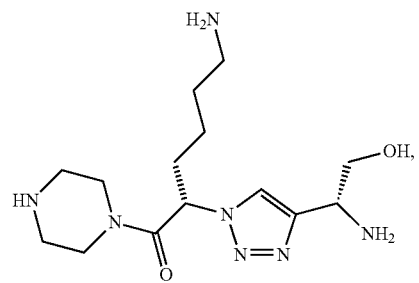
S″
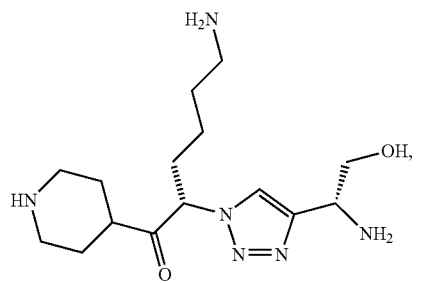
r″
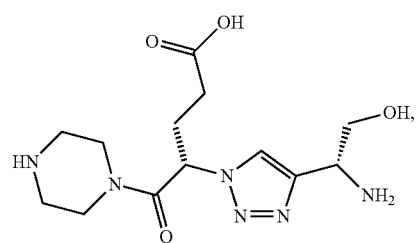
T″
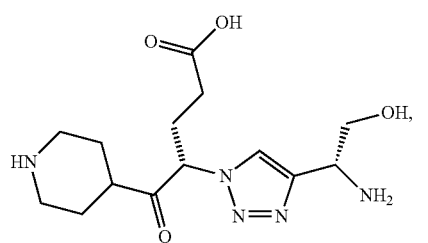

-continued
u″ 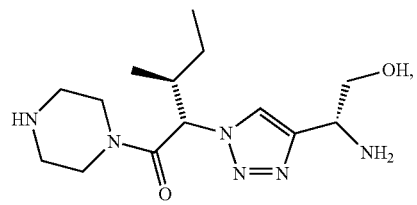
v″ 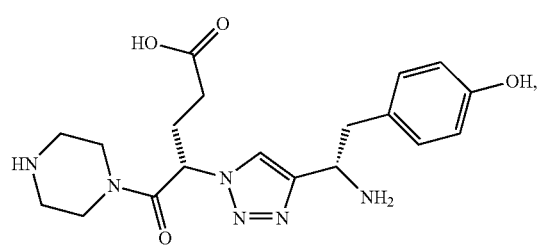
w″ 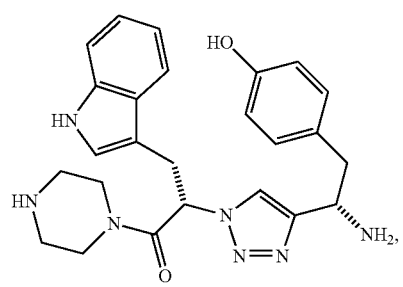
U″ 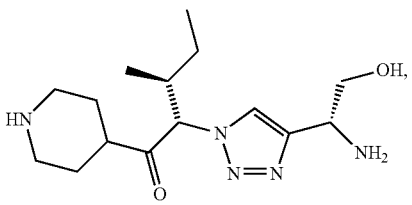
V″ 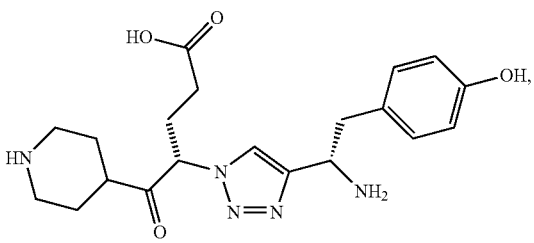
W″ 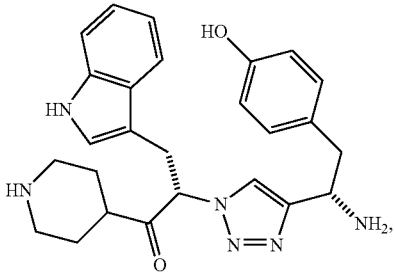
x″ 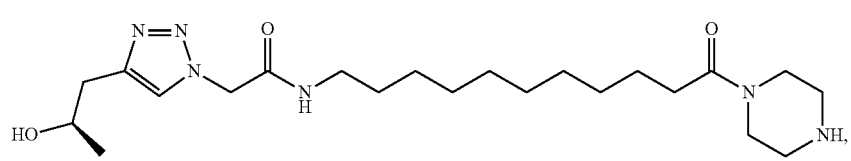
X″ 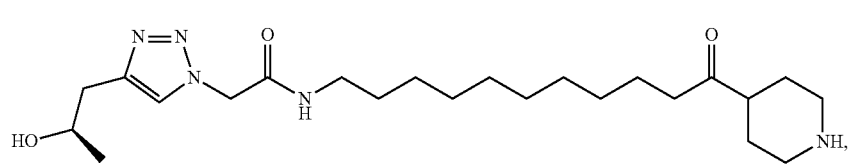
y″ 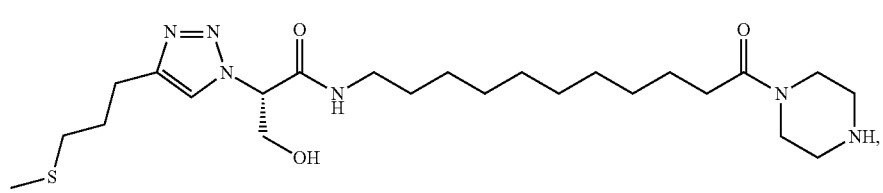
Y″ 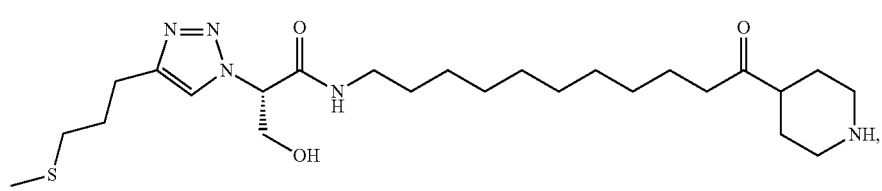

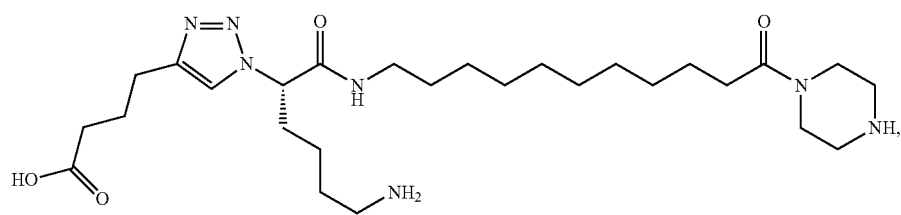 z''
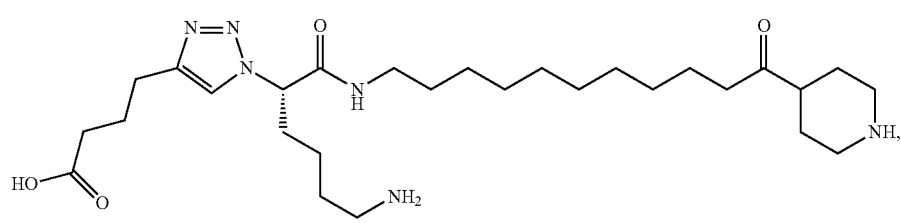 Z''
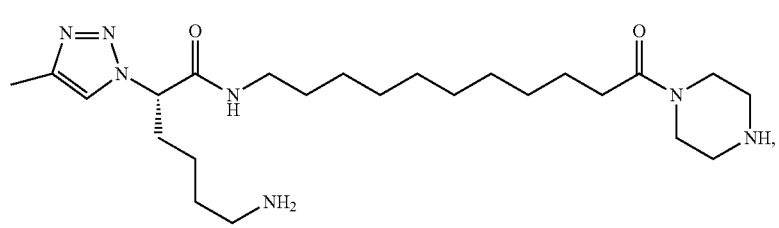 a'''
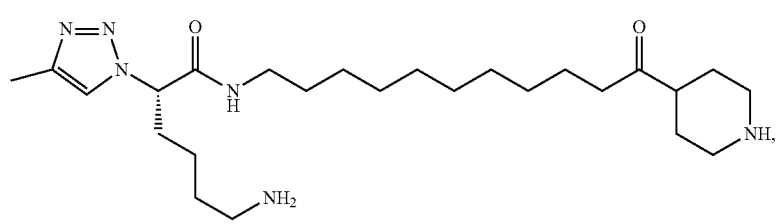 A'''
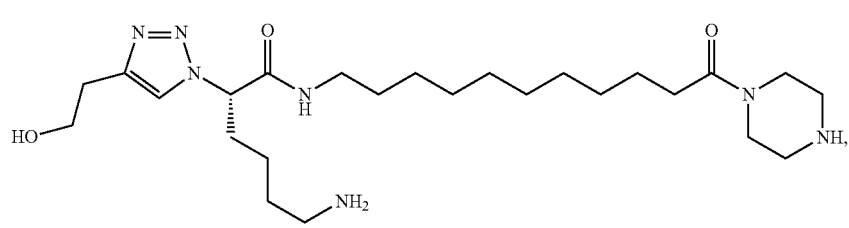 b'''
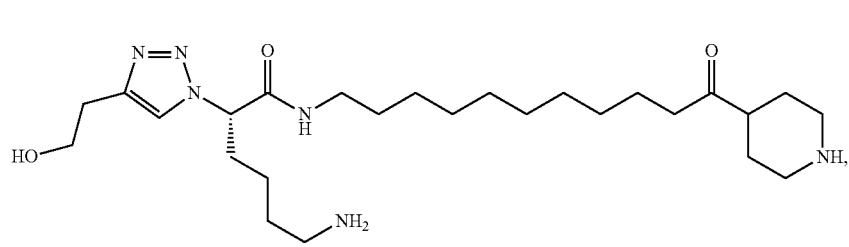 B'''
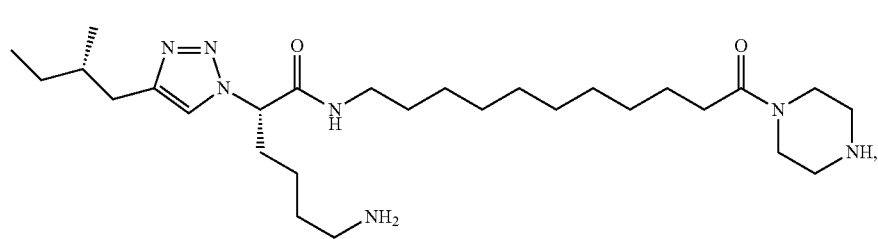 c'''

-continued
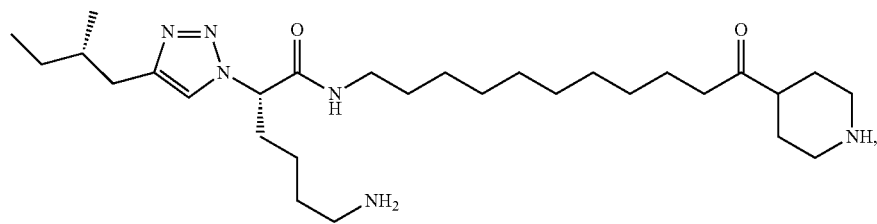
C'''
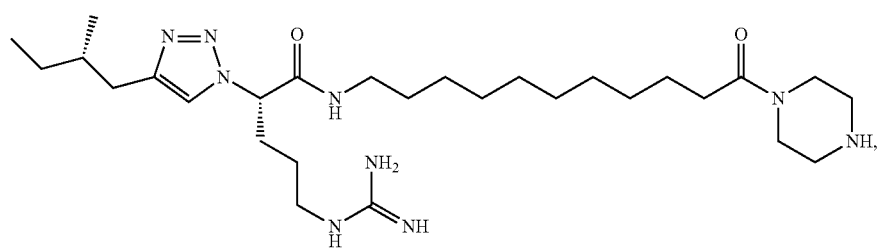
d'''
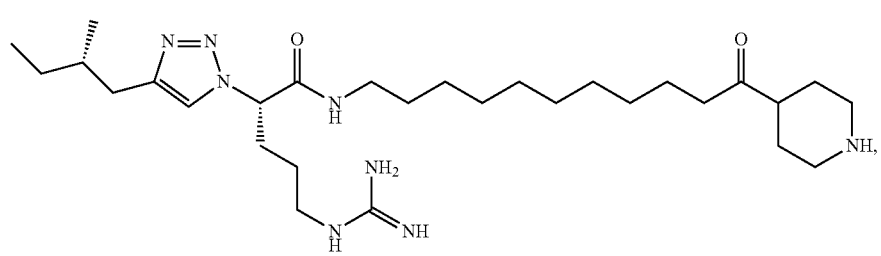
D'''
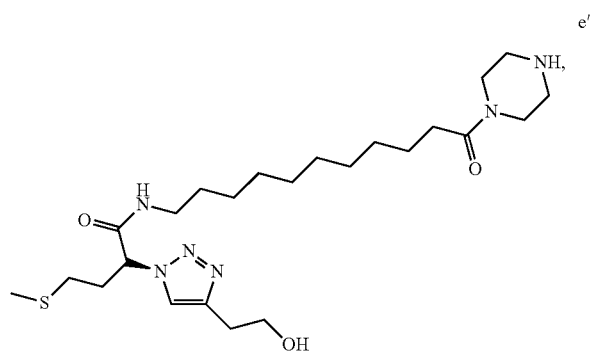
e'''
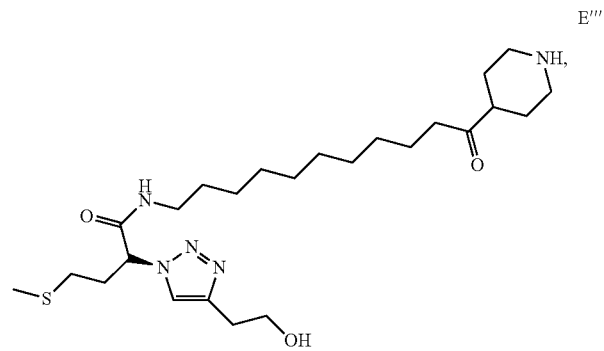
E'''
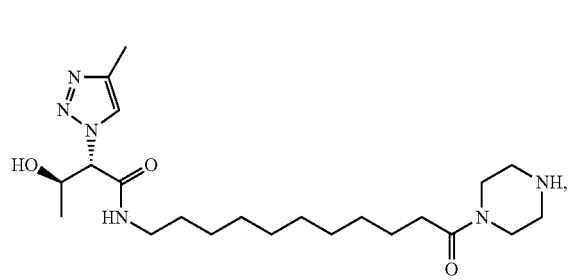
f'''
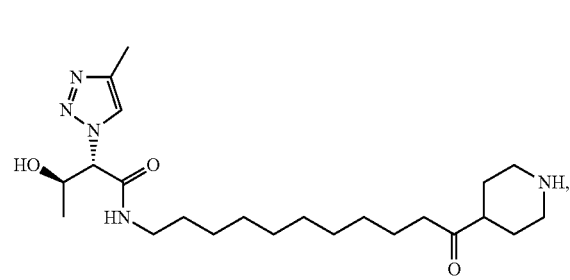
F'''
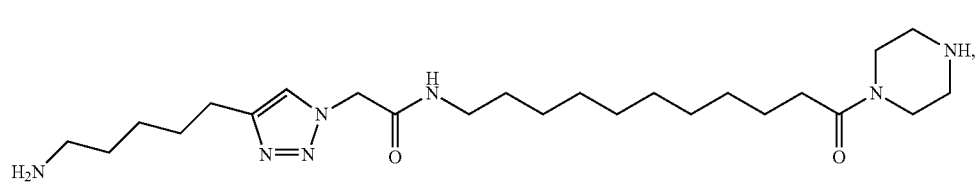
g'''

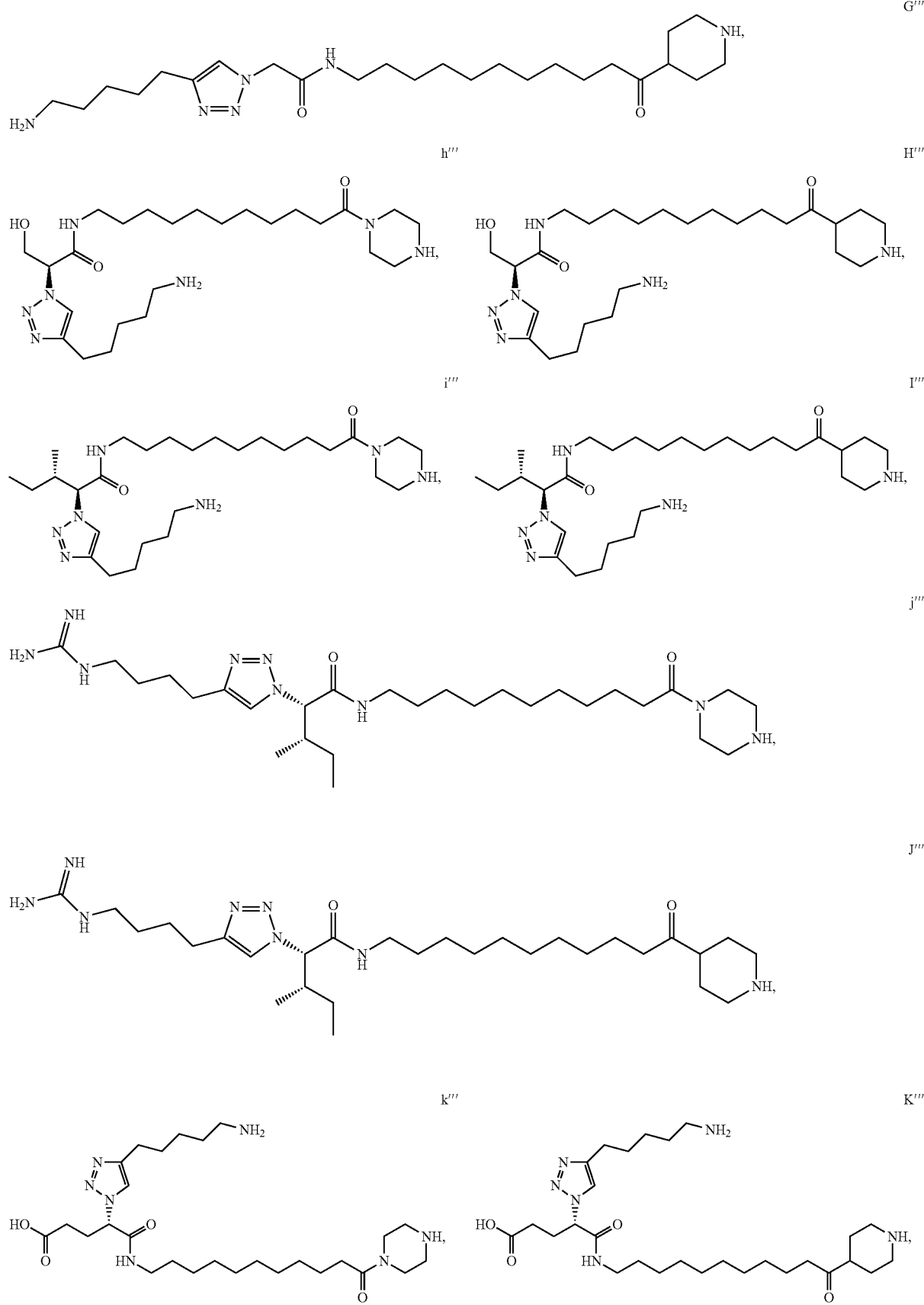

-continued
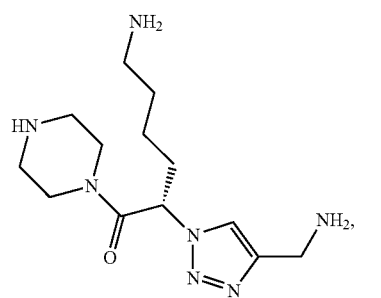 l'''
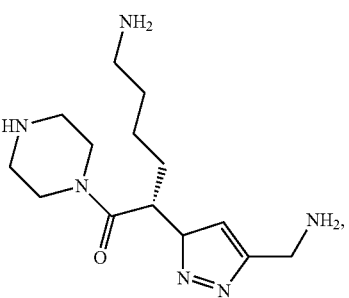 L'''
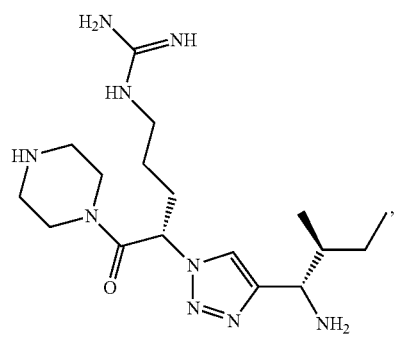 m'''
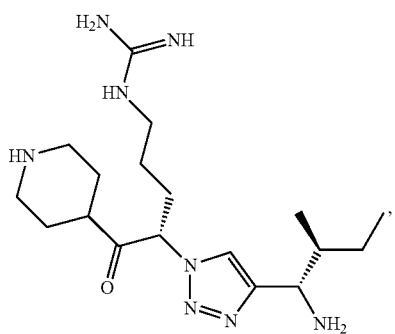 M'''
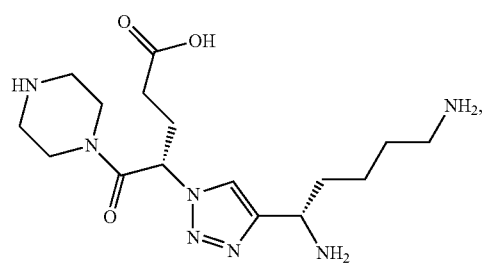 n'''
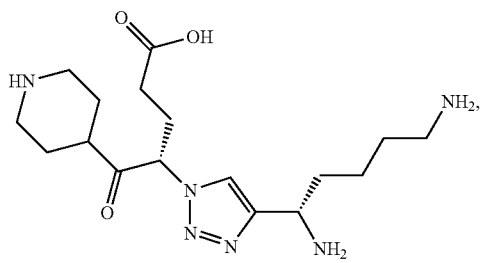 N'''
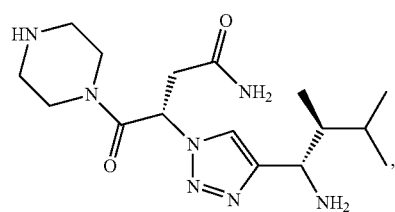 o'''
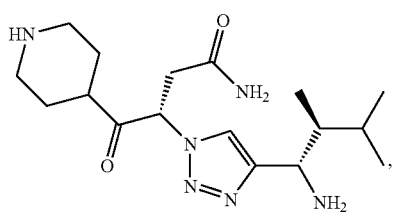 O'''
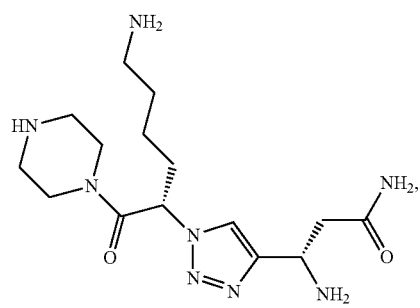 p'''
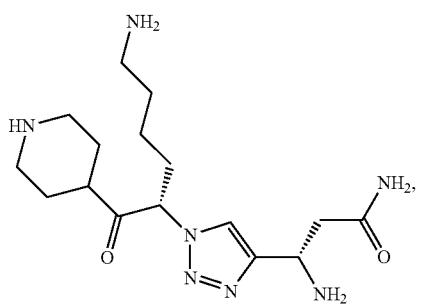 P'''
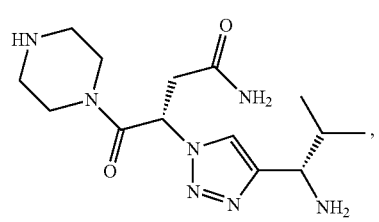 q'''
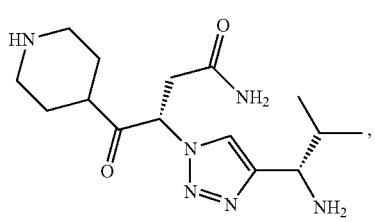 Q'''

-continued
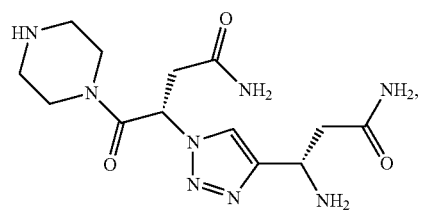 r'''
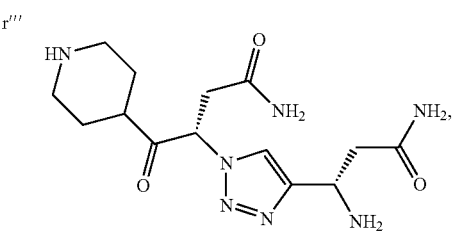 R'''
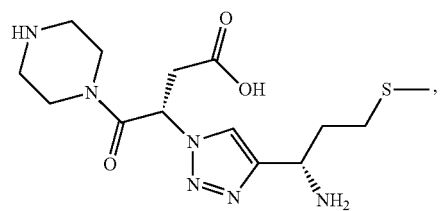 s'''
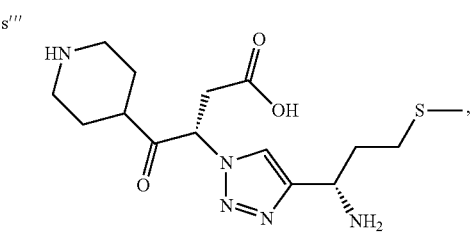 S'''
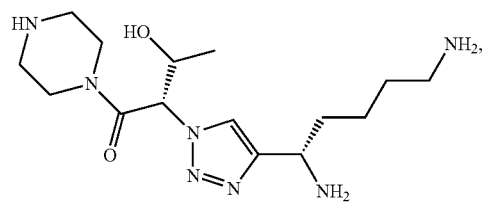 t'''
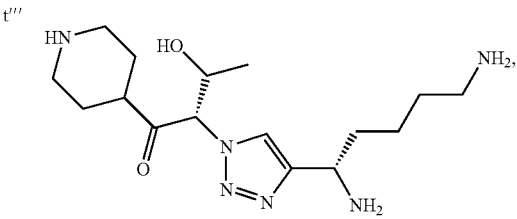 T'''
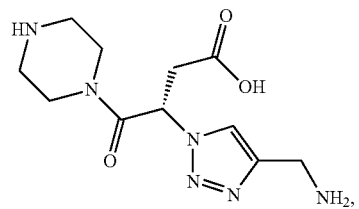 u'''
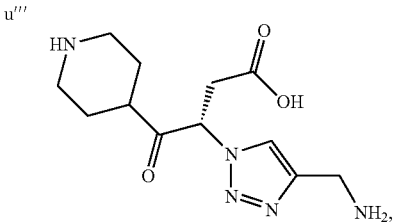 U'''
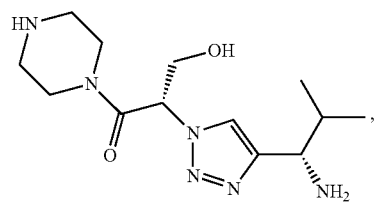 v'''
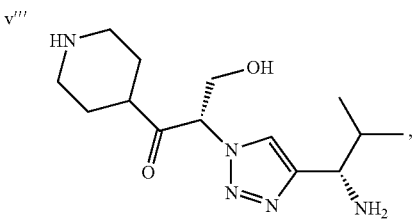 V'''
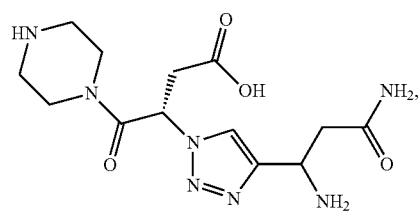 w'''
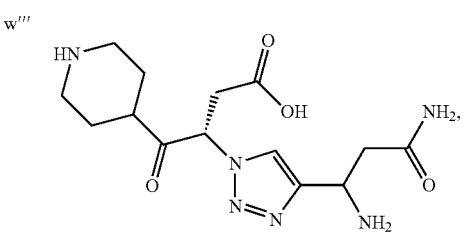 W'''
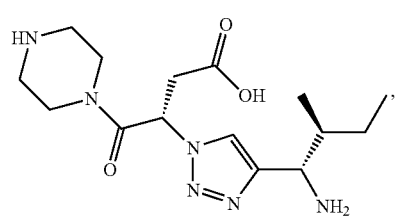 x'''
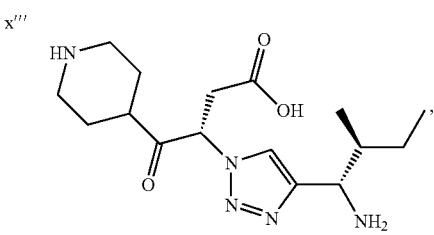 X'''

-continued
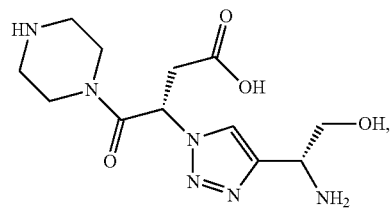
y''''
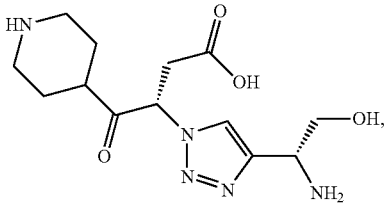
Y''''
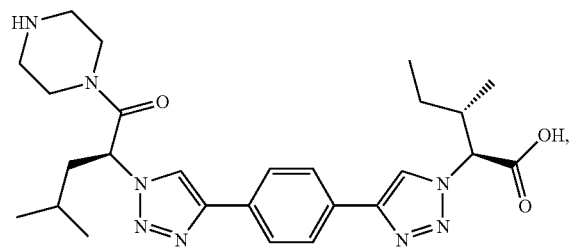
z''''
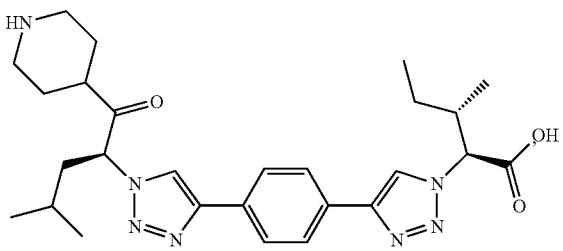
Z''''
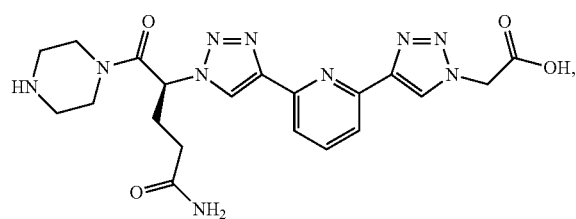
a''''
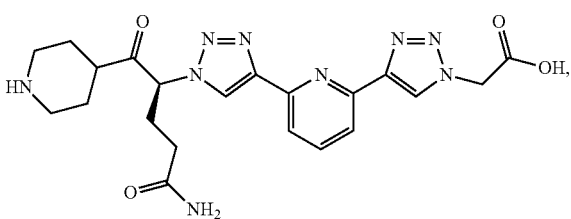
A''''
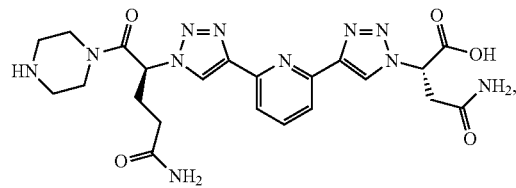
b''''
and
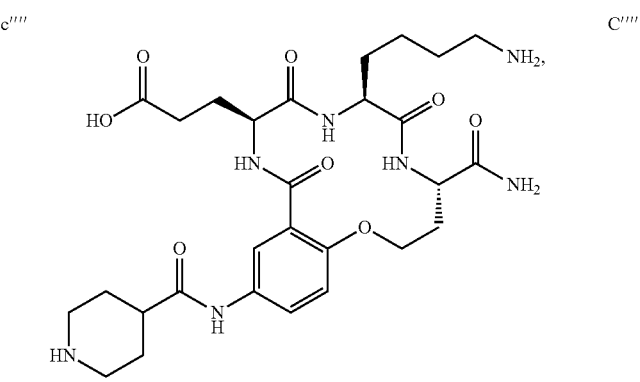
B''''
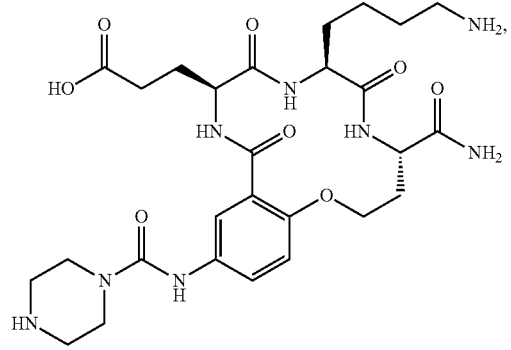
c''''
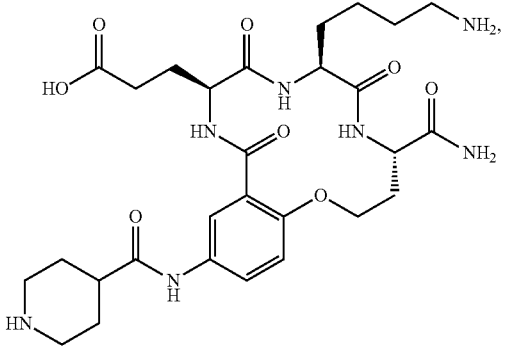
C''''
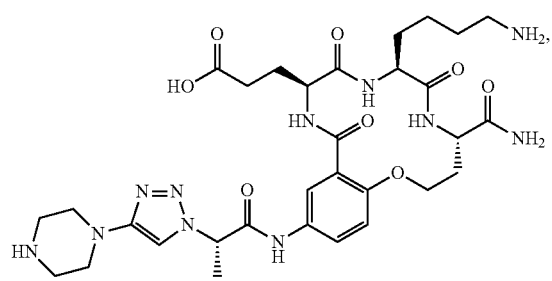
d''''
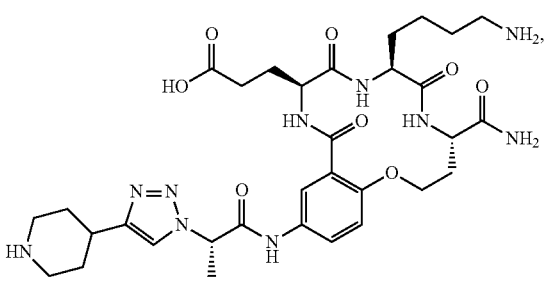
D''''

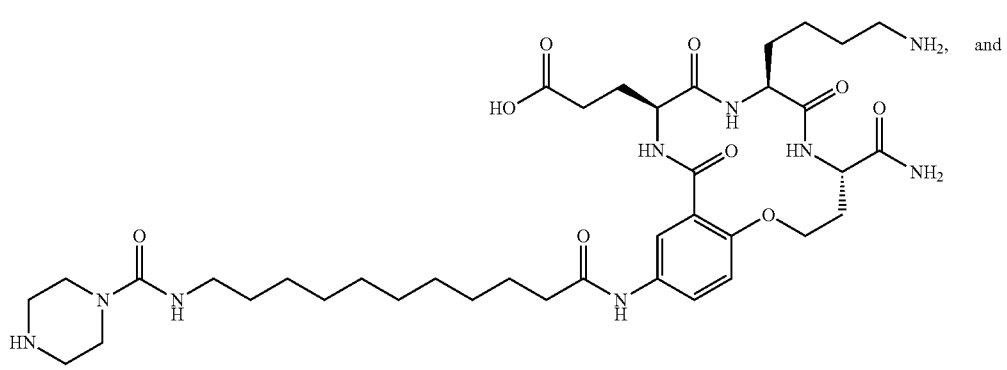

e''''′, and

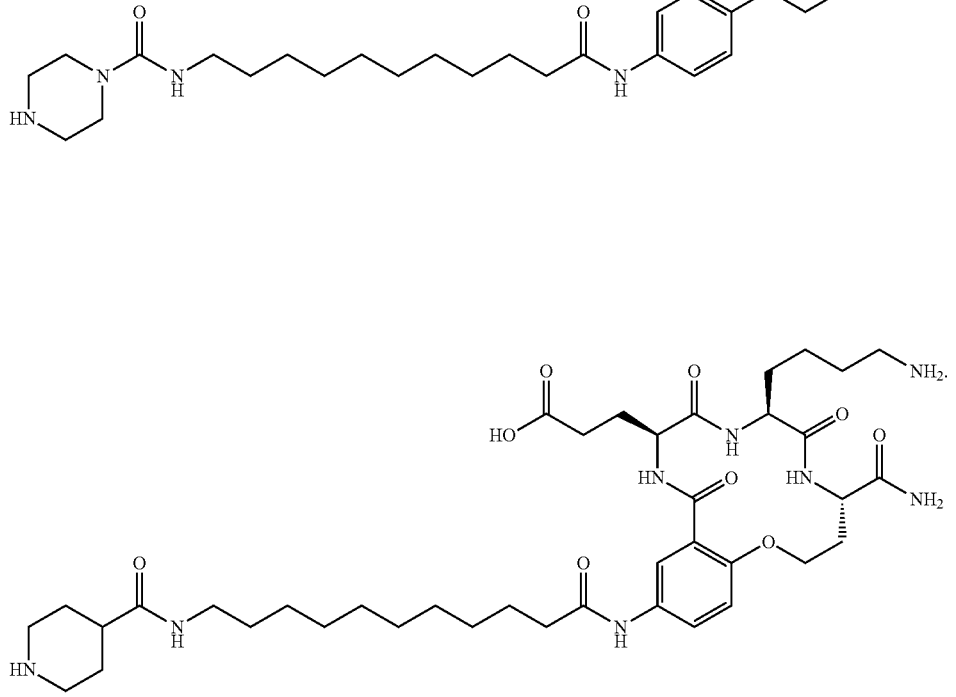

E''''′

A general aspect of the disclosure describes compounds having the structure

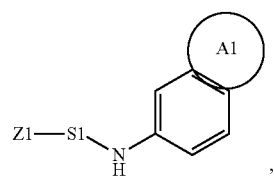

wherein A1 comprises a macrocyclic ring comprising at least two amino acids. The at least two amino acids are bound to each other in a ring comprising at least one peptide bond. Z1 comprises a nucleophilic moiety selected from the group consisting of piperidine, piperazine, pyrrolidine, azetidine, and any derivative or analog thereof. S1 comprises a spacer group having at least one carbonyl moiety, wherein S1 does not comprise glycine. In certain embodiments, the compound has a structure selected from the group of compounds, including but not limited to:

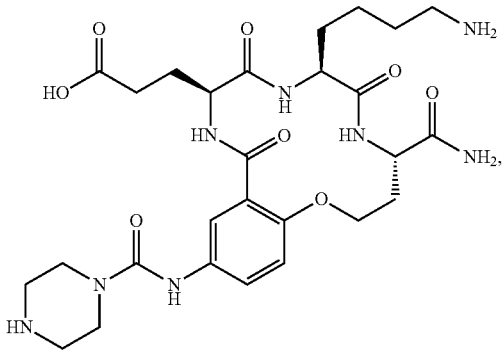 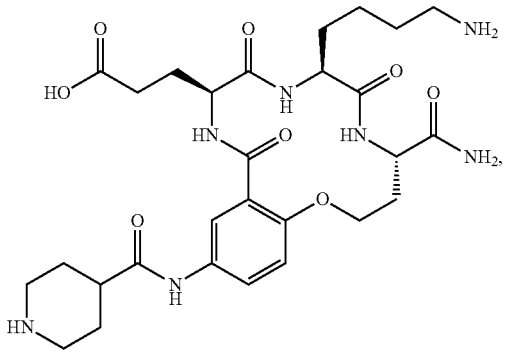

-continued

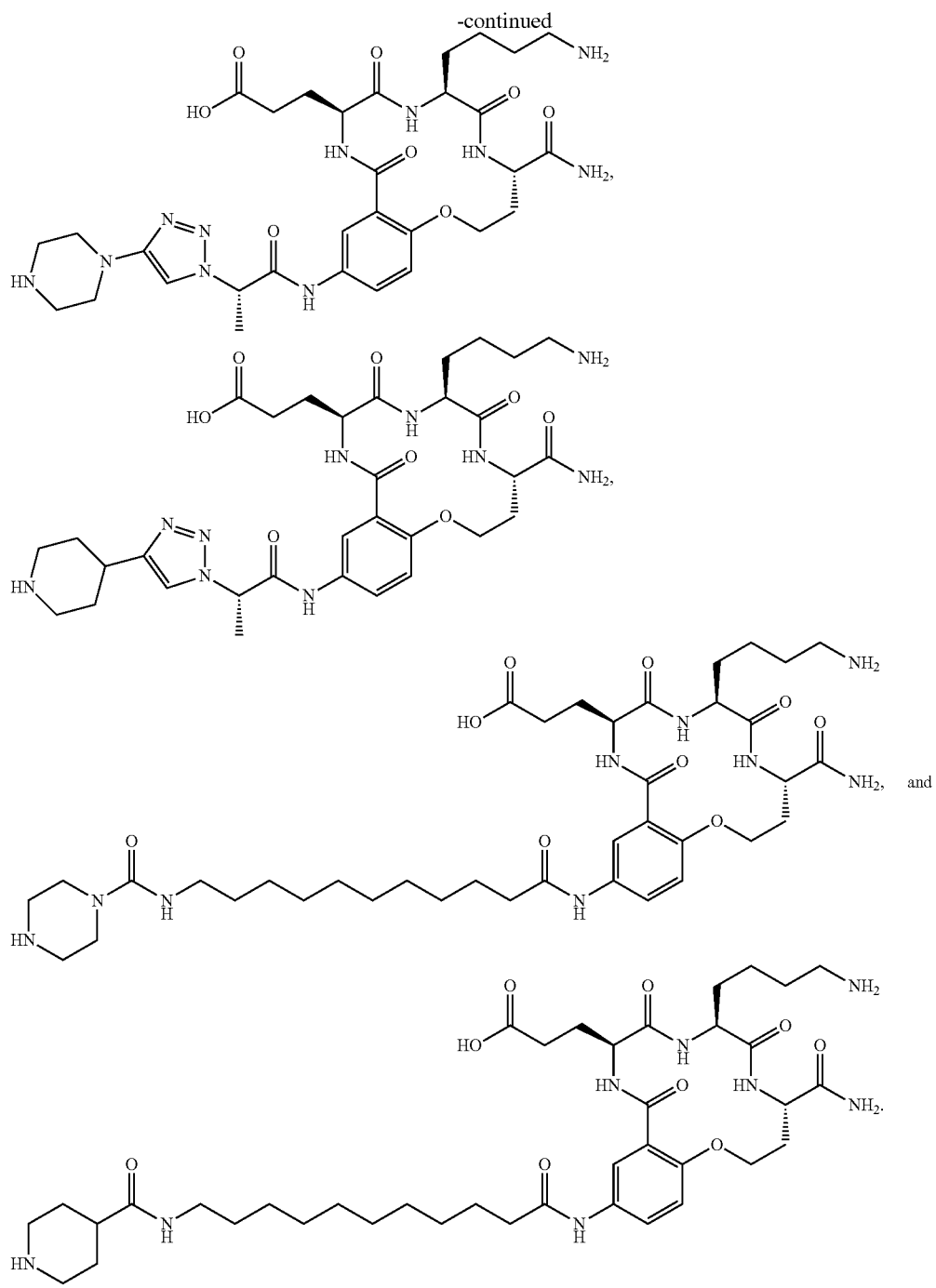

Compounds produced hereinabove may be useful as monovalent diamino acid mimics. The compounds may also be useful as pharmaceuticals or pharmaceutical leads. They demonstrate utility in that two of these monovalent amino acid mimics may be assembled into one molecule to give a bivalent amino acid mimic. The monovalent compounds may be assembled into bivalent compounds using a their appended nucleophile in a non-limiting example. In practicing the disclosure to form monovalent and bivalent amino acid mimics, the compounds disclosed hereinabove may be synthesized in a protected form. Such a protected form may comprise protecting groups known to those skilled in the art. In non-limiting examples, amino groups may be protected with a tert-butoxycarbonyl group and carboxylic acids may be protected as t-butyl esters. Other protecting groups may be more advantageous for use with certain moieties, and the utility of substituting different protecting groups for a given situation will be evident to those skilled in the art.

The compounds disclosed hereinabove may comprise a fragment of a larger molecule, wherein the fragment comprises removal of a hydrogen atom from the secondary nitrogen of the piperidine or piperazine ring of any of the compounds. Said fragment may be bonded to any other molecule conceivable to one skilled in the art. In an embodiment, the compounds disclosed hereinabove may comprise a bivalent amino acid mimic.

An advantage of the compounds disclosed hereinabove as monovalent amino acid mimics is that the syntheses of most of the compounds may be conducted directly from amino acid starting materials. This feature allows a wide range of amino acid side chains to be incorporated into the monovalent compounds. Through methods known to those skilled in the art, side chains that are analogs, derivatives, or homologues of naturally-occurring amino acid side chains may be incorporated into the molecules as well. In another aspect, amino acid side chains may be incorporated into the compounds to mimic proteins that are involved in any protein-protein interaction of interest. In a non-limiting example, the amino acid side chains may be those derived from the group including, but not limited to, Trp, Arg, Tyr, Lys, Glu, Ser, Asn and Leu. Another advantage of the monovalent amino acid mimics is that the amino acid side chains may be incorporated at a variety of separations and presentation angles by choice of the core molecule. Further, the organic framework is relatively rigid. These differences in distance and presentation angle may correspond to proximal amino acids in any secondary structural element, such as turns, helices, sheets, and loops, in a protein of interest. In yet another advantage, syntheses of the compounds do not require amino acid protection. Yet another advantage of the compounds, is that they contain a nucleophilic group, which allows the monovalent compounds to be assembled into bivalent compounds, again without the requirement for protecting groups. Said nucleophilic group may or may not influence the pharmacological or biological activity in the monovalent or bivalent compounds. In summary, the compounds present the following advantages: 1) convenient preparation of a plurality of amino acid side chains and derivatives, 2) rigid frameworks to which the amino acid side-chains are bound, 3) variable separation and presentation angles of the amino acid side chains, allowing mimicking of various protein secondary structures, and 4) incorporation of a nucleophilic group which allows assembly of the monovalent compounds into divalent compounds.

Another aspect of the present disclosure is a compound having the structure

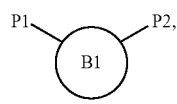

wherein B1 is a core molecule selected from the group consisting of heteroarylenes, arylenes, and heterocyclenes. P1 and P2 are independently selected and comprise an organic moiety comprising removal of a hydrogen atom from any of the compounds disclosed hereinabove. The compound may be further comprised by a labeling tag T1 which is bound to B1. In embodiments of the disclosure, T1 may be a group such as a fluorescein tag, a biotin tag, a polyether tag, or a 1,2,3-triazole-functionalized polyether tag, in non-limiting examples. The compound may also be further comprised by a third organic moiety comprising removal of a hydrogen atom from the compounds disclosed hereinabove bound to B1, wherein said third organic moiety is selected independently of P1 and P2.

In another general aspect of the disclosure, a compound having the structure

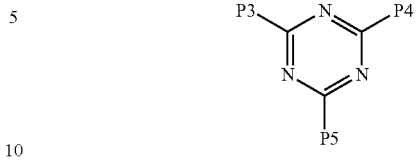

is described, wherein P3 and P4 comprise an organic moiety comprising removal of a hydrogen atom from the nitrogen atom of the piperidine or piperazine ring of the compounds disclosed hereinabove. P3 and P4 are independently selected. P5 comprises a moiety selected from the group consisting of an organic moiety comprising removal of a hydrogen atom from the nitrogen atom of the piperidine or piperazine ring of the compounds disclosed hereinabove and a labeling tag T1. P5 is selected independently of P3 and P4. In an embodiment, the compound has the structure

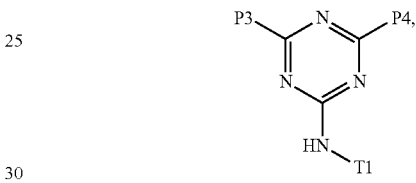

wherein P3, P4, and T1 are defined as described hereinabove. In a further embodiment, at least one of P3 and P4 may further comprise a morpholinyl group (structure p below), with the proviso that both P3 and P4 are not a morpholinyl group.

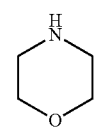

In embodiments wherein there is a labeling tag T1, T1 may be a group such as a fluorescein tag, a biotin tag, a polyether tag, or a 1,2,3-triazole-functionalized polyether tag, in non-limiting examples. In certain embodiments, the labeling tag T1 may be selected from the group, including but not limited to the following structures:

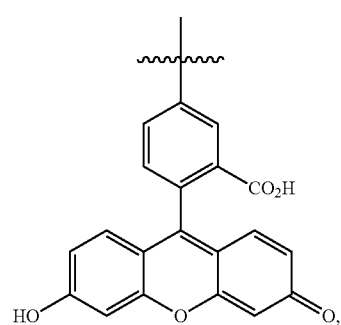

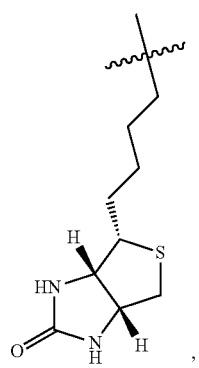

These labeling tags are representative of the groups that may be useful for tagging the library and should not be considered limiting of the disclosure. For example, fragment 1, may be useful for fluorescence detection assays. Fragment 2 may be useful in strepavidin-based assays. Fragment 3 may be useful for conveying improved water solubility. Fragment 3 also bears functionality beneficial for synthesizing fragment 4, which has a 1,2,3-triazine moiety appended to its polyether chain. Fragment 4 may be useful for impregnation of the compounds comprising fragment 4 into a liposome structure.

Compounds comprising P3, P4, and T1 may comprise a combinatorial library. By way of non-limiting example, an exemplary member of the library of bivalent compounds may be made from a P3 fragment comprising removal of a hydrogen atom from the piperazine ring of b, a P4 fragment comprising removal of a hydrogen atom from the piperazine ring of d, and a labeling tag comprising 1. Such a library member has the structure:

The fragments comprising P3 and P4 may be chosen from any compound disclosed hereinabove, with the proviso that both P3 and P4 are not morpholinyl. Further any valid combination of P3 and P4 may be combined with any combination of T1. Members of the library may be expressed in the shorthand form P3P4T1, wherein P3, P4, and T1 describe the individual fragments bound to the central triazine core comprising the library. P3 may be selected from the group including, but not limited to, a, A, b, B, c, C, d, D, e, E, f, F, g, G, h, H, i, I, j, J, k, K, l, L, m, M, n, N, o, O, p, q, Q, r, R, s, S, t, T, u, U, v, V, w, W, x, X, y, Y, z, Z, a', A', b', B', c', C', d', D', e', E', f', F', g', G', h', H', i', I', j', J', k', K', l', L', m', M', n', N', o', O', p', P', q', Q', r', R', s', S', t', T', u', U', v', V', w', W', x', X', y', Y', z', Z', a", A", b", B", c", C", d", D", e", E", f", F", g", G", h", H", i", I", j", J", k", K", l", L", m", M", n", N", o", O", p", P", q", Q", r", R", s", S", t", T", u", U", v", V", w", W", x", X", y", Y", z", Z", a'", A'", b'", B'", c'", C'", d'", D'", e'", E'", f'", F'", g'", G'", h'", H'", i'", I'", j'", J'", k'", K'", l'", L'", m'", M'", n'", N'", o'", O'", p'", P'", q'", Q'", r'", R'", s'", S'", t'", T'", u'", U'", v'", V'", w'", W'", x'", X'", y'", Y'", z'", Z'", a'''', A'''', b'''', B'''', c'''', C'''', d'''', D'''', e'''', and E''''. P4 may be selected from the group including, but not limited to, a, A, b, B, c, C, d, D, e, E, f, F, g, G, h, H, i, I, j, J, k, K, l, L, m, M, n, N, o, O, p, q, Q, r, R, s, S, t, T, u, U, v, V, w, W, x, X, y, Y, z, Z, a', A', b', B', c', C', d', D', e', E', f', F', g', G', h', H', i', I', j', J', k', K', l', L', m', M', n', N', o', O', p', P', q', Q', r', R', s', S', t', T', u', U', v', V', w', W', x', X', y', Y', z', Z', a", A", b", B", c", C", d", D", e", E", f", F", g", G", h", H", i", I", j", J", k", K", l", L", m", M", n", N", o", O", p", P", q", Q", r", R", s", S", t", T", u", U", v", V", w", W", x", X", y", Y", z", Z", a'", A'", b'", B'", c'", C'", d'", D'", e'", E'", f'", F'", g'", G'", h'", H'", i'", I'", j'", J'", k'", K'", l'", L'", m'", M'", n'", N'", o'", O'", p'", P'", q'", Q'", r'", R'", s'", S'", t'", T'", u'", U'", v'", V'", w'", W'", x'", X'", y'", Y'", z'", Z'", a'''', A'''', b'''', B'''', c'''', C'''', d'''', D'''', e'''', and E''''. T1 may be selected from the group including, but not limited to, 1, 2, 3, and 4. All allowable combinations may comprise the library. For the non-limiting example presented hereinabove, the shorthand notation describing the library compound is bd1.

In another general aspect, the present disclosure provides a method of producing a library of compounds comprising: 1) providing

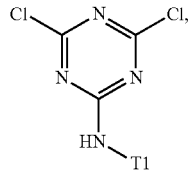

wherein T1 comprises a labeling tag; 2) reacting a first equivalent of any of the monovalent compounds described hereinabove or morpholine with the compound of step 1 in the presence of a base and a solvent; 3) removing the solvent; and 4) reacting a second equivalent of any of the monovalent compounds described hereinabove or morpholine with the compound produced in step 2 of the method. Selection of said first equivalent and said second equivalent is conducted with the proviso that said first equivalent and said second equivalent are not both morpholine. In certain embodiments of the method, the base is potassium carbonate. In certain embodiments of the method, T1 is selected from the group including, but not limited to

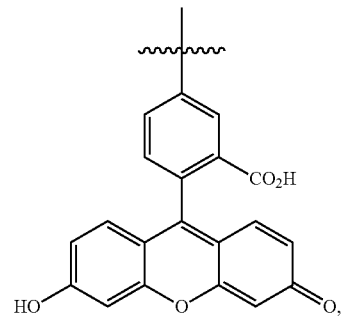

1

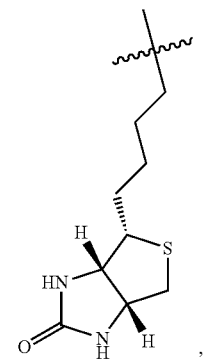

2

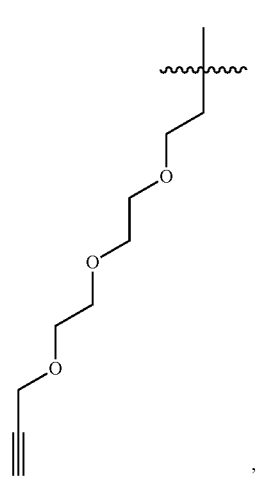

3

, and

4

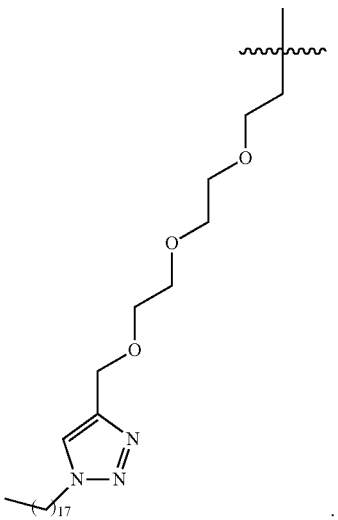

The method used to prepare the library of bivalent compounds is advantageous in that it is an entirely solution phase method. An additional advantage of the method is that the intermediate produced in step 2 may generally be used without further purification following removal of the solvent in step 3. Finally, the library may be synthesized from monovalent fragments comprising the monovalent compounds hereinabove, wherein the amino acid side chain moieties of the monovalent compounds do not require protection. It is further notable that the nucleophilic group comprising the monovalent compounds was designed specifically to ensure chemoselective reaction over the protein amino acid side chains. Further, the method utilizes different solvents in steps 2 and 4 to ensure monoaddition to the triazine core during coupling of the first monovalent compound.

Any of the monovalent and bivalent compounds described hereinabove and derivatives thereof may be pharmaceuticals. Any of the monovalent and bivalent compounds described hereinabove may pharmaceutical leads. A derivative or analog of a pharmaceutical lead may be a pharmaceutical. In another embodiment of the disclosure, compounds having a labeling tag may be useful for conducting pharmacological assays. In another embodiment, compounds having a labeling tag may be pharmacological probes. For example, a non-limiting use of the monovalent and divalent compounds may comprise demonstrating protein-protein interactions.

The compounds disclosed hereinabove have been designed to mimic certain proteins implicated in protein-protein interactions of particular interest. For instance, certain monovalent compounds have been designed with sidechains that correspond to amino acid residues at putative 'hot-spots' for the neurotrophins (NGF, BDNF, NT-3, NT-4) interacting with their receptors (TrkA, TrkB, TrkC, and p75), for the tumor necrosis factors (TNFα and TNFβ) interacting with their receptors (including p55 and p75), and for the so called "BH3-only proteins" (Bad, Bim, Bid, and Noxa) interacting with other Bcl2 proteins (eg Bcl2, Mcl1, BclW, BclB, Bax, Bak and Bok). These protein targets are merely exemplary and are not meant to be limiting of the protein targets that may interact with the compounds described in the disclosure.

EXAMPLES

The following experimental examples are included to demonstrate particular aspects of the present disclosure. It should be appreciated by those of skill in the art that the methods described in the examples that follow merely represent exemplary embodiments of the disclosure. Those of skill in the art should, in light of the present disclosure, appreciate that many changes can be made in the specific embodiments described and still obtain a like or similar result without departing from the spirit and scope of the present disclosure.

Example 1

Synthesis and Characterization of Protected Monovalent Compounds

Monovalent compounds were synthesized with their amino groups protected as t-butoxycarbonyl derivatives. For compounds having carboxylic acid groups, the carboxylic acid was protected as the t-butyl ester derivative. Phenols were either protected as the t-butyl ester derivative or left unprotected. The protecting groups are removed only just prior to coupling with a with a triazine derivative to prepare a library compound. Analyses, including $^1$H and $^{13}$C NMR, MS, and HPLC were conducted on the fully protected monovalent precursor compounds. The following experimental data was obtained:

The following general method may be used to prepare protected monovalent compounds a through o (Scheme 1). Synthesis of protected monovalent compound 1 is demonstrated in Scheme 2 as a representative example.

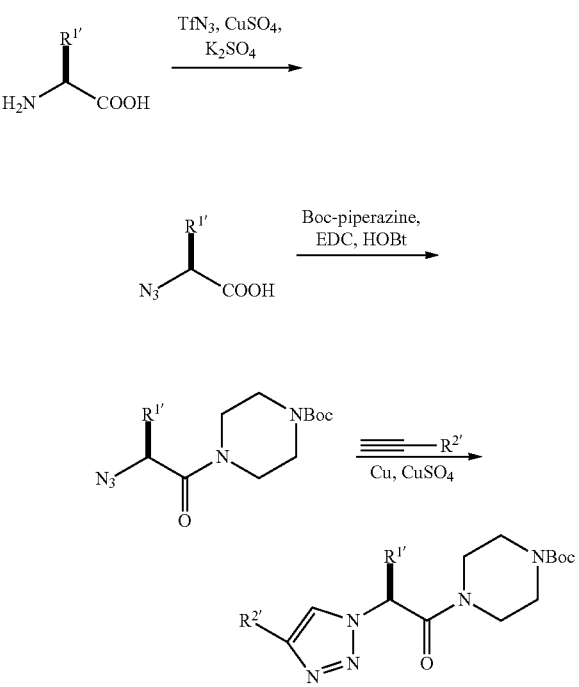

Scheme 1

Scheme 2

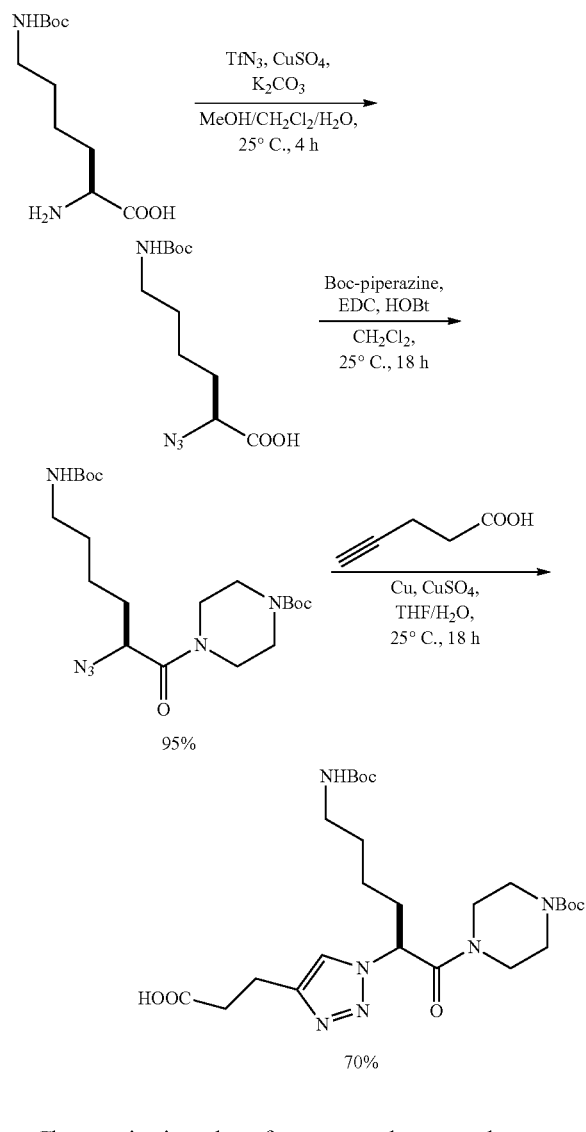

95%

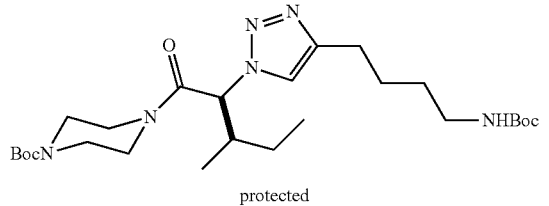

70%

Characterization data for protected monovalent compounds a through o follows:

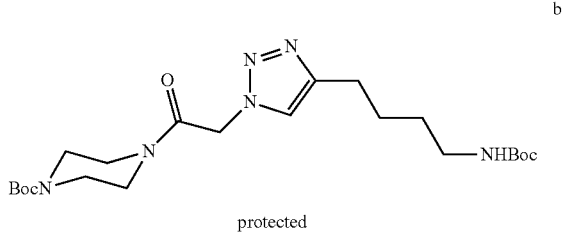 [SMILES: CC(C)(C)OC(=O)NCCCCc1cn(CC(=O)N2CCN(C(=O)OC(C)(C)C)CC2)nn1]
a

¹H NMR (300 MHz, CDCl₃) δ 5.42 (d, 1H, J=10.5 Hz), 5.28 (s, 1H), 4.56 (s, 2H), 3.67-3.29 (m, 12H), 2.36 (m, 1H), 1.04 (s, 18H), 1.02-0.78 (m, 8H); ¹³C NMR (75 MHz, CDCl₃) δ 166.9, 156.2, 154.6, 145.5, 121.7, 80.8, 79.5, 64.7, 46.3, 44.0 (b), 42.5, 40.5, 38.2, 28.7, 28.5, 28.4, 26.3, 25.0, 24.7, 15.9, 10.6; MS (ESI, m/z) 531 (M+Li)⁺.

b protected

¹H NMR (300 MHz, CDCl₃) δ 7.48 (s, 1H), 5.21 (s, 2H), 4.60 (s, 1H), 3.61-3.52 (m, 8H), 3.12 (m, 2H), 2.75 (t, 2H, J=7.5 Hz), 1.71 (m, 2H), 1.55 (m, 2H), 1.52 (s, 9H), 1.43 (s, 9H); ¹³C NMR (75 MHz, CDCl₃) δ 164.0, 156.2, 154.6, 148.4, 122.7, 80.9, 79.3, 51.2, 45.3, 43.8 (b), 42.4, 40.5, 29.8, 28.7, 28.6, 26.7, 25.5; MS (ESI, m/z) 467 (M+H)⁺.

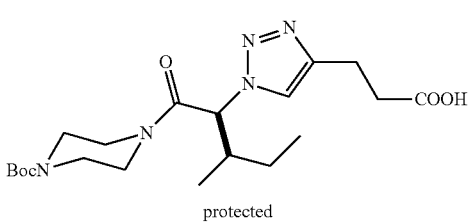
c protected

¹H NMR (300 MHz, CDCl₃) δ 8.75 (b, 1H), 7.71 (s, 1H), 5.40 (d, 1H, J=10.5 Hz), 3.67-3.04 (m, 8H), 3.02 (t, 2H, J=7.2 Hz), 2.74 (t, 2H, 7.2 Hz), 1.23 (s, 9H), 0.97-0.76 (m, 8H); ¹³C NMR (75 MHz, CDCl₃) δ 176.4, 167.0, 154.8, 147.0, 120.6, 80.9, 63.6, 46.3, 44.0 (b), 42.5, 38.1, 33.6, 28.5, 24.7, 21.1, 15.9, 10.7; MS (ESI, m/z) 422 (M−H)⁺.

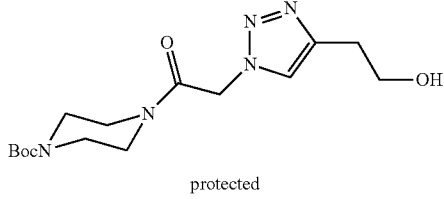
d protected

¹H NMR (300 MHz, CD₃OD) δ 7.75 (b, 1H), 5.45 (s, 2H), 3.82 (t, 2H, J=6.3 Hz), 3.60-3.52 (m, 8H), 2.91 (t, 2H, J=6.3 Hz), 1.47 (s, 9H); ¹³C NMR (75 MHz, CDCl₃) δ 164.1, 154.6, 146.2, 123.7, 80.9, 61.7, 51.1, 45.4, 43.8 (b), 42.4, 31.2, 28.6; MS (ESI, m/z) 340 (M+H)⁺.

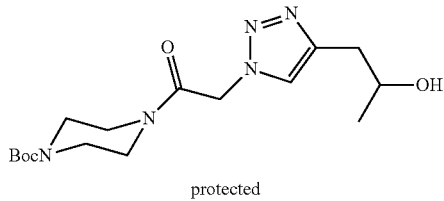
e protected

¹H NMR (300 MHz, CD₃OD) δ 7.74 (s, 1H), 5.49 (s, 2H), 4.00 (m, 1H), 3.60-3.54 (m, 8H), 2.81 (d, 2H, J=6.3 Hz), 1.47 (s, 9H), 1.20 (d, 3H, J=6.3 Hz); ¹³C NMR (75 MHz, CDCl₃) δ 164.1, 154.6, 145.8, 123.9, 80.9, 67.3, 51.1, 45.4, 44.0 (b), 42.4, 35.2, 28.6, 23.2; MS (ESI, m/z) 360 (M+Li)⁺.

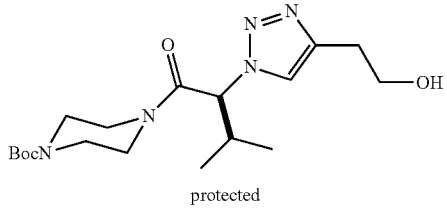

f protected

¹H NMR (300 MHz, CDCl₃) δ 7.74 (s, 1H), 5.28 (d, 1H, 7.5 Hz), 3.89 (s, 2H), 3.72-3.17 (m, 8H), 2.94 (m, 4H), 2.55 (m, 1H), 1.42 (s, 9H), 0.99 (m, 3H), 0.74 (m, 3H); ¹³C NMR (75 MHz, CDCl₃) δ 166.9, 154.6, 146.2, 120.7, 80.8, 65.1, 61.0, 46.3, 44.2 (b), 43.6, 42.5, 32.2, 28.6, 19.7, 18.6; MS (ESI, m/z) 382 (M+H)⁺.

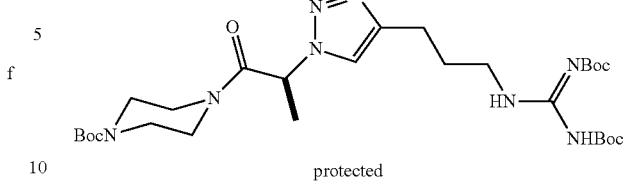

i protected

¹H NMR (300 MHz, CD₃OD) δ 7.95 (s, 1H), 6.00 (q, 1H, J=6.6 Hz), 3.68-3.34 (m, 10H), 2.83 (t, 2H, J=7.5 Hz), 1.80 (m, 2H), 1.76 (d, 3H, J=6.6 Hz), 1.74 (s, 9H), 1.54 (s, 9H); ¹³C NMR (75 MHz, CD₃OD) δ 168.0, 163.5, 156.5, 155.0, 153.0, 147.2, 121.5, 83.3, 80.6, 79.2, 55.7, 45.4, 44.0 (b), 42.3, 40.0, 28.7, 27.4, 27.1, 22.5, 17.2; MS (ESI, m/z) 609 (M+H)⁺.

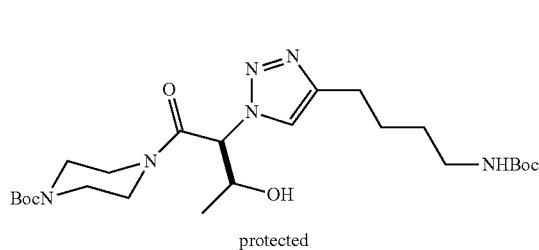

g protected

¹H NMR (300 MHz, CD₃OD) δ 7.98 (s, 1H), 5.74 (d, 1H, J=5.7 Hz), 4.83 (s, 2H), 4.46 (m, 1H), 3.66-3.12 (m, 8H), 3.05 (t, 2H, J=6.6 Hz), 2.73 (m, 2H), 1.67 (m, 2H), 1.54 (m, 2H), 1.48 (s, 9H), 1.44 (s, 9H), 1.13 (d, 3H, J=6.3 Hz); ¹³C NMR (75 MHz, CD₃OD) δ 167.2, 158.3, 156.0, 148.3, 124.0, 81.6, 79.7, 68.3, 66.1, 46.8, 43.5 (b), 43.3, 40.9, 30.3, 28.8, 28.6, 27.6, 25.9, 20.1; MS (ESI, m/z) 511 (M+H)⁺.

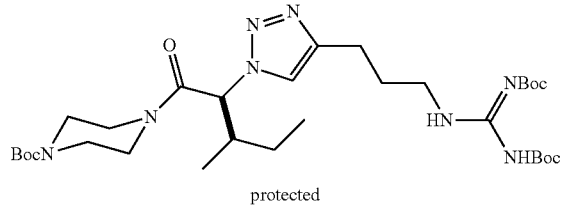

j protected

¹H NMR (300 MHz, CDCl₃) δ 11.44 (s, 1H), 8.36 (s, 1H), 7.62 (s, 1H), 5.33 (d, 1H, J=9.9 Hz), 3.61-3.11 (m, 10H), 2.71 (m, 2H), 2.32 (s, 1H), 1.93 (m, 2H), 1.43 (s, 18H), 1.32 (s, 9H), 0.94 (m, 5H), 0.74 (m, 3H); ¹³C NMR (75 MHz, CDCl₃) δ 166.9, 163.7, 156.4, 154.5, 153.4, 147.6, 119.8, 83.2, 80.5, 79.3, 63.4, 46.2, 43.4, 42.4 (b), 38.4, 37.9, 34.0, 28.8, 28.4, 28.2, 24.6, 23.3, 15.9, 10.6; MS (ESI, m/z) 651 (M+H)⁺.

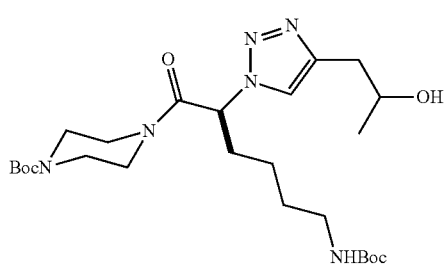

protected h

¹H NMR (300 MHz, CD₃OD) δ 7.93 (s, 1H), 5.88 (t, 1H, J=7.2 Hz), 4.05 (m, 1H), 3.71-3.05 (m, 8H), 2.86 (m, 2H), 2.84 (d, 2H, J=6.3 Hz), 2.14 (m, 2H), 1.39 (m, 11H), 1.27 (m, 1H), 1.20 (d, 3H, J=6.3 Hz); ¹³C NMR (75 MHz, CD₃OD) δ 167.5, 157.4, 155.0, 145.2, 122.4, 80.6, 78.7, 66.8, 59.9, 45.6, 43.6 (b), 42.3, 39.6, 35.0, 31.9, 29.2, 27.7, 27.5, 22.7, 21.9; MS (ESI, m/z) 531 (M+Li)⁺.

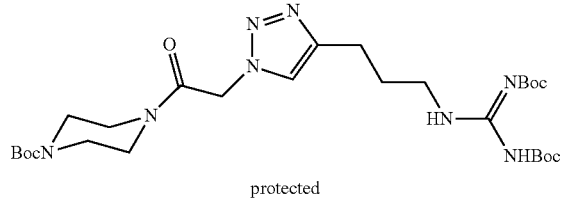

k protected

¹H NMR (3000 MHz, CD₃OD) δ 7.89 (s, 1H), 7.79 (s, 1H), 5.44 (s, 2H), 3.56-3.30 (m, 10H), 2.77 (t, 2H, J=7.5 Hz), 1.94 (m, 2H), 1.52 (s, 9H), 1.46 (s, 18H); ¹³C NMR (75 MHz, CD₃OD) δ 165.3, 163.4, 156.5, 155.0, 153.0, 147.0, 124.2, 83.3, 80.6, 79.2, 50.9, 44.7, 43.4, 42.7 (b), 42.0, 39.8, 28.8, 27.5, 27.1, 22.4; MS (ESI, m/z) 595 (M+H)⁺.

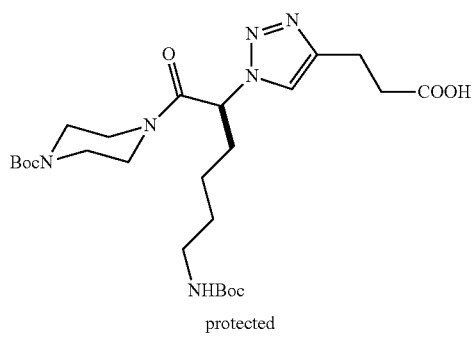

l
protected

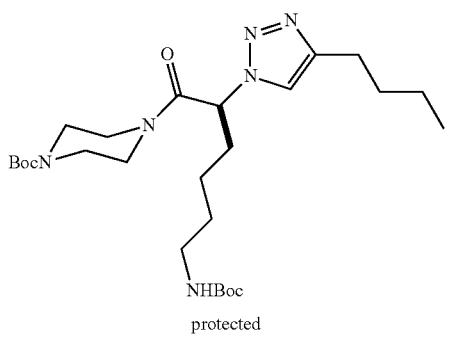

o
protected

¹H NMR (300 MHz, CD₃OD) δ 7.91 (s, 1H), 5.87 (t, 1H, J=7.2 Hz), 3.72-3.33 (m, 8H), 3.04 (t, 2H, J=7.5 Hz), 2.74 (t, 2H, J=7.2 Hz), 2.18 (m, 2H), 1.69 (2 Hz); ¹³C NMR (75 MHz, CD₃OD) δ 167.4, 157.3, 154.9, 121.3, 80.5, 78.6, 59.9, 47.1, 45.6, 44.0 (b), 42.3, 39.7, 31.9, 31.6, 29.3, 27.8, 27.6, 25.0, 22.7, 22.1, 13.1; MS (ESI, m/z) 537 (M−H)⁺.

¹H NMR (300 MHz, CD₃OD) δ 7.91 (s, 1H), 6.5.4 (s, 1H), 5.87 (t, 1H, J=7.2 Hz), 3.72-3.33 (m, 8H), 3.04 (t, 2H, J=7.5 Hz), 2.74 (t, 2H, J=7.2 Hz), 2.18 (m, 2H), 1.69 (2 Hz); ¹³C NMR (75 MHz, CD₃OD) δ 167.4, 157.3, 154.9, 121.3, 80.5, 78.6, 59.9, 47.1, 45.6, 43.6 (b), 42.3, 39.7, 31.9, 31.6, 29.3, 27.8, 27.6, 25.0, 22.7, 22.1, 13.1; MS (ESI, m/z) 523 (M+H)⁺.

The following general method may be used to prepare protected monovalent compounds q through e' (Scheme 3). Synthesis of protected monovalent compound q is demonstrated in Scheme 4 as a representative example.

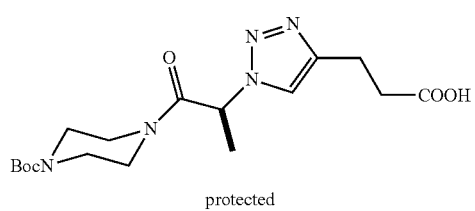

m
protected

¹H NMR (300 MHz, CDCl₃) δ 7.62 (b, 1H), 7.27 (s, 1H), 5.81 (q, 1H, J=7.2 Hz), 3.75-3.20 (m, 8H), 3.03 (t, 2H, J=7.2 Hz), 2.75 (t, 2H, J=7.2 Hz), 1.68 (d, 3H, J=7.2 Hz), 1.43 (s, 9H); ¹³C NMR (75 MHz, CDCl₃) δ 176.4, 167.1, 154.9, 146.9, 120.6, 80.9, 55.4, 45.8, 44.0 (b), 42.6, 33.5, 28.6, 21.1, 18.9; MS (ESI, m/z) 380 (M−H)⁺.

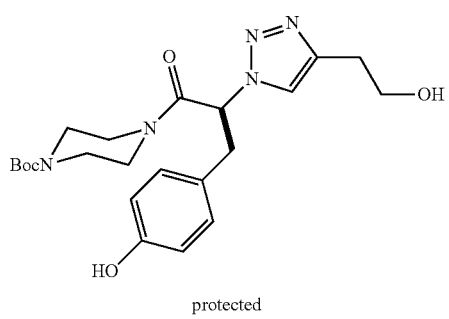

n
protected

¹H NMR (300 MHz, CDCl₃) δ 7.88 (s, 1H), 6.92 (d, 2H, J=8.4 Hz), 6.72 (d, 2H, J=8.4 Hz), 5.88 (t, 1H, J=7.8 Hz), 3.87 (t, 2H, J=6.0 Hz), 3.52-3.16 (m, 9H), 2.93 (m, 3H), 1.43 (s, 9H); ¹³C NMR (75 MHz, CDCl₃) δ 166.8, 156.6, 154.7, 145.7, 130.6, 125.8, 121.8, 116.1, 81.0, 61.5, 60.6, 46.0, 43.4, 42.7 (b), 42.5, 39.1, 28.6; MS (ESI, m/z) 446 (M+H)⁺.

Scheme 3

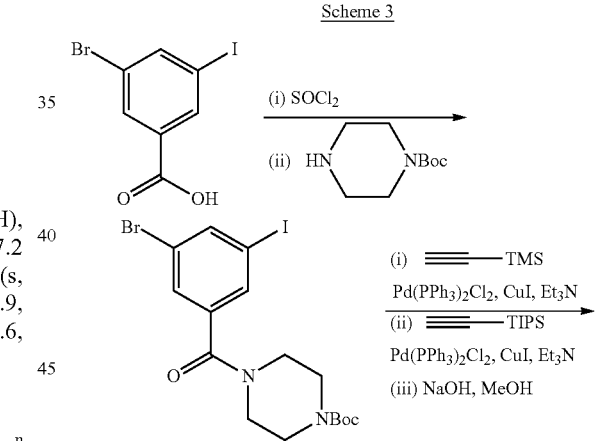

86%

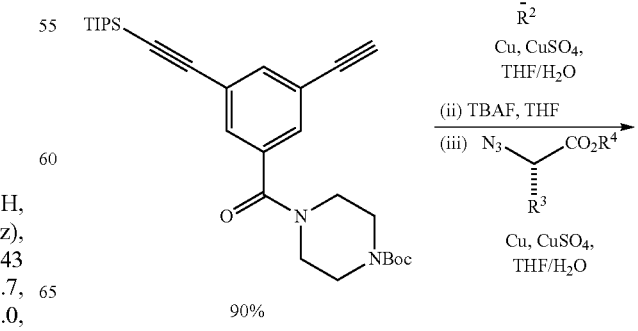

90%

-continued

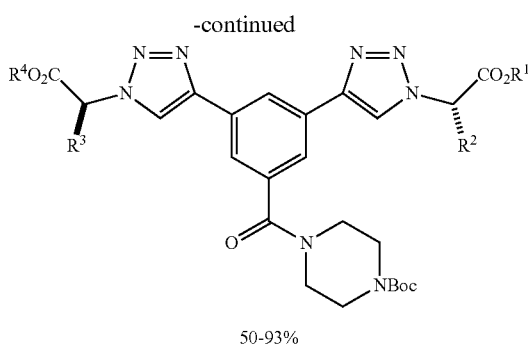

50-93%

Scheme 4

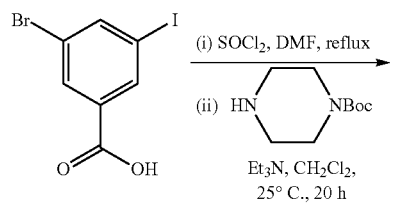

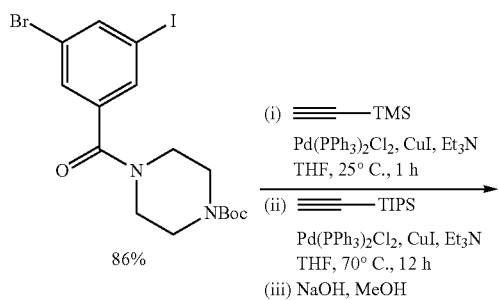

86%

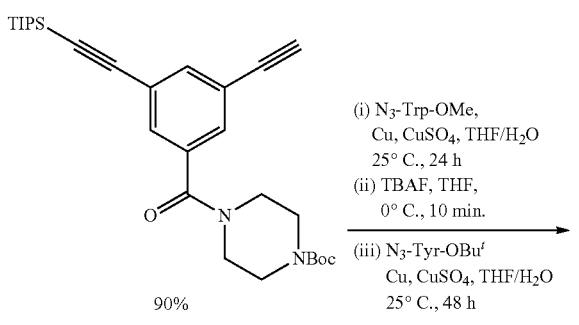

90%

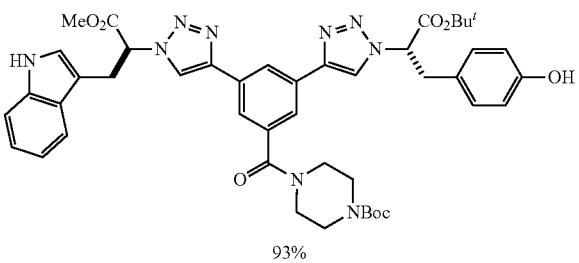

93%

Characterization data for protected monovalent compounds q through e' follows:

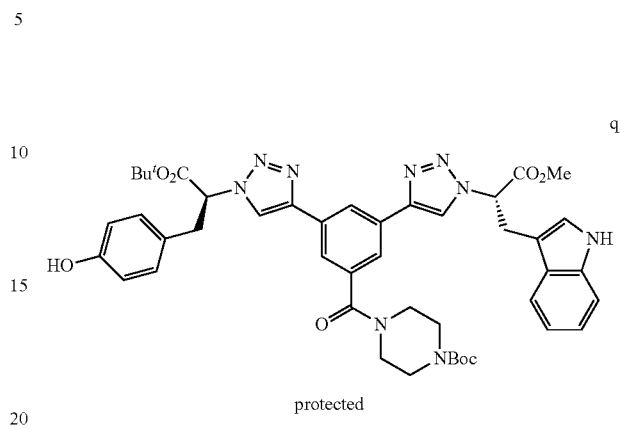

q protected

¹H NMR (500 MHz, CD₃OD) δ 8.44 (d, J=3.0 Hz, 1H), 8.34 (d, J=11.0 Hz, 1H), 8.21 (d, J=9.5 Hz, 1H), 7.79 (s, 1H), 7.71 (s, 1H), 7.44 (d, J=7.5 Hz, 1H), 7.27 (d, J=8.0 Hz, 1H), 7.04 (t, J=7.5 Hz, 1H), 6.98-6.95 (m, 3H), 6.89 (s, 1H), 6.62 (d, J=8.5 Hz, 2H), 5.80-5.77 (m, 1H), 5.55 (dd, J=9.5, 6.0 Hz, 1H), 3.81-3.67 (m, 15H), 1.45 (s, 9H), 1.42 (s, 9H); ¹³C NMR (125 MHz, CD₃OD) δ 171.7, 170.3, 168.8, 157.7, 156.2, 147.2, 138.1, 137.8, 133.0, 131.2, 128.2, 127.4, 125.0, 124.79, 124.76, 124.5, 123.5, 123.2, 122.6, 120.1, 118.8, 116.3, 112.4, 109.3, 84.5, 81.6, 66.5, 65.2, 53.6, 44.8, 43.2, 38.2, 29.3, 28.6, 28.0; MS (MALDI) calcd for $C_{45}H_{52}N_9O_8$ (M+H)⁺ 846. found 846.

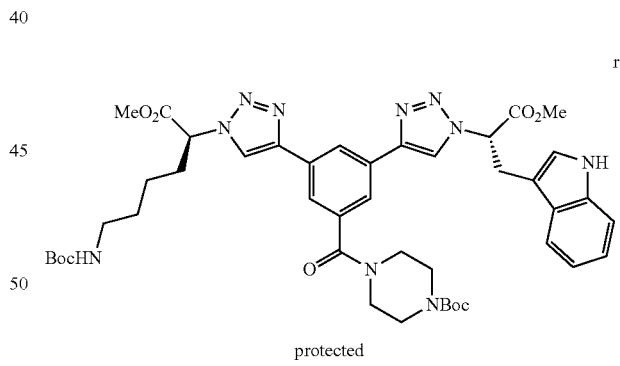

r protected

¹H NMR (500 MHz, CD₃OD) δ 8.53 (s, 1H), 8.36 (s, 1H), 8.27 (s, 1H), 7.84 (s, 1H), 7.72 (s, 1H), 7.45 (d, J=8.0 Hz, 1H), 7.27 (d, J=8.5 Hz, 1H), 7.21 (s, 1H), 7.04 (t, J=7.5 Hz, 1H), 6.96 (t, J=7.3 Hz, 1H), 6.90 (s, 1H), 5.80-5.77 (m, 1H), 5.49-5.46 (m, 1H), 3.77-3.38 (m, 16H), 2.98 (t, J=6.5, 2 H), 2.31-2.23 (m, 2H), 1.45 (s, 9H), 1.34 (s, 9H), 1.33-1.14 (m, 4H); ¹³C NMR (125 MHz, CDCl₃) δ 171.6, 170.6, 170.4, 158.4, 156.2, 147.6, 138.1, 137.8, 132.9, 129.4, 128.8, 128.6, 128.1, 125.0, 124.8, 124.5, 123.5, 122.9, 122.6, 120.1, 118.8, 112.4, 109.3, 81.6, 79.8, 67.2, 65.1, 64.2, 53.6, 45.0 (br), 43.2, 40.7, 32.5, 30.1, 29.3, 28.7, 28.6, 24.0; MS (MALDI) calcd for $C_{44}H_{57}N_{10}O_9$ (M+H)⁺ 869 found 869.

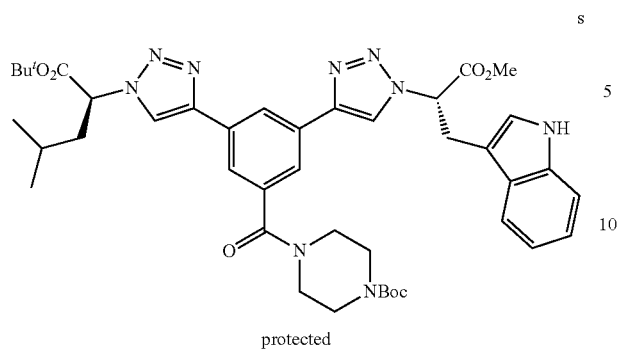

s

u

¹H NMR (500 MHz, CDCl₃) δ 8.38 (s, 1H), 8.27 (d, J=5.0 Hz, 1H), 8.10 (s, 1H), 7.93 (s, 1H), 7.89 (s, 1H), 7.77 (s, 1H), 7.51 (d, J=7.5 Hz, 1H), 7.35 (d, J=8.0 Hz, 1H), 7.18 (t, J=7.5 Hz, 1H), 7.12 (t, J=7.5 Hz, 1H), 6.81 (s, 1H), 5.76-5.73 (m, 1H), 5.41 (dd, J=9.5, 6.0 Hz, 1H), 3.79 (s, 3H), 3.75-3.35 (m, 10H), 2.05-2.01 (m, 1H), 1.49 (s, 9H), 1.48 (s, 9H), 1.47-1.37 (m, 2H), 0.99 (d, J=3.3 Hz, 3H), 0.95 (d, J=3.3 Hz, 3H); ¹³C NMR (125 MHz, CDCl₃) δ 169.8, 168.9, 168.8, 168.3, 154.5, 146.5, 146.3, 136.7, 136.0, 131.6, 131.5, 126.7, 124.0, 123.8, 123.2, 122.4, 120.7, 119.8, 119.7, 118.0, 111.5, 108.7, 83.6, 80.3, 63.4, 62.1, 53.2, 47.6, 43.7 (br), 42.1, 41.6, 29.0, 28.3, 27.9, 24.7, 22.6, 21.3; MS (MALDI) calcd for $C_{42}H_{54}N_9O_7$ (M+H)⁺ 796. found 796.

¹H NMR (500 MHz, CD₃OD) δ 9.53 (s, 1H), 8.30 (d, J=4.0 Hz, 1H), 8.19 (d, J=5.0 Hz, 1H), 7.80 (s, 1H), 7.68 (s, 1H), 7.44 (d, J=8.0 Hz, 1H), 7.26 (d, J=8.5 Hz, 1H), 7.02 (t, J=7.5 Hz, 1H), 6.95 (t, J=7.5 Hz, 1H), 6.87 (s, 1H), 5.75 (dd, J=9.5, 5.0 Hz, 1H), 5.66 (dd, J=6.0, 3.5 Hz, 1H), 4.36 (dd, J=12.0, 5.5 Hz, 1H), 4.14 (dd, J=12.5, 3.5 Hz, 1H), 3.77 (s, 3H), 3.75 (s, 3H), 3.74-3.38 (m, 10H), 1.44 (s, 9H); ¹³C NMR (125 MHz, CDCl₃) δ 171.6, 170.4, 169.1, 156.2, 147.2, 147.1, 138.1, 137.8, 133.0, 132.9, 128.2, 125.0, 124.9, 124.5, 123.7, 123.4, 122.6, 120.1, 118.8, 112.5, 109.4, 81.6, 66.3, 65.1, 62.8, 53.62, 53.61, 42.4 (br), 43.2, 29.3, 28.6; MS (MALDI) calcd for $C_{36}H_{42}N_9O_8$ (M+H)⁺ 728. found 728.

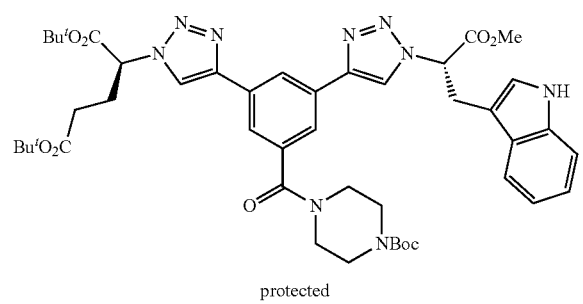

t

v

¹H NMR (300 MHz, CD₃OD) δ 8.56 (s, 1H), 8.37 (s, 1H), 8.28 (s, 1H), 7.86 (s, 1H), 7.74 (s, 1H), 7.45 (d, J=7.8 Hz, 1H), 7.28 (d, J=8.4 Hz, 1H), 7.05 (t, J=7.4 Hz, 1H), 6.97 (t, J=7.4 Hz, 1H), 6.90 (s, 1H), 5.80 (dd, J=9.3, 5.4 Hz, 1H), 5.47 (dd, J=9.9, 5.4 Hz, 1H), 3.79 (s, 3H), 3.78-3.40 (m, 10H), 2.61-2.38 (m, 2H), 2.45 (t, J=6.9 Hz, 2H), 1.47 (s, 9H), 1.46 (s, 9H), 1.41 (s, 9H); ¹³C NMR (75 MHz, CDCl₃) δ 171.7, 170.6, 169.2, 167.7, 155.0, 146.5, 146.0, 137.1, 136.7, 131.9, 131.9, 127.0, 123.9, 123.6, 123.4, 123.3, 122.3, 121.9, 121.5, 118.9, 117.6, 111.3, 108.2, 83.5, 80.9, 80.5, 64.0, 62.9, 52.4, 43.7 (br), 42.1, 30.9, 28.2, 27.4, 27.1, 27.0, 26.9; MS (MALDI) calcd for $C_{45}H_{58}N_9O_9$ (M+H)⁺ 868. found 868.

¹H NMR (500 MHz, CD₃OD) δ 8.64 (t, J=1.5 Hz, 1H), 8.51 (s, 1H), 8.38 (t, J=1.5 Hz, 1H), 7.88 (s, 1H), 7.83 (t, J=1.5 Hz, 1H), 6.96 (d, J=8.5 Hz, 2H), 6.63 (d, J=8.5 Hz, 2H), 5.57 (dd, J=10.0, 6.0 Hz, 1H), 5.44 (dd, J=11.0, 5.5 Hz, 1H), 3.77-3.38 (m, 10H), 2.28-2.22 (m, 1H), 2.10-2.04 (m, 1H), 1.47 (s, 9H), 1.46 (s, 9H), 1.43 (s, 9H), 1.42-1.39 (m, 1H), 0.98 (d, J=6.5 Hz, 3H), 0.94 (d, J=5.0 Hz, 3H); ¹³C NMR (125 MHz, CD₃OD δ 171.7, 169.6, 168.8, 157.7, 156.2, 147.5, 147.2, 138.3, 133.2, 131.2, 127.4, 125.0, 124.5, 123.2, 122.8, 116.4, 84.5, 84.4, 81.7, 66.6, 63.5, 44.0 (br), 43.3, 41.6, 38.3, 28.6, 28.11, 28.09, 26.1, 23.0, 21.5; MS (MALDI) calcd for $C_{43}H_{58}N_8O_8Na$ (M+Na)⁺ 837. found 837.

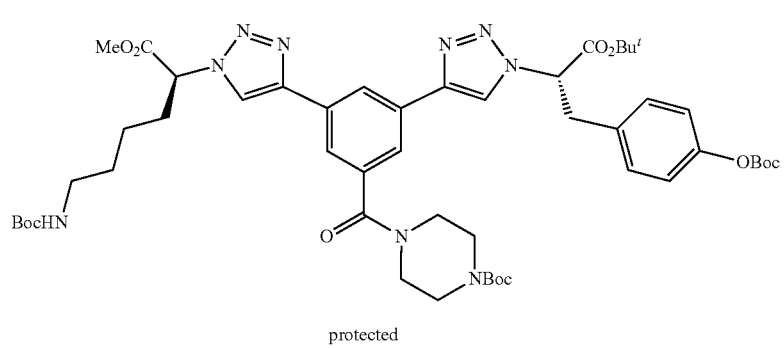

protected

¹H NMR (500 MHz, CDCl₃) δ 8.33 (s, 1H), 8.13 (s, 1H), 8.08 (s, 1H), 7.90 (s, 1H), 7.84 (s, 1H), 7.12 (d, J=8.0 Hz, 2H), 7.06 (d, J=8.0 Hz, 2H), 5.50 (t, J=7.3 Hz, 1H), 5.40 (dd, J=9.0, 5.0 Hz, 1H), 4.60 (s, 1H, N—H), 3.78 (s, 6H), 3.75-3.38 (m, 10H), 3.07 (br, 2H), 2.25-2.13 (m, 2H), 1.53-1.23 (m, 40H); ¹³C NMR (125 MHz, CDCl₃) δ 169.7, 169.1, 167.0, 155.9, 154.4, 151.5, 150.3, 146.8, 146.3, 136.7, 132.2, 131.5, 131.4, 129.9, 124.0, 123.8, 123.7, 121.5, 120.2, 119.8, 84.0, 83.5, 80.2, 64.6, 62.7, 53.1, 47.6, 43.5 (br), 42.1, 39.8, 38.3, 32.4, 29.2, 28.28, 28.26, 27.7, 27.6, 22.8; MS (MALDI) calcd for $C_{50}H_{68}N_9O_{12}$ (M+H)⁺ 988. found 988.

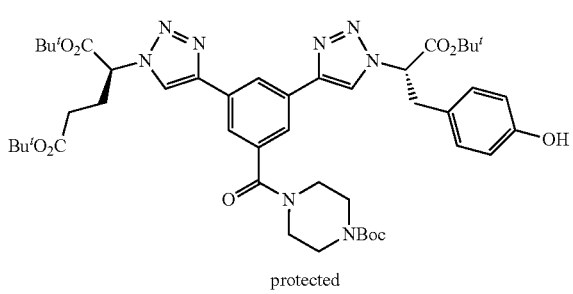

protected

¹H NMR (500 MHz, CD₃OD) δ 8.60 (s, 1H), 8.50 (s, 1H), 8.37 (s, 1H), 7.88 (s, 1H), 7.83 (s, 1H), 6.97 (d, J=8.0 Hz, 2H), 6.63 (d, J=8.0 Hz, 2H), 5.57 (dd, J=10.0, 6.5 Hz, 1H), 5.48 (dd, J=9.5, 5.5 Hz, 1H), 3.77-3.39 (m, 10H), 2.60-2.56 (m, 1H), 2.49-2.42 (m, 1H), 2.26 (m, 2H), 1.47 (s, 9H), 1.46 (s, 9H), 1.43 (s, 9H), 1.42 (s, 9H); ¹³C NMR (125 MHz, CD₃OD) δ 172.9, 171.8, 168.9, 168.8, 157.7, 156.2, 147.6, 147.2, 138.3, 133.2, 133.1, 131.2, 127.4, 125.0, 124.6, 124.5, 123.3, 123.1, 116.4, 84.7, 84.5, 82.1, 81.7, 66.6, 64.1, 44.4 (br), 43.3, 38.3, 32.1, 28.6, 28.32, 28.25, 28.12, 28.10; MS (MALDI) calcd for $C_{46}H_{63}N_8O_{10}$ (M+H)⁺ 887. found 887.

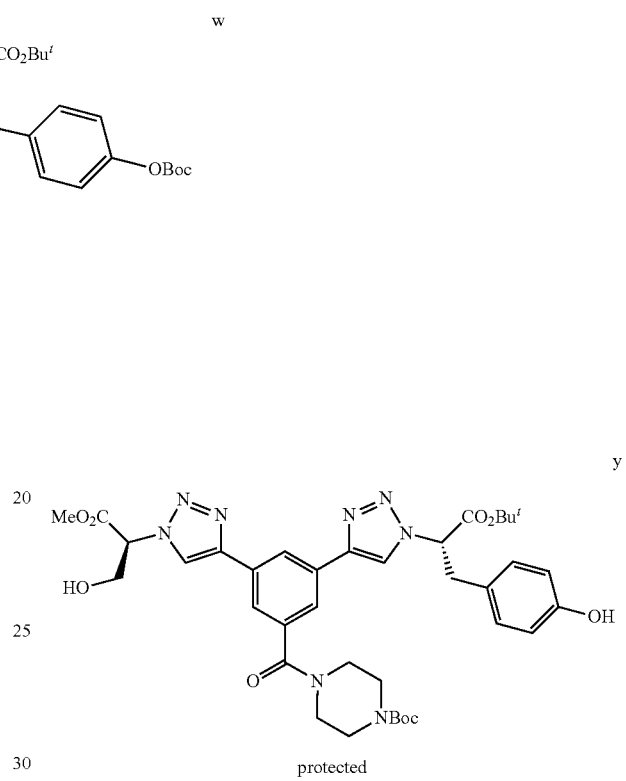

protected

¹H NMR (500 MHz, CD₃OD) δ 8.64 (s, 1H), 8.52 (s, 1H), 8.39 (s, 1H), 7.89 (s, 1H), 7.84 (s, 1H), 6.97 (d, J=8.0 Hz, 2H), 6.63 (d, J=8.5 Hz, 2H), 5.71 (dd, J=6.5, 4.0 Hz, 1H), 5.57 (dd, J=9.5, 6.0 Hz, 1H), 4.38 (dd, J=12.0, 6.5 Hz, 1H), 4.16 (dd, J=12.0, 3.0 Hz, 1H), 3.82 (s, 3H), 3.79-3.39 (m, 10H), 1.46 (s, 9H), 1.44 (s, 9H); ¹³C NMR (125 MHz, CD₃OD) δ 171.8, 169.1, 168.8, 157.7, 156.2, 147.3, 147.2, 138.3, 133.2, 133.1, 131.2, 127.4, 125.0, 124.55, 124.49, 123.8, 123.5, 116.3, 84.6, 81.6, 66.6, 66.4, 62.8, 53.6, 44.5 (br), 43.3, 38.3, 28.6, 28.1; MS (MALDI) calcd for $C_{37}H_{47}N_8O_9$ (M+H)⁺ 747. found 747.

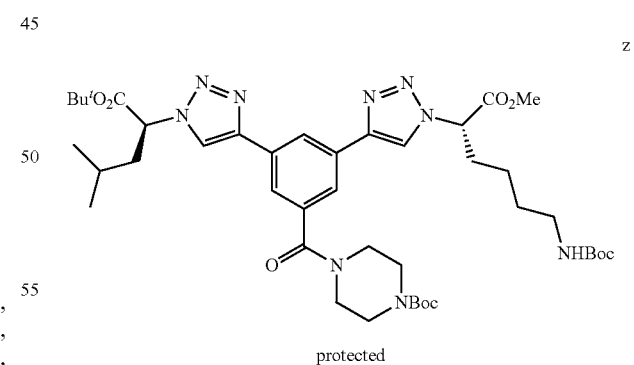

protected

¹H NMR (500 MHz, CDCl₃) δ 8.39 (s, 1H), 8.14 (s, 2H), 7.91 (s, 2H), 5.44-5.40 (m, 2H), 4.56 (br, 1H, N—H), 3.80 (s, 3H), 3.78-3.40 (m, 8H), 3.08 (br, 2H), 2.34-2.26 (m, 1H), 2.21-2.17 (m, 1H), 2.08-1.98 (m, 2H), 1.54-1.24 (m, 32H), 0.98 (d, J=6.5 Hz, 3H), 0.94 (d, J=6.5 Hz, 3H); ¹³C NMR (125 MHz, CDCl₃) δ 169.8, 169.1, 168.3, 155.9, 154.5, 146.9, 146.7, 136.8, 131.7, 131.5, 124.0, 123.9, 123.8, 119.8, 119.6, 83.5, 80.3, 79.2, 62.8, 62.0, 53.1, 47.7, 43.6

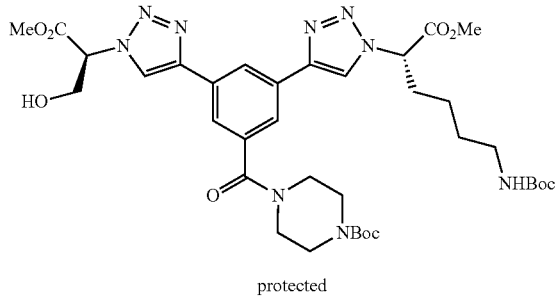

a' protected

¹H NMR (500 MHz, CD₃OD) δ 8.61 (s, 1H), 8.60 (s, 1H), 8.34 (s, 1H), 7.85 (s, 2H), 5.72-5.70 (m, 1H), 5.44 (dd, J=9.0, 5.5 Hz, 1H), 4.38 (dd, J=12.0, 6.0 Hz, 1H), 4.17 (d, J=9.5 Hz, 1H), 3.82 (s, 3H), 3.78 (s, 3H), 3.77-3.42 (m, 8H), 3.00 (t, J=6.5 Hz, 2H), 2.37-2.25 (m, 2H), 1.58-1.19 (m, 22H); ¹³C NMR (125 MHz, CDCl₃) δ 171.6, 170.7, 169.1, 158.4, 156.2, 147.6, 147.3, 138.2, 133.1, 132.9, 125.0, 124.5, 124.4, 123.7, 122.9, 81.6, 79.8, 66.3, 64.2, 62.8, 53.6, 44.4 (br), 43.3, 40.8, 32.5, 30.2, 28.8, 28.7, 28.6, 24.1; MS (MALDI) calcd for $C_{36}H_{52}N_9O_{10}$ (M+H)⁺ 770. found 770.

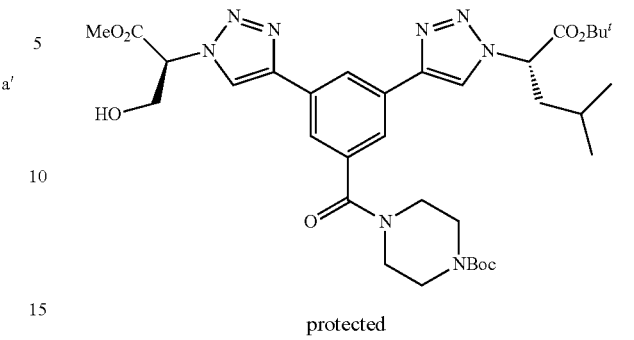

c' protected

¹H NMR (500 MHz, CD₃OD) δ 8.86 (s, 1H), 8.64 (s, 1H), 8.42 (s, 1H), 7.89 (s, 2H), 5.71 (dd, J=6.0, 3.5 Hz, 1H), 5.45 (dd, J=10.5, 5.0 Hz, 1H), 4.38 (dd, J=12.0, 6.0 Hz, 1H), 4.16 (dd, J=12.0, 3.0 Hz, 1H), 3.82 (s, 3H), 3.81-3.45 (m, 8H), 2.29-2.22 (m, 1H), 2.10-2.04 (m, 1H), 1.47 (s, 9H), 1.46 (s, 9H), 1.46-1.34 (m, 1H), 0.98 (d, J=6.5 Hz, 3H), 0.95 (d, J=6.5 Hz, 3H); ¹³C NMR (125 MHz, CDCl₃) δ 171.7, 169.6, 169.0, 156.2, 147.5, 147.2, 138.2, 133.1, 133.0, 125.0, 124.5, 124.4, 123.8, 122.9, 84.4, 81.6, 66.3, 63.5, 62.8, 53.6, 44.5 (br), 43.2, 41.5, 28.6, 28.1, 26.0, 23.0, 21.5; MS (ESI) calcd for $C_{34}H_{49}N_8O_8$ (M+H)⁺ 697. found 697.

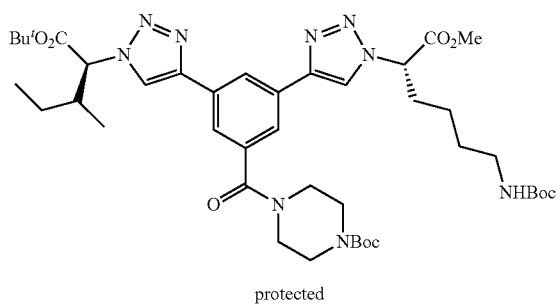

b' protected

¹H NMR (500 MHz, CDCl₃) δ 8.39 (s, 1H), 8.24 (s, 1H), 8.14 (s, 1H), 7.92 (s, 2H), 5.42 (dd, J=10.0, 5.0 Hz, 1H), 5.18 (d, J=8.5 Hz, 1H), 4.54 (br, 1H, N—H), 3.81 (s, 3H), 3.80-3.42 (m, 8H), 3.10-3.07 (m, 2H), 2.31-2.04 (m, 3H), 1.63-1.26 (m, 33H), 1.05 (d, J=6.5 Hz, 3H), 0.91 (t, J=7.5 Hz, 3H); ¹³C NMR (125 MHz, CDCl₃) δ 169.8, 169.1, 167.8, 155.9, 154.5, 146.9, 146.5, 136.8, 131.8, 131.5, 124.0, 123.9, 123.8, 119.9, 119.7, 83.6, 80.3, 68.4, 62.8, 53.1, 47.6, 43.4 (br), 42.1, 39.9, 38.8, 32.5, 29.3, 28.3, 27.9, 25.1, 22.8, 15.5, 10.8; MS (MALDI) calcd for $C_{42}H_{64}N_9O_9$ (M+H)⁺ 838. found 838.

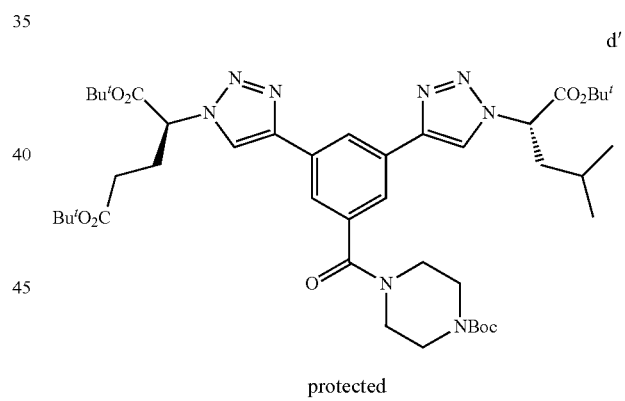

d' protected

¹H NMR (500 MHz, CD₃OD) δ 8.66 (s, 1H), 8.62 (s, 1H), 8.44 (s, 1H), 7.90 (s, 2H), 5.50-5.44 (m, 2H), 3.82-3.45 (m, 8H), 2.60-2.55 (m, 1H), 2.48-2.44 (m, 1H), 2.27-2.22 (m, 3H), 2.10-2.04 (m, 1H), 1.48 (s, 9H), 1.47 (s, 9H), 1.46 (s, 9H), 1.42 (s, 9H), 1.41-1.34 (m, 1H), 0.98 (d, J=6.5 Hz, 3H), 0.95 (d, J=7.0 Hz, 3H); ¹³C NMR (125 MHz, CDCl₃) δ 172.9, 171.8, 169.6, 168.9, 156.2, 147.7, 147.6, 138.4, 133.2, 133.1, 125.0, 124.6, 123.1, 122.9, 84.7, 84.5, 82.1, 81.7, 64.1, 63.5, 44.8 (br), 43.3, 41.6, 32.1, 28.6, 28.32, 28.27, 28.12, 28.11, 26.1, 23.0, 21.5; MS (MALDI) calcd for $C_{37}H_{53}N_8O_{10}$ (M+H)⁺ 769. found 769.

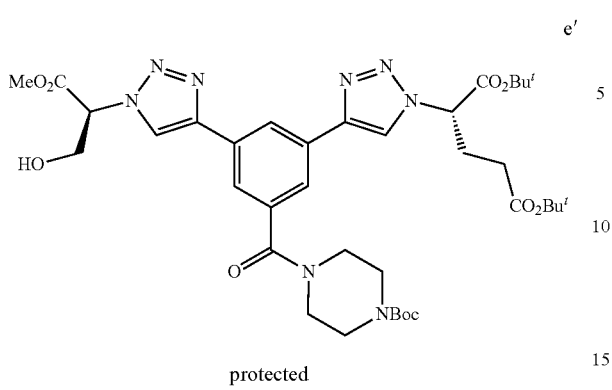

protected

¹H NMR (500 MHz, CD₃OD) δ 8.62 (s, 1H), 8.60 (s, 1H), 8.38 (s, 1H), 7.87 (s, 2H), 5.70 (dd, J=6.0, 3.5 Hz, 1H), 5.48 (dd, J=10.0, 5.5 Hz, 1H), 4.49 (dd, J=12.0, 6.0 Hz, 1H), 4.17 (dd, J=11.5, 3.0 Hz, 1H), 3.82 (s, 3H), 3.81-3.45 (m, 8H), 2.60-2.55 (m, 1H), 2.50-2.43 (m, 1H), 2.27 (t, J=7.3 Hz, 2H), 1.47 (s, 9H), 1.45 (s, 9H), 1.42 (s, 9H); ¹³C NMR (125 MHz, CDCl₃) δ 172.8, 171.7, 169.1, 168.9, 156.2, 147.7, 147.4, 138.3, 133.2, 133.0, 125.0, 124.6, 124.5, 123.8, 123.1, 84.7, 82.1, 81.6, 66.3, 64.1, 62.9, 53.6, 44.5 (br), 43.3, 32.2, 28.6, 28.3, 28.2, 28.1; MS (ESI) calcd for $C_{43}H_{65}N_8O_9$ $(M+H)^+$ 837. found 837.

The following general methods may be used to prepare protected monovalent compounds f' through m' (Schemes 5 and 6). Synthesis of a protected monovalent compound from this group is demonstrated in Scheme 7 as a representative example.

Scheme 5

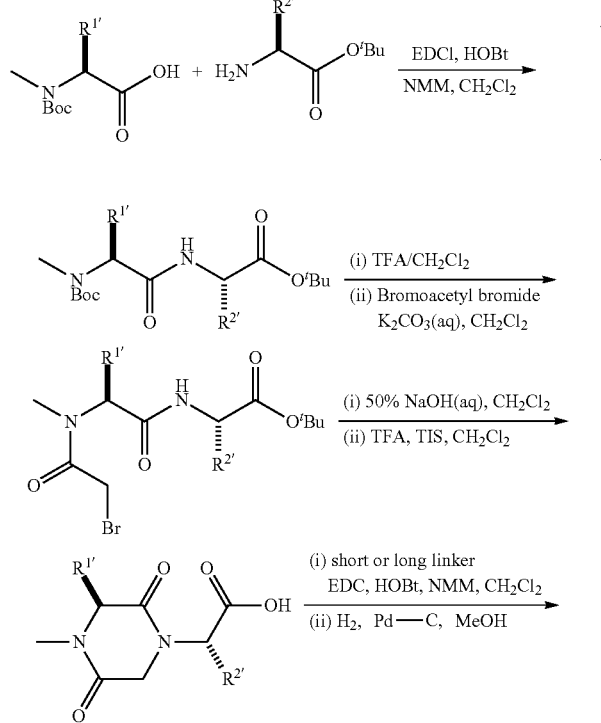

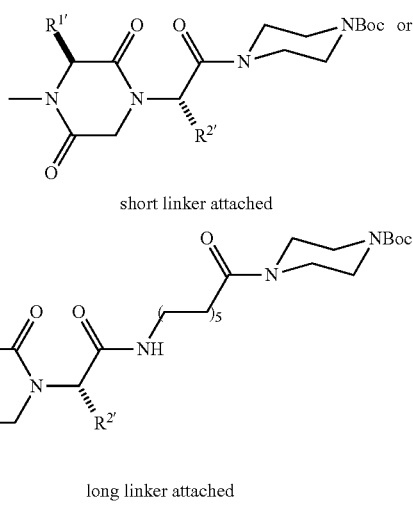

short linker attached long linker attached

Scheme 6

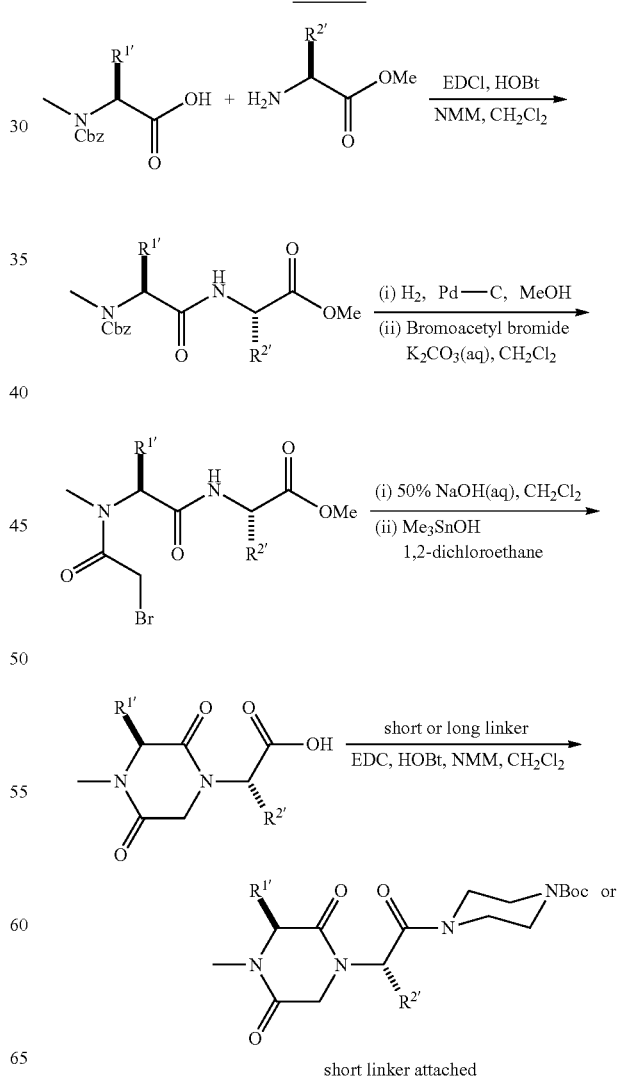

short linker attached

-continued

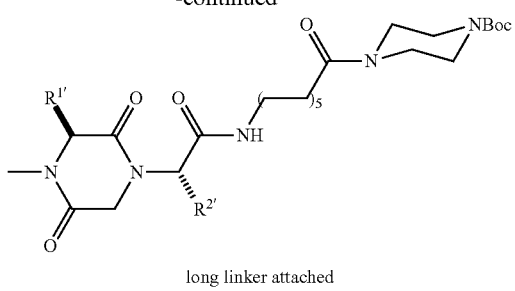

long linker attached

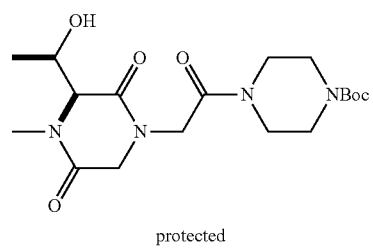

protected

¹H NMR (500 MHz, CDCl₃) δ 4.93 (br, 1H), 4.85 (d, 1H, J=16.1 Hz), 4.42-4.32 (m, 2H), 3.77 (d, 1H, J=1.7 Hz), 3.66 (d, 1H, J=16.1 Hz), 3.62-3.32 (m, 8H), 3.06 (s, 3H), 1.43 (s, 9H), 1.27 (d, 3H, J=6.5 Hz). ¹³C NMR (125 MHz, CDCl₃) δ 168.0, 165.4, 164.7, 154.2, 80.5, 71.2, 68.7, 52.0, 47.8, 44.4, 42.0, 36.1, 28.2, 19.7. Desired MS 399.22 (M+H). MS Found (ESI, m/z) 399.22 (M+H)

Scheme 7

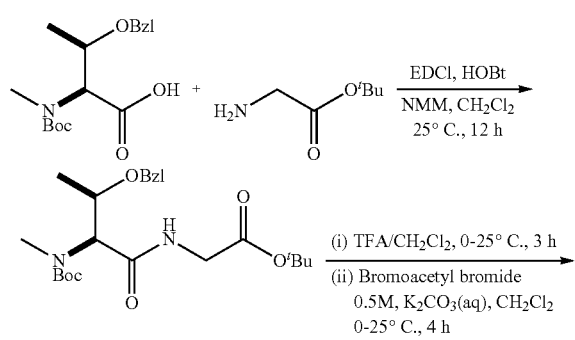

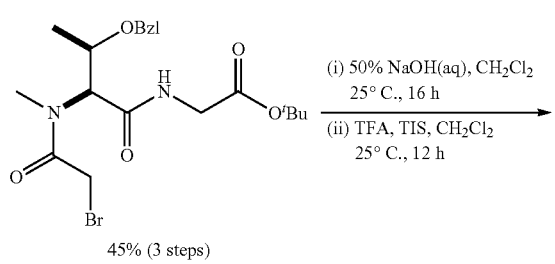

45% (3 steps)

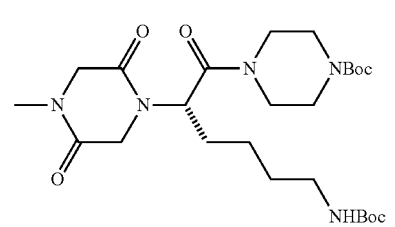

protected

¹H NMR (500 MHz, CDCl₃) δ 5.26 (t, 1H, J=7.6 Hz), 4.69 (br, 1H), 4.03 (d, 1H, J=17.4 Hz), 3.96-3.81 (m, 3H), 3.58-3.30 (m, 6H), 3.27-3.18 (m, 2H), 3.03-2.93 (m, 2H), 2.87 (s, 3H), 1.80-1.58 (m, 2H), 1.45-1.37 (m, 2H), 1.35 (s, 9H), 1.31 (s, 9H), 1.20-1.12 (m, 2H). Desired MS 548.32 (M+Na). MS Found (ESI, m/z) 548.30 (M+Na)

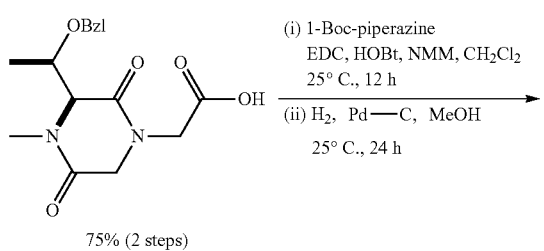

75% (2 steps)

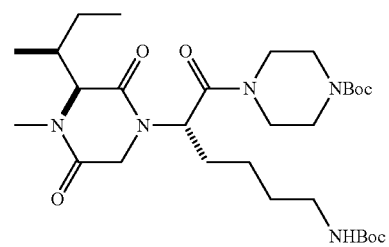

protected

¹H NMR (500 MHz, CDCl₃) δ 5.26 (t, 1H, J=7.6 Hz), 4.60 (br, 1H), 4.11 (br, 1H), 3.83 (d, 1H, J=17.6 Hz), 3.74 (d, 1H, J=4.3 Hz), 3.60-3.31 (m, 6H), 3.27-3.11 (m, 2H), 3.04-2.97 (m, 2H), 2.88 (s, 3H), 1.88-1.78 (m, 2H), 1.59-1.47 (m, 2H), 1.47-1.39 (m, 2H), 1.35 (s, 9H), 1.33 (s, 9H), 1.31-1.24 (m, 1H), 1.24-1.14 (m, 2H), 0.89 (t, 3H, J=7.3 Hz), 0.83 (d, 3H, J=6.8 Hz). ¹³C NMR (125 MHz, CDCl₃) δ 167.8, 162.9, 164.0, 155.8, 154.2, 80.1, 78.9, 66.6, 51.1, 45.6, 45.2, 41.9, 39.8, 38.6, 33.3, 29.5, 28.3, 28.2, 28.1, 26.2, 23.2, 14.5, 11.7. Desired MS 582.38 (M+H). MS Found (ESI, m/z) 582.39 (M+H).

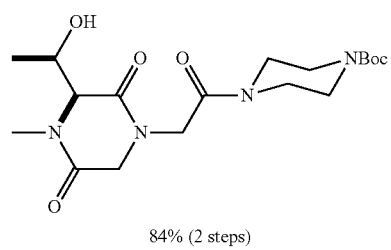

84% (2 steps)

Characterization data for protected monovalent compounds f' through m' follows:

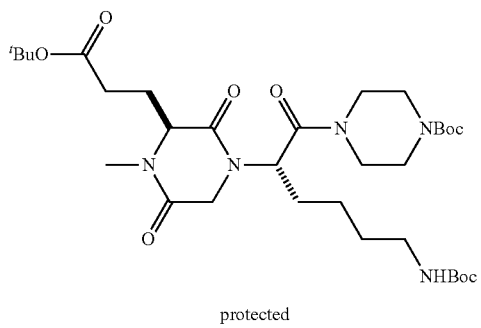

protected

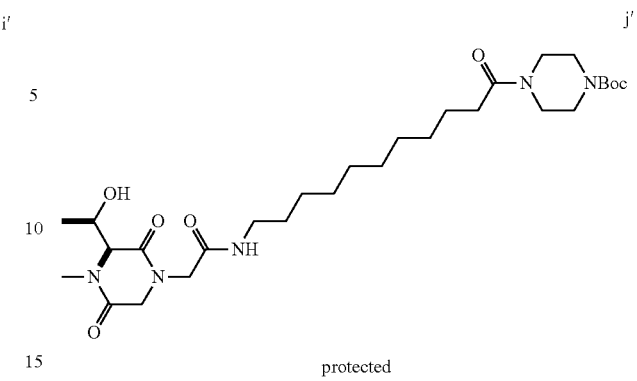

protected

¹H NMR (500 MHz, CDCl₃) δ 5.22 (t, 1H, J=7.6 Hz), 4.69 (br, 1H), 4.10 (br, 1H), 3.88-3.78 (m, 2H), 3.60-3.09 (m, 8H), 3.05-2.96 (m, 2H), 2.89 (s, 3H), 2.30-2.17 (m, 2H), 2.13-2.04 (m, 1H), 1.95-1.85 (m, 1H), 1.85-1.76 (m, 1H), 1.67-1.57 (m, 1H), 1.49-1.28 (m, 29H), 1.23-1.12 (m, 2H). ¹³C NMR (125 MHz, CDCl₃) δ 171.1, 167.6, 165.6, 163.5, 155.8, 154.2, 81.0, 80.1, 78.8, 61.6, 51.2, 45.2, 45.0, 41.9, 39.8, 32.2, 30.3, 29.5, 28.2, 28.1, 28.0, 27.9, 26.3, 23.0. Desired MS 676.40 (M+H). MS Found (ESI, m/z) 676.40 (M+H)

¹H NMR (500 MHz, CDCl₃) δ 6.76 (t, 1H, J=5.6 Hz), 4.83 (d, 1H, J=4.8 Hz), 4.67 (d, 1H, J=16.3 Hz), 4.40-4.33 (m, 2H), 3.77 (d, 1H, J=1.9 Hz), 3.68 (d, 1H, J=16.3 Hz), 3.55-3.49 (m, 2H), 3.42-3.32 (m, 6H), 3.17 (q, 2H, J=6.7 Hz), 3.04 (s, 3H), 2.31-2.15 (m, 4H), 1.59-1.51 (m, 2H), 1.42 (s, 9H), 1.32-1.17 (m, 15H). ¹³C NMR (125 MHz, CDCl₃) δ 171.9, 167.4, 167.0, 164.9, 154.5, 80.3, 71.6, 68.6, 51.9, 49.4, 45.3, 41.2, 39.7, 36.2, 33.2, 29.1, 29.1, 29.0, 29.0, 28.3, 26.6, 25.1, 20.1. Desired MS 582.38 (M+H). MS Found (ESI, m/z) 582.38 (M+H).

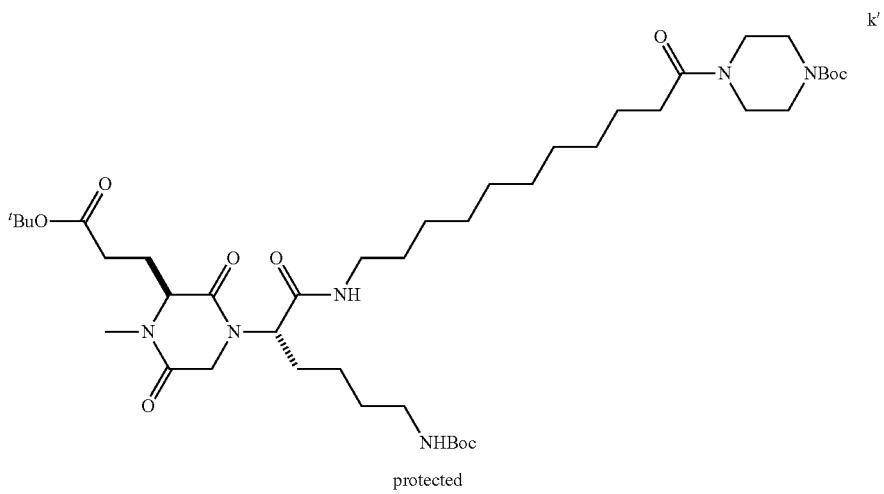

protected

¹H NMR (500 MHz, CDCl₃) δ 6.22 (t, 1H, J=5.6 Hz), 4.82-4.74 (m, 1H), 4.71 (t, 1H, J=7.8 Hz), 4.07 (d, 1H, J=17.3 Hz), 3.87-3.79 (m, 2H), 3.50-3.44 (m, 2H), 3.35-3.25 (m, 6H), 3.15-2.94 (m, 4H), 2.87 (s, 3H), 2.28-2.04 (m, 5H), 1.96-1.81 (m, 2H), 1.63-1.38 (m, 5H), 1.35 (s, 9H), 1.33 (s, 9H), 1.31 (s, 9H), 1.24-1.09 (m, 16H). ¹³C NMR (125 MHz, CDCl₃) δ 171.6, 171.1, 168.6, 166.0, 163.2, 155.8, 154.3, 80.9, 80.0, 78.7, 61.6, 55.6, 45.5, 45.2, 41.0, 39.8, 39.3, 38.4, 33.1, 32.1, 30.2, 29.3, 29.2, 29.1, 29.1, 28.9, 28.2, 28.1, 27.8, 26.9, 26.5, 26.5, 25.0, 23.0. Desired MS 837.56 (M+H). MS Found (ESI, m/z) 837.57 (M+H).

I'

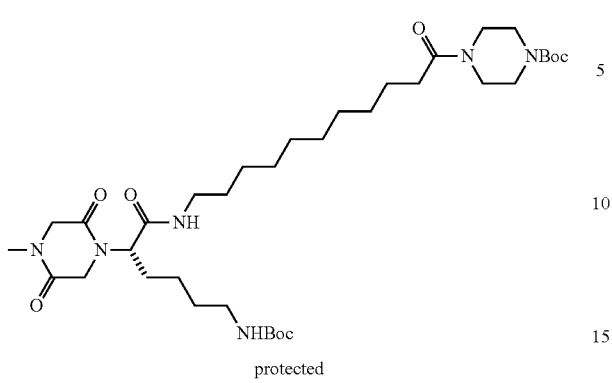

protected $^{13}$C NMR (125 MHz, CDCl$_3$) δ 171.7, 168.8, 164.4, 163.4, 155.9, 154.4, 80.1, 79.1, 78.9, 55.4, 51.6, 45.6, 45.2, 41.1, 39.3, 33.2, 33.0, 29.3, 29.2, 29.2, 29.2, 29.2, 29.0, 28.3, 28.2, 28.2, 26.7, 26.6, 25.1, 22.8. Desired MS 709.48 (M+H). MS Found (ESI, m/z) 709.47 (M+H).

m'

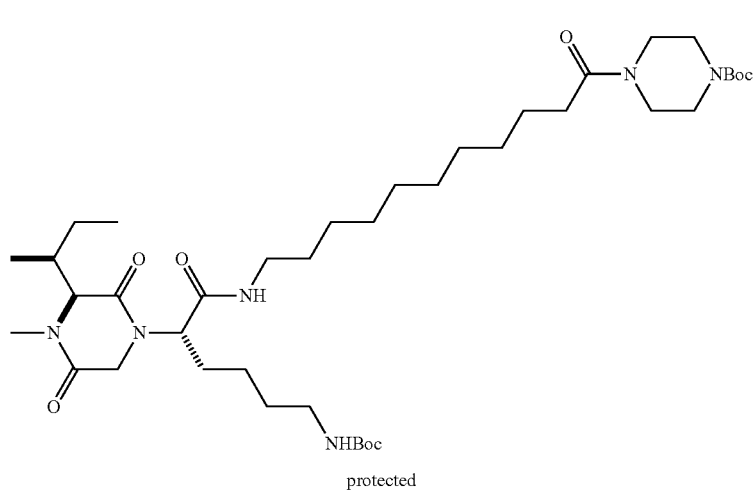

protected $^1$H NMR (500 MHz, CDCl$_3$) δ 6.30 (t, 1H, J=5.0 Hz), 4.75-4.69 (m, 2H), 4.07 (d, 1H, J=17.5 Hz), 3.83 (d, 1H, J=17.5 Hz), 3.76 (d, 1H, J=4.1 Hz), 3.50-3.44 (m, 2H), 3.35-3.25 (m, 6H), 3.15-2.94 (m, 4H), 2.86 (s, 3H), 2.21 (t, 2H, J=7.5 Hz), 1.88-1.76 (m, 2H), 1.57-1.38 (m, 6H), 1.35 (s, 9H), 1.31 (s, 9H), 1.29-1.09 (m, 17H), 0.88 (t, 3H, J=7.2 Hz), 0.80 (d, 3H, J=6.8 Hz). $^{13}$C NMR (125 MHz, CDCl$_3$) δ 171.6, 168.8, 165.2, 163.7, 155.8, 154.3, 80.0, 78.8, 66.4, 55.6, 46.0, 45.1, 41.0, 39.8, 39.2, 38.4, 33.1, 33.1, 29.3, 29.2, 29.1, 29.1, 28.9, 28.2, 28.1, 26.9, 26.5, 26.1, 25.0, 23.1, 14.3, 11.7. Desired MS 765.54 (M+H). MS Found (ESI, m/z) 765.54 (M+H).

The following general method may be used to prepare protected monovalent compounds n' through g'" (Schemes 8 and 9). Synthesis of protected monovalent compound v' is demonstrated in Scheme 10 as a representative example.

Scheme 8

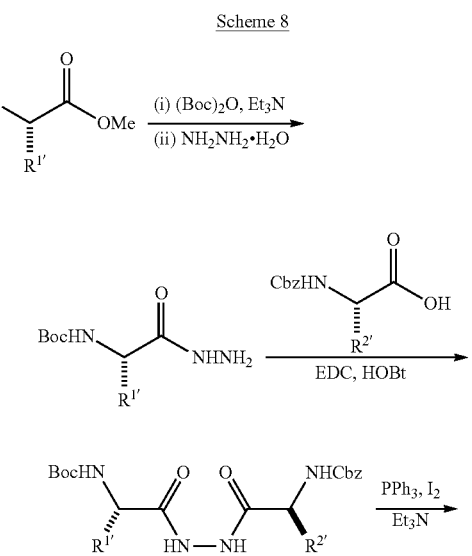

-continued

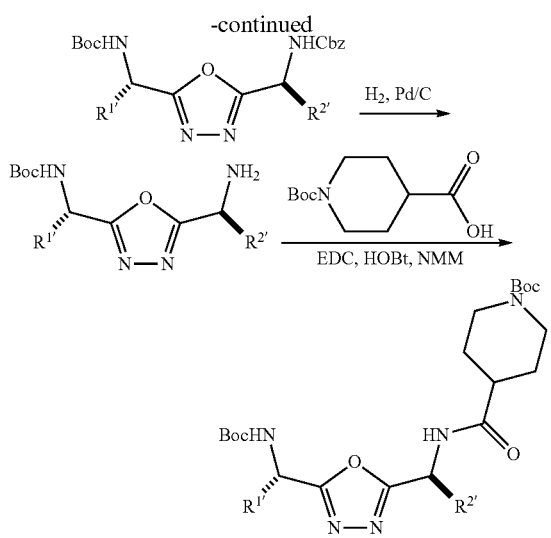

Scheme 9
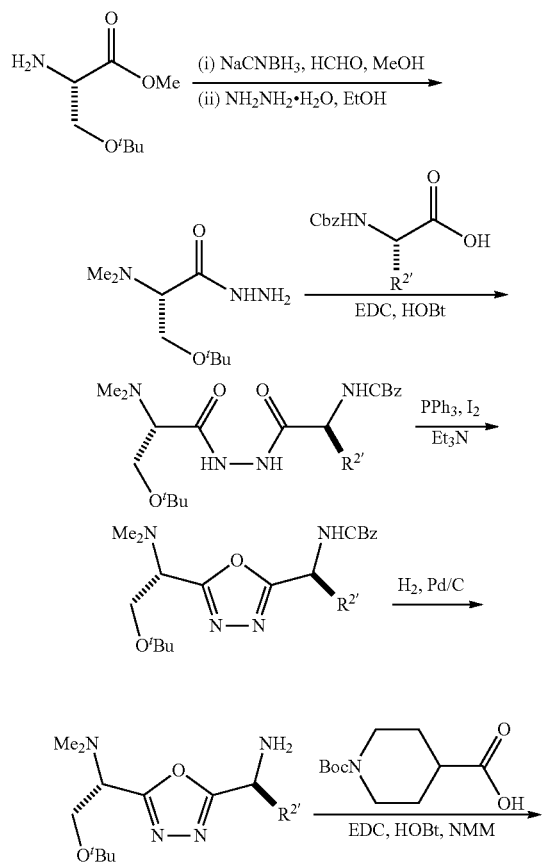
Scheme 10
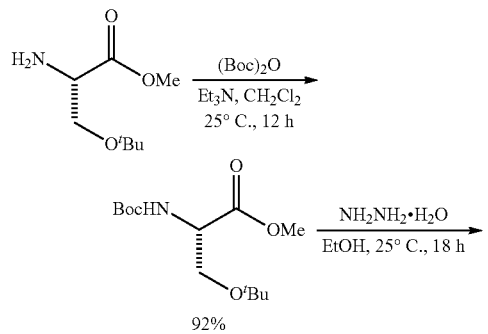
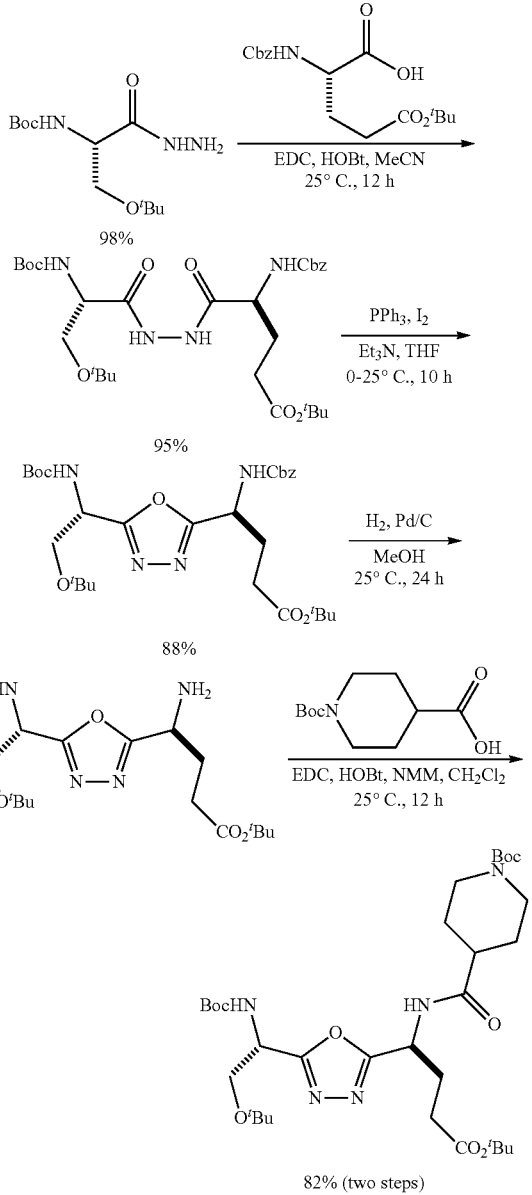
Characterization data for protected monovalent compounds n' through g''' follows:
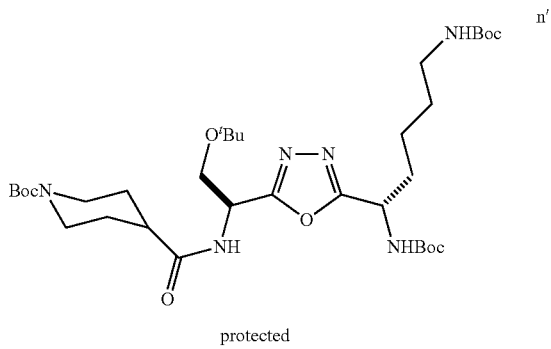 [SMILES: CC(C)(C)OC[C@H](NC(=O)C1CCN(C(=O)OC(C)(C)C)CC1)c1nnc([C@H](CCCCNC(=O)OC(C)(C)C)NC(=O)OC(C)(C)C)o1]
protected ¹H NMR (500 MHz, CDCl₃) δ 6.59 (d, 1H, J=8.2 Hz), 5.42-5.36 (m, 1H), 5.22 (d, 1H, J=8.5 Hz), 4.98-4.89 (m, 1H), 4.65 (br, 1H), 4.10 (br, 2H), 3.78 (dd, 1H, J=3.2, 9.4 Hz), 3.15-2.94 (dd, 1H, J=3.9, 9.4 Hz), 3.12-2.99 (m, 2H), 2.81-2.65 (br, 2H), 2.39-2.30 (m, 1H), 1.94-1.75 (m, 4H), 1.70-1.57 (m, 2H), 1.51-1.31 (m, 31H), 1.06 (s, 9H). ¹³C NMR (125 MHz, CDCl₃) δ 174.2, 167.1, 165.4, 156.1, 155.0, 154.6, 80.3, 80.0, 79.6, 79.1, 73.8, 62.1, 46.9, 46.5, 42.9, 39.9, 33.2, 29.4, 28.4, 28.4, 28.3, 28.2, 27.2, 22.3. Desired MS 719.44 (M+Na). MS Found (ESI, m/z) 719.42 (M+Na).

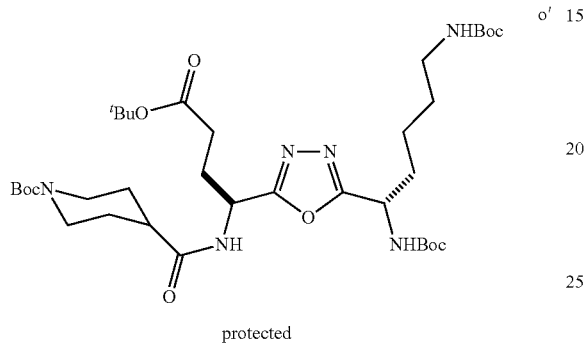

protected o'

¹H NMR (500 MHz, CDCl₃) δ 6.77 (br, 1H), 5.32-5.23 (m, 2H), 4.98-4.89 (m, 1H), 4.70 (br, 1H), 4.09 (br, 2H), 3.12-3.01 (m, 2H), 2.72 (br, 2H), 2.41-2.17 (m, 4H), 2.12-2.02 (m, 1H), 1.96-1.74 (m, 4H), 1.69-1.55 (m, 2H), 1.52-1.32 (m, 40H). ¹³C NMR (125 MHz, CDCl₃) δ 174.4, 172.2, 167.3, 166.4, 156.1, 155.1, 154.6, 81.2, 80.4, 79.6, 79.1, 47.1, 45.3, 42.9, 39.9, 33.2, 31.2, 29.4, 28.5, 28.4, 28.4, 28.3, 28.3, 28.0, 22.3. Desired MS 761.45 (M+Na). MS Found (MALDI, m/z) 761.06 (M+Na).

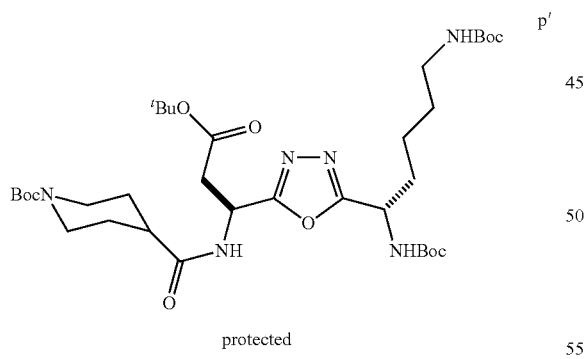

protected p'

¹H NMR (500 MHz, CDCl₃) δ 6.95 (br, 1H), 5.66-5.58 (m, 1H), 5.24-5.13 (m, 1H), 5.03-4.93 (m, 1H), 4.73-4.63 (m, 1H), 4.25-4.05 (br, 2H), 3.16-3.06 (m, 2H), 3.06-2.97 (m, 1H), 2.88 (ddd, 1H, J=2.3, 5.2, 16.5 Hz), 2.78 (br, 2H), 2.35 (tt, 1H, J=3.7, 11.5 Hz), 2.00-1.79 (m, 4H), 1.73-1.62 (m, 2H), 1.57-1.36 (m, 40H). ¹³C NMR (125 MHz, CDCl₃) δ 174.0, 169.6, 167.4, 165.6, 156.1, 155.0, 154.6, 82.3, 80.4, 79.6, 79.2, 47.0, 43.0, 42.2, 40.0, 37.6, 33.4, 33.2, 29.4, 28.4, 28.3, 28.3, 28.0, 22.3, 22.2. Desired MS 747.44 (M+Na). MS Found (MALDI, m/z) 747.16 (M+Na).

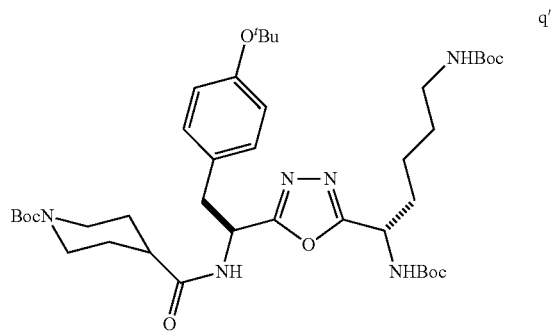

protected q'

¹H NMR (500 MHz, CDCl₃) δ 6.92 (d, 2H, J=8.5 Hz), 6.85 (d, 2H, J=8.5 Hz), 6.34 (d, 1H, J=8.2 Hz), 5.58-5.51 (m, 1H), 5.22 (d, 1H, J=8.5 Hz), 4.96-4.86 (m, 1H), 4.69 (br, 1H), 4.05 (br, 2H), 3.21 (dd, 1H, J=6.2, 14.0 Hz), 3.15-3.01 (m, 3H), 2.74-2.60 (br, 2H), 2.21 (tt, 1H, J=3.7, 11.5 Hz), 1.91-1.60 (m, 4H), 1.60-1.30 (m, 33H), 1.28 (s, 9H). ¹³C NMR (125 MHz, CDCl₃) δ 174.0, 171.2, 167.3, 166.2, 156.1, 155.1, 154.6, 129.8, 129.7, 124.3, 80.4, 79.2, 78.6, 47.0, 45.5, 42.9, 39.9, 38.7, 33.1, 29.4, 28.8, 28.6, 28.4, 28.4, 28.3, 28.1, 22.3. Desired MS 795.47 (M+Na). MS Found (MALDI, m/z) 795.17 (M+Na).

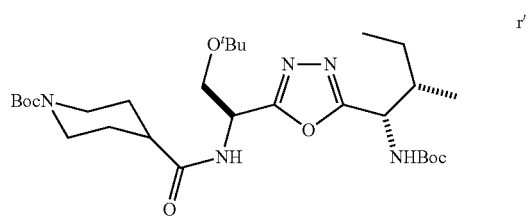 [SMILES: CC[C@H](C)[C@H](NC(=O)OC(C)(C)C)c1nnc([C@H](COC(C)(C)C)NC(=O)C2CCN(C(=O)OC(C)(C)C)CC2)o1]

r'

¹H NMR (500 MHz, CDCl₃) δ 6.53 (d, 1H, J=8.6 Hz), 5.44 (dt, 1H, J=3.5, 8.6 Hz), 5.18 (d, 1H, J=9.2 Hz), 4.98-4.90 (m, 1H), 4.14 (br, 2H), 3.81 (dd, 1H, J=2.6, 9.2 Hz), 3.66 (dd, 1H, J=3.7, 9.2 Hz), 2.78 (br, 2H), 2.37 (tt, 1H, J=3.7, 11.5 Hz), 1.97-1.61 (m, 5H), 1.51-1.38 (m, 19H), 1.24-1.13 (m, 1H), 1.10 (s, 9H), 0.95-0.87 (m, 6H). ¹³C NMR (125 MHz, CDCl₃) δ 174.1, 166.5, 165.2, 155.1, 154.6, 80.3, 79.6, 73.8, 62.3, 51.6, 46.5, 43.0, 38.9, 28.5, 28.4, 28.3, 28.2, 27.2, 25.0, 15.1, 11.3. Desired MS 582.38 (M+H). MS Found (MALDI, m/z) 583.08 (M+H).

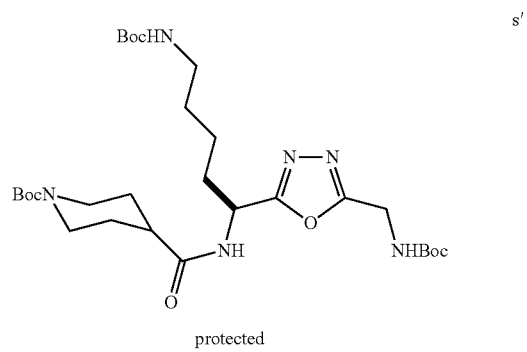 [SMILES: CC(C)(C)OC(=O)NCCCC[C@H](NC(=O)C1CCN(C(=O)OC(C)(C)C)CC1)c1nnc(CNC(=O)OC(C)(C)C)o1]

protected s'

¹H NMR (300 MHz, CDCl₃) δ 6.80 (d, 1H, J=7.8 Hz), 5.44 (br, 1H), 5.35-5.21 (m, 1H), 4.71 (br, 1H), 4.49 (d, 2H, J=5.9 Hz), 4.07 (br, 2H), 3.14-2.96 (m, 2H), 2.80-2.60 (m, 2H), 2.40-2.24 (m, 1H), 2.01-1.56 (m, 6H), 1.54-1.25 (m, 31H). ¹³C NMR (75 MHz, CDCl₃) δ 174.5, 167.2, 164.5, 156.2, 155.5, 154.6, 80.5, 79.6, 79.2, 77.2, 45.2, 42.9, 39.8, 35.8, 33.0, 29.3, 28.5, 28.4, 28.4, 28.2, 22.2. Desired MS 633.37 (M+H). MS Found (ESI, m/z) 633.19 (M+H).

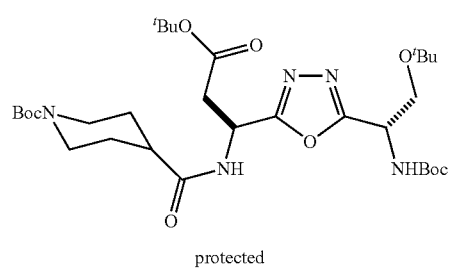

t′ protected

¹H NMR (500 MHz, CDCl₃) δ 6.91-6.82 (m, 1H), 5.58 (dt, 1H, J=4.9, 8.8 Hz), 5.43 (d, 1H, J=8.8 Hz), 5.06 (br, 1H), 4.10 (br, 2H), 3.80-3.71 (m, 1H), 3.65 (dd, 1H, J=4.1, 9.2 Hz), 2.97 (dt, 1H, J=4.5, 16.5 Hz), 2.82 (ddd, 1H, J=2.6, 5.2, 16.5 Hz), 2.73 (br, 2H), 2.33-2.25 (m, 1H), 1.87-1.76 (m, 2H), 1.68-1.57 (m, 2H), 1.42 (br, 18H), 1.39 (s, 9H), 1.08 (s, 9H). ¹³C NMR (125 MHz, CDCl₃) δ 173.8, 169.6, 166.3, 165.5, 155.1, 154.6, 82.2, 80.4, 79.6, 73.8, 62.3, 48.2, 43.0, 42.2, 37.6, 28.4, 28.4, 28.3, 28.2, 27.9, 27.2. Desired MS 662.38 (M+Na). MS Found (MALDI, m/z) 661.93 (M+Na).

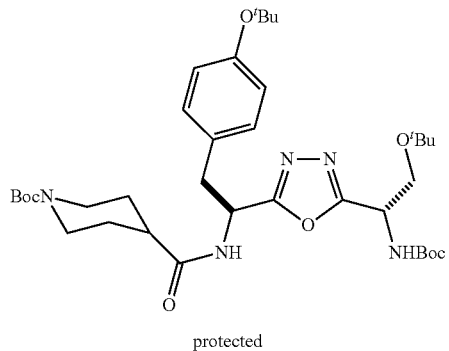

u′ protected

¹H NMR (500 MHz, CDCl₃) δ 6.92-6.81 (m, 4H), 6.15 (d, 1H, J=8.4 Hz), 5.59-5.53 (m, 1H), 5.43 (d, 1H, J=8.4 Hz), 5.11-5.02 (m, 1H), 4.04 (br, 2H), 3.80-3.72 (m, 1H), 3.23 (dd, 1H, J=6.0, 14.1 Hz), 3.09 (dd, 1H, J=6.5, 14.1 Hz), 2.67 (dd, 1H, J=4.1, 9.3 Hz), 2.19 (tt, 1H, J=3.7, 11.5 Hz), 1.75-1.47 (m, 4H), 1.43 (s, 9H), 1.42 (s, 9H), 1.28 (s, 9H), 1.10 (s, 9H). ¹³C NMR (125 MHz, CDCl₃) δ 173.8, 166.3, 165.9, 155.1, 154.6, 154.5, 129.8, 129.6, 124.2, 80.5, 79.6, 78.5, 73.9, 62.4, 48.2, 46.4, 42.9, 38.5, 28.8, 28.6, 28.4, 28.3, 28.1, 27.2. Desired MS 710.42 (M+Na). MS Found (MALDI, m/z) 710.03 (M+Na).

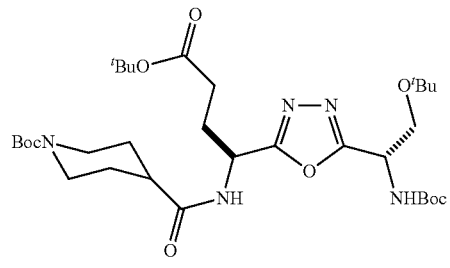

v′ protected

¹H NMR (500 MHz, CDCl₃) δ 6.62 (d, 1H, J=8.0 Hz), 5.46 (d, 1H, J=8.5 Hz), 5.35-5.26 (m, 1H), 5.06 (br, 1H), 4.09 (br, 2H), 3.78-3.70 (br, 1H), 3.65 (dd, 1H, J=4.0, 9.2 Hz), 2.71 (br, 2H), 2.38-2.15 (m, 4H), 2.11-2.01 (m, 1H), 1.83-1.74 (m, 2H), 1.68-1.54 (m, 2H), 1.49-1.31 (m, 27H), 1.07 (s, 9H). ¹³C NMR (125 MHz, CDCl₃) δ 174.5, 172.3, 166.5, 155.4, 154.9, 81.4, 80.7, 79.8, 74.1, 62.8, 48.5, 45.4, 43.2, 31.4, 28.7, 28.7, 28.6, 28.5, 28.3, 27.5. Desired MS 676.40 (M+Na). MS Found (MALDI, m/z) 676.06 (M+Na).

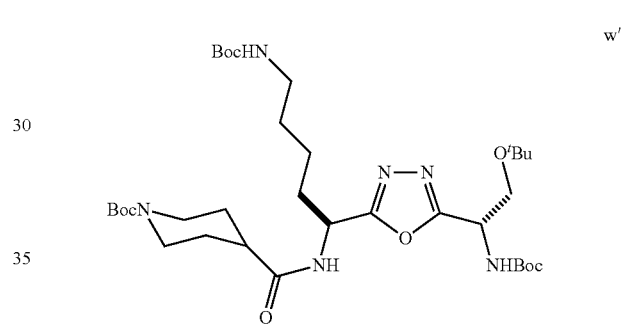

w′ protected

¹H NMR (500 MHz, CDCl₃) δ 7.20 (d, 1H, J=7.6 Hz), 5.59 (d, 1H, J=8.5 Hz), 5.32-5.19 (m, 1H), 4.99 (br, 1H), 4.84 (br, 1H), 4.01 (br, 2H), 3.73-3.55 (m, 2H), 3.05-2.87 (m, 2H), 2.62 (br, 2H), 2.33-2.21 (m, 1H), 1.90-1.50 (m, 6H), 1.49-1.23 (m, 31H), 1.01 (s, 9H). ¹³C NMR (125 MHz, CDCl₃) δ 174.5, 166.9, 166.0, 156.0, 155.1, 154.4, 80.2, 79.3, 78.8, 73.7, 62.3, 48.1, 44.9, 42.6, 39.8, 33.0, 29.1, 28.5, 28.3, 28.2, 28.1, 28.0, 27.1, 22.1. Desired MS 697.44 (M+H). MS Found (MALDI, m/z) 697.13 (M+H).

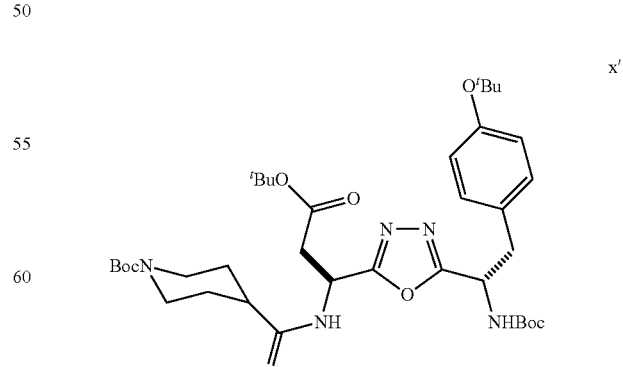

x′ protected

¹H NMR (300 MHz, CDCl₃) δ 6.99-6.72 (m, 4H), 5.59-5.50 (m, 2H), 5.28-4.96 (m, 2H), 4.11 (br, 2H), 3.23-2.90 (m, 3H), 2.87-2.88 (m, 3H), 2.35-2.21 (m, 1H), 1.86-1.52 (m, 4H), 1.48-1.32 (m, 27H), 1.29 (s, 9H). ¹³C NMR (75 MHz, CDCl₃) δ 174.0, 169.8, 169.7, 166.9, 166.8, 165.7, 154.6, 129.9, 129.8, 124.2, 82.3, 80.4, 79.6, 78.5, 48.4, 43.0, 42.2, 39.3, 37.6, 28.8, 28.4, 28.4, 28.3, 28.2, 28.0. Desired MS 738.42 (M+Na). MS Found (MALDI, m/z) 738.05 (M+Na).

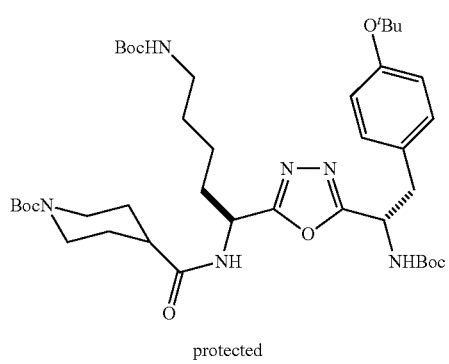

y' protected

¹H NMR (500 MHz, CDCl₃) δ 6.97 (d, 2H, J=8.3 Hz), 6.86 (d, 2H, J=8.3 Hz), 6.54-6.41 (br, 1H), 5.30-5.13 (m, 3H), 4.73 (t, 1H, J=5.7 Hz), 4.10 (br, 2H), 3.20-2.98 (m, 4H), 2.71 (br, 2H), 2.34-2.24 (m, 1H), 1.92-1.69 (m, 4H), 1.51-1.20 (m, 40H). ¹³C NMR (125 MHz, CDCl₃) δ 174.4, 166.8, 156.2, 154.8, 154.6, 154.5, 130.1, 129.7, 124.3, 80.4, 79.6, 79.1, 78.5, 48.4, 45.2, 42.9, 39.9, 39.2, 33.1, 29.3, 28.8, 28.6, 28.4, 28.4, 28.3, 28.2, 22.2. Desired MS 795.47 (M+Na). MS Found (MALDI, m/z) 795.18 (M+Na).

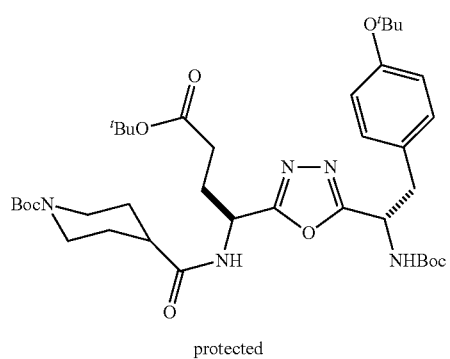

z' protected

¹H NMR (500 MHz, CDCl₃) δ 6.99 (d, 2H, J=8.3 Hz), 6.89 (d, 2H, J=8.3 Hz), 6.52 (d, 1H, J=7.6 Hz), 5.32-5.18 (m, 2H), 5.11 (d, 1H, J=8.4 Hz), 4.13 (br, 2H), 3.19 (dd, 1H, J=6.5, 14.0 Hz), 3.13 (dd, 1H, J=6.6, 14.0 Hz), 2.77 (br, 2H), 2.43-2.16 (m, 4H), 2.14-2.04 (m, 1H), 1.90-1.56 (m, 4H), 1.50-1.34 (m, 27H), 1.32 (s, 9H). ¹³C NMR (125 MHz, CDCl₃) δ 174.3, 172.2, 166.7, 166.3, 154.7, 154.6, 154.6, 130.0, 129.8, 124.3, 81.3, 80.4, 79.6, 78.5, 48.4, 45.3, 43.0, 39.2, 34.6, 31.2, 28.8, 28.5, 28.4, 28.3, 28.2, 28.0. Desired MS 752.43 (M+Na). MS Found (MALDI, m/z) 752.11 (M+Na).

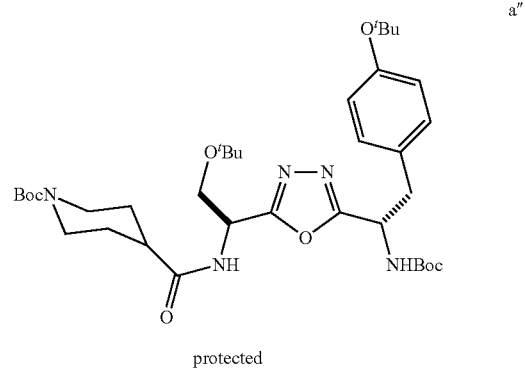 [SMILES: CC(C)(C)OC[C@H](NC(=O)C1CCN(C(=O)OC(C)(C)C)CC1)c1nnc([C@H](Cc2ccc(OC(C)(C)C)cc2)NC(=O)OC(C)(C)C)o1]

a'' protected

¹H NMR (500 MHz, CDCl₃) δ 6.96 (d, 2H, J=8.4 Hz), 6.87 (d, 2H, J=8.4 Hz), 6.35 (d, 1H, J=8.3 Hz), 5.38 (dt, 1H, J=3.5, 8.4 Hz), 5.25-5.15 (m, 1H), 5.04 (d, 1H, J=8.3 Hz), 4.12 (br, 2H), 3.79 (dd, 1H, J=2.7, 9.2 Hz), 3.63 (dd, 1H, J=3.6, 9.2 Hz), 3.21-3.04 (m, 2H), 2.76 (t, 2H, J=12.2 Hz), 2.32 (tt, 1H, J=3.7, 11.5 Hz), 1.86-1.76 (m, 2H), 1.71-1.54 (m, 2H), 1.44 (s, 9H), 1.38 (s, 9H), 1.29 (s, 9H), 1.09 (s, 9H). ¹³C NMR (125 MHz, CDCl₃) δ 174.2, 166.6, 165.4, 154.7, 154.6, 154.5, 130.0, 129.8, 124.2, 80.4, 79.6, 78.5, 73.9, 62.1, 48.3, 46.5, 43.0, 39.2, 28.8, 28.5, 28.4, 28.3, 28.2, 27.3. Desired MS 710.42 (M+Na). MS Found (MALDI, m/z) 710.07 (M+Na).

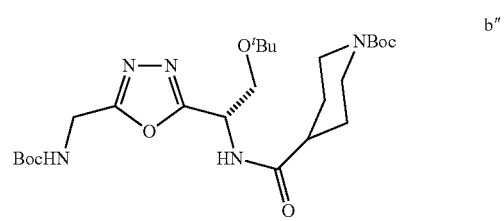

b'' protected

¹H NMR (500 MHz, CDCl₃) δ 6.61 (t, 1H, J=5.4 Hz), 5.48 (d, 1H, J=8.6 Hz), 5.07-4.99 (m, 1H), 4.62 (d, 2H, J=5.4 Hz), 3.76 (dd, 1H, J=3.2, 9.3 Hz), 3.66 (dd, 1H, J=4.0, 9.3 Hz), 2.71 (br, 2H), 2.32 (tt, 1H, J=3.7, 11.5 Hz), 1.84-1.74 (m, 2H), 1.69-1.57 (m, 2H), 1.41 (s, 18H), 1.07 (s, 9H). ¹³C NMR (125 MHz, CDCl₃) δ 174.6, 166.4, 163.8, 155.2, 154.6, 80.4, 79.6, 73.9, 62.2, 48.2, 42.8, 34.4, 28.4, 28.2, 27.2. Desired MS 548.32 (M+Na). MS Found (MALDI, m/z) 547.84 (M+Na).

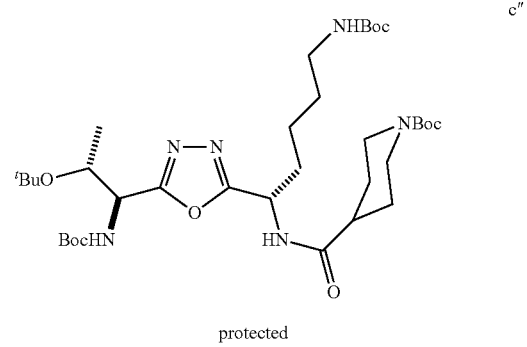 [SMILES: C[C@@H](OC(C)(C)C)[C@H](NC(=O)OC(C)(C)C)c1nnc([C@H](CCCCNC(=O)OC(C)(C)C)NC(=O)C2CCN(C(=O)OC(C)(C)C)CC2)o1]

c'' protected

¹H NMR (500 MHz, CDCl₃) δ 6.47 (d, 1H, J=8.5 Hz), 5.49 (d, 1H, J=9.5 Hz), 5.33-5.22 (m, 1H), 4.86 (dd, 1H, J=1.7, 9.5 Hz), 4.70-4.60 (m, 1H), 4.22-3.96 (m, 3H), 3.13-2.98 (m, 2H), 2.70 (br, 2H), 2.29 (tt, 1H, J=3.7, 11.5 Hz), 1.98-1.86 (m, 2H), 1.85-1.71 (m, 2H), 1.69-1.55 (m, 2H), 1.54-1.21 (m, 31H), 1.22 (d, 3H, J=6.2 Hz), 0.92 (s, 9H). ¹³C NMR (125 MHz, CDCl₃) δ 174.2, 166.6, 166.5, 156.1, 155.7, 154.6, 80.3, 79.6, 79.1, 74.4, 68.1, 53.3, 45.1, 42.9, 39.9, 33.2, 29.3, 28.7, 28.5, 28.4, 28.4, 28.3, 28.0, 22.3, 20.1. Desired MS 711.46 (M+H). MS Found (MALDI, m/z) 711.03 (M+H).

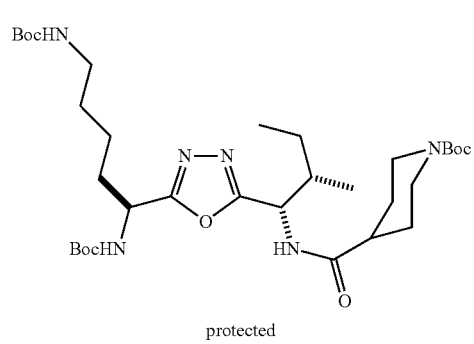

d″ protected

¹H NMR (500 MHz, CDCl₃) δ 6.65 (d, 1H, J=7.2 Hz), 5.36 (d, 1H, J=7.8 Hz), 5.30-5.21 (m, 1H), 4.93 (br, 1H), 4.69 (br, 1H), 4.08 (br, 2H), 3.13-2.99 (m, 2H), 2.70 (br, 2H), 2.32 (tt, 1H, J=3.7, 11.5 Hz), 1.99-1.70 (m, 5H), 1.69-1.55 (m, 2H), 1.54-1.29 (m, 32H), 1.19-1.07 (m, 1H), 0.91-0.80 (m, 6H). ¹³C NMR (125 MHz, CDCl₃) δ 174.3, 167.2, 166.3, 156.1, 155.1, 154.6, 80.3, 79.6, 79.1, 49.7, 47.0, 42.9, 39.9, 38.7, 33.1, 29.4, 28.7, 28.4, 28.3, 28.2, 28.1, 25.0, 22.3, 15.1, 11.3. Desired MS 667.43 (M+H). MS Found (MALDI, m/z) 667.04 (M+H).

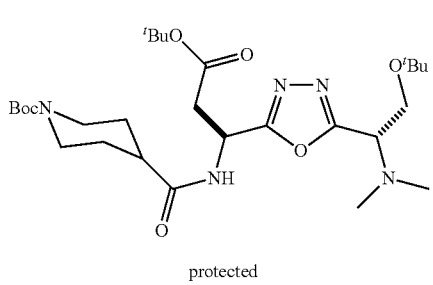

e″ protected

¹H NMR (500 MHz, CDCl₃) δ 6.91 (d, 1H, J=8.8 Hz), 5.55 (dt, 1H, J=5.0, 8.8 Hz), 4.16-3.92 (m, 3H), 3.80-3.66 (m, 2H), 2.96 (ddd, 1H, J=1.5, 4.7, 16.6 Hz), 2.83 (dd, 1H, J=5.1, 16.6 Hz), 2.71 (br, 2H), 2.28 (tt, 1H, J=3.7, 11.5 Hz), 2.23 (s, 6H), 1.84-1.72 (m, 2H), 1.66-1.54 (m, 2H), 1.45-1.28 (m, 18H), 1.09 (s, 9H). ¹³C NMR (125 MHz, CDCl₃) δ 173.9, 169.6, 165.4, 165.0, 154.5, 82.1, 79.5, 73.4, 61.2, 61.0, 60.8, 42.9, 42.3, 42.3, 42.1, 37.7, 28.3, 27.9, 27.2. Desired MS 568.36 (M+H). MS Found (MALDI, m/z) 568.04 (M+H).

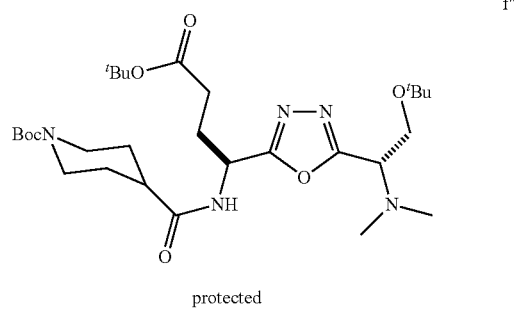 [SMILES: CN(C)[C@@H](COC(C)(C)C)c1nnc([C@H](CCC(=O)OC(C)(C)C)NC(=O)C2CCN(C(=O)OC(C)(C)C)CC2)o1]

f″ protected

¹H NMR (500 MHz, CDCl₃) δ 6.74 (br, 1H), 5.32 (dt, 1H, J=4.9, 8.2 Hz), 4.20-3.90 (m, 3H), 3.82-3.67 (m, 2H), 2.70 (br, 2H), 2.37-2.15 (m, 10H), 2.13-2.01 (m, 1H), 1.78 (br, 2H), 1.67-1.54 (m, 2H), 1.42-1.35 (m, 18H), 1.09 (s, 9H). ¹³C NMR (125 MHz, CDCl₃) δ 174.2, 172.0, 166.2, 165.1, 154.5, 81.1, 79.5, 73.4, 61.2, 60.9, 45.3, 42.9, 42.2, 42.2, 31.1, 28.4, 28.3, 28.2, 28.0, 27.3. Desired MS 582.38 (M+H). MS Found (MALDI, m/z) 581.97 (M+H).

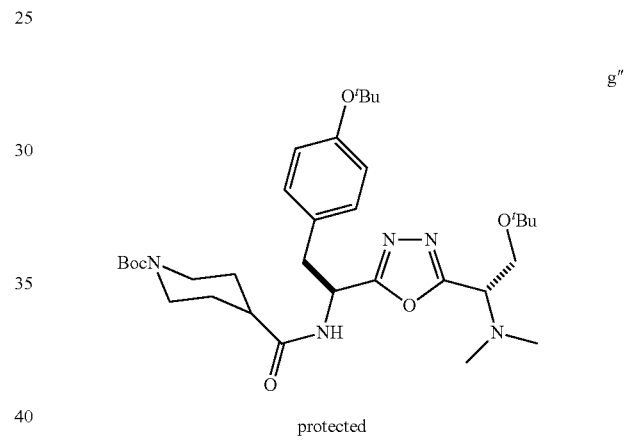

g″ protected

¹H NMR (500 MHz, CDCl₃) δ 6.96-6.75 (m, 4H), 6.36 (br, 1H), 5.65-5.51 (m, 1H), 4.20-3.88 (m, 3H), 3.86-3.66 (m, 2H), 3.21 (dd, 1H, J=5.8, 13.6 Hz), 3.08 (dd, 1H, J=5.7, 13.6 Hz), 2.66 (br, 2H), 2.30-2.16 (m, 7H), 1.75-1.61 (m, 2H), 1.60-1.46 (m, 2H), 1.40 (s, 9H), 1.26 (s, 9H), 1.12 (s, 9H). ¹³C NMR (125 MHz, CDCl₃) δ 173.8, 166.0, 165.1, 154.6, 154.5, 129.8, 129.5, 124.1, 79.5, 78.4, 73.5, 61.2, 61.0, 60.9, 46.5, 42.8, 42.2, 38.7, 38.6, 28.7, 28.3, 27.3. Desired MS 616.40 (M+H). MS Found (MALDI, m/z) 616.05 (M+H).

The following general method may be used to prepare protected monovalent compounds h″ through w″ and through y‴ (Scheme 11). Synthesis of protected monovalent compound o″ is demonstrated in Scheme 12 as a representative example.

Scheme 11

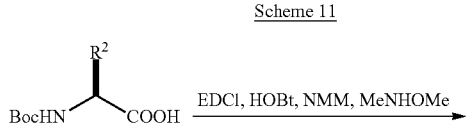

95
-continued
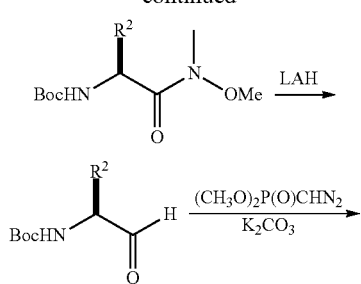
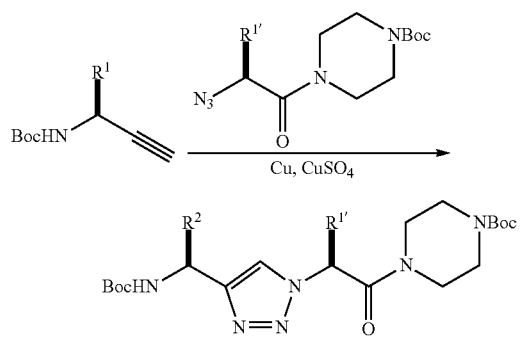
Scheme 12
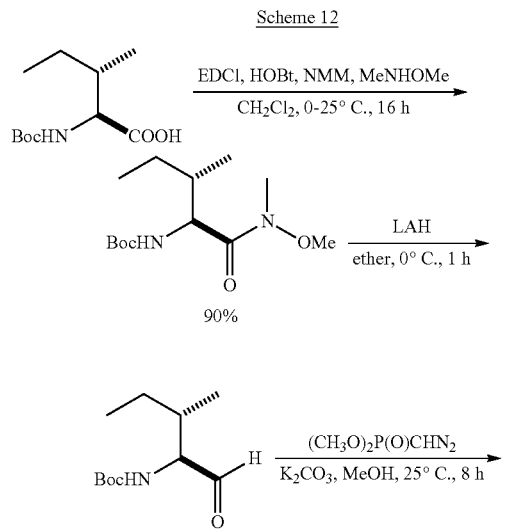
58% (2 steps)
96
-continued
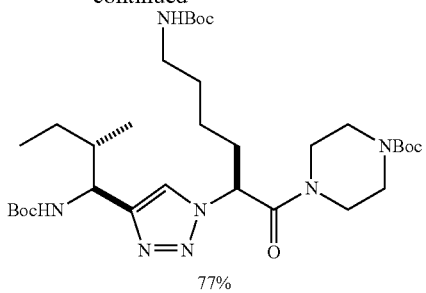
77%
The following general method may be used to prepare protected monovalent compounds x″ through k‴ (Scheme 13). Synthesis of protected monovalent compound i‴ is demonstrated in Scheme 14 as a representative example.
Scheme 13
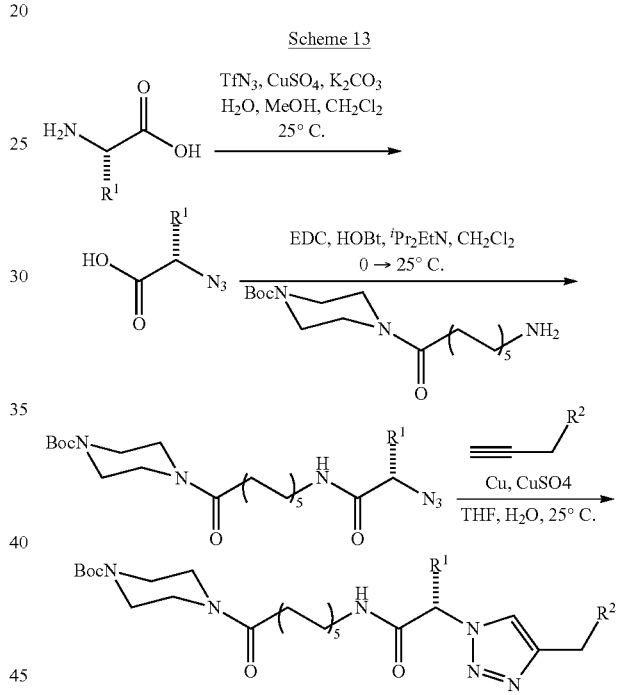
Scheme 14
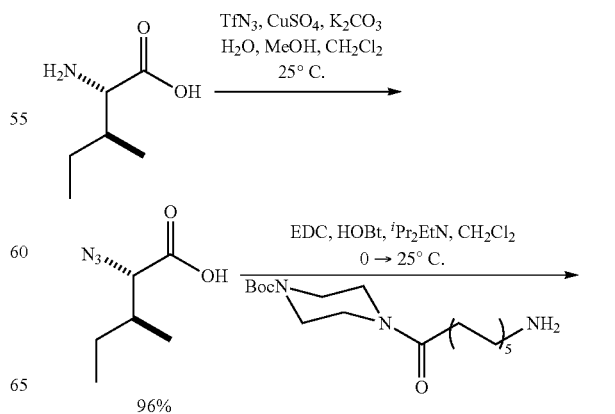
96%

-continued

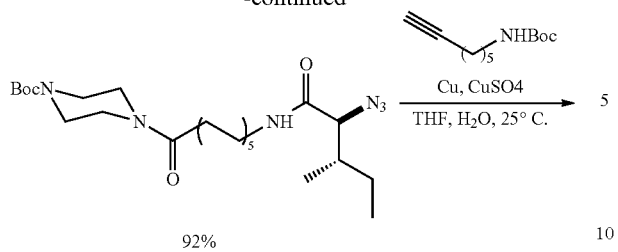

92%

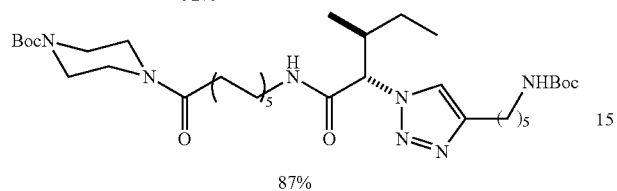

87%

Characterization data for protected monovalent compounds h″ through y′″ follows:

h″

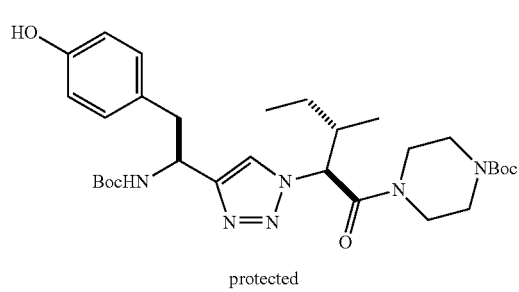

protected $^1$H NMR (500 MHz, CDCl$_3$) δ 7.38 (s, 1H), 6.78-6.91 (m, 2H), 6.50-6.68 (m, 2H), 5.16-5.36 (m, 1H), 4.99 (s, 1H), 3.33-3.92 (m, 6H), 2.90-3.33 (m, 4H), 2.16-2.40 (m, 1H), 1.46 (s, 9H), 1.41 (s, 9H), 1.18-1.33 (m, 1H), 0.94 (t, J=6.6 Hz, 3H), 0.84-0.91 (m, 2H), 0.80 (d, J=6.3 Hz, 3H). $^{13}$C NMR (125 MHz, CDCl$_3$) δ 166.4, 154.8, 152.7, 148.1, 130.6, 130.4, 128.6, 120.1, 115.3, 80.8, 79.8, 63.6, 48.6, 42.2, 40.5, 29.7, 28.4, 28.3, 24.3, 15.8, 10.4. MS (ESI) for C$_{30}$H$_{47}$N$_6$O$_6$ [M+H]$^+$ calcd 587.73. found 587.33.

i″

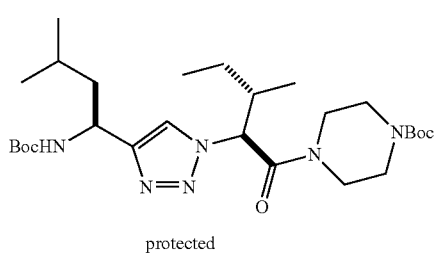

protected $^1$H NMR (500 MHz, CDCl$_3$) δ 7.75 (s, 1H), 5.38 (d, J=10.5 Hz, 1H), 4.94-5.03 (m, 1H), 4.82-4.92 (m, 1H), 3.66-3.78 (m, 2H), 3.55-3.66 (b, 1H), 3.43-3.55 (m, 3H), 3.20-3.32 (b, 1H), 3.00-3.22 (b, 1H), 2.32-2.42 (m, 1H), 1.74 (t, J=7.5 Hz, 2H), 1.52-1.66 (m, 1H), 1.46 (s, 9H), 1.41 (s, 9H), 0.90-1.06 (m, 2H), 1.00 (d, J=6.5 Hz, 3H), 0.93 (d, J=6.5 Hz, 6H), 0.82 (t, J=7.5 Hz, 3H). $^{13}$C NMR (125 MHz, CDCl$_3$) δ 166.8, 155.5, 154.6, 150.0, 120.1, 80.8, 79.7, 63.7, 46.3, 45.6, 44.5, 42.5, 38.1, 28.6, 25.0, 24.7, 23.0, 22.5, 16.0, 10.7. MS (ESI) for C$_{27}$H$_{49}$N$_6$O$_5$ [M+H]$^+$ calcd 537.38. found 537.38.

j″

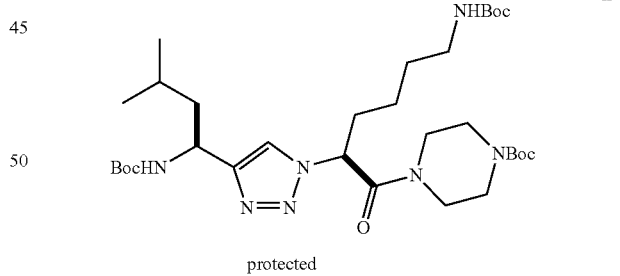

protected $^1$H NMR (500 MHz, CDCl$_3$) δ 8.39 (s, 1H), 7.95 (s, 1H), 7.60 (d, J=8 Hz, 1H), 7.37 (d, J=8 Hz, 1H), 7.21-7.24 (m, 1H), 7.15-7.18 (m, 1H), 6.99 (d, J=2 Hz, 1H), 6.02 (t, J=5 Hz, 1H), 5.07 (d, J=8 Hz, 1H), 4.93 (d, J=8 Hz, 1H), 3.70 (dd, J=4.5, 9 Hz, 1H), 3.48-3.56 (m, 1H), 3.26-3.44 (m, 4H), 3.06-3.14 (b, 1H), 2.82-3.06 (b, 1H), 2.36-2.58 (b, 1H), 1.88-2.05 (b, 1H), 1.76 (t, J=7.5 Hz, 2H), 1.62 (m, 1H), 1.45 (s, 9H), 1.41 (s, 9H), 0.96 (d, J=6.5 Hz, 6H). $^{13}$C NMR (125 MHz, CDCl$_3$) δ 167.0, 155.5, 154.5, 149.8, 136.3, 127.1, 123.6, 122.8, 120.6, 120.3, 118.5, 111.8, 109.3, 80.6, 79.7, 59.4, 46.0, 45.6, 44.9, 42.4, 30.3, 28.6, 28.5, 25.0, 22.9, 22.5. MS (ESI) for C$_{32}$H$_{48}$N$_7$O$_5$ [M+H]$^+$ calcd 610.37. found 610.37.

k″

[structure: BocHN-CH(iBu)-triazole-CH(C(O)NBoc-piperazine)-CH2CH2CH2CH2-NHBoc]

protected $^1$H NMR (500 MHz, CDCl$_3$) δ 7.70 (s, 1H), 5.65 (t, J=8 Hz, 1H), 5.05-5.15 (m, 1H), 4.82-4.97 (m, 1H), 4.56 (s, 1H), 3.68-3.80 (b, 1H), 3.61-3.68 (m, 1H), 3.38-3.60 (m, 4H), 3.20-3.32 (b, 1H), 2.98-3.19 (m, 3H), 2.15-2.24 (m, 1H), 1.86-2.10 (m, 2H), 1.76 (t, J=7.5 Hz, 2H), 1.54-1.68 (m, 1H), 1.46 (s, 9H), 1.44 (s, 9H), 1.43 (s, 9H), 1.22-1.35 (m, 1H), 1.16-1.22 (m, 1H), 0.94 (d, J=6.5 Hz, 6H) $^{13}$C NMR (125 MHz, CDCl$_3$) δ 166.5, 156.3, 155.5, 154.6, 150.0, 120.1, 80.8, 79.7, 79.5, 59.7, 46.0, 45.6, 42.6, 40.0, 32.7, 29.7, 28.7, 28.6, 28.5, 25.1, 22.9, 22.8, 22.5. MS (ESI) for C$_{32}$H$_{58}$N$_7$O$_7$ [M+H]$^+$ calcd 652.44. found 652.44.

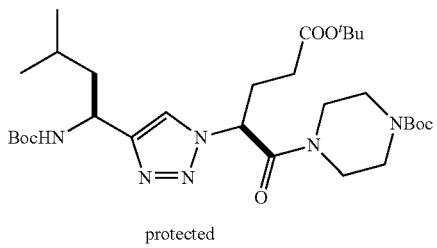

l″ protected

¹H NMR (500 MHz, CDCl₃) δ 7.75 (s, 1H), 5.80-5.95 (m, 1H), 5.05 (d, J=8 Hz, 1H), 4.80-4.95 (m, 1H), 3.59-3.74 (b, 3H), 3.42-3.58 (m, 3H), 3.27-3.35 (m, 1H), 3.10-3.27 (b, 1H), 2.30-2.40 (m, 1H), 2.05-2.28 (m, 2H), 1.93-2.07 (m, 1H), 1.75 (t, J=7.5 Hz, 2H), 1.52-1.68 (m, 1H), 1.46 (s, 9H), 1.44 (s, 9H), 1.42 (s, 9H), 0.93 (d, J=7 Hz, 6H). ¹³C NMR (125 MHz, CDCl₃) δ 171.7, 166.6, 155.5, 154.6, 150.0, 120.4, 81.5, 80.7, 79.7, 58.7, 45.9, 45.6, 44.8, 42.5, 30.4, 28.6, 28.6, 28.3, 25.0, 22.9, 22.5. MS (ESI) for $C_{32}H_{53}N_6O_7$ $[M+H]^+$ calcd 609.40. found 609.40.

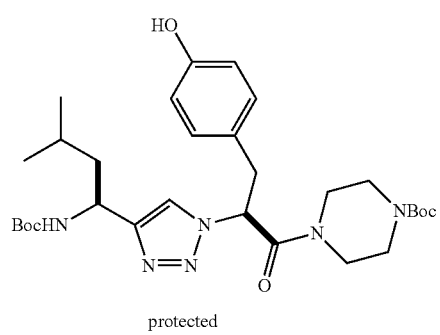

m″ protected

¹H NMR (500 MHz, CDCl₃) δ 7.85 (s, 1H), 6.99 (d, J=8.5 Hz, 2H), 6.76 (d, J=8 Hz, 2H), 5.80-5.90 (b, 1H), 5.09 (d, J=8.5 Hz, 1H), 4.90 (d, J=6.5 Hz, 1H), 3.46-3.62 (b, 2H), 3.18-3.46 (m, 5H), 3.02-3.18 (m, 2H), 2.86-3.00 (b, 1H), 1.68-1.82 (m, 2H), 1.52-1.68 (m, 1H), 1.45 (s, 9H), 1.44 (s, 9H), 0.94 (d, J=6.5 Hz, 6H). ¹³C NMR (125 MHz, CDCl₃) δ 166.4, 156.1, 154.5, 149.8, 130.7, 125.9, 120.7, 116.1, 80.9, 79.9, 60.4, 46.0, 45.5, 44.7, 42.5, 39.3, 28.6, 28.5, 25.0, 22.9, 22.5. MS (ESI) for $C_{30}H_{47}N_6O_6$ $[M+H]^+$ calcd 587.36. found 587.35.

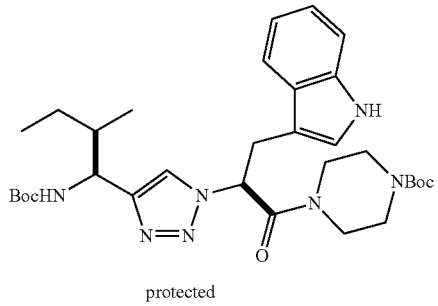

n″ protected

¹H NMR (500 MHz, CDCl₃) δ 8.77 (s, 1H), 7.86 (s, 1H), 7.56 (d, J=7.8 Hz, 1H), 7.32 (d, J=8.1 Hz, 1H), 7.09-7.30 (m, 2H), 6.94 (s, 1H), 5.95-6.05 (b, 1H), 5.42 (d, J=8.4 Hz, 1H), 4.77 (t, J=7.2 Hz, 1H), 3.61-3.78 (m, 2H), 3.08-3.59 (m, 5H), 2.72-3.09 (m, 3H), 2.20-2.60 (b, 1H), 1.84-2.04 (b, 1H), 1.42 (s, 9H), 1.38 (s, 9H), 0.99-1.25 (m, 2H), 0.84-0.99 (m, 3H), 0.75-0.83 (m, 3H). ¹³C NMR (125 MHz, CDCl₃) δ 166.6, 155.4, 154.1, 147.4, 136.0, 126.8, 123.4, 122.4, 120.7, 119.8, 118.1, 111.5, 108.7, 80.3, 79.4, 59.1, 51.5, 45.6, 42.0, 39.3, 30.0, 28.3, 28.2, 25.2, 15.1, 11.4. MS (ESI) for $C_{32}H_{47}N_7O_5$ $[M+H]^+$ calcd 610.37. found 610.35.

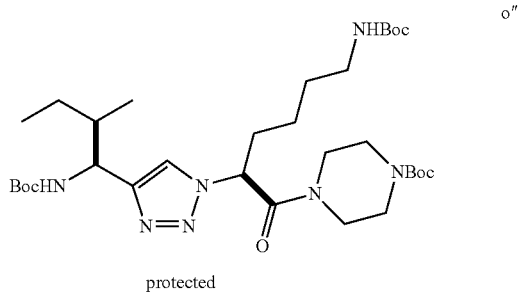 [SMILES: CCC(C)[C@H](NC(=O)OC(C)(C)C)c1cn([C@@H](CCCCNC(=O)OC(C)(C)C)C(=O)N2CCN(C(=O)OC(C)(C)C)CC2)nn1]

o″ protected

¹H NMR (500 MHz, CDCl₃) δ 7.57 (s, 1H), 5.55-5.60 (m, 1H), 5.32 (d, J=8.7 Hz, 1H), 4.67-4.70 (m, 1H), 4.48-4.60 (b, 1H), 3.26-3.78 (m, 7H), 2.83-3.25 (m, 4H), 1.78-2.20 (m, 4H), 1.38 (s, 18H), 1.36 (s, 9H), 1.12-1.28 (m, 2H), 0.92-1.12 (m, 2H), 0.84 (t, J=7.2 Hz, 3H), 0.74 (d, J=6.6 Hz, 3H). ¹³C NMR (125 MHz, CDCl₃) δ 166.2, 156.0, 155.4, 154.3, 147.9, 120.0, 80.5, 79.4, 79.2, 59.3, 51.5, 45.6, 42.3, 39.7, 39.3, 32.4, 29.4, 28.3, 28.3, 28.2, 25.3, 22.5, 15.1, 11.5. MS (ESI) for $C_{32}H_{58}N_7O_7$ $[M+H]^+$ calcd 652.44. found 652.45.

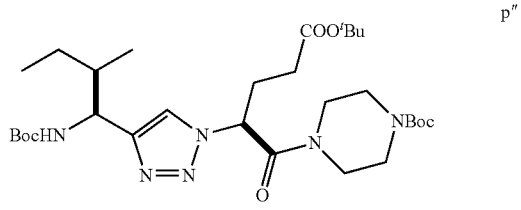

p″ protected

¹H NMR (500 MHz, CDCl₃) δ 7.63 (s, 1H), 5.78-5.90 (b, 1H), 5.37 (d, J=8.4 Hz, 1H), 4.59-4.73 (b, 1H), 3.54-3.78 (b, 3H), 3.32-3.53 (m, 3H), 3.00-3.32 (m, 2H), 2.23-2.40 (m, 1H), 2.04-2.22 (m, 3H), 1.75-2.04 (m, 2H), 1.40 (s, 9H), 1.38 (s, 9H), 1.37 (s, 9H), 0.93-1.13 (m, 1H), 0.85 (t, J=7.2 Hz, 3H), 0.75 (d, J=6.6 Hz, 3H). ¹³C NMR (125 MHz, CDCl₃) δ 171.4, 166.1, 155.3, 154.2, 147.5, 120.4, 81.1, 80.3, 79.2, 58.3, 51.4, 45.5, 43.3, 42.2, 39.2, 30.0, 28.2, 28.1, 27.9, 25.2, 15.0, 11.4. MS (ESI) for $C_{30}H_{53}N_5O_7$ $[M+H]^+$ calcd 609.40. found 609.39.

q″

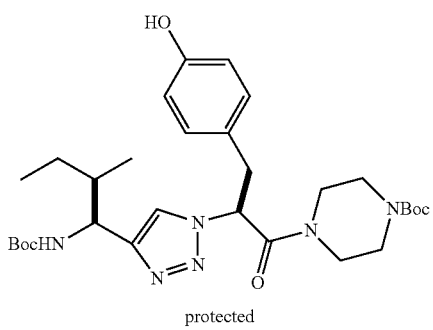

protected

¹H NMR (500 MHz, CDCl₃) δ 7.75 (s, 1H), 6.92 (d, J=7.8 Hz, 2H), 6.72 (d, J=8.1 Hz, 2H), 5.75-5.87 (b, 1H), 5.37 (d, J=8.7 Hz, 1H), 4.71 (t, J=7.5 Hz, 1H), 3.42-3.59 (b, 2H), 2.98-3.42 (m, 7H), 2.78-2.98 (b, 1H), 1.78-2.00 (b, 2H), 1.40 (s, 9H), 1.39 (s, 9H), 0.97-1.16 (m, 2H), 0.87 (t, J=7.2 Hz, 3H), 0.77 (d, J=6.6 Hz, 3H). ¹³C NMR (125 MHz, CDCl₃) δ 166.1, 156.0, 155.6, 154.3, 147.9, 130.3, 125.9, 120.9, 115.9, 80.6, 79.6, 60.1, 51.5, 45.7, 42.2, 39.2, 30.9, 28.3, 28.2, 25.2, 15.2, 11.4. MS (ESI) for $C_{30}H_{47}N_6O_6$ $[M+H]^+$ calcd 587.36. found 587.32.

protected r″

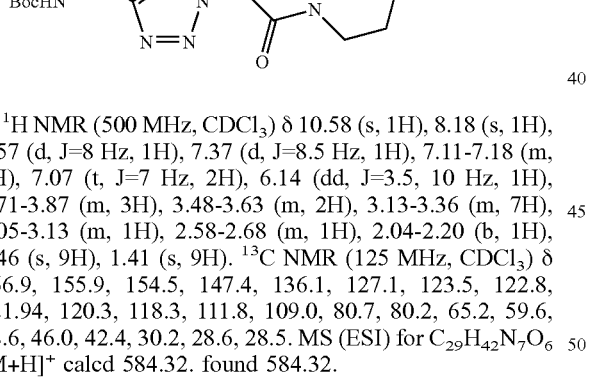

¹H NMR (500 MHz, CDCl₃) δ 10.58 (s, 1H), 8.18 (s, 1H), 7.57 (d, J=8 Hz, 1H), 7.37 (d, J=8.5 Hz, 1H), 7.11-7.18 (m, 2H), 7.07 (t, J=7 Hz, 2H), 6.14 (dd, J=3.5, 10 Hz, 1H), 3.71-3.87 (m, 3H), 3.48-3.63 (m, 2H), 3.13-3.36 (m, 7H), 3.05-3.13 (m, 1H), 2.58-2.68 (m, 1H), 2.04-2.20 (b, 1H), 1.46 (s, 9H), 1.41 (s, 9H). ¹³C NMR (125 MHz, CDCl₃) δ 166.9, 155.9, 154.5, 147.4, 136.1, 127.1, 123.5, 122.8, 121.94, 120.3, 118.3, 111.8, 109.0, 80.7, 80.2, 65.2, 59.6, 48.6, 46.0, 42.4, 30.2, 28.6, 28.5. MS (ESI) for $C_{29}H_{42}N_7O_6$ $[M+H]^+$ calcd 584.32. found 584.32.

protected s″

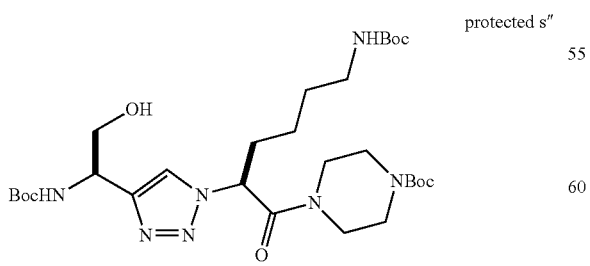

¹H NMR (500 MHz, CDCl₃) δ 7.86 (s, 1H), 5.45-5.81 (m, 2H), 4.92 (s, 1H), 4.60 (s, 1H), 4.12 (s, 1H), 3.91 (s, 1H), 3.41-3.80 (m, 6H), 2.93-3.41 (m, 5H), 2.37-2.86 (b, 2H), 2.18 (s, 1H), 2.05 (s, 1H), 1.46 (s, 9H), 1.44 (s, 9H), 1.43 (s, 9H), 1.08-1.37 (m, 2H). ¹³C NMR (125 MHz, CDCl₃) δ 166.5, 156.3, 155.9, 154.6, 147.7, 121.5, 80.8, 80.2, 79.5, 65.3, 59.8, 48.7, 46.1, 42.6, 40.0, 32.7, 29.6, 28.7, 28.6, 28.5, 22.8. MS (ESI) for $C_{29}H_{52}N_7O_8$ $[M+H]^+$ calcd 626.39. found 626.38.

protected t″

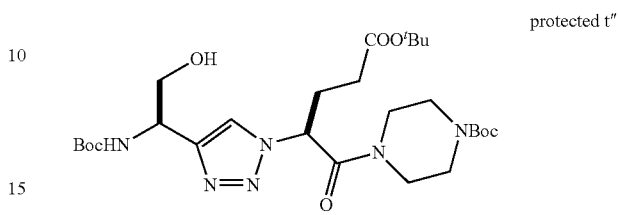

¹H NMR (500 MHz, CDCl₃) δ 7.88 (s, 1H), 5.90 (q, J=4.5 Hz, 1H), 5.48-5.69 (m, 1H), 4.92 (s, 1H), 4.01-4.18 (m, 1H), 3.85-3.96 (m, 1H), 3.59-3.78 (b, 3H), 3.41-3.59 (m, 3H), 3.21-3.41 (m, 2H), 2.56-3.16 (b, 1H), 2.30-2.43 (m, 1H), 2.16-2.29 (m, 2H), 1.96-2.10 (m, 1H), 1.46 (s, 9H), 1.44 (s, 18H). ¹³C NMR (125 MHz, CDCl₃) δ 171.7, 166.5, 155.9, 154.6, 147.6, 121.7, 155.9, 154.6, 147.6, 81.6, 80.8, 80.2, 65.3, 58.8, 45.9, 42.6, 30.4, 28.6, 28.3. MS (ESI) for $C_{27}H_{47}N_6O_8$ $[M+H]^+$ calcd 583.35. found 583.31.

protected u″

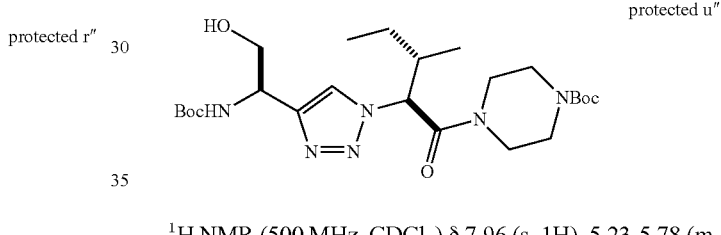

¹H NMR (500 MHz, CDCl₃) δ 7.96 (s, 1H), 5.23-5.78 (m, 2H), 4.78-5.05 (b, 1H), 4.0-4.26 (m, 1H), 3.80-4.00 (m, 1H), 3.60-3.78 (b, 3H), 3.40-3.60 (m, 3H), 3.19-3.40 (m, 1H), 3.13-3.19 (b, 1H), 2.44-2.86 (b, 2H), 1.46 (s, 9H), 1.44 (s, 9H), 0.89-1.35 (m, 5H), 0.83 (q, J=6 Hz, 3H). ¹³C NMR (125 MHz, CDCl₃) δ 166.8, 155.9, 154.6, 147.7, 121.5, 80.8, 80.2, 65.3, 63.6, 48.6, 46.4, 42.5, 38.2, 28.6, 28.5, 24.8, 15.9, 10.7. MS (ESI) for $C_{24}H_{43}N_6O_6$ $[M+H]^+$ calcd 511.33. found 511.32.

protected v″

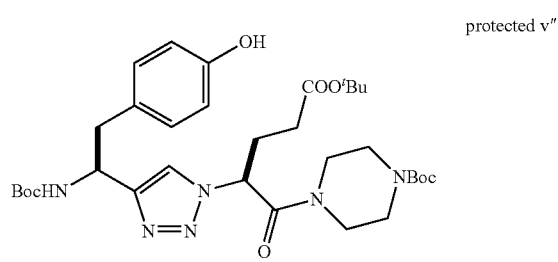

¹H NMR (500 MHz, CDCl₃) δ 7.35 (s, 1H), 6.78-6.92 (m, 2H), 6.56-6.72 (m, 2H), 5.72-5.85 (b, 1H), 5.24-5.44 (m, 1H), 4.90-5.08 (m, 1H), 3.31-3.78 (b, 7H), 3.09-3.26 (m, 2H), 2.84-3.09 (m, 2H), 2.21-2.40 (m, 1H), 2.02-2.20 (m, 2H), 1.45 (s, 9H), 1.41 (s, 9H), 1.39 (s, 9H). ¹³C NMR (125 MHz, CDCl₃) δ 171.6, 166.1, 155.1, 154.4, 148.1, 130.5, 128.3, 120.3, 115.3, 81.4, 80.7, 79.7, 58.3, 48.6, 48.5, 45.3, 42.1, 41.0, 40.7, 30.1, 28.3, 28.0, 27.9. MS (ESI) for $C_{33}H_{51}N_6O_8$ $[M+H]^+$ calcd 659.38. found 659.34.

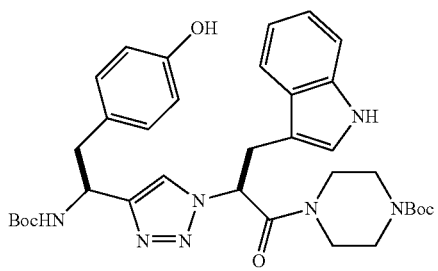

protected w″

¹H NMR (500 MHz, CDCl₃) δ 8.57 (s, 1H), 7.40-7.62 (m, 2H), 7.27-7.36 (m, 1H), 7.03-7.21 (m, 2H), 6.80-6.94 (m, 2H), 6.77 (s, 1H), 6.3 (d, J=8.4 Hz, 2H), 5.77-5.97 (b, 1H), 5.24-5.46 (m, 1H), 4.96-5.12 (m, 1H), 2.81-3.68 (m, 12H), 1.42 (s, 9H), 1.41 (s, 9H). ¹³C NMR (125 MHz, CDCl₃) δ 166.2, 155.2, 154.9, 148.0, 137.9, 136.0, 130.5, 128.6, 126.8, 123.5, 122.4, 120.3, 119.9, 118.0, 111.5, 108.8, 80.8, 79.8, 59.4, 48.6, 45.4, 42.1, 40.6, 29.5, 28.3. MS (ESI) for $C_{35}H_{46}N_7O_6$ [M+H]⁺ calcd 660.35. found 660.34.

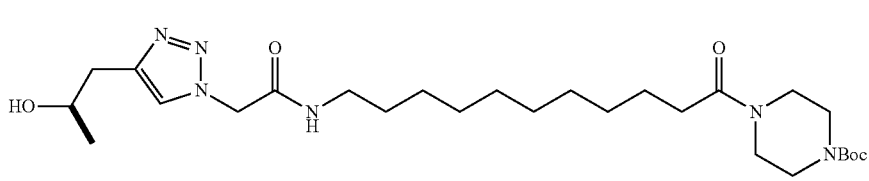

protected x″

¹H NMR (CDCl₃) δ 7.57 (s, 1H), 6.31 (s, 1H), 5.01 (s, 1H), 4.14 (m, 1H), 3.56 (t, 2H, J=4.5, J=5.7), 3.44 (s, 4H), 3.40 (t, 2H, J=5.7, J=4.8), 3.23 (q, 2H, J=6.6, J=6.3, J=6.9), 2.95 (s, 1H), 2.91 (dd, 1H, J=3.9, J=11.1, J=3.6), 2.80 (dd, 1H, J=7.1, J=6.9, J=8.1), 2.32 (t, 2H, J=7.5, J=7.8), 1.62 (m, 2H), 1.47 (s, 11H), 1.29-1.21 (m, 15H); HRMS (ESI, m/z): (M+H)⁺ calcd for $C_{27}H_{49}N_6O_5$ 537.3759. found 537.3538.

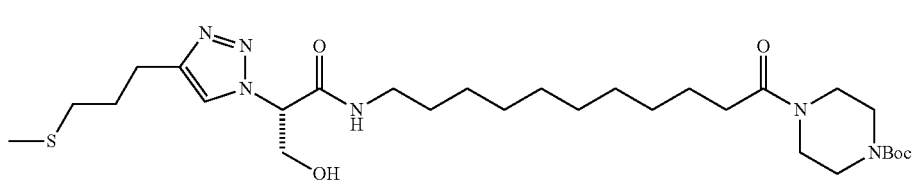

protected y″

¹H NMR (CDCl₃) δ 7.69 (s, 1H), 7.06 (t, 1H, J=5.4, J=5.7), 5.28 (t, 1H, J=5.1, J=5.7), 4.37 (t, 1H, J=6, J=6.3), 4.39-4.08 (m, 2H), 3.53 (t, 2H, J=4.5, J=5.7), 3.40 (s, 4H), 3.35 (t, 2H, J=5.7, J=4.8), 3.18 (q, 2H, J=6.6, J=7.2, J=6.3), 2.77 (t, 2H, J=7.5, J=7.8), 2.50 (t, 1H, J=6.9, J=7.5), 2.27 (t, 2H, J=7.5, J=7.8), 2.06 (s, 3H), 1.93 (p, 2H, J=7.5, J=7.5, J=7.2, J=7.2), 1.56 (m, 2H), 1.42 (s, 11H), 1.24 (br, 4H), 1.78 (br, 8H); ¹³C NMR (CDCl₃) δ 172.2, 167.12, 154.8, 147.6, 122.0, 80.5, 77.0, 65.1, 63.0, 45.7, 41.6, 40.0, 33.8, 33.6, 29.6, 29.5, 29.4, 29.3, 29.3, 28.7, 28.6, 26.9, 25.4, 24.7, 15.6; HRMS (ESI, m/z): (M+H)⁺ calcd for $C_{29}H_{53}N_6O_5S$. 597.3793, found 597.3770.

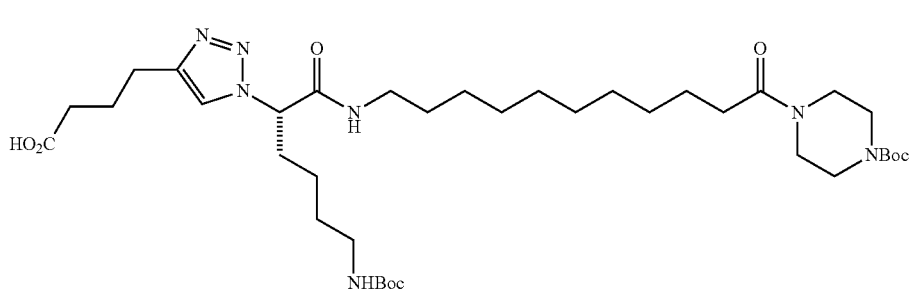

protected z″

¹H NMR (CDCl₃) δ 7.60 (s, 1H), 6.79 (t, 1H, J=5.4, J=5.4), 5.11 (t, 1H, J=7.8, J=6.9), 4.75 (s, 1H), 3.59 (t, 2H, J=4.5, J=5.7), 3.45 (s, 4H), 3.40 (t, 2H, J=6.0, J=4.5), 3.20 (q, 2H, J=6.6, J=7.2, J=6.3), 3.07 (m, 2H), 2.18 (t, 2H, J=7.2, J=7.2), 2.40 (br, 2H), 2.34 (t, 2H, J=7.5, J=7.8), 2.21-2.15 (br, 2H), 2.03 (p, 2H, J=7.2, J=6.9, J=6.9, J=7.2), 1.60 (m, 2H), 1.55-1.46 (m, 1H), 1.42 (s, 9H), 1.28-1.25 (m, 4H), 1.22 (br, 12H); ¹³C NMR (CDCl₃) δ 176.16, 172.55, 168.39, 156.46, 154.86, 147.40, 121.53, 80.64, 79.51, 64.45, 45.71, 41.63, 40.22, 40.04, 33.56, 33.51, 33.79, 29.57, 29.51, 29.32, 28.64, 28.60, 26.95, 25.51, 25.04, 24.52, 23.06; HRMS (ESI, m/z): (M+H)⁺ calcd for $C_{37}H_{66}N_7O_8$ 736.4967. found 736.4785.

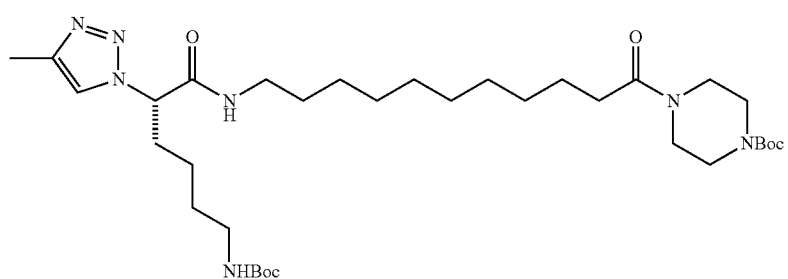

protected a'''

¹H NMR (CDCl₃) δ 7.54 (s, 1H), 6.74 (s, 1H), 5.09 (q, 1H, J=6.0, J=3.6, J=5.7), 4.66 (s, 1H), 3.60 (t, 2H, J=4.8, J=5.4), 3.45 (s, 4H), 3.41 (t, 2H, J=5.4, J=5.1), 3.21 (q, 2H, J=6.6, J=6.9, J=6.6), 3.06 (m, 2H), 2.37 (s, 3H), 2.33 (t, 2H, J=9.9, J=7.8), 2.29-2.05 (m, 2H), 1.62 (m, 2H), 1.51 (m, 2H), 1.48 (s, 9H), 1.44 (s, 9H), 1.30 (br, 6H), 1.23 (br, 10H); HRMS (ESI, m/z): (M+H)⁺ calcd for $C_{34}H_{62}N_7O_6$ 664.4756. found 664.24.

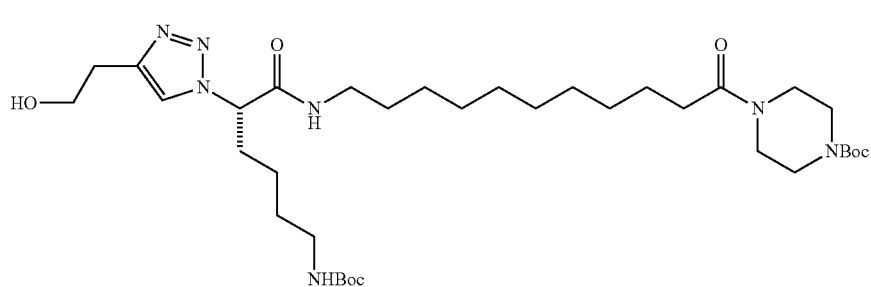

protected b'''

¹H NMR (CDCl₃) δ 7.70 (s, 1H), 7.27 (s, 1H), 5.15 (t, 1H, J=8.7, J=6.6), 4.88 (s, 1H), 3.85 (t, 2H, J=6, J=6.3), 3.53 (t, 2H, J=4.5, J=5.7), 3.39 (s, 4H), 3.34 (t, 2H, J=5.4, J=4.8), 3.14 (m, 2H), 2.998 (q, 2H, J=6.3, J=6.6, J=6.9), 2.90 (t, 2H, J=6.0, J=6.3), 2.28 (t, 2H, J=7.2, J=6.3), 2.16-2.02 (m, 2H), 1.53 (m, 2H), 1.42 (m, 11H), 1.37 (s, 9H), 1.23 (br, 4H), 1.18 (br, 12H); HRMS (ESI, m/z): (M+H)⁺ calcd for $C_{35}H_{64}N_7O_7$ 694.4862. found 694.4270.

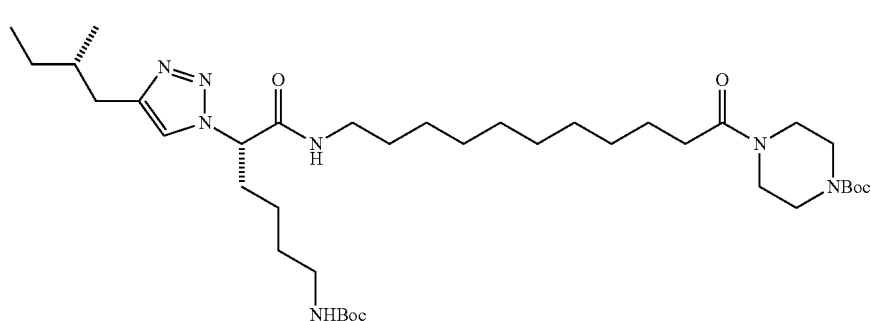

protected c'''

¹H NMR (CDCl₃) δ 7.48 (s, 1H), 6.69 (s, 1H), 5.06 (q, 1H, J=6.0, J=3.3, J=6.0), 4.62 (s, 1H), 3.58 (t, 2H, J=4.5, J=5.4), 3.43 (s, 4H), 3.39 (t, 2H, J=5.4, J=4.8), 3.19 (q, 2H, J=6.3, J=7.2, J=6.3), 3.05 (m 2H), 2.71 (dd, 1H, J=5.7, J=8.7, J=6.0), 2.51 (dd, 1H, J=8.1, J=6.6, J=7.8), 2.32 (t, 2H, J=7.2, J=8.1), 2.370-2.10 (m, 2H), 1.73 (m, 2H), 1.50 (m, 2H), 1.46 (s, 9H), 1.42 (s, 2H), 1.37 (m, 2H), 1.33-1.26 (br, 6H), 1.26-1.12 (br, 10H), 2.90 (t, 3H, J=7.2, J=6.6), 0.87 (d, 3H, J=6.6); HRMS (ESI, m/z): (M+H)⁺ calcd for C₃₈H₇₀N₇O₆ 720.5382, found 720.5566.

protected d'''

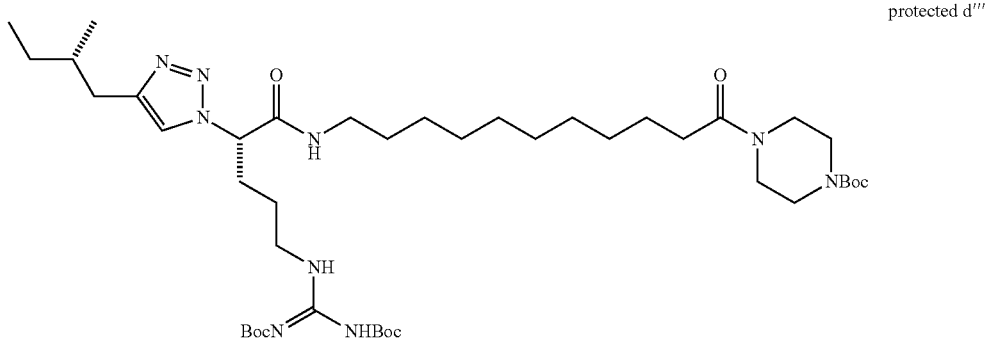

¹H NMR (CDCl₃) δ 11.43 (s, 1H), 8.40 (t, 1H, J=5.5, J=5.7), 7.58 (s, 1H), 6.83 (t, 1H, J=5.4, J=6.0), 5.29 (q, 1H, J=6.3, J=3.3, J=5.7), 3.46 (m, 2H), 3.43 (s, 4H), 3.39 (m, 2H), 3.25-4.14 (m, 2H), 2.71 (dd, 1H, J=6.3, J=8.4, J=5.7), 2.51 (dd, 1H, J=8.1, J=6.3, J=7.8), 2.31 (t, 2H, J=7.5, J=7.8), 2.33-2.10 (m, 2H), 1.73 (m, 1H), 1.60 (m, 2H), 1.49 (s, 22H), 1.46 (s, 9H), 1.27 (br, 4H), 1.22 (br, 10H), 0.89 (t, 3H, J=7.5, J=5.1), 0.87 (d, 3H, J=6.6); ¹³C NMR (CDCl₃) δ 171.80, 167.98, 162.46, 156.12, 154.46, 153.00, 147.27, 121.14, 83.51, 80.16, 63.14, 45.30, 41.19, 39.66, 39.43, 34.78, 33.26, 32.57, 30.10, 29.29, 29.25, 29.21, 29.12, 29.00, 28.25, 28.13, 27.92, 26.82, 25.32, 25.15, 18.28, 11.29; HRMS (ESI, m/z): (M+H)⁺ calcd for C₄₃H₇₈N₉O₈ 848.5968. found 848.7464.

protected e'''

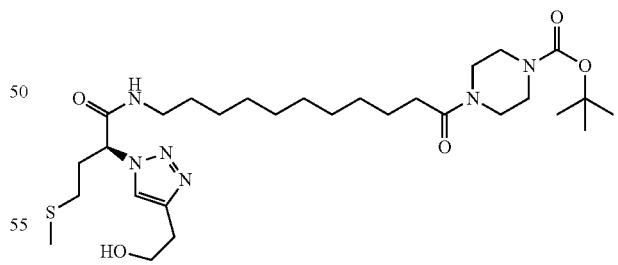

¹H NMR (500 MHz, DMSO-d₆): δ=8.46 (t, J=5.5 Hz, 1H), 7.94 (s, 1H), 5.30 (m, 1H), 4.69 (t, J=, 1H), 3.64 (dd, 2H), 3.41-3.34 (m, 10H), 3.10-3.00 (m, 2H), 2.76 (t, J=, 2H), 2.29-2.26 (m, 6H), 2.03 (s, 3H), 1.40 (m, 11H), 1.22 (m, J=, 12H); ¹³C NMR (126 MHz, DMSO-d₆): δ=171.48, 167.85, 154.46, 145.06, 122.06, 79.78, 62.23, 60.97, 55.60, 41.39, 40.68, 39.38, 32.98, 32.25, 29.91, 29.64, 29.59 29.57, 29.47, 29.36, 29.32, 28.70, 15.06. TOF MS calcd for C₂₉H₅₂N₆O₅S. 596.83. found: 597.55.

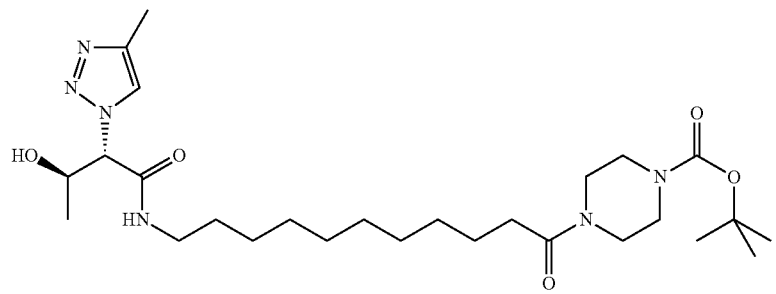
protected f'''
¹H NMR (500 MHz, DMSO-d₆): δ=8.49 (t, J=5.5 Hz, 1H), 7.85 (s, 1H), 5.13 (d, J=6 Hz, 1H), 5.012 (d, J=6 Hz, 1H), 4.23 (m, 1H), 3.40-3.26 (m, 10H), 3.11-2.98 (m, 2H), 2.29 (t, J=7.5 Hz, 2H), 2.22 (s, 3H), 1.47 (m, 14H), 1.24 (m, 12H), 1.06 (d, J=6 Hz, 3H); ¹³C NMR (126 MHz, DMSO-d₆): δ=171.46, 167.22, 154.45, 141.89, 122.34, 79.76, 69.77, 67.09, 45.31, 41.38, 39.26, 32.97, 29.61, 29.58, 29.56, 29.47, 29.34, 29.31, 28.69, 26.96, 25.42, 20.94, 11.26. TOF MS calcd for $C_{27}H_{48}N_6O_5$ 536.71. found: 537.49.
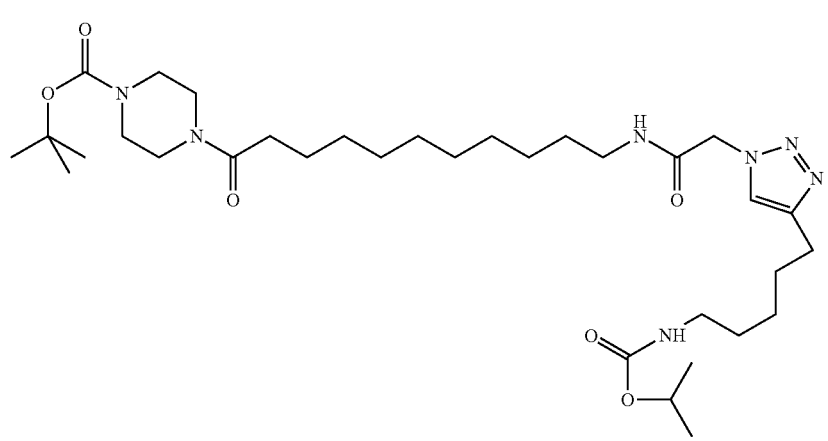
protected g'''
¹H NMR (500 MHz, DMSO-d₆): δ=8.26 (t, J=5.5 Hz, 1H), 7.76 (s, 1H), 6.79 (t, J=6 Hz, 1H), 4.98 (s, 2H), 3.41-3.25 (m, 10H), 3.08 (q, J=7.5 Hz, 2H), 2.90 (q, J=6.5 Hz, 2H), 2.60 (t, J=7.5 Hz, 2H), 2.29 (t, J=7.5 Hz, 2H), 1.40-1.36 (m, 30H), 1.24 (m, 16H); ¹³C NMR (126 MHz, DMSO-d₆): δ=171.46, 165.94, 156.22, 154.45, 147.19, 123.88, 79.76, 77.94, 55.60, 52.19, 45.31, 41.38, 39.39, 32.97, 29.92, 29.65, 29.62, 29.58, 29.47, 29.40, 29.37, 28.94, 28.69, 27.03, 26.58, 25.64, 25.42. TOF MS calcd for $C_{34}H_{61}N_7O_6$ 663.89. found: 664.49.
protected h'''
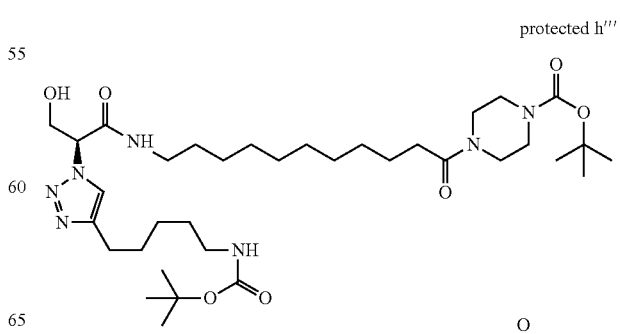

¹H NMR (500 MHz, DMSO-d₆): δ=8.40 (t, J=5.5 Hz, 1H), 7.86 (s, 1H), 6.79 (t, J=6 Hz, 1H), 5.28-5.22 (m, 2H), 3.92 (t, J=6 Hz, 2H), 3.41-3.25 (m, 10H), 3.06 (q, J=7.5 Hz, 2H), 2.97 (q, J=7.5 Hz, 2H), 2.60 (t, J=6 Hz, 2H), 2.29 (t, J=6 Hz, 2H), 1.59 (m, 2H), 1.40 (m, 28H), 1.24 (m, 16H); ¹³C NMR (126 MHz, DMSO-d₆): δ=171.47, 166.86, 156.22, 154.45, 147.04, 121.73, 79.76, 77.95, 65.45, 62.06, 45.31, 41.39, 39.36, 32.97, 29.92, 29.63, 29.60, 29.58, 29.47, 29.42, 29.34, 28.94, 28.69, 26.92, 26.67, 25.77, 25.43. TOF MS calcd for $C_{35}H_{63}N_7O_7$ 693.92. found: 694.51.

protected i'''

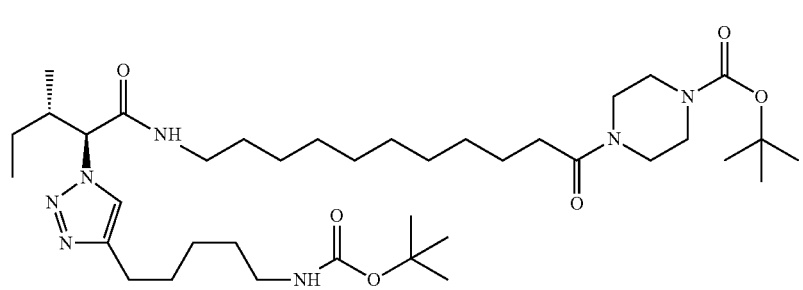

¹H NMR (500 MHz, DMSO-d₆): δ=8.55 (t, J=5.5 Hz, 1H), 7.88 (s, 1H), 6.77 (t, J=6 Hz, 1H), 4.95 (d, J=11 Hz, 1H), 3.41-3.25 (m, 8H), 3.15-2.95 (m, 2H), 2.89 (q, J=7.5 Hz, 2H), 2.59 (t, J=6 Hz, 2H), 2.29 (t, J=6 Hz, 2H), 2.20 (m, 1H), 1.58 (m, 2H), 1.39 (m, 24H), 1.26 (m, 15H), 0.90 (d, J=6.5 Hz, 3H), 0.75 (t, J=7 Hz, 3H); ¹³C NMR (126 MHz, DMSO-d₆): δ=171.45, 168.07, 156.21, 154.44, 147.57, 120.94, 95.00, 79.75, 77.92, 67.75, 45.31, 41.38, 39.18, 37.17, 32.97, 29.85, 29.62, 29.56, 29.46, 29.32, 29.28, 28.93, 28.68, 26.94, 26.60, 25.73, 25.42, 24.96, 15.65, 10.53. TOF MS calcd for $C_{38}H_{69}N_7O_8$ 720.00. found: 720.58.

protected j'''

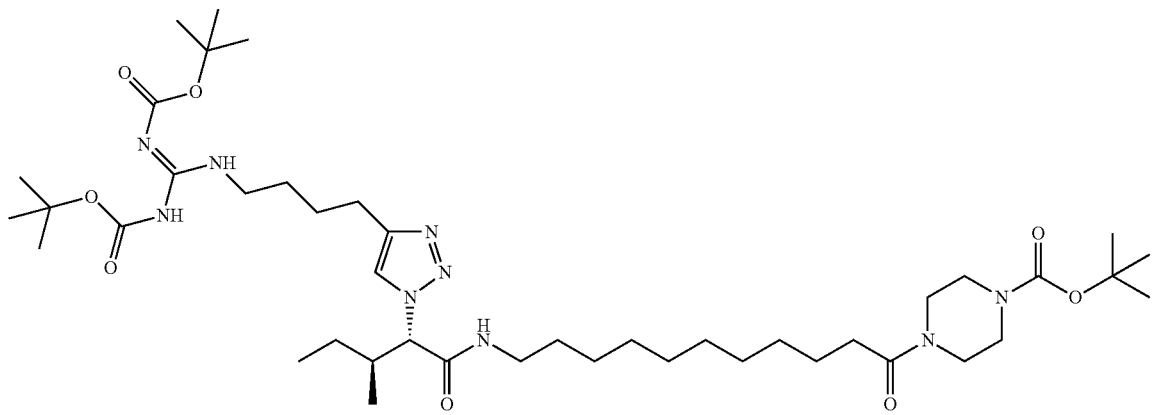

¹H NMR (500 MHz, DMSO-d₆): δ=11.50 (s, 1H), 8.54 (t, J=5.5 Hz, 1H), 8.30 (t, J=5.5 Hz, 1H), 7.90 (s, 1H), 4.96 (d, J=11 Hz, 1H), 3.40-3.25 (m, 10H), 3.16 (m, 1H), 3.10 (m, 1H), 2.64 (t, J=6 Hz, 2H), 2.29 (t, J=6 Hz, 2H), 2.19 (m, 1H), 1.60 (m, 2H), 1.51 (m, 15H), 1.39 (m, 22H), 1.20 (m, 12H), 0.95 (d, J=6.5 Hz, 3H), 0.75 (t, J=7 Hz, 3H); ¹³C NMR (126 MHz, DMSO-d₆): δ=171.44, 168.04, 163.81, 155.89, 154.44, 152.76, 147.36, 121.05, 83.50, 79.75, 78.72, 67.75, 55.59, 45.31, 41.38, 39.17, 37.20, 32.97, 29.61, 29.55, 29.46, 29.32, 29.26, 28.83, 28.68, 28.65, 28.27, 26.92, 25.41, 25.35, 24.96, 15.65, 10.52. TOF MS calcd for $C_{43}H_{77}N_9O_8$ 848.13. found: 848.57.

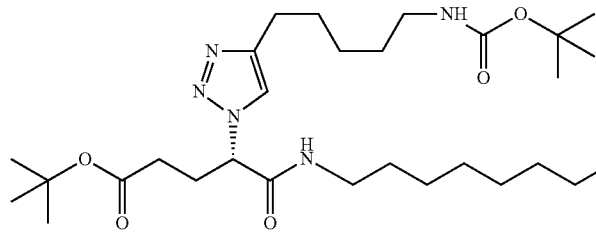

protected k'''

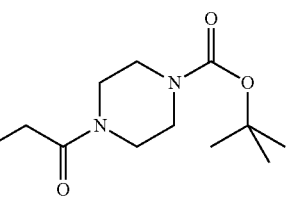

¹H NMR (500 MHz, DMSO-$d_6$): δ=8.42 (t, J=5.5 Hz, 1H), 7.88 (s, 1H), 6.78 (t, J=6 Hz, 1H), 5.19 (t, J=8 Hz, 1H), 3.40-3.25 (m, 8H), 3.11-2.99 (m, 2H), 2.90 (q, J=6.5 Hz, 2H), 2.59 (t, J=6 Hz, 2H), 2.29-2.04 (m, 6H), 1.58 (m, 2H), 1.39 (m, 37H), 1.21 (m, 14H); ¹³C NMR (126 MHz, DMSO-$d_6$): δ=171.52, 171.45, 167.82, 156.20, 154.44, 147.55, 121.35, 80.69, 79.75, 77.92, 62.48, 45.31, 41.38, 39.31, 32.97, 31.51, 29.88, 29.67, 29.60, 29.58, 29.46, 29.33, 29.27, 28.93, 28.68, 28.36, 28.00, 26.91, 26.62, 25.73, 25.42. TOF MS calcd for $C_{41}H_{73}N_7O_8$ 792.06. found: 792.64.

¹³C NMR (75 MHz, $CDCl_3$) δ: 171.2, 166.1, 155.9, 155.2, 154.1, 149.3, 120.0, 80.9, 80.1, 79.1, 87.5, 58.2, 46.9, 45.4, 42.1, 40.0, 34.9, 30.0, 29.3, 28.2 28.1, 27.8, 22.8.

MS (MALDI) calculated [M+H]: 724.45. found: 724.19.

protected l'''

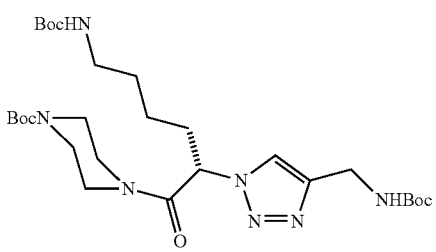

protected o'''

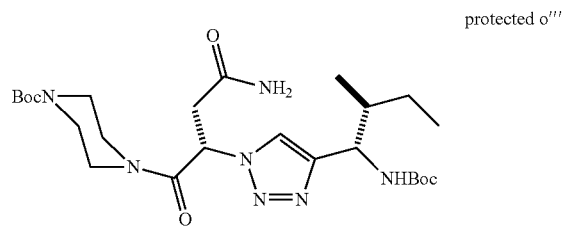 [SMILES: CC[C@H](C)[C@H](NC(=O)OC(C)(C)C)c1cn([C@@H](CC(N)=O)C(=O)N2CCN(C(=O)OC(C)(C)C)CC2)nn1]

¹³C NMR (75 MHz, $CDCl_3$) δ: 166.6, 156.4, 156.1, 154.6, 146.3, 121.0, 80.8, 80.0, 79.5, 59.7, 46.0, 42.6, 40.0, 36.6, 32.7, 29.7, 28.7, 28.6, 22.9. MS (MALDI) calculated [M+H]: 596.37. found: 596.03.

¹³C NMR (75 MHz, $CDCl_3$) δ: 171.4, 165.8, 155.9, 154.5, 148.5, 121.3, 80.7, 79.6, 56.2, 51.8, 46.0, 42.9, 39.3, 38.7, 28.6, 25.5, 25.5, 15.6, 11.6. MS (MALDI) calculated [M+H]: 538.33. found: 538.06.

protected m'''

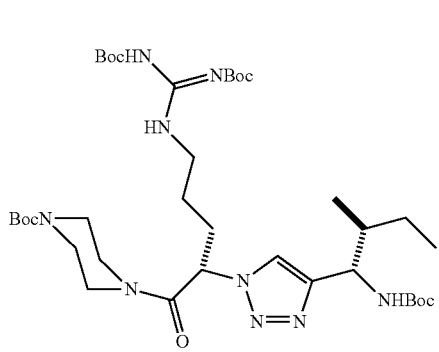

protected p'''

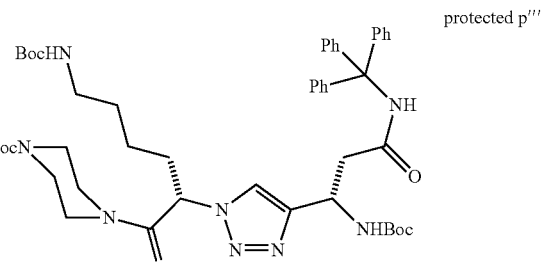

¹³C NMR (75 MHz, $CDCl_3$) δ: 166.2, 163.6, 156.5, 155.6, 154.5, 153.4, 120.2, 83.5, 80.6, 79.6, 58.9, 51.8, 45.9, 43.6, 42.6, 39.6, 30.0, 28.5, 25.2, 25.4, 15.4, 11.7. MS (MALDI) calculated [M+H]: 780.49. found: 780.30.

¹³C NMR (75 MHz, $CDCl_3$) δ: 169.9, 166.2, 156.2, 155.6, 154.4, 149.3, 144.5, 128.7, 127.0, 120.8, 80.5, 79.7, 79.1, 70.6, 68.0, 59.4, 45.7, 45.2, 42.4, 40.4, 39.8, 32.6, 29.4, 28.5, 25.7, 22.8. MS (MALDI) calculated [M+Na]: 917.49. found: 917.27.

protected q'''

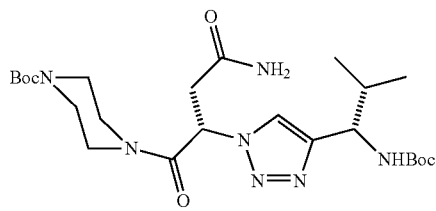

¹³C NMR (75 MHz, CDCl₃) δ: 171.5, 165.8, 156.0, 154.5, 148.7, 121.3, 80.6, 79.5, 56.2, 52.9, 45.9, 42.8, 38.7, 33.0, 28.5, 19.3, 18.7. MS (MALDI) calculated [M+H]: 524.31, 524.06.

protected r'''

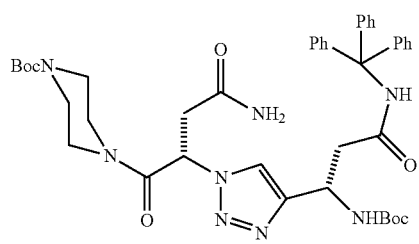

¹³C NMR (75 MHz, CDCl₃) δ: 171.2, 170.2, 168.0, 165.9, 155.7, 154.5, 144.7, 132.6, 131.2, 129.0, 128.9, 127.1, 121.8, 80.5, 79.8, 70.7, 68.4, 56.0, 42.7, 38.9, 38.4, 30.6, 29.1, 28.6.
MS (MALDI) calculated [M+Na]: 803.39. found: 803.19.

protected s'''

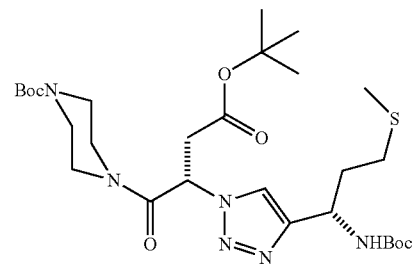

¹³C NMR (75 MHz, CDCl₃) δ: 168.6, 165.4, 155.3, 154.4, 149.2, 120.1, 82.2, 80.5, 79.7, 55.5, 46.4, 45.9, 42.7, 38.7, 34.7, 30.5, 28.5, 28.4, 15.5. MS (MALDI) calculated [M+H]: 613.33, 613.40.

protected t'''

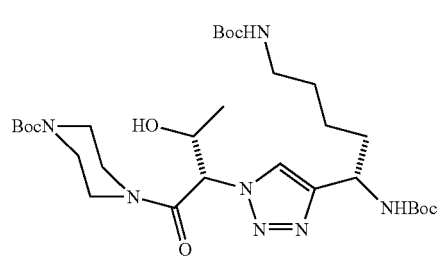

¹³C NMR (75 MHz, CDCl₃) δ: 166.8, 156.4, 155.7, 154.5, 121.5, 80.9, 799, 79.3, 67.6, 63.1, 47.5, 45.9, 42.6, 40.5, 35.3, 29.8, 28.7, 28.6, 23.1, 18.9. MS (MALDI) calculated [M+H]: 640.40. found, 640.52.

protected u'''

¹³C NMR (75 MHz, CDCl₃) δ: 168.9, 165.6, 154.6, 120.8, 82.5, 80.8, 55.7, 46.1, 44.0, 42.6, 38.9, 36.5, 28.7, 28.3. MS (MALDI) calculated [M+H]: 539.31. found 539.41.

protected v'''

¹³C NMR (75 MHz, CDCl₃) δ: 165.8, 156.0, 154.6, 148.2, 121.6, 80.8, 79.7, 63.0, 60.7, 52.8, 45.9, 42.5, 33.1, 28.5, 19.2, 18.5. MS (MALDI) calculated [M+H]: 497.30. found: 497.44.

protected w'''

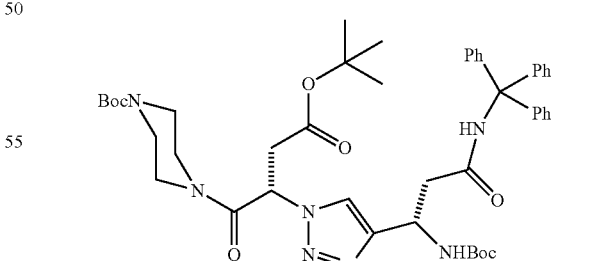

¹³C NMR (75 MHz, CDCl₃) δ: 170.0, 168.8, 165.2, 155.6, 154.4, 149.9, 144.5, 128.8, 128.2, 127.1, 121.0, 120.7, 82.1, 800.4, 79.8, 70.7, 55.4, 45.8, 45.2, 42.7, 40.2, 38.7, 28.5, 28.2.

MS (MALDI) calculated [M+H]: 838.44. found: 838.58.

protected x'''

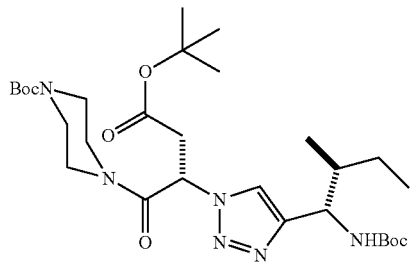

¹³C NMR (75 MHz, CDCl₃) δ: 168.6, 165.3, 155.5, 154.3, 148.4, 120.1, 82.0, 80.4, 79.4, 55.6, 51.6, 45.8, 42.7, 39.2, 38.7, 28.4, 28.0, 25.3, 15.4, 11.6. MS (MALDI) calculated [M+H]: 595.37. found: 595.51.

protected y'''

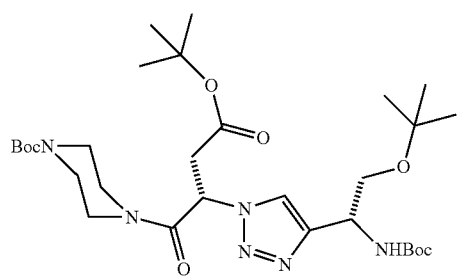

¹³C NMR (75 MHz, CDCl₃) δ: 168.5, 165.1, 155.2, 154.1, 120.4, 81.8, 80.1, 79.4, 73.1, 63.4, 55.5, 48.0, 45.6, 44.5, 42.5, 38.5, 28.8, 28.2, 27.9, 27.4. MS (MALDI) calculated [M+H]: 625.38. found: 625.45.

The following method may be used to prepare protected monovalent compound z''' (Scheme 15).

Scheme 15

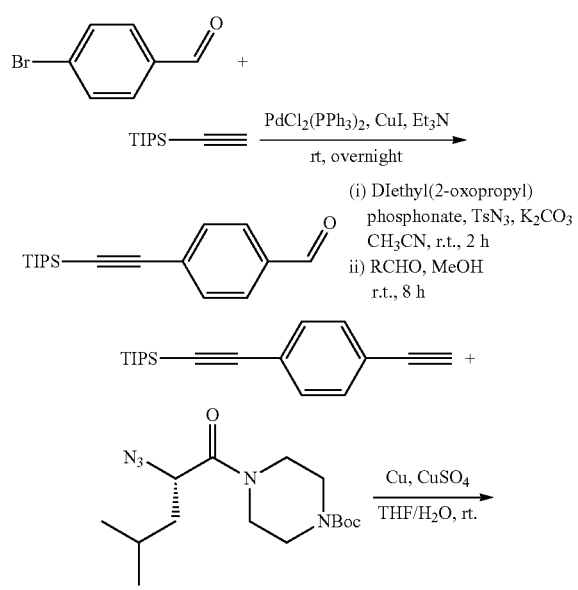

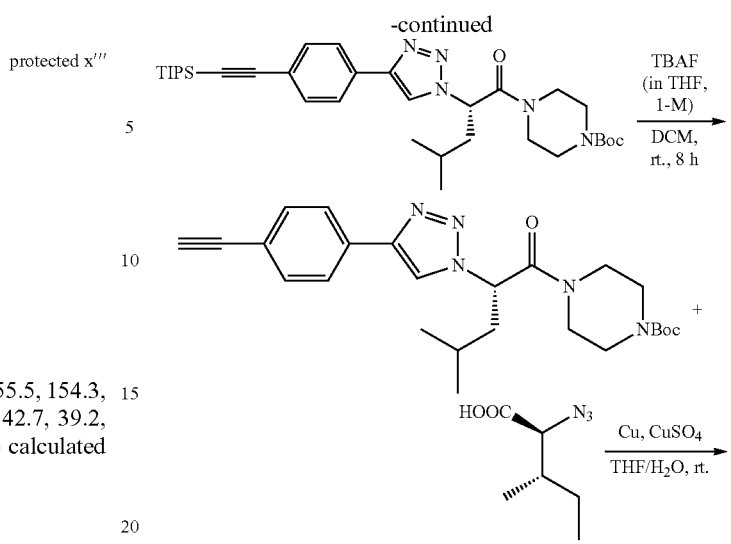

Characterization data for protected monovalent compound z''' follows:

Protected z'''

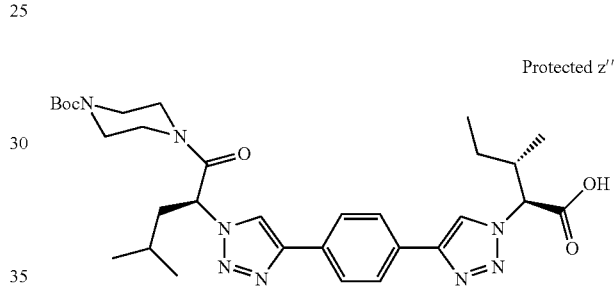

¹H NMR (CDCl₃, 300 MHz): δ 8.24-8.14 (m, 2H), 7.97-7.87 (s, 4H), 5.89-5.81 (m, 1H), 5.36-5.30 (m, 1H), 3.80-3.14 (m, 8H), 2.15-1.90 (m, 6H), 1.50-1.42 (s, 9H), 1.29-1.22 (m, 3H), 1.14-1.07 (m, 3H), 1.03-0.98 (m, 3H), 0.96-0.90 (m, 3H). Mass Spec (ESI) Calculated for [M+1]: 609.34. found: 609.35.

The following general method may be used to prepare protected monovalent compounds a'''' through b'''' (Scheme 16).

Scheme 16

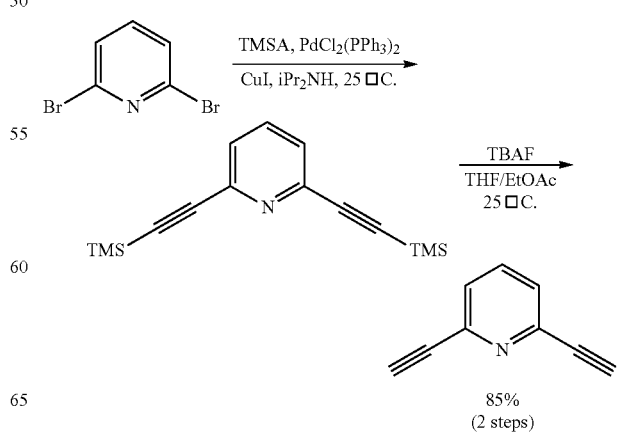

85%
(2 steps)

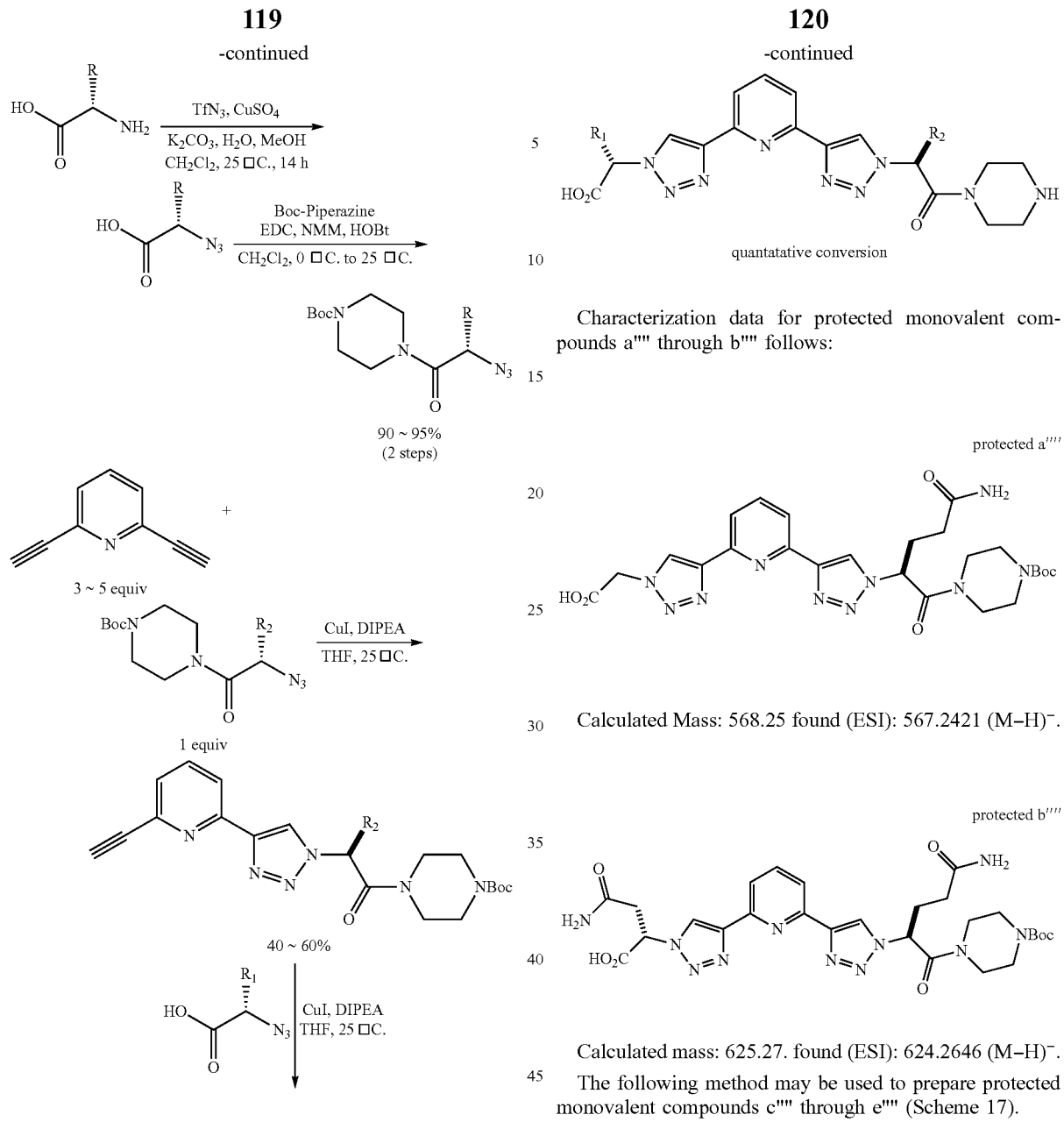
Characterization data for protected monovalent compounds a'''' through b'''' follows:
*protected a''''*
Calculated Mass: 568.25 found (ESI): 567.2421 (M–H)⁻.
*protected b''''*
Calculated mass: 625.27. found (ESI): 624.2646 (M–H)⁻.
The following method may be used to prepare protected monovalent compounds c'''' through e'''' (Scheme 17).
Scheme 17
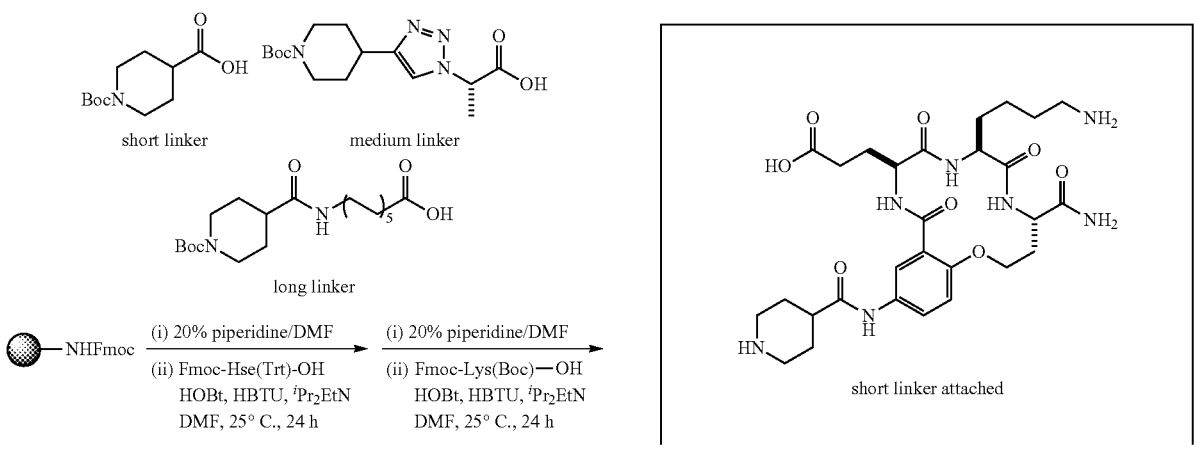

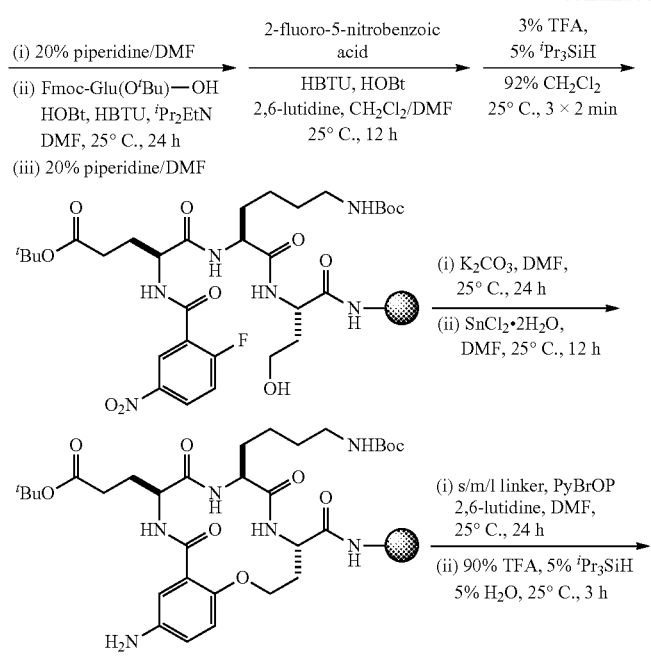
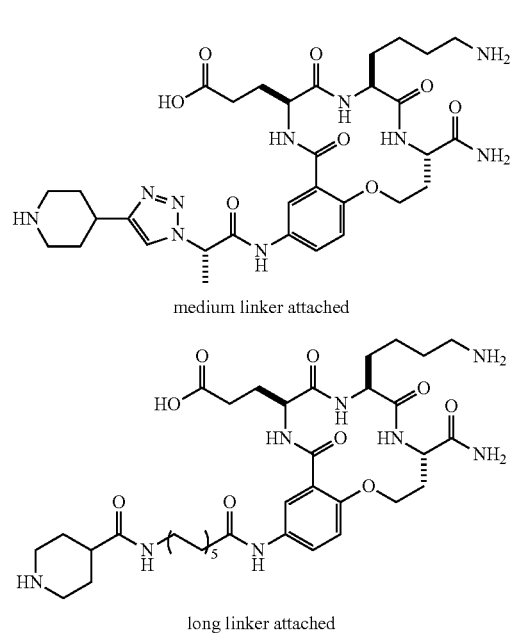

Characterization data for protected monovalent compounds c'''' through e'''' follows:

Desired MS 699.35 (M+H). MS Found (MALDI, m/z) 699.20 (M+H).

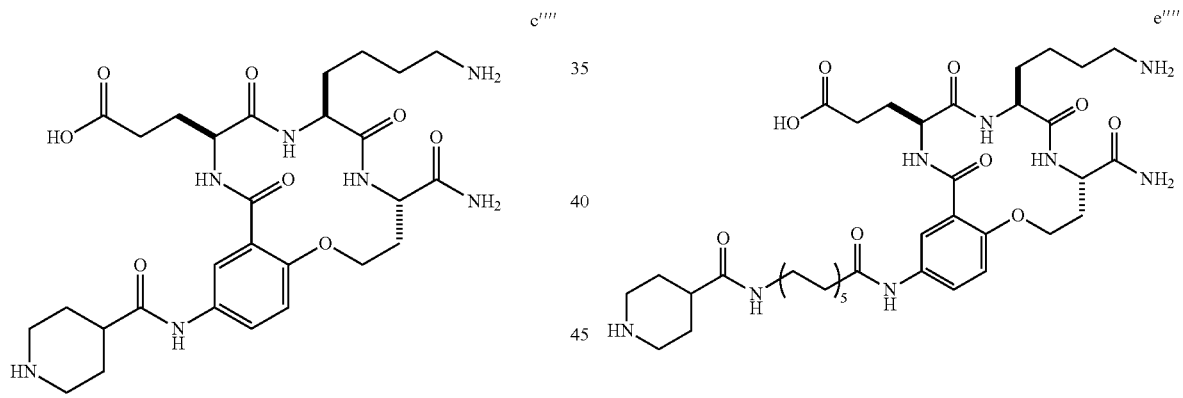

Desired MS 604.30 (M+H). MS Found (MALDI, m/z) 604.34 (M+H).

Desired MS 787.46 (M+H). MS Found (ESI, m/z) 787.46 (M+H).

Example 2

Synthesis of Bivalent Compounds Having a Triazine Core

The protected monovalent compounds may be reacted with a 1,3,5-triazine moiety having a labeling tag attached. An exemplary but non-limiting general procedure for synthesizing the 1,3,5-triazine bivalent compounds follows: The protected monovalent compound was deprotected with TFA in $CH_2Cl_2$. The deprotected monovalent compound was dissolved in THF and reacted at room temperature with a dichlorotriazine derivative in the presence of $K_2CO_3$. In the example that follows, the dichlorotriazine derivative is

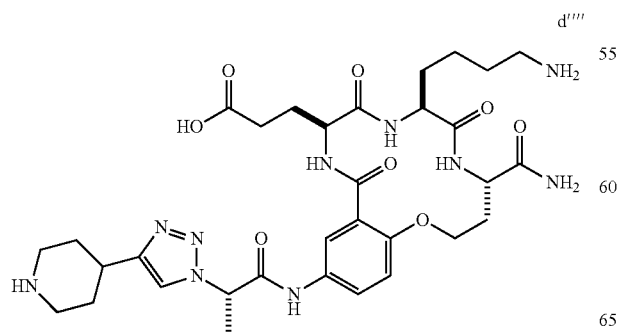

labeled with a fluorescein tag (i.e., DTAF). The solvent was removed at reduced pressure, and the product was sufficiently pure to use without further purification. The crude product was redissolved in DMSO, and a second equivalent of a deprotected monovalent compound was reacted at room temperature in the presence of $K_2CO_3$. Following workup and purification, bivalent peptide mimics having a 1,3,5-triazine core and a labeling tag were obtained. Morpholine may also be used in the first or second coupling steps. A representative synthesis of the 1,3,5-triazine bivalent compounds is presented in Scheme 18.

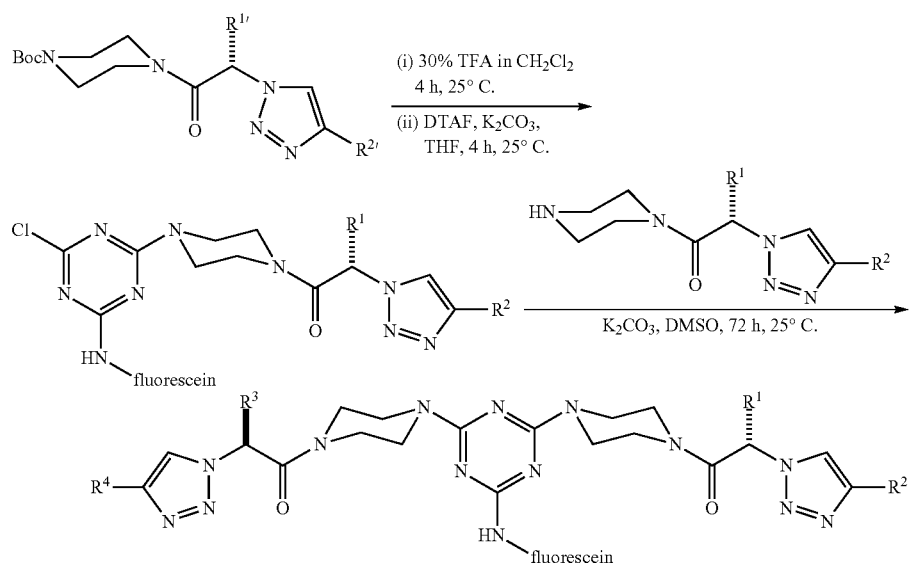

Scheme 18

Example 3

Listing of Bivalent Triazine Compounds Prepared

Tables 1-7 provide listings of bivalent compounds prepared and experimental characterization of those compounds when available.

TABLE 1

| Bivalent Compounds from Monovalent Compounds a-o | | | |
|---|---|---|---|
| Monovalent Compound | Tag | HPLC Purity (%) UV 254 nm | Sedex |
| ap | 1 | 100 | 100 |
| aa | 1 | 100 | 100 |
| bp | 1 | 93 | 100 |
| ba | 1 | 86 | 100 |
| bb | 1 | 91 | 100 |
| cp | 1 | 100 | 100 |
| ca | 1 | 86 | 92 |
| cb | 1 | 85 | 92 |
| cc | 1 | 100 | 100 |
| dp | 1 | 85 | 92 |
| da | 1 | 86 | 100 |
| db | 1 | 92 | 100 |
| dc | 1 | 90 | 100 |
| dd | 1 | 92 | 100 |
| ep | 1 | 86 | 90 |
| ea | 1 | 92 | 94 |
| eb | 1 | 100 | 100 |
| ec | 1 | 94 | 100 |
| ed | 1 | 100 | 100 |
| ee | 1 | 100 | 100 |
| fp | 1 | 100 | 100 |
| fa | 1 | 100 | 100 |
| fb | 1 | 90 | 100 |
| fc | 1 | 100 | 100 |
| fd | 1 | 91 | 100 |
| fe | 1 | 89 | 100 |
| ff | 1 | 100 | 94 |
| gp | 1 | 88 | 98 |
| ga | 1 | 86 | 92 |
| gb | 1 | 100 | 100 |
| gc | 1 | 96 | 98 |
| gd | 1 | 87 | 00 |
| ge | 1 | 94 | 100 |
| gf | 1 | 96 | 100 |
| gg | 1 | 86 | 100 |
| hp | 1 | 98 | 100 |
| ha | 1 | 89 | 93 |
| hb | 1 | 93 | 100 |
| hc | 1 | 93 | 100 |
| hd | 1 | 93 | 100 |
| he | 1 | 93 | 100 |
| hf | 1 | 87 | 94 |
| hg | 1 | 96 | 98 |
| hh | 1 | 91 | 100 |
| ip | 1 | 92 | 87 |
| ia | 1 | 93 | 91 |
| ib | 1 | 100 | 100 |
| ic | 1 | 91 | 100 |
| id | 1 | 90 | 100 |
| ie | 1 | 100 | 100 |
| if | 1 | 100 | 100 |

TABLE 1-continued

Bivalent Compounds from Monovalent Compounds a-o

| Monovalent Compound | Tag | HPLC Purity (%) UV 254 nm | Sedex |
|---|---|---|---|
| ig | 1 | 98 | 97 |
| ih | 1 | 92 | 100 |
| ii | 1 | 89 | 96 |
| jp | 1 | 100 | 100 |
| ja | 1 | 100 | 100 |
| jb | 1 | 100 | 100 |
| jc | 1 | 100 | 100 |
| jd | 1 | 100 | 100 |
| je | 1 | 100 | 100 |
| jf | 1 | 100 | 100 |
| jg | 1 | 96 | 100 |
| jh | 1 | 96 | 100 |
| ji | 1 | 100 | 100 |
| jj | 1 | 100 | 100 |
| kp | 1 | 94 | 99 |
| ka | 1 | 90 | 95 |
| kb | 1 | 100 | 100 |
| kc | 1 | 94 | 100 |
| kd | 1 | 100 | 100 |
| ke | 1 | 100 | 100 |
| kf | 1 | 86 | 93 |
| kg | 1 | 93 | 90 |
| kh | 1 | 100 | 100 |
| ki | 1 | 100 | 100 |
| kj | 1 | 100 | 100 |
| kk | 1 | 86 | 100 |
| lp | 1 | 87 | 100 |
| la | 1 | 88 | 94 |
| lb | 1 | 100 | 100 |
| lc | 1 | 97 | 100 |
| ld | 1 | 100 | 100 |
| le | 1 | 100 | 100 |
| lf | 1 | 87 | 100 |
| lg | 1 | 100 | 100 |
| lh | 1 | 100 | 100 |
| li | 1 | 100 | 100 |
| lj | 1 | 100 | 100 |
| lk | 1 | 100 | 100 |
| ll | 1 | 95 | 100 |
| mp | 1 | 92 | 97 |
| ma | 1 | 92 | 100 |
| mb | 1 | 86 | 92 |
| mc | 1 | 97 | 100 |
| md | 1 | 100 | 100 |
| me | 1 | 89 | 100 |
| mf | 1 | 100 | 100 |
| mg | 1 | 88 | 96 |
| mh | 1 | 88 | 87 |
| mi | 1 | 100 | 100 |
| mj | 1 | 100 | 100 |
| mk | 1 | 100 | 100 |
| ml | 1 | 100 | 100 |
| mm | 1 | 100 | 100 |
| np | 1 | 100 | 100 |
| na | 1 | 100 | 96 |
| nb | 1 | 100 | 100 |
| nc | 1 | 100 | 100 |
| nd | 1 | 100 | 100 |
| ne | 1 | 100 | 100 |
| nf | 1 | 100 | 98 |
| ng | 1 | 86 | 100 |
| nh | 1 | 92 | 100 |
| ni | 1 | 100 | 100 |
| nj | 1 | 100 | 100 |
| nk | 1 | 100 | 100 |
| nl | 1 | 100 | 100 |
| nm | 1 | 100 | 100 |
| nn | 1 | 100 | 100 |
| op | 1 | 100 | 100 |
| oa | 1 | 100 | 93 |
| ob | 1 | 87 | 93 |
| oc | 1 | 100 | 100 |
| od | 1 | 87 | 86 |
| oe | 1 | 90 | 92 |
| of | 1 | 100 | 100 |
| og | 1 | 90 | 94 |
| oh | 1 | 89 | 93 |
| oi | 1 | 89 | 95 |
| oj | 1 | 100 | 98 |
| ok | 1 | 88 | 93 |
| ol | 1 | 90 | 90 |
| om | 1 | 100 | 100 |
| on | 1 | 100 | 100 |
| oo | 1 | 100 | 91 |
| ap | 2 | 100 | 98 |
| aa | 2 | 93 | 100 |
| bp | 2 | 100 | 100 |
| ba | 2 | 90 | 100 |
| bb | 2 | 97 | 100 |
| cp | 2 | 100 | 100 |
| ca | 2 | 91 | 91 |
| cb | 2 | 86 | 91 |
| cc | 2 | 100 | 87 |
| dp | 2 | 100 | 100 |
| da | 2 | 100 | 100 |
| db | 2 | 87 | 100 |
| dc | 2 | 97 | 100 |
| dd | 2 | 100 | 100 |
| ep | 2 | 100 | 100 |
| ea | 2 | 100 | 100 |
| eb | 2 | 89 | 100 |
| ec | 2 | 86 | 92 |
| ed | 2 | 87 | 100 |
| ee | 2 | 100 | 100 |
| fp | 2 | 100 | 100 |
| fa | 2 | 90 | 85 |
| fb | 2 | 98 | 100 |
| fc | 2 | 87 | 91 |
| fd | 2 | 89 | 94 |
| fe | 2 | 89 | 93 |
| ff | 2 | 100 | 99 |
| gp | 2 | 100 | 100 |
| ga | 2 | 87 | 90 |
| gb | 2 | 91 | 92 |
| gc | 2 | 89 | 94 |
| gd | 2 | 89 | 100 |
| ge | 2 | 85 | 89 |
| gf | 2 | 100 | 100 |
| gg | 2 | 89 | 97 |
| hp | 2 | 89 | 87 |
| ha | 2 | 89 | 91 |
| hb | 2 | 90 | 87 |
| hc | 2 | 88 | 91 |
| hd | 2 | 92 | 89 |
| he | 2 | 89 | 90 |
| hf | 2 | 100 | 100 |
| hg | 2 | 100 | 100 |
| hh | 2 | 87 | 89 |
| ip | 2 | 100 | 100 |
| ia | 2 | 95 | 100 |
| ib | 2 | 98 | 100 |
| ic | 2 | 97 | 96 |
| id | 2 | 91 | 90 |
| ie | 2 | 92 | 100 |
| if | 2 | 96 | 92 |
| ig | 2 | 100 | 92 |
| ih | 2 | 93 | 91 |
| ii | 2 | 91 | 95 |
| jp | 2 | 100 | 97 |
| ja | 2 | 100 | 88 |
| jb | 2 | 95 | 100 |
| jc | 2 | 93 | 100 |
| jd | 2 | 87 | 91 |
| je | 2 | 87 | 88 |
| jf | 2 | 100 | 94 |
| jg | 2 | 100 | 100 |
| jh | 2 | 95 | 100 |
| ji | 2 | 90 | 91 |
| jj | 2 | 96 | 100 |
| kp | 2 | 100 | 100 |

TABLE 1-continued

Bivalent Compounds from Monovalent Compounds a-o

| Monovalent Compound | Tag | HPLC Purity (%) UV 254 nm | Sedex |
|---|---|---|---|
| ka | 2 | 95 | 100 |
| kb | 2 | 100 | 100 |
| kc | 2 | 96 | 95 |
| kd | 2 | 92 | 90 |
| ke | 2 | 97 | 94 |
| kf | 2 | 90 | 92 |
| kg | 2 | 100 | 92 |
| kh | 2 | 94 | 93 |
| ki | 2 | 87 | 90 |
| kj | 2 | 91 | 92 |
| kk | 2 | 98 | 97 |
| lp | 2 | 96 | 100 |
| la | 2 | 99 | 100 |
| lb | 2 | 90 | 88 |
| lc | 2 | 88 | 86 |
| ld | 2 | 86 | 85 |
| le | 2 | 86 | 89 |
| lf | 2 | 86 | 98 |
| lg | 2 | 86 | 86 |
| lh | 2 | 87 | 87 |
| li | 2 | 89 | 86 |
| lj | 2 | 88 | 85 |
| lk | 2 | 87 | 88 |
| ll | 2 | 91 | 96 |
| mp | 2 | 100 | 100 |
| ma | 2 | 86 | 86 |
| mb | 2 | 100 | 100 |
| mc | 2 | 86 | 100 |
| md | 2 | 87 | 94 |
| me | 2 | 96 | 100 |
| mf | 2 | 86 | 85 |
| mg | 2 | 90 | 90 |
| mh | 2 | 89 | 88 |
| mi | 2 | 100 | 100 |
| mj | 2 | 89 | 95 |
| mk | 2 | 94 | 100 |
| ml | 2 | 92 | 92 |
| mm | 2 | 91 | 89 |
| np | 2 | 100 | 100 |
| na | 2 | 89 | 100 |
| nb | 2 | 85 | 100 |
| nc | 2 | 93 | 90 |
| nd | 2 | 92 | 100 |
| ne | 2 | 90 | 95 |
| nf | 2 | 100 | 92 |
| ng | 2 | 85 | 90 |
| nh | 2 | 97 | 88 |
| ni | 2 | 87 | 94 |
| nj | 2 | 87 | 92 |
| nk | 2 | 85 | 87 |
| nl | 2 | 87 | 86 |
| nm | 2 | 86 | 100 |
| nn | 2 | 96 | 96 |
| op | 2 | 100 | 98 |
| oa | 2 | 92 | 87 |
| ob | 2 | 86 | 100 |
| oc | 2 | 90 | 85 |
| od | 2 | 100 | 100 |
| oe | 2 | 85 | 100 |
| of | 2 | 87 | 100 |
| og | 2 | 85 | 92 |
| oh | 2 | 88 | 93 |
| oi | 2 | 95 | 100 |
| oj | 2 | 100 | 100 |
| ok | 2 | 94 | 100 |
| ol | 2 | 94 | 100 |
| om | 2 | 87 | 97 |
| on | 2 | 91 | 85 |
| oo | 2 | 90 | 92 |
| ap | 3 | 76 | 100 |
| aa | 3 | 95 | 100 |
| bp | 3 | 70 | 92 |
| ba | 3 | 88 | 96 |
| bb | 3 | 80 | 93 |
| cp | 3 | 75 | 94 |
| ca | 3 | 80 | 96 |
| cb | 3 | 83 | 95 |
| cc | 3 | 93 | 93 |
| dp | 3 | 94 | 100 |
| da | 3 | 80 | 95 |
| db | 3 | 81 | 96 |
| dc | 3 | 95 | 92 |
| dd | 3 | 92 | 100 |
| ep | 3 | 96 | 100 |
| ea | 3 | 89 | 97 |
| eb | 3 | 88 | 94 |
| ec | 3 | 99 | 100 |
| ed | 3 | 95 | 98 |
| ee | 3 | 96 | 100 |
| fp | 3 | 96 | 99 |
| fa | 3 | 89 | 93 |
| fb | 3 | 85 | 95 |
| fc | 3 | 76 | 91 |
| fd | 3 | 92 | 92 |
| fe | 3 | 93 | 97 |
| ff | 3 | 95 | 94 |
| gp | 3 | 76 | 94 |
| ga | 3 | 83 | 91 |
| gb | 3 | 85 | 98 |
| gc | 3 | 80 | 93 |
| gd | 3 | 85 | 90 |
| ge | 3 | 94 | 97 |
| gf | 3 | 75 | 94 |
| gg | 3 | 85 | 96 |
| hp | 3 | 95 | 100 |
| ha | 3 | 85 | 100 |
| hb | 3 | 84 | 91 |
| hc | 3 | 81 | 98 |
| hd | 3 | 85 | 100 |
| he | 3 | 86 | 94 |
| hf | 3 | 85 | 96 |
| hg | 3 | 80 | 100 |
| hh | 3 | 80 | 90 |
| ip | 3 | 93 | 100 |
| ia | 3 | 85 | 94 |
| ib | 3 | 95 | 100 |
| ic | 3 | 93 | 100 |
| id | 3 | 92 | 95 |
| ie | 3 | 92 | 87 |
| if | 3 | 87 | 100 |
| ig | 3 | 93 | 95 |
| ih | 3 | 95 | 100 |
| ii | 3 | 90 | 88 |
| jp | 3 | 96 | 100 |
| ja | 3 | 91 | 94 |
| jb | 3 | 91 | 95 |
| jc | 3 | 91 | 94 |
| jd | 3 | 92 | 100 |
| je | 3 | 91 | 86 |
| jf | 3 | 92 | 94 |
| jg | 3 | 89 | 97 |
| jh | 3 | 88 | 91 |
| ji | 3 | 95 | 100 |
| jj | 3 | 95 | 100 |
| kp | 3 | 95 | 100 |
| ka | 3 | 88 | 94 |
| kb | 3 | 88 | 91 |
| kc | 3 | 94 | 100 |
| kd | 3 | 93 | 100 |
| ke | 3 | 92 | 90 |
| kf | 3 | 91 | 100 |
| kg | 3 | 92 | 95 |
| kh | 3 | 90 | 89 |
| ki | 3 | 90 | 87 |
| kj | 3 | 95 | 100 |
| kk | 3 | 90 | 87 |
| lp | 3 | 85 | 100 |
| la | 3 | 85 | 100 |
| lb | 3 | 87 | 92 |
| lc | 3 | 87 | 95 |

TABLE 1-continued

Bivalent Compounds from Monovalent Compounds a-o

| Monovalent Compound | Tag | HPLC Purity (%) UV 254 nm | Sedex |
|---|---|---|---|
| ld | 3 | 85 | 97 |
| le | 3 | 93 | 94 |
| lf | 3 | 78 | 92 |
| lg | 3 | 87 | 97 |
| lh | 3 | 86 | 90 |
| li | 3 | 92 | 90 |
| lj | 3 | 87 | 90 |
| lk | 3 | 93 | 94 |
| ll | 3 | 85 | 93 |
| mp | 3 | 98 | 100 |
| ma | 3 | 93 | 96 |
| mb | 3 | 81 | 100 |
| mc | 3 | 74 | 100 |
| md | 3 | 94 | 97 |
| me | 3 | 93 | 94 |
| mf | 3 | 96 | 98 |
| mg | 3 | 93 | 100 |
| mh | 3 | 82 | 97 |
| mi | 3 | 90 | 91 |
| mj | 3 | 95 | 100 |
| mk | 3 | 91 | 97 |
| ml | 3 | 89 | 94 |
| mm | 3 | 98 | 99 |
| np | 3 | 91 | 100 |
| na | 3 | 78 | 95 |
| nb | 3 | 82 | 95 |
| nc | 3 | 77 | 90 |
| nd | 3 | 90 | 93 |
| ne | 3 | 94 | 96 |
| nf | 3 | 96 | 100 |
| ng | 3 | 78 | 94 |
| nh | 3 | 78 | 94 |
| ni | 3 | 95 | 100 |
| nj | 3 | 91 | 94 |
| nk | 3 | 89 | 91 |
| nl | 3 | 81 | 94 |
| nm | 3 | 94 | 95 |
| nn | 3 | 95 | 100 |
| op | 3 | 78 | 95 |
| oa | 3 | 89 | 96 |
| ob | 3 | 85 | 92 |
| oc | 3 | 90 | 94 |
| od | 3 | 86 | 97 |
| oe | 3 | 85 | 91 |
| of | 3 | 85 | 100 |
| og | 3 | 85 | 94 |
| oh | 3 | 92 | 97 |
| oi | 3 | 95 | 100 |
| oj | 3 | 91 | 91 |
| ok | 3 | 93 | 98 |
| ol | 3 | 85 | 94 |
| om | 3 | 85 | 100 |
| on | 3 | 95 | 100 |
| oo | 3 | 86 | 92 |
| ap | 4 | | |
| aa | 4 | | |
| bp | 4 | | |
| ba | 4 | | |
| bb | 4 | | |
| cp | 4 | | |
| ca | 4 | | |
| cb | 4 | | |
| cc | 4 | | |
| dp | 4 | | |
| da | 4 | | |
| db | 4 | | |
| dc | 4 | | |
| dd | 4 | | |
| ep | 4 | | |
| ea | 4 | | |
| eb | 4 | | |
| ec | 4 | | |
| ed | 4 | | |
| ee | 4 | | |
| fp | 4 | | |
| fa | 4 | | |
| fb | 4 | | |
| fc | 4 | | |
| fd | 4 | | |
| fe | 4 | | |
| ff | 4 | | |
| gp | 4 | | |
| ga | 4 | | |
| gb | 4 | | |
| gc | 4 | | |
| gd | 4 | | |
| ge | 4 | | |
| gf | 4 | | |
| gg | 4 | | |
| hp | 4 | | |
| ha | 4 | | |
| hb | 4 | | |
| hc | 4 | | |
| hd | 4 | | |
| he | 4 | | |
| hf | 4 | | |
| hg | 4 | | |
| hh | 4 | | |
| ip | 4 | | |
| ia | 4 | | |
| ib | 4 | | |
| ic | 4 | | |
| id | 4 | | |
| ie | 4 | | |
| if | 4 | | |
| ig | 4 | | |
| ih | 4 | | |
| ii | 4 | | |
| jp | 4 | | |
| ja | 4 | | |
| jb | 4 | | |
| jc | 4 | | |
| jd | 4 | | |
| je | 4 | | |
| jf | 4 | | |
| jg | 4 | | |
| jh | 4 | | |
| ji | 4 | | |
| jj | 4 | | |
| kp | 4 | | |
| ka | 4 | | |
| kb | 4 | | |
| kc | 4 | | |
| kd | 4 | | |
| ke | 4 | | |
| kf | 4 | | |
| kg | 4 | | |
| kh | 4 | | |
| ki | 4 | | |
| kj | 4 | | |
| kk | 4 | | |
| lp | 4 | | |
| la | 4 | | |
| lb | 4 | | |
| lc | 4 | | |
| ld | 4 | | |
| le | 4 | | |
| lf | 4 | | |
| lg | 4 | | |
| lh | 4 | | |
| li | 4 | | |
| lj | 4 | | |
| lk | 4 | | |
| ll | 4 | | |
| mp | 4 | | |
| ma | 4 | | |
| mb | 4 | | |
| mc | 4 | | |
| md | 4 | | |
| me | 4 | | |

TABLE 1-continued

Bivalent Compounds from Monovalent Compounds a-o

| Monovalent Compound | Tag | HPLC Purity (%) UV 254 nm | Sedex |
|---|---|---|---|
| mf | 4 | | |
| mg | 4 | | |
| mh | 4 | | |
| mi | 4 | | |
| mj | 4 | | |
| mk | 4 | | |
| ml | 4 | | |
| mm | 4 | | |
| np | 4 | | |
| na | 4 | | |
| nb | 4 | | |
| nc | 4 | | |
| nd | 4 | | |
| ne | 4 | | |
| nf | 4 | | |
| ng | 4 | | |
| nh | 4 | | |
| ni | 4 | | |
| nj | 4 | | |
| nk | 4 | | |
| nl | 4 | | |
| nm | 4 | | |
| nn | 4 | | |
| op | 4 | | |
| oa | 4 | | |
| ob | 4 | | |
| oc | 4 | | |
| od | 4 | | |
| oe | 4 | | |
| of | 4 | | |
| og | 4 | | |
| oh | 4 | | |
| oi | 4 | | |
| oj | 4 | | |
| ok | 4 | | |
| ol | 4 | | |
| om | 4 | | |
| on | 4 | | |
| oo | 4 | | |

TABLE 2

Representative Mass Spec Results for Bivalent Compounds of Monovalent Compounds a-o

| Monovalent Compound | Tag | Mass (M + H)+ theoretical | found |
|---|---|---|---|
| ba | 1 | 1012 | 1012 |
| cp | 1 | 1070 | 1070 |
| dd | 1 | 902 | 902 |
| ed | 1 | 916 | 916 |
| gf | 1 | 1015 | 1015 |
| gg | 1 | 1044 | 1044 |
| ia | 1 | 1054 | 1054 |
| ib | 1 | 998 | 998 |
| ig | 1 | 1041 | 1041 |
| jp | 1 | 860 | 860 |
| jf | 1 | 1055 | 1055 |
| jh | 1 | 1098 | 1098 |
| jj | 1 | 1124 | 1124 |
| kg | 1 | 1027 | 1027 |
| kj | 1 | 1068 | 1068 |
| le | 1 | 1015 | 1015 |
| mp | 1 | 986 | 986 |
| ml | 1 | 1043 | 1043 |
| np | 1 | 1114 | 1114 |
| ne | 1 | 1021 | 1021 |
| nf | 1 | 1050 | 1050 |
| ng | 1 | 1078 | 1078 |
| nh | 1 | 1093 | 1093 |
| nj | 1 | 1119 | 1119 |
| nk | 1 | 1063 | 1063 |
| nm | 1 | 1050 | 1050 |
| og | 1 | 1055 | 1055 |
| oj | 1 | 1096 | 1096 |
| aa | 2 | 936 | 936 |
| cc | 2 | 938 | 938 |
| da | 2 | 853 | 853 |
| ea | 2 | 867 | 867 |
| ff | 2 | 854 | 854 |
| ic | 2 | 923 | 923 |
| ii | 2 | 908 | 908 |
| jb | 2 | 908 | 908 |
| jc | 2 | 965 | 965 |
| jf | 2 | 923 | 923 |
| kp | 2 | 672 | 672 |
| kb | 2 | 852 | 852 |
| kc | 2 | 909 | 909 |
| mk | 2 | 867 | 867 |
| ml | 2 | 911 | 911 |
| mm | 2 | 854 | 854 |
| np | 2 | 723 | 723 |
| nc | 2 | 960 | 960 |
| nd | 2 | 876 | 876 |
| nn | 2 | 982 | 982 |
| oj | 2 | 964 | 964 |
| ok | 2 | 908 | 908 |
| oo | 2 | 936 | 936 |
| cc | 3 | 909 | 909 |
| dp | 3 | 589 | 598 |
| dd | 3 | 741 | 741 |
| ee | 3 | 769 | 769 |
| hc | 3 | 911 | 911 |
| ip | 3 | 658 | 658 |
| if | 3 | 852 | 852 |
| oi | 3 | 894 | 894 |
| la | 3 | 924 | 924 |
| ll | 3 | 940 | 940 |
| mg | 3 | 854 | 854 |
| ml | 3 | 882 | 882 |
| kp | 3 | 644 | 644 |
| ok | 3 | 880 | 880 |
| kk | 3 | 852 | 852 |
| ne | 3 | 861 | 861 |
| on | 3 | 931 | 931 |
| ja | 3 | 936 | 936 |
| ji | 3 | 922 | 922 |
| jj | 3 | 964 | 964 |

TABLE 3

Bivalent Compounds from Monovalent Compounds f' to m'

| Monovalent Compound | Tag | mass (desired) | mass (found) | HPLC purity (%) UV (254 nm) |
|---|---|---|---|---|
| pp | 2 | 465.23 | 465.03 | 100 |
| g'p | 2 | 703.37 | 703.28 | 100 |
| g'g' | 2 | 941.52 | 941.48 | 100 |
| h'p | 2 | 759.44 | 759.36 | 100 |
| h'g' | 2 | 997.58 | 997.55 | 100 |
| h'h' | 2 | 1053.64 | 1053.65 | 100 |
| k'p | 2 | 958.56 | 958.67 | 100 |
| k'g' | 2 | 1196.70 | 1196.79 | 100 |
| k'h' | 2 | 1252.76 | 1252.82 | 100 |
| k'k' | 2 | 1451.88 | 1452.05 | 100 |
| i'p | 2 | 775.40 | 775.31 | 100 |
| i'g' | 2 | 1013.54 | 1013.52 | 100 |
| i'h' | 2 | 1069.60 | 1069.49 | 100 |

TABLE 3-continued

Bivalent Compounds from Monovalent Compounds f to m'

| Monovalent Compound | Tag | mass (desired) | mass (found) | HPLC purity (%) UV (254 nm) |
|---|---|---|---|---|
| i'k' | 2 | 1268.72 | 1268.83 | 97 |
| i'i' | 2 | 1085.56 | 1085.51 | 100 |
| l'p | 2 | 886.54 | 886.55 | 100 |
| l'g' | 2 | 1124.68 | 1124.70 | 100 |
| l'h' | 2 | 1180.74 | 1180.96 | 100 |
| l'k' | 2 | 1379.86 | 1379.95 | 100 |
| l'i' | 2 | 1196.70 | 1196.78 | 100 |
| l'l' | 2 | 1307.84 | 1308.06 | 100 |
| m'p | 2 | 942.60 | 942.74 | 100 |
| m'g' | 2 | 1180.74 | 1180.83 | 100 |
| m'h' | 2 | 1236.81 | 1236.86 | 100 |
| m'k' | 2 | 1435.93 | 1436.04 | 100 |
| m'i' | 2 | 1252.76 | 1252.87 | 100 |
| m'l' | 2 | 1363.90 | 1364.08 | 100 |
| m'm' | 2 | 1419.97 | 1420.04 | 100 |
| j'p | 2 | 859.49 | 859.37 | 100 |
| j'g' | 2 | 1097.63 | 1097.69 | 100 |
| j'h' | 2 | 1153.70 | 1153.79 | 100 |
| j'k' | 2 | 1352.82 | 1352.93 | 100 |
| j'i' | 2 | 1169.65 | 1169.72 | 100 |
| j'l' | 2 | 1280.80 | 1280.79 | 100 |
| j'm' | 2 | 1336.86 | 1336.87 | 100 |
| j'j' | 2 | 1253.75 | 1253.73 | 100 |
| fp | 2 | 676.33 | 676.31 | 100 |
| fg' | 2 | 914.47 | 914.32 | 98 |
| fh' | 2 | 970.53 | 970.54 | 100 |
| fk' | 2 | 1169.65 | 1169.82 | 100 |
| fi' | 2 | 986.49 | 986.41 | 100 |
| fl' | 2 | 1097.63 | 1097.72 | 100 |
| fm' | 2 | 1153.70 | 1153.71 | 100 |
| fj' | 2 | 1070.59 | 1070.69 | 100 |
| ff | 2 | 887.42 | 887.36 | 100 |

TABLE 4

Bivalent Compounds from Monovalent Compounds h" to w"

| Monovalent Compounds | Tag | HPLC Purity (%) UV 254 nm | Sedex |
|---|---|---|---|
| h"p | 1 | 98 | 99 |
| h"h" | 1 | 97 | 97 |
| i"p | 1 | 99 | 99 |
| i"h" | 1 | 90 | 95 |
| i"i" | 1 | 100 | 97 |
| j"p | 1 | 95 | 100 |
| j"h" | 1 | 94 | 100 |
| j"i" | 1 | 92 | 100 |
| j"j" | 1 | 87 | 97 |
| k"p | 1 | 97 | 100 |
| k"h" | 1 | 91 | 97 |
| k"i" | 1 | 90 | 96 |
| k"j" | 1 | 86 | 98 |
| k"k" | 1 | 95 | 100 |
| l"p | 1 | 95 | 100 |
| l"h" | 1 | 90 | 98 |
| l"i" | 1 | 94 | 99 |
| l"j" | 1 | 87 | 100 |
| l"k" | 1 | 94 | 100 |
| l"l" | 1 | 100 | 100 |
| m"p | 1 | 99 | 100 |
| m"h" | 1 | 99 | 99 |
| m"i" | 1 | 91 | 96 |
| m"j" | 1 | 85 | 97 |
| m"k" | 1 | 91 | 97 |
| m"l" | 1 | 90 | 96 |
| m"m" | 1 | 100 | 98 |
| n"p | 1 | 95 | 99 |
| n"h" | 1 | 92 | 100 |
| n"i" | 1 | 92 | 99 |
| n"j" | 1 | 86 | 91 |
| n"k" | 1 | 88 | 100 |
| n"l" | 1 | 88 | 100 |
| n"m" | 1 | 92 | 97 |
| n"n" | 1 | 87 | 100 |
| o"p | 1 | 97 | 100 |
| o"h" | 1 | 90 | 97 |
| o"i" | 1 | 94 | 96 |
| o"j" | 1 | 90 | 96 |
| o"k" | 1 | 94 | 100 |
| o"l" | 1 | 92 | 98 |
| o"m" | 1 | 93 | 96 |
| o"n" | 1 | 93 | 97 |
| o"o" | 1 | 92 | 100 |
| p"p | 1 | 92 | 98 |
| p"h" | 1 | 90 | 96 |
| p"i" | 1 | 92 | 96 |
| p"j" | 1 | 87 | 97 |
| p"k" | 1 | 87 | 100 |
| p"l" | 1 | 100 | 100 |
| p"m" | 1 | 94 | 98 |
| p"n" | 1 | 90 | 98 |
| p"o" | 1 | 86 | 98 |
| p"p" | 1 | 100 | 100 |
| q"p | 1 | 100 | 100 |
| q"h" | 1 | 96 | 96 |
| q"i" | 1 | 91 | 94 |
| q"j" | 1 | 90 | 97 |
| q"k" | 1 | 86 | 97 |
| q"l" | 1 | 88 | 97 |
| q"m" | 1 | 99 | 99 |
| q"n" | 1 | 90 | 95 |
| q"o" | 1 | 85 | 97 |
| q"p" | 1 | 90 | 97 |
| q"q" | 1 | 100 | 98 |
| r"p | 1 | 100 | 100 |
| r"h" | 1 | 86 | 98 |
| r"i" | 1 | 100 | 100 |
| r"j" | 1 | 96 | 96 |
| r"k" | 1 | 95 | 95 |
| r"l" | 1 | 90 | 99 |
| r"m" | 1 | 90 | 100 |
| r"n" | 1 | 100 | 100 |
| r"o" | 1 | 98 | 100 |
| r"p" | 1 | 85 | 100 |
| r"q" | 1 | 87 | 100 |
| r"r" | 1 | 86 | 100 |
| s"p | 1 | 98 | 100 |
| s"h" | 1 | 97 | 98 |
| s"i" | 1 | 85 | 95 |
| s"j" | 1 | 85 | 97 |
| s"k" | 1 | 85 | 93 |
| s"l" | 1 | 86 | 97 |
| s"m" | 1 | 92 | 98 |
| s"n" | 1 | 92 | 10 |
| s"o" | 1 | 95 | 100 |
| s"p" | 1 | 99 | 97 |
| s"q" | 1 | 92 | 99 |
| s"r" | 1 | 88 | 99 |
| s"s" | 1 | 98 | 100 |
| t"p | 1 | 88 | 94 |
| t"h" | 1 | 85 | 95 |
| t"i" | 1 | 90 | 97 |
| t"j" | 1 | 98 | 100 |
| t"k" | 1 | 90 | 98 |
| t"l" | 1 | 87 | 95 |
| t"m" | 1 | 95 | 96 |
| t"n" | 1 | 93 | 100 |
| t"o" | 1 | 98 | 100 |
| t"p" | 1 | 97 | 100 |
| t"q" | 1 | 99 | 95 |
| t"r" | 1 | 85 | 89 |
| t"s" | 1 | 86 | 91 |
| t"t" | 1 | 85 | 86 |

TABLE 4-continued

Bivalent Compounds from Monovalent Compounds h" to w"

| Monovalent Compounds | Tag | HPLC Purity (%) UV 254 nm | Sedex |
|---|---|---|---|
| u"p | 1 | 100 | 100 |
| u"h" | 1 | 87 | 90 |
| u"i" | 1 | 85 | 96 |
| u"j" | 1 | 85 | 97 |
| u"k" | 1 | 85 | 95 |
| u"l" | 1 | 93 | 97 |
| u"m" | 1 | 91 | 97 |
| u"n" | 1 | 97 | 95 |
| u"o" | 1 | 98 | 100 |
| u"p" | 1 | 85 | 88 |
| u"q" | 1 | 100 | 100 |
| u"r" | 1 | 99 | 96 |
| u"s" | 1 | 95 | 100 |
| u"t" | 1 | 91 | 99 |
| u"u" | 1 | 99 | 100 |
| v"p | 1 | 93 | 98 |
| v"h" | 1 | 86 | 95 |
| v"i" | 1 | 88 | 95 |
| v"j" | 1 | 88 | 96 |
| v"k" | 1 | 100 | 100 |
| v"l" | 1 | 99 | 99 |
| v"m" | 1 | 87 | 96 |
| v"n" | 1 | 87 | 96 |
| v"o" | 1 | 99 | 99 |
| v"p" | 1 | 97 | 97 |
| v"q" | 1 | 90 | 90 |
| v"r" | 1 | 85 | 93 |
| v"s" | 1 | 85 | 85 |
| v"t" | 1 | 85 | 94 |
| v"u" | 1 | 85 | 94 |
| v"v" | 1 | 96 | 96 |
| w"p | 1 | 91 | 95 |
| w"h" | 1 | 90 | 98 |
| w"i" | 1 | 95 | 95 |
| w"j" | 1 | 90 | 90 |
| w"k" | 1 | 90 | 90 |
| w"l" | 1 | 85 | 85 |
| w"m" | 1 | 85 | 85 |
| w"n" | 1 | 88 | 88 |
| w"o" | 1 | 85 | 85 |
| w"p" | 1 | 90 | 90 |
| w"q" | 1 | 97 | 97 |
| w"r" | 1 | 90 | 90 |
| w"s" | 1 | 88 | 88 |
| w"t" | 1 | 87 | 87 |
| w"u" | 1 | 85 | 85 |
| w"v" | 1 | 90 | 90 |
| w"w" | 1 | 90 | 90 |
| h"p | 3 | 99 | 100 |
| h"h" | 3 | 94 | 90 |
| i"p | 3 | 100 | 100 |
| i"h" | 3 | 92 | 90 |
| i"i" | 3 | 100 | 98 |
| j"p | 3 | 100 | 100 |
| j"h" | 3 | 96 | 100 |
| j"i" | 3 | 93 | 98 |
| j"j" | 3 | 95 | 90 |
| k"p | 3 | 99 | 97 |
| k"h" | 3 | 100 | 100 |
| k"i" | 3 | 100 | 100 |
| k"j" | 3 | 94 | 100 |
| k"k" | 3 | 95 | 95 |
| l"p | 3 | 100 | 100 |
| l"h" | 3 | 96 | 100 |
| l"i" | 3 | 99 | 100 |
| l"j" | 3 | 100 | 100 |
| l"k" | 3 | 100 | 100 |
| l"l" | 3 | 91 | 100 |
| m"p | 3 | 98 | 100 |
| m"h" | 3 | 97 | 92 |
| m"i" | 3 | 91 | 90 |
| m"j" | 3 | 100 | 100 |
| m"k" | 3 | 100 | 100 |
| m"l" | 3 | 100 | 97 |
| m"m" | 3 | 100 | 100 |
| n"p | 3 | 100 | 100 |
| n"h" | 3 | 98 | 100 |
| n"i" | 3 | 88 | 97 |
| n"j" | 3 | 100 | 100 |
| n"k" | 3 | 97 | 97 |
| n"l" | 3 | 100 | 100 |
| n"m" | 3 | 94 | 100 |
| n"n" | 3 | 100 | 100 |
| o"p | 3 | 91 | 95 |
| o"h" | 3 | 90 | 100 |
| o"i" | 3 | 97 | 100 |
| o"j" | 3 | 100 | 100 |
| o"k" | 3 | 100 | 100 |
| o"l" | 3 | 96 | 100 |
| o"m" | 3 | 97 | 91 |
| o"n" | 3 | 92 | 100 |
| o"o" | 3 | 93 | 93 |
| p"p | 3 | 100 | 100 |
| p"h" | 3 | 97 | 97 |
| p"i" | 3 | 98 | 100 |
| P"j" | 3 | 100 | 100 |
| p"k" | 3 | 100 | 100 |
| p"l" | 3 | 97 | 100 |
| p"m" | 3 | 98 | 100 |
| p"n" | 3 | 100 | 100 |
| p"o" | 3 | 100 | 100 |
| p"p" | 3 | 94 | 90 |
| q"p | 3 | 100 | 100 |
| q"h" | 3 | 94 | 100 |
| q"i" | 3 | 97 | 99 |
| q"j" | 3 | 100 | 100 |
| q"k" | 3 | 100 | 100 |
| q"l" | 3 | 95 | 100 |
| q"m" | 3 | 96 | 100 |
| q"n" | 3 | 100 | 100 |
| q"o" | 3 | 98 | 100 |
| q"p" | 3 | 100 | 100 |
| q"q" | 3 | 97 | 92 |
| s"p | 3 | 93 | 100 |
| s"h" | 3 | 92 | 91 |
| s"i" | 3 | 100 | 100 |
| s"j" | 3 | 100 | 100 |
| s"k" | 3 | 100 | 100 |
| s"l" | 3 | 100 | 100 |
| s"m" | 3 | 81 | 100 |
| s"n" | 3 | 91 | 98 |
| s"o" | 3 | 100 | 100 |
| s"p" | 3 | 100 | 100 |
| s"q" | 3 | 92 | 93 |
| s"s" | 3 | 86 | 96 |
| t"p | 3 | 98 | 99 |
| t"h" | 3 | 93 | 98 |
| t"i" | 3 | 100 | 100 |
| t"j" | 3 | 95 | 100 |
| t"k" | 3 | 100 | 100 |
| t"l" | 3 | 100 | 100 |
| t"m" | 3 | 100 | 100 |
| t"n" | 3 | 92 | 100 |
| t"o" | 3 | 100 | 100 |
| t"p" | 3 | 100 | 100 |
| t"q" | 3 | 100 | 100 |
| t"s" | 3 | 86 | 91 |
| t"t" | 3 | 97 | 100 |
| u"p | 3 | 98 | 95 |
| u"h" | 3 | 100 | 100 |
| u"i" | 3 | 100 | 100 |
| u"j" | 3 | 84 | 100 |
| u"k" | 3 | 100 | 100 |
| u"l" | 3 | 100 | 100 |
| u"m" | 3 | 95 | 98 |
| u"n" | 3 | 89 | 91 |
| u"o" | 3 | 100 | 100 |
| u"p" | 3 | 100 | 100 |

TABLE 4-continued

Bivalent Compounds from Monovalent Compounds h" to w"

| Monovalent Compounds | Tag | HPLC Purity (%) UV 254 nm | Sedex |
|---|---|---|---|
| u"q" | 3 | 92 | 97 |
| u"s" | 3 | 100 | 100 |
| u"t" | 3 | 100 | 100 |
| u"u" | 3 | 100 | 100 |
| v"p | 3 | 100 | 100 |
| v"h" | 3 | 82 | 100 |
| v"i" | 3 | 100 | 100 |
| v"j" | 3 | 100 | 100 |
| v"k" | 3 | 96 | 96 |
| v"l" | 3 | 100 | 97 |
| v"m" | 3 | 100 | 100 |
| v"n" | 3 | 100 | 100 |
| v"o" | 3 | 99 | 100 |
| v"p" | 3 | 100 | 100 |
| v"q" | 3 | 96 | 100 |
| v"s" | 3 | 100 | 99 |
| v"t" | 3 | 94 | 100 |
| v"u" | 3 | 100 | 100 |
| v"v" | 3 | 100 | 100 |
| w"p | 3 | 98 | 100 |
| w"h" | 3 | 82 | 90 |
| w"i" | 3 | 96 | 100 |
| w"j" | 3 | 100 | 100 |
| w"k" | 3 | 90 | 95 |
| w"l" | 3 | 97 | 100 |
| w"m" | 3 | 100 | 100 |
| w"n" | 3 | 92 | 92 |
| w"o" | 3 | 100 | 100 |
| w"p" | 3 | 91 | 91 |
| w"q" | 3 | 100 | 100 |
| w"s" | 3 | 89 | 90 |
| w"t" | 3 | 93 | 100 |
| w"u" | 3 | 97 | 100 |
| w"v" | 3 | 100 | 100 |
| w"w" | 3 | 100 | 100 |

TABLE 5

Representative Mass Spec Results for Bivalent Compounds of Monovalent Compounds h" to w"

| Monovalent Compounds | Tag | Mass theoretical | found |
|---|---|---|---|
| h"h" | 1 | 1233.53 (M + K) | 1233.52 |
| i"i" | 1 | 1096.62 (M + 2) | 1096.62 |
| k"p | 1 | 861.42 (M + 1) | 861.45 |
| l"k" | 1 | 1127.58 (M + 2) | 1127.56 |
| m"h" | 1 | 1233.52 (M + K) | 1233.56 |
| n"n" | 1 | 1279 (M + K) | 1279.60 |
| o"i" | 1 | 1148 (M + K) | 1148.62 |
| o"o" | 1 | 1126.64 (M + 2) | 1126.64 |
| p"o" | 1 | 1164.53 (M + K) | 1164.54 |
| r"p | 1 | 893.36 (M + 2) | 893.37 |
| r"j" | 1 | 1237.52 (N + Na) | 1237.61 |
| s"p" | 1 | 1100.51 (M + 1) | 1100.57 |
| s"s" | 1 | 1095.49 (M + Na) | 1095.56 |
| t"o" | 1 | 1100.52 (M + 1) | 1100.61 |
| t"t" | 1 | 1075.41 (M + 1) | 1075.47 |
| u"n" | 1 | 1164.52 (M + Na) | 1164.56 |
| u"u" | 1 | 1043.49 (M + 1) | 1043.62 |
| v"l" | 1 | 1178.50 (M + 2) | 1178.59 |
| w"i" | 1 | 1256.54 (M + K) | 1256.54 |
| w"r" | 1 | 1287.50 (M + Na) | 1287.55 |
| h"h" | 3 | 1035.60 (M + H) | 1035.63 |
| i"i" | 3 | 935.64 (M + H) | 935.64 |
| l"j" | 3 | 1024.60 (M + H) | 1024.64 |
| m"m" | 3 | 1035.60 (M + H) | 1035.64 |
| n"k" | 3 | 1023.65 (M + H) | 1023.68 |
| o"o" | 3 | 965.67 (M + H) | 965.71 |

TABLE 5-continued

Representative Mass Spec Results for Bivalent Compounds of Monovalent Compounds h" to w"

| Monovalent Compounds | Tag | Mass theoretical | found |
|---|---|---|---|
| p"i" | 3 | 951.60 (M + H) | 951.64 |
| p"n" | 3 | 1024.60 (M + H) | 1024.64 |
| q"h" | 3 | 1035.60 (M + H) | 1035.57 |
| q"l" | 3 | 1001.58 (M + H) | 1001.62 |
| q"q" | 3 | 1035.60 (M + H) | 1035.60 |
| s"j" | 3 | 997.60 (M + H) | 997.57 |
| s"o" | 3 | 939.61 (M + H) | 939.65 |
| s"s" | 3 | 913.56 (M + H) | 913.58 |
| t"p | 3 | 1035.60 (M + H) | 1035.57 |
| t"l" | 3 | 941.51 (M + H) | 941.55 |
| u"n" | 3 | 982.59 (M + H) | 982.61 |
| u"u" | 3 | 883.54 (M + H) | 883.56 |
| v"i" | 3 | 1001.58 (M + H) | 1001.61 |
| v"p" | 3 | 1017.54 (M + H) | 1017.56 |
| w"m" | 3 | 1108.60 (M + H) | 1108.63 |

TABLE 6

Bivalent Compounds from Monovalent Compounds x" to k'"

| Monovalent Compounds | Tag | Mass Spec (M + H)+ calculated | found | HPLC Purity (%) UV 254 nm | SEDEX |
|---|---|---|---|---|---|
| x"x" | 3 | 1135.74 | 1135.50 | 88 | 100 |
| x"y" | 3 | 1195.74 | 1195.54 | 97 | 100 |
| x"z" | 3 | 1234.81 | 1234.59 | 98 | 100 |
| x"a'" | 3 | 1162.79 | 1162.51 | 93 | 100 |
| x"b'" | 3 | 1192.8 | 1192.78 | 98 | 100 |
| x"c'" | 3 | 1218.85 | 1218.61 | 100 | 100 |
| x"d'" | 3 | 1246.86 | 1246.74 | 100 | 100 |
| y"y" | 3 | 1255.75 | 1255.72 | 100 | 100 |
| y"z" | 3 | 1294.81 | 1294.78 | 91 | 95 |
| y"a'" | 3 | 1222.79 | 1222.62 | 100 | 100 |
| y"b'" | 3 | 1252.80 | 1252.66 | 95 | 100 |
| y"c'" | 3 | 1278.85 | 1278.70 | 93 | 100 |
| y"d'" | 3 | 1306.86 | 1306.68 | 99 | 100 |
| z"z" | 3 | 1333.88 | 1333.81 | 90 | 99 |
| z"a'" | 3 | 1261.85 | 1261.88 | 89 | 90 |
| z"b'" | 3 | 1291.87 | 1291.96 | 99 | 100 |
| z"c'" | 3 | 1317.92 | 1317.97 | 94 | 100 |
| z"d'" | 3 | 1345.92 | 1345.91 | 99 | 98 |
| a'"a'" | 3 | 1189.83 | 1189.64 | 100 | 100 |
| a'"b'" | 3 | 1219.84 | 1219.71 | 98 | 95 |
| a'"c'" | 3 | 1245.92 | 1245.73 | 98 | 99 |
| a'"d'" | 3 | 1273.90 | 1273.83 | 87 | 96 |
| b'"b'" | 3 | 1249.85 | 1249.71 | 98 | 99 |
| b'"c'" | 3 | 1275.91 | 1275.68 | 94 | 99 |
| b'"d'" | 3 | 1303.91 | 1303.74 | 98 | 100 |
| c'"c'" | 3 | 1301.96 | 1301.80 | 98 | 100 |
| c'"d'" | 3 | 1329.96 | 1329.85 | 100 | 100 |
| d'"d'" | 3 | 1357.97 | 1357.69 | 100 | 100 |
| x"p | 3 | 786.49 | 786.26 | 91 | 100 |
| y"p | 3 | 846.49 | 846.26 | 100 | 100 |
| z"p | 3 | 885.56 | 885.47 | 98 | 100 |
| a'"p | 3 | 813.54 | 813.34 | 95 | 100 |
| b'"p | 3 | 843.55 | 843.31 | 91 | 99 |
| c'"p | 3 | 869.6 | 869.40 | 82 | 94 |
| d'"p | 3 | 897.61 | 897.41 | 95 | 100 |
| k'"p | 3 | 885.11 | 885.52 | 100 | 100 |
| j'"p | 3 | 897.16 | 897.58 | 100 | 100 |

TABLE 6-continued

Bivalent Compounds from Monovalent Compounds x'' to k'''

| Monovalent Compounds | Tag | Mass Spec (M + H)+ calculated | found | HPLC Purity (%) UV 254 nm | SEDEX |
|---|---|---|---|---|---|
| h'''p | 3 | 843.07 | 843.54 | 100 | 100 |
| g'''p | 3 | 813.04 | 813.37 | 100 | 100 |
| f'''p | 3 | 785.98 | 786.49 | 100 | 100 |
| i'''p | 3 | 869.15 | 869.40 | 100 | 100 |
| e'''p | 3 | 846.09 | 846.33 | 100 | 100 |
| i'''i''' | 3 | 1301.8 | 1302.04 | 100 | 100 |
| i'''g''' | 3 | 1245.69 | 1245.87 | 100 | 100 |
| i'''k''' | 3 | 1317.75 | 1317.93 | 100 | 100 |
| i'''h''' | 3 | 1275.72 | 1275.82 | 100 | 100 |
| i'''f''' | 3 | 1218.62 | 1218.89 | 100 | 100 |
| i'''j''' | 3 | 1329.81 | 1329.98 | 100 | 100 |
| i'''e''' | 3 | 1278.74 | 1278.85 | 100 | 100 |
| g'''g''' | 3 | 1189.58 | 1189.73 | 100 | 100 |
| g'''k''' | 3 | 1261.65 | 1261.98 | 100 | 100 |
| g'''h''' | 3 | 1219.61 | 1219.75 | 100 | 100 |
| g'''f''' | 3 | 1162.52 | 1162.69 | 100 | 100 |
| g'''j''' | 3 | 1273.70 | 1273.76 | 100 | 100 |
| g'''e''' | 3 | 1222.63 | 1222.82 | 100 | 100 |
| k'''k''' | 3 | 1333.71 | 1333.86 | 100 | 100 |
| k'''h''' | 3 | 1291.67 | 1291.86 | 100 | 100 |
| k'''f''' | 3 | 1234.58 | 1234.73 | 100 | 100 |
| k'''j''' | 3 | 1345.77 | 1345.84 | 100 | 100 |
| k'''e''' | 3 | 1294.70 | 1294.78 | 100 | 100 |
| h'''h''' | 3 | 1249.64 | 1249.78 | 100 | 100 |
| h'''f''' | 3 | 1192.54 | 1192.80 | 100 | 100 |
| h'''j''' | 3 | 1303.73 | 1303.86 | 100 | 100 |
| h'''e''' | 3 | 1252.66 | 1252.79 | 100 | 100 |
| f'''f''' | 3 | 1135.45 | 1135.60 | 100 | 100 |
| f'''j''' | 3 | 1246.64 | 1246.85 | 100 | 100 |
| f'''e''' | 3 | 1195.57 | 1195.64 | 100 | 100 |
| j'''j''' | 3 | 1357.82 | 1357.93 | 98 | 100 |
| j'''e''' | 3 | 1306.75 | 1306.68 | 100 | 100 |
| e'''e''' | 3 | 1255.68 | 1255.68 | 100 | 100 |
| h'''y'' | 3 | 1252.66 | 1252.53 | 100 | 100 |
| k'''y'' | 3 | 1294.70 | 1294.58 | 100 | 100 |
| g'''y'' | 3 | 1222.63 | 1222.59 | 100 | 100 |
| j'''y'' | 3 | 1306.75 | 1306.63 | 100 | 100 |
| e'''y'' | 3 | 1255.68 | 1255.62 | 100 | 100 |
| i'''c''' | 3 | 1301.8 | 1301.76 | 100 | 100 |
| e'''c''' | 3 | 1278.74 | 1278.73 | 100 | 100 |
| f'''c''' | 3 | 1218.62 | 1218.68 | 100 | 100 |
| h'''c''' | 3 | 1275.72 | 1275.78 | 100 | 100 |
| e'''x'' | 3 | 1195.57 | 1195.61 | 97 | 100 |
| e'''b''' | 3 | 1252.66 | 1252.61 | 100 | 100 |
| i'''b''' | 3 | 1275.72 | 1275.64 | 100 | 100 |
| j'''x'' | 3 | 1246.64 | 1246.61 | 95 | 99 |
| g'''c''' | 3 | 1245.69 | 1246.04 | 100 | 100 |
| k'''c''' | 3 | 1317.75 | 1318.13 | 99 | 100 |
| i'''z'' | 3 | 1317.75 | 1318.07 | 100 | 100 |
| k'''z'' | 3 | 1333.71 | 1333.88 | 100 | 100 |
| h'''z'' | 3 | 1291.67 | 1291.94 | 100 | 100 |
| f'''z'' | 3 | 1234.58 | 1234.77 | 99 | 100 |
| j'''z'' | 3 | 1345.77 | 1346.13 | 100 | 100 |
| e'''z'' | 3 | 1294.70 | 1294.92 | 100 | 100 |
| f'''a''' | 3 | 1162.52 | 1162.87 | 98 | 100 |
| f'''b''' | 3 | 1192.54 | 1192.93 | 100 | 100 |
| i'''x'' | 3 | 1218.62 | 1218.96 | 100 | 100 |
| g'''x'' | 3 | 1162.52 | 1162.88 | 100 | 100 |
| k'''x'' | 3 | 1234.58 | 1234.94 | 100 | 100 |
| f'''x'' | 3 | 1135.45 | 1135.90 | 100 | 100 |
| gi'''d''' | 3 | 1273.70 | 1274.06 | 100 | 100 |
| f'''d''' | 3 | 1246.64 | 1247.00 | 100 | 100 |
| i'''y'' | 3 | 1278.74 | | 100 | 100 |
| i'''d''' | 3 | 1329.81 | | | |
| i'''a''' | 3 | 1245.69 | | 98 | 100 |
| g'''z'' | 3 | 1261.65 | | | |
| g'''a''' | 3 | 1189.58 | | | |
| k'''d''' | 3 | 1345.77 | | | |
| k'''a''' | 3 | 1261.65 | | 99 | 100 |
| g'''b''' | 3 | 1219.61 | | 95 | 100 |
| k'''b''' | 3 | 1291.67 | | 97 | 100 |
| h'''a''' | 3 | 1219.61 | | 100 | 100 |
| h'''b''' | 3 | 1249.64 | | 98 | 100 |
| h'''x'' | 3 | 1192.54 | | | |
| h'''d''' | 3 | 1303.73 | | 99 | 100 |
| f''y'' | 3 | 1195.57 | | | |
| j'''c''' | 3 | 1329.81 | | | |
| j'''a''' | 3 | 1273.7 | | | |
| j'''b''' | 3 | 1303.73 | | 94 | 99 |
| j'''d''' | 3 | 1357.82 | | 100 | 100 |
| e'''a''' | 3 | 1222.63 | | | |
| e'''d''' | 3 | 1306.75 | | | |

TABLE 7

Bivalent Compounds from Monovalent Compounds c'''' to e''''

| Monovalent Compounds | Tag | Mass (desired) | Mass (found) | HPLC purity UV 254 nm (%) |
|---|---|---|---|---|
| c''''c'''' | 1 | 1629.67 | 1629.65 | 100 |
| c''''d'''' | 1 | 1724.72 | 1724.49 | 100 |
| d''''d'''' | 1 | 1819.77 | 1819.62 | 100 |
| c''''e'''' | 1 | 1812.83 | 1812.94 | 98 |
| d''''e'''' | 1 | 1907.88 | 1907.91 | 100 |
| e''''e'''' | 1 | 1995.99 | 1996.06 | 100 |
| c''''c'''' | 3 | 1469.71 | 1469.68 | 100 |
| d''''d'''' | 3 | 1659.81 | 1659.91 | 100 |
| e''''e'''' | 3 | 1836.03 | 1836.27 | 100 |

From the foregoing description, one skilled in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure, which is defined in the following claims.

What is claimed is:

1. A dipeptide mimic having the structure:

wherein R0 is a fluorescein tag, a biotin tag or a polyether tag.

2. A protein mimic having the structure:

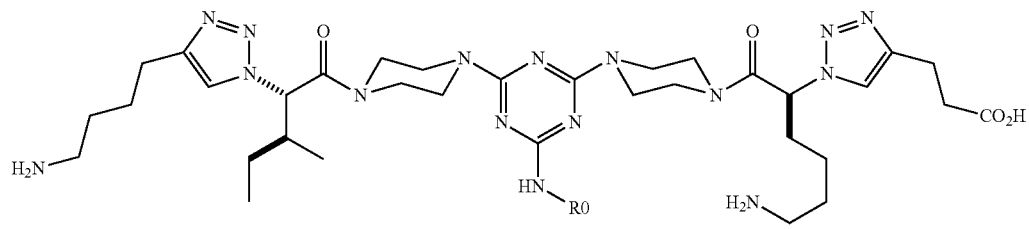

wherein R0 is a fluorescein tag, a biotin tag or a polyether tag.

3. A protein mimic having the structure:

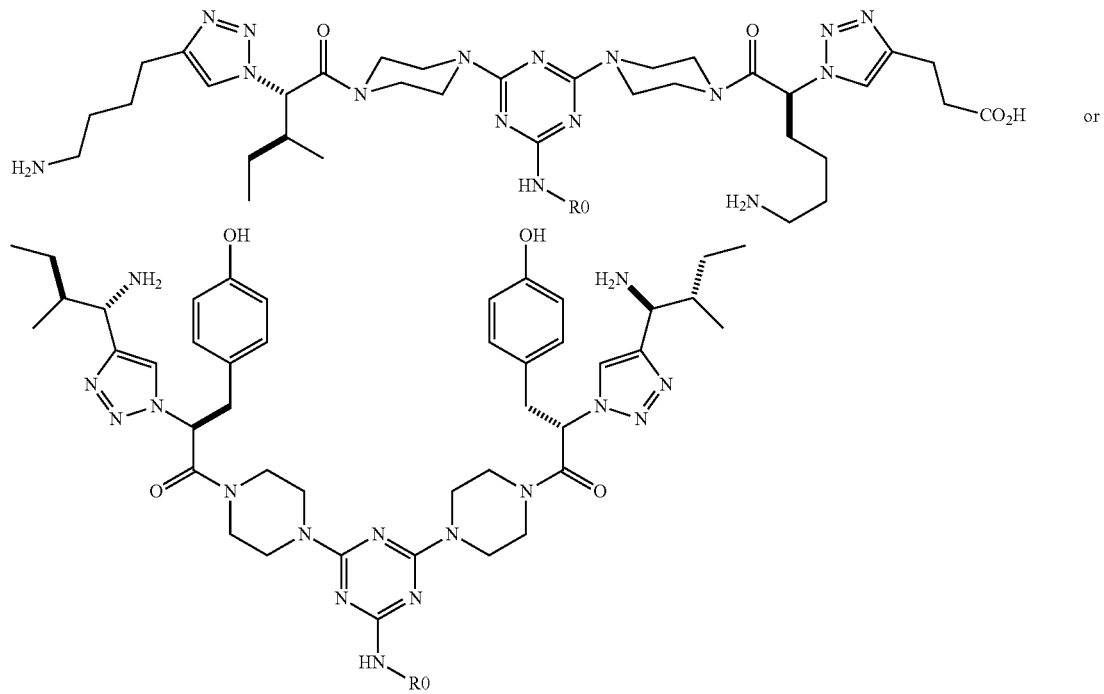

wherein R0 is a fluorescein tag, a biotin tag or a polyether tag.

4. A dipeptide mimic to mimic proteins in a protein-protein interactions having the structure

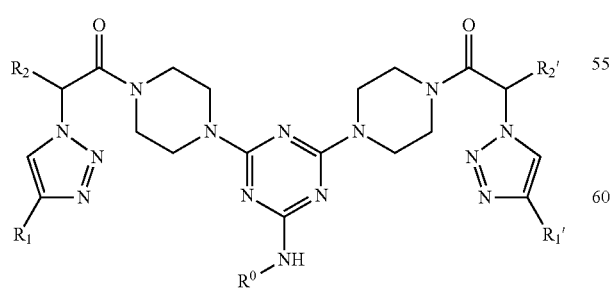

wherein R0 is a fluorescein tag and wherein R1, R2 and R1' and R2' are selected from (a) R1 is $(CH_2)_4NH_2$, R2 is $CHCH_3CH_2CH_3$;
(b) R1 is —$(CH_2)_4NH_2$, R2 is —H;
(c) R1 is —$CH_2CH_2COOH$, R2 is —$CHCH_3CH_2CH_3$;
(d) R1 is —$CH_2CH_2OH$, R2 is —H;
(e) R1 is —$CH_2CHCH_3OH$, R2 is —H;
(f) R1 is —$CH_2CH_2OH$, R2 is —$CH(CH_3)_2$;
(g) R1 is —$(CH_2)_4NH_2$, R2 is —$CHCH_3OH$;
(h) R1 is —$CH_2CHCH_3OH$, R2 is —$(CH_2)_4NH_2$;
(i) R1 is —$(CH_2)_3NHCNHNH_2$, R2 is —$CH_3$;
(j) R1 is —$(CH_2)_3NHCNHNH_2$, R2 is —$CHCH_3CH_2CH_3$;
(k) R1 is —$(CH_2)_3NHCNHNH_2$, R2 is —H;
(l) R1 is —$CH_2CH_2COOH$, R2 is —$(CH_2)_4NH_2$;
(m) R1 is —$CH_2CH_2COOH$, R2 is —$CH_3$;
(n) R1 is —$CH_2CH_2COOH$, R2 is

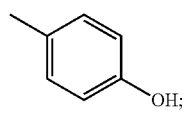

(o) R1 is —$(CH_2)_4CH_3$, R2 is —$(CH_2)_4NH_2$;
(h") R1

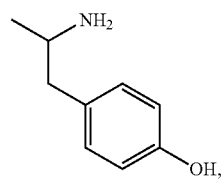

R2 is —CHCH₃CH₂CH₃;

(i") R1 is —CHNH₂CH₂CH(CH₃)₂, R2 is —CHCH₃CH₂CH₃;

(j") R1 is —CHNH₂CH₂CH(CH₃)₂, R2 is

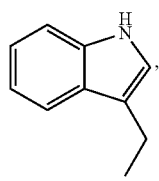

(k") R1 is —CHNH₂CH₂CH(CH₃)₂, R2 is —(CH₂)₄NH₂;

(l") R1 is —CHNH₂CH₂CH(CH₃)₂, R2 is —CH₂CH₂COOH;

(m") R1 is —CHNH₂CH₂CH(CH₃)₂, R2 is

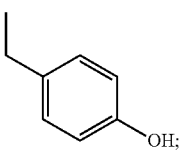

(n") R1 is —CHNH₂CHCH₃CH₂CH₃, R2 is

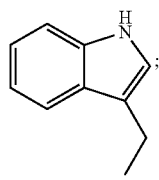

(o") R1 is —CHNH₂CHCH₃CH₂CH₃, R2 is —(CH₂)₄NH₂;

(p") R1 is —CHNH₂CHCH₃CH₂CH₃, R2 is —CH₂CH₂COOH;

(q") R1 is —CHNH₂CHCH₃CH₂CH₃, R2 is

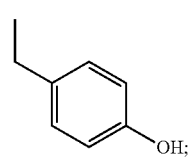

(r") R1 is —CHNH₂CH₂OH, R2 is

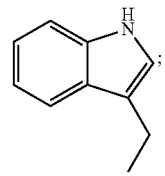

(s") R1 is —CHNH₂CH₂OH, R2 is —(CH₂)₄NH₂;
(t") R1 is —CHNH₂CH₂OH, R2 is —CH₂CH₂COOH;
(u") R1 is —CHNH₂CH₂OH, R2 is —CHCH₃CH₂CH₃;
(v") R1 is

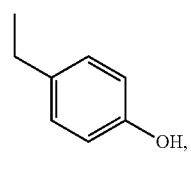

R2 is —CH₂CH₂COOH;

(w") R1 is

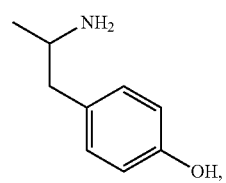

R2 is

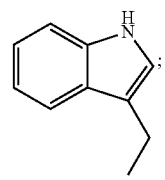

(l''') R1 is —CH₂NH₂, R2 is —(CH₂)₄NH₂;
(m''') R1 is —CHNH₂CHCH₃CH₂CH₃, R2 is —(CH₂)₃NHCNHNH₂;
(n''') R1 is —CHNH₂(CH₂)₄NH₂, R2 is —CH₂CH₂COOH;
(o''') R1 is —CHNH₂CHCH₃CH₂CH₃, R2 is —CH₂CONH₂;
(p''') R1 is —CHNH₂CH₂CONH₂, R2 is —(CH₂)₄NH₂;
(q''') R1 is —CHNH₂CH(CH₃)₂, R2 is —CH₂CONH₂;
(r''') R1 is —CHNH₂CH₂CONH₂, R2 is —CH₂CONH₂;
(s''') R1 is —(CH₂)₂SCH₃, R2 is —CH₂CH₂COOH;
(t''') R1 is —CHNH₂(CH₂)₄NH₂, R2 is —CHCH₃OH;
(u''') R1 is —CH₂NH₂, R2 is —CH₂COOH;
(v''') R1 is —CHNH₂, CH(CH₃)₂, R2 is —CH₂OH;
(w''') R1 is —CHNH₂CH₂CONH₂, R2 is —CH₂COOH;
(x''') R1 is —CHNH₂CHCH₃CH₂CH₃, R2 is —CH₂COOH
(y''') R1 is —CHNH₂CH₂OH, R2 is —CH₂COOH
(z") R1 is —C₆H₆C₂HN₃CHCOOHCHCH₃CH₂CH₃, R2 is —CH₂CH(CH₃)₂;

(a"") R1 is —C$_5$H$_3$NC$_2$HN$_3$CH$_2$COOH, R2 is —CH$_2$CH$_2$CONH$_2$; or
(b"") R1 is —C$_5$H$_3$NC$_2$HN$_3$CHCOOHCH$_2$CCONH$_2$, R2 is —CH$_2$CH$_2$CONH$_2$; and
(a) R1' is —(CH$_2$)$_4$NH$_2$, R2' is —CHCH$_3$CH$_2$CH$_3$;
(b) R1' is —(CH$_2$)$_4$NH$_2$, R2' is —H;
(c) R1' is —CH$_2$CH$_2$COOH, R2' is —CHCH$_3$CH$_2$CH$_3$;
(d) R1' is —CH$_2$CH$_2$OH, R2' is —H;
(e) R1' is —CH$_2$CHCH$_3$OH, R2' is —H;
(f) R1' is —CH$_2$CH$_2$OH, R2' is —CH(CH$_3$)$_2$;
(g) R1' is —(CH$_2$)$_4$NH$_2$, R2' is —CHCH$_3$OH;
(h) R1' is —CH$_2$CHCH$_3$OH, R2' is —(CH$_2$)$_4$NH$_2$;
(i) R1' is —(CH$_2$)$_3$NHCNHNH$_2$, R2' is —CH$_3$;
(j) R1' is —(CH$_2$)$_3$NHCNHNH$_2$, R2' is —CHCH$_3$CH$_2$CH$_3$;
(k) R1' is —(CH$_2$)$_3$NHCNHNH$_2$, R2' is —H;
(l) R1' is —CH$_2$CH$_2$COOH, R2' is —(CH$_2$)$_4$NH$_2$;
(m) R1' is —CH$_2$CH$_2$COOH, R2' is —CH$_3$;
(n) R1' is —CH$_2$CH$_2$OH, R2' is

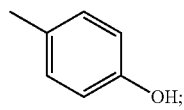

(o) R1' is —(CH$_2$)$_4$CH$_3$, R2' is —(CH$_2$)$_4$NH$_2$;
(h") R1'

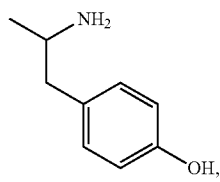

R2' is —CHCH$_3$CH$_2$CH$_3$;
(i") R1' is —CHNH$_2$CH$_2$CH(CH$_3$)$_2$, R2' is —CHCH$_3$CH$_2$CH$_3$;
(j") R1' is —CHNH$_2$CH$_2$CH(CH$_3$)$_2$, R2' is

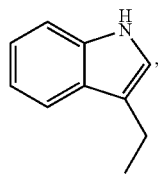

(k") R1' is —CHNH$_2$CH$_2$CH(CH$_3$)$_2$, R2' is —(CH$_2$)$_4$NH$_2$;
(l") R1' is —CHNH$_2$CH$_2$CH(CH$_3$)$_2$, R2' is —CH$_2$CH$_2$COOH;
(m") R1' is —CHNH$_2$CH$_2$CH(CH$_3$)$_2$, R2' is

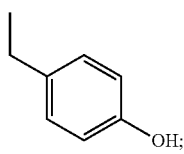

(n") R1' is —CHNH$_2$CHCH$_3$CH$_2$CH$_3$, R2' is

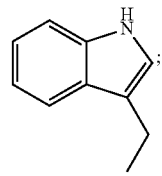

(o") R1' is —CHNH$_2$CHCH$_3$CH$_2$CH$_3$, R2' is —(CH$_2$)$_4$NH$_2$;
(p") R1' is —CHNH$_2$CHCH$_3$CH$_2$CH$_3$, R2' is —CH$_2$CH$_2$COOH;
(q") R1' is —CHNH$_2$CHCH$_3$CH$_2$CH$_3$, R2' is

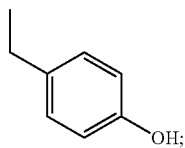

(r") R1' is —CHNH$_2$CH$_2$OH, R2' is

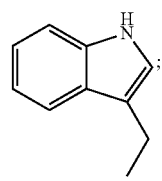

(s") R1' is —CHNH$_2$CH$_2$OH, R2' is —(CH$_2$)$_4$NH$_2$;
(t") R1' is —CHNH$_2$CH$_2$OH, R2' is —CH$_2$CH$_2$COOH;
(u") R1' is —CHNH$_2$CH$_2$OH, R2' is —CHCH$_3$CH$_2$CH$_3$;
(v") R1' is

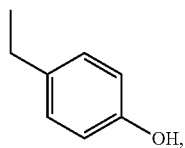

R2' is —CH$_2$CH$_2$COOH;
(w") R1'

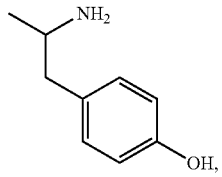

R2' is

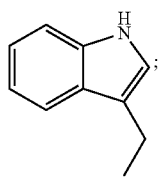

(l''') R1' is —CH₂NH₂, R2' is —(CH₂)₄NH₂;
(m''') R1' is —CHNH₂CHCH₃CH₂CH₃, R2' is —(CH₂)₃NHCNHNH₂;
(n''') R1' is —CHNH₂(CH₂)₄NH₂, R2' is —CH₂CH₂COOH;
(o''') R1' is —CHNH₂CHCH₃CH₂CH₃, R2' is —CH₂CONH₂;
(p''') R1' is —CHNH₂CH₂CONH₂, R2' is —(CH₂)₄NH₂;
(q''') R1' is —CHNH₂CH(CH₃)₂, R2' is —CH₂CONH₂;
(r''') R1' is —CHNH₂CH₂CONH₂, R2' is —CH₂CONH₂;
(s''') R1' is —CHNH₂(CH₂)₂SCH₃, R2' is —CH₂CH₂COOH;
(t''') R1' is —CHNH₂(CH₂)₄NH₂, R2' is —CHCH₃OH;
(u''') R1' is —CH₂NH₂, R2' is —CH₂CH₂COOH;
(v''') R1' is —CHNH₂CH(CH₃)₂, R2' is —CH₂OH;
(w''') R1' is —CHNH₂CH₂CONH₂, R2' is —CH₂CH₂COOH;
(x''') R1' is —CHNH₂CHCH₃CH₂CH₃, R2' is —CH₂CH₂COOH; or
(y''') R1' is —CHNH₂CH₂OH, R2' is —CH₂COOH.

5. A dipeptide mimic to mimic proteins in a protein-protein interactions having the structure

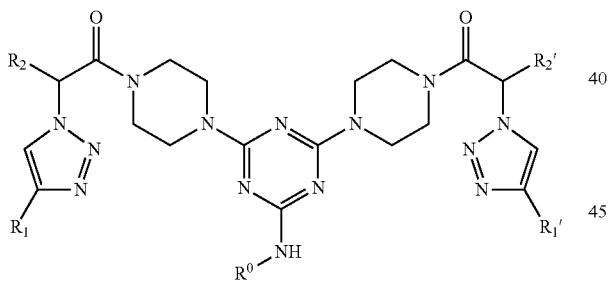

wherein R0 is a biotin tag and wherein R1, R2 and R1' and R2' are selected from

R1 is —(CH₂)₄NH₂, R2 is —CHCH₃CH₂CH₃;
R1 is —(CH₂)₄NH₂, R2 is —H;
R1 is —CH₂CH₂COOH, R2 is —CHCH₃CH₂CH₃;
R1 is —CH₂CH₂OH, R2 is —H;
R1 is —CH₂CHCH₃OH, R2 is —H;
R1 is —CH₂CH₂OH, R2 is —CH(CH₃)₂;
R1 is —(CH₂)₄NH₂, R2 is —CHCH₃OH;
R1 is —CH₂CHCH₃OH, R2 is —(CH₂)₄NH₂;
R1 is —(CH₂)₃NHCNHNH₂, R2 is —CH₃;
R1 is —(CH₂)₃NHCNHNH₂, R2 is —CHCH₃CH₂CH₃;
R1 is —(CH₂)₃NHCNHNH₂, R2 is —H;
R1 is —CH₂CH₂COOH, R2 is —(CH₂)₄NH₂;
R1 is —CH₂CH₂COOH, R2 is —CH₃;
R1 is —CH₂CH₂COOH, R2 is

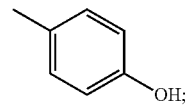

R1 is —(CH₂)₄CH₃, R2 is —(CH₂)₄NH₂;
R1 is

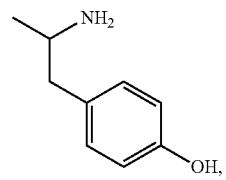

R2 is —CHCH₃CH₂CH₃;
R1 is —CHNH₂CH₂CH(CH₃)₂, R2 is —CHCH₃CH₂CH₃;
R1 is —CHNH₂CH₂CH(CH₃)₂, R2 is

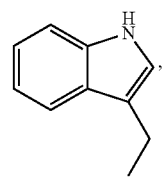

R1 is —CHNH₂CH₂CH(CH₃)₂, R2 is —(CH₂)₄NH₂;
R1 is —CHNH₂CH₂CH(CH₃)₂, R2 is —CH₂CH₂COOH;
R1 is —CHNH₂CH₂CH(CH₃)₂, R2 is

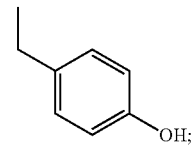

R1 is —CHNH₂CHCH₃CH₂CH₃, R2 is

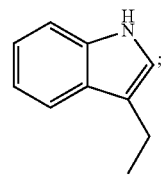

R1 is —CHNH₂CHCH₃CH₂CH₃, R2 is —(CH₂)₄NH₂;
R1 is —CHNH₂CHCH₃CH₂CH₃, R2 is —CH₂CH₂COOH;

149

R1 is —CHNH₂CHCH₃CH₂CH₃, R2 is

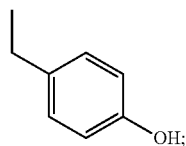

R1 is —CHNH₂CH₂OH, R2 is

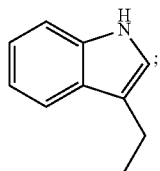

R1 is —CHNH₂CH₂OH, R2 is —(CH₂)₄NH₂;
R1 is —CHNH₂CH₂OH, R2 is —CH₂CH₂COOH;
R1 is —CHNH₂CH₂OH, R2 is —CHCH₃CH₂CH₃;
R1 is

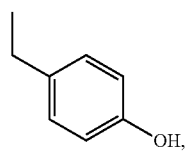

R2 is —CH₂CH₂COOH;
R1 is

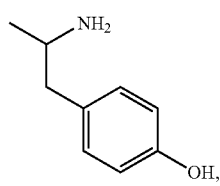

R2 is

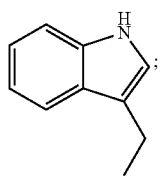

R1 is —CH₂NH₂, R2 is —(CH₂)₄NH₂;
R1 is —CHNH₂CHCH₃CH₂CH₃, R2 is —(CH₂)₃NHC-NHNH₂;
R1 is —CHNH₂(CH₂)₄NH₂, R2 is —CH₂CH₂COOH;
R1 is —CHNH₂CHCH₃CH₂CH₃, R2 is —CH₂CONH₂;
R1 is —CHNH₂CH₂CONH₂, R2 is —(CH₂)₄NH₂;
R1 is —CHNH₂CH(CH₃)₂, R2 is —CH₂CONH₂;
R1 is —CHNH₂CH₂CONH₂, R2 is —CH₂CONH₂;
R1 is —CHNH₂(CH₂)₂SCH₃, R2 is —CH₂CH₂COOH;
R1 is —CHNH₂(CH₂)₄NH₂, R2 is —CHCH₃OH;

150

R1 is —CH₂NH₂, R2 is —CH₂COOH;
R1 is —CHNH₂, CH(CH₃)₂, R2 is —CH₂OH;
R1 is —CHNH₂CH₂CONH₂, R2 is —CH₂COOH;
R1 is —CHNH₂CHCH₃CH₂CH₃, R2 is —CH₂COOH
R1 is —CHNH₂CH₂OH, R2 is —CH₂COOH
R1 is —C₆H₆C₂HN₃CHCOOHCHCH₃CH₂CH₃, R2 is —CH₂CH(CH₃)₂;
R1 is —C₅H₃NC₂HN₃CH₂COOH, R2 is —CH₂CH₂CONH₂; or
R1 is —C₅H₃NC₂HN₃CHCOOHCH₂CCONH₂, R2 is —CH₂CH₂CONH₂; and
R1' is —(CH₂)₄NH₂, R2' is —CHCH₃CH₂CH₃;
R1' is —(CH₂)₄NH₂, R2' is —H;
R1' is —CH₂CH₂COOH, R2' is —CHCH₃CH₂CH₃;
R1' is —CH₂CH₂OH, R2' is —H;
R1' is —CH₂CHCH₃OH, R2' is —H;
R1' is —CH₂CH₂OH, R2' is —CH(CH₃)₂;
R1' is —(CH₂)₄NH₂, R2' is —CHCH₃OH;
R1' is —CH₂CHCH₃OH, R2' is —(CH₂)₄NH₂;
R1' is —(CH₂)₃NHCNHNH₂, R2' is —CH₃;
R1' is —(CH₂)₃NHCNHNH₂, R2' is —CHCH₃CH₂CH₃;
R1' is —(CH₂)₃NHCNHNH₂, R2' is —H;
R1' is —CH₂CH₂COOH, R2' is —(CH₂)₄NH₂;
R1' is —CH₂CH₂COOH, R2' is —CH₃;
R1' is —CH₂CH₂OH, R2' is

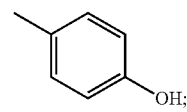

R1' is —(CH₂)₄CH₃, R2' is —(CH₂)₄NH₂;
R1'

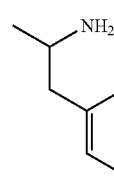

R2' is —CHCH₃CH₂CH₃;
R1' is —CHNH₂CH₂CH(CH₃)₂, R2' is —CHCH₃CH₂CH₃;
R1' is —CHNH₂CH₂CH(CH₃)₂, R2' is

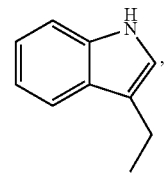

R1' is —CHNH₂CH₂CH(CH₃)₂, R2' is —(CH₂)₄NH₂;
R1' is —CHNH₂CH₂CH(CH₃)₂, R2' is —CH₂CH₂COOH;

R1' is —CHNH₂CH₂CH(CH₃)₂, R2' is

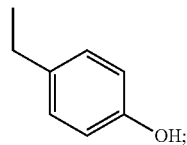

R1' is —CHNH₂CHCH₃CH₂CH₃, R2' is

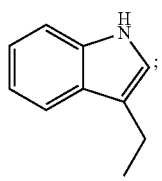

R1' is —CHNH₂CHCH₃CH₂CH₃, R2' is —(CH₂)₄NH₂;
R1' is —CHNH₂CHCH₃CH₂CH₃, R2' is —CH₂CH₂COOH;
R1' is —CHNH₂CHCH₃CH₂CH₃, R2' is

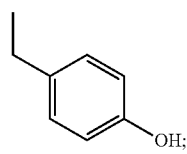

R1' is —CHNH₂CH₂OH, R2' is

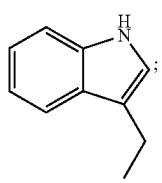

R1' is —CHNH₂CH₂OH, R2' is —(CH₂)₄NH₂;
R1' is —CHNH₂CH₂OH, R2' is —CH₂CH₂COOH;
R1' is —CHNH₂CH₂OH, R2' is —CHCH₃CH₂CH₃;
R1' is

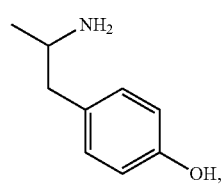

R2' is —CH₂CH₂COOH;

R1'

R2' is

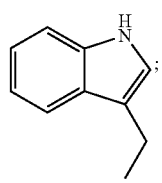

R1' is —CH₂NH₂, R2' is —(CH₂)₄NH₂;
R1' is —CHNH₂CHCH₃CH₂CH₃, R2' is —(CH₂)₃NHC-NHNH₂;
R1' is —CHNH₂(CH₂)₄NH₂, R2' is —CH₂CH₂COOH;
R1' is —CHNH₂CHCH₃CH₂CH₃, R2' is —CH₂CONH₂;
R1' is —CHNH₂CH₂CONH₂, R2' is —(CH₂)₄NH₂;
R1' is —CHNH₂CH(CH₃)₂, R2' is —CH₂CONH₂;
R1' is —CHNH₂CH₂CONH₂, R2' is —CH₂CONH₂;
R1' is —CHNH₂(CH₂)₂SCH₃, R2' is —CH₂CH₂COOH;
R1' is —CHNH₂(CH₂)₄NH₂, R2' is —CHCH₃OH;
R1' is —CH₂NH₂, R2' is —CH₂CH₂COOH;
R1' is —CHNH₂CH(CH₃)₂, R2' is —CH₂OH;
R1' is —CHNH₂CH₂CONH₂, R2' is —CH₂CH₂COOH;
R1' is —CHNH₂CHCH₃CH₂CH₃, R2' is —CH₂CH₂COOH; or
R1' is —CHNH₂CH₂OH, R2' is —CH₂COOH.

6. A dipeptide mimic to mimic proteins in a protein-protein interactions having the structure

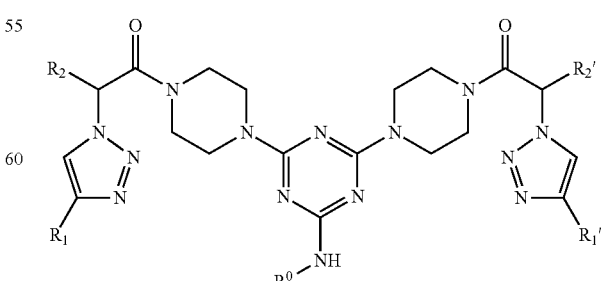

wherein R0 is a polyether tag having the structure

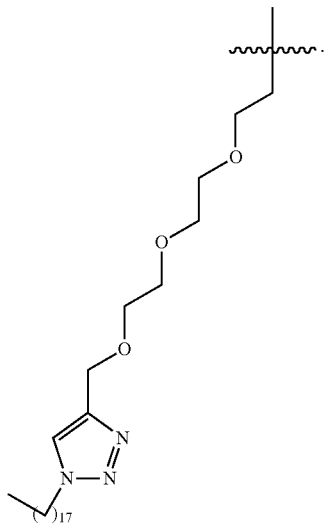

and
wherein R1, R2 and R1' and R2' are selected from
R1 is —(CH$_2$)$_4$NH$_2$, R2 is —CHCH$_3$CH$_2$CH$_3$;
R1 is —(CH$_2$)$_4$NH$_2$, R2 is —H;
R1 is —CH$_2$CH$_2$COOH, R2 is —CHCH$_3$CH$_2$CH$_3$;
R1 is —CH$_2$CH$_2$OH, R2 is —H;
R1 is —CH$_2$CHCH$_3$OH, R2 is —H;
R1 is —CH$_2$CH$_2$OH, R2 is —CH(CH$_3$)$_2$;
R1 is —(CH$_2$)$_4$NH$_2$, R2 is —CHCH$_3$OH;
R1 is —CH$_2$CHCH$_3$OH, R2 is —(CH$_2$)$_4$NH$_2$;
R1 is —(CH$_2$)$_3$NHCNHNH$_2$, R2 is —CH$_3$;
R1 is —(CH$_2$)$_3$NHCNHNH$_2$, R2 is —CHCH$_3$CH$_2$CH$_3$;
R1 is —(CH$_2$)$_3$NHCNHNH$_2$, R2 is —H;
R1 is —CH$_2$CH$_2$COOH, R2 is —(CH$_2$)$_4$NH$_2$;
R1 is —CH$_2$CH$_2$COOH, R2 is —CH$_3$;
R1 is —CH$_2$CH$_2$COOH, R2 is

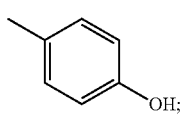

R1 is —(CH$_2$)$_4$CH$_3$, R2 is —(CH$_2$)$_4$NH$_2$;
R1 is

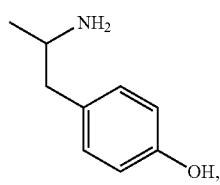

R2 is —CHCH$_3$CH$_2$CH$_3$;
R1 is —CHNH$_2$CH$_2$CH(CH$_3$)$_2$, R2 is —CHCH$_3$CH$_2$CH$_3$;

R1 is —CHNH$_2$CH$_2$CH(CH$_3$)$_2$, R2 is

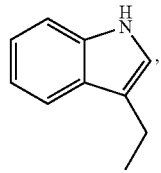

R1 is —CHNH$_2$CH$_2$CH(CH$_3$)$_2$, R2 is —(CH$_2$)$_4$NH$_2$;
R1 is —CHNH$_2$CH$_2$CH(CH$_3$)$_2$, R2 is —CH$_2$CH$_2$COOH;
R1 is —CHNH$_2$CH$_2$CH(CH$_3$)$_2$, R2 is

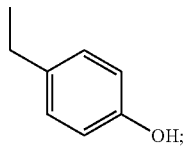

R1 is —CHNH$_2$CHCH$_3$CH$_2$CH$_3$, R2 is

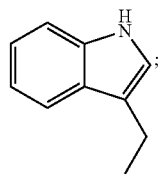

R1 is —CHNH$_2$CHCH$_3$CH$_2$CH$_3$, R2 is —(CH$_2$)$_4$NH$_2$;
R1 is —CHNH$_2$CHCH$_3$CH$_2$CH$_3$, R2 is —CH$_2$CH$_2$COOH;
R1 is —CHNH$_2$CHCH$_3$CH$_2$CH$_3$, R2 is

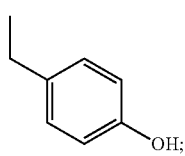

R1 is —CHNH$_2$CH$_2$OH, R2 is

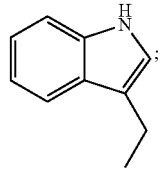

R1 is —CHNH$_2$CH$_2$OH, R2 is —(CH$_2$)$_4$NH$_2$;
R1 is —CHNH$_2$CH$_2$OH, R2 is —CH$_2$CH$_2$COOH;
R1 is —CHNH$_2$CH$_2$OH, R2 is —CHCH$_3$CH$_2$CH$_3$;

R1 is

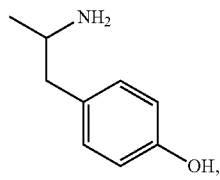

R2 is —CH₂CH₂COOH;
R1 is

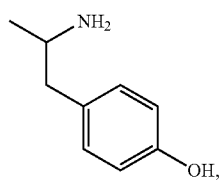

R2 is

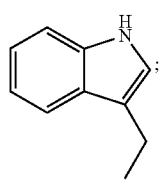;

R1 is —CH₂NH₂, R2 is —(CH₂)₄NH₂;
R1 is —CHNH₂CHCH₃CH₂CH₃, R2 is —(CH₂)₃NHC-NHNH₂;
R1 is —CHNH₂(CH₂)₄NH₂, R2 is —CH₂CH₂COOH;
R1 is —CHNH₂CHCH₃CH₂CH₃, R2 is —CH₂CONH₂;
R1 is —CHNH₂CH₂CONH₂, R2 is —(CH₂)₄NH₂;
R1 is —CHNH₂CH(CH₃)₂, R2 is —CH₂CONH₂;
R1 is —CHNH₂CH₂CONH₂, R2 is —CH₂CONH₂;
R1 is —CHNH₂(CH₂)₂SCH₃, R2 is —CH₂CH₂COOH;
R1 is —CHNH₂(CH₂)₄NH₂, R2 is —CHCH₃OH;
R1 is —CH₂NH₂, R2 is —CH₂COOH;
R1 is —CHNH₂, CH(CH₃)₂, R2 is —CH₂OH;
R1 is —CHNH₂CH₂CONH₂, R2 is —CH₂COOH;
R1 is —CHNH₂CHCH₃CH₂CH₃, R2 is —CH₂COOH
R1 is —CHNH₂CH₂OH, R2 is —CH₂COOH
R1 is —C₆H₆C₂HN₃CHCOOHCHCH₃CH₂CH₃, R2 is —CH₂CH(CH₃)₂;
R1 is —C₅H₃NC₂HN₃CH₂COOH, R2 is —CH₂CH₂CONH₂; or
R1 is -C₅H₃N C₂HN₃CHCOOHCH₂CCONH₂, R2 is —CH₂CH₂CONH₂; and
R1' is —(CH₂)₄NH₂, R2' is —CHCH₃CH₂CH₃;
R1' is —(CH₂)₄NH₂, R2' is —H;
R1' is —CH₂CH₂COOH, R2' is —CHCH₃CH₂CH₃;
R1' is —CH₂CH₂OH, R2' is —H;
R1' is —CH₂CHCH₃OH, R2' is —H;
R1' is —CH₂CH₂OH, R2' is —CH(CH₃)₂;
R1' is —(CH₂)₄NH₂, R2' is —CHCH₃OH;
R1' is —CH₂CHCH₃OH, R2' is —(CH₂)₄NH₂;
R1' is —(CH₂)₃NHCNHNH₂, R2' is —CH₃;
R1' is —(CH₂)₃NHCNHNH₂, R2' is —CHCH₃CH₂CH₃;
R1' is —(CH₂)₃NHCNHNH₂, R2' is —H;
R1' is —CH₂CH₂COOH, R2' is —(CH₂)₄NH₂;

R1' is —CH₂CH₂COOH, R2' is —CH₃;
R1' is —CH₂CH₂OH, R2' is

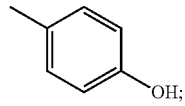;

R1' is —(CH₂)₄CH₃, R2' is —(CH₂)₄NH₂;
R1'

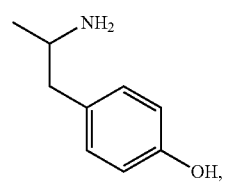

R2' is —CHCH₃CH₂CH₃;
R1' is —CHNH₂CH₂CH(CH₃)₂, R2' is —CHCH₃CH₂CH₃;
R1' is —CHNH₂CH₂CH(CH₃)₂, R2' is

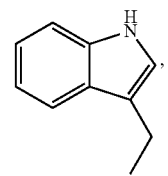

R1' is αCHNH₂CH₂CH(CH₃)₂, R2' is —(CH₂)₄NH₂;
R1' is —CHNH₂CH₂CH(CH₃)₂, R2' is —CH₂CH₂COOH;
R1' is —CHNH₂CH₂CH(CH₃)₂, R2' is

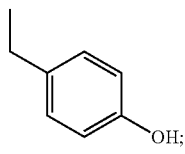

R1' is —CHNH₂CHCH₃CH₂CH₃, R2' is

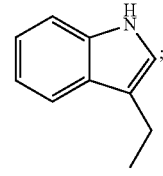;

R1' is —CHNH₂CHCH₃CH₂CH₃, R2' is —(CH₂)₄NH₂;
R1' is —CHNH₂CHCH₃CH₂CH₃, R2' is —CH₂CH₂COOH;

R1' is —CHNH₂CHCH₃CH₂CH₃, R2' is

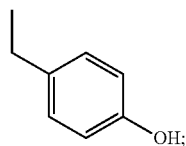

R1' is —CHNH₂CH₂OH, R2' is

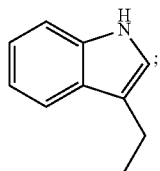

R1' is —CHNH₂CH₂OH, R2' is —(CH₂)₄NH₂;
R1' is —CHNH₂CH₂OH, R2' is —CH₂CH₂COOH;
R1' is —CHNH₂CH₂OH, R2' is —CHCH₃CH₂CH₃;
R1' is

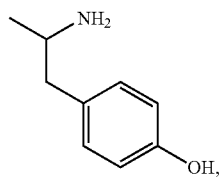

R2' is —CH₂CH₂COOH;
R1'

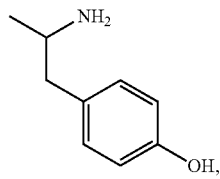

R2' is

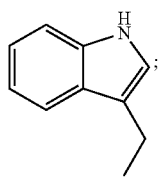

R1' is —CH₂NH₂, R2' is —(CH₂)₄NH₂;
R1' is —CHNH₂CHCH₃CH₂CH₃, R2' is —(CH₂)₃NHC-NHNH₂;
R1' is —CHNH₂(CH₂)₄NH₂, R2' is —CH₂CH₂COOH;
R1' is —CHNH₂CHCH₃CH₂CH₃, R2' is —CH₂CONH₂;
R1' is —CHNH₂CH₂CONH₂, R2' is —(CH₂)₄NH₂;
R1' is —CHNH₂CH(CH₃)₂, R2' is —CH₂CONH₂;
R1' is —CHNH₂CH₂CONH₂, R2' is —CH₂CONH₂;
R1' is —CHNH₂(CH₂)₂SCH₃, R2' is —CH₂CH₂COOH;

R1' is —CHNH₂(CH₂)₄NH₂, R2' is —CHCH₃OH;
R1' is —CH₂NH₂, R2' is —CH₂CH₂COOH;
R1' is —CHNH₂CH(CH₃)₂, R2' is —CH₂OH;
R1' is —CHNH₂CH₂CONH₂, R2' is —CH₂CH₂COOH;
R1' is —CHNH₂CHCH₃CH₂CH₃, R2' is —CH₂CH₂COOH; or
R1' is —CHNH₂CH₂OH, R2' is —CH₂COOH.

7. A dipeptide mimic to mimic proteins in a protein-protein interactions having the structure

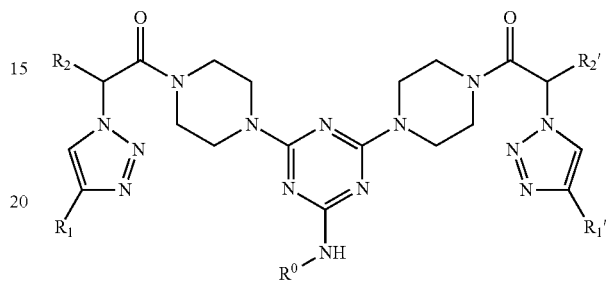

wherein R0 is a 1,2,3-triazole-functionalized polyether tag and wherein R1, R2 and R1' and R2' are selected from R1 is —(CH₂)₄NH₂, R2 is —CHCH₃CH₂CH₃;
R1 is —(CH₂)₄NH₂, R2 is —H;
R1 is —CH₂CH₂COOH, R2 is —CHCH₃CH₂CH₃;
R1 is —CH₂CH₂OH, R2 is —H;
R1 is —CH₂CHCH₃OH, R2 is —H;
R1 is —CH₂CH₂OH, R2 is —CH(CH₃)₂;
R1 is —(CH₂)₄NH₂, R2 is —CHCH₃OH;
R1 is —CH₂CHCH₃OH, R2 is —(CH₂)₄NH₂;
R1 is —(CH₂)₃NHCNHNH₂, R2 is —CH₃;
R1 is —(CH₂)₃NHCNHNH₂, R2 is —CHCH₃CH₂CH₃;
R1 is —(CH₂)₃NHCNHNH₂, R2 is —H;
R1 is —CH₂CH₂COOH, R2 is —(CH₂)₄NH₂;
R1 is —CH₂CH₂COOH, R2 is —CH₃;
R1 is —CH₂CH₂COOH, R2 is R1 is —(CH₂)₄CH₃, R2 is —(CH₂)₄NH₂;
R1 is R2 is —CHCH₃CH₂CH₃;
R1 is —CHNH₂CH₂CH(CH₃)₂, R2 is —CHCH₃CH₂CH₃;

R1 is —CHNH$_2$CH$_2$CH(CH$_3$)$_2$, R2 is

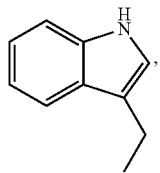

R1 is —CHNH$_2$CH$_2$CH(CH$_3$)$_2$, R2 is —(CH$_2$)$_4$NH$_2$;
R1 is —CHNH$_2$CH$_2$CH(CH$_3$)$_2$, R2 is —CH$_2$CH$_2$COOH;
R1 is —CHNH$_2$CH$_2$CH(CH$_3$)$_2$, R2 is

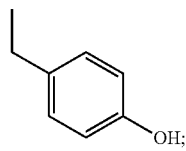

R1 is —CHNH$_2$CHCH$_3$CH$_2$CH$_3$, R2 is

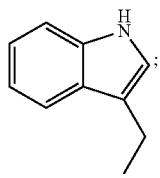

R1 is —CHNH$_2$CHCH$_3$CH$_2$CH$_3$, R2 is —(CH$_2$)$_4$NH$_2$;
R1 is —CHNH$_2$CHCH$_3$CH$_2$CH$_3$, R2 is —CH$_2$CH$_2$COOH;
R1 is —CHNH$_2$CHCH$_3$CH$_2$CH$_3$, R2 is

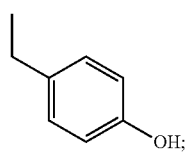

R1 is —CHNH$_2$CH$_2$OH, R2 is

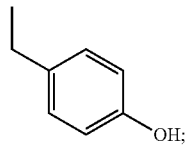

R1 is —CHNH$_2$CH$_2$OH, R2 is —(CH$_2$)$_4$NH$_2$;
R1 is —CHNH$_2$CH$_2$OH, R2 is —CH$_2$CH$_2$COOH;
R1 is —CHNH$_2$CH$_2$OH, R2 is —CHCH$_3$CH$_2$CH$_3$;

R1 is

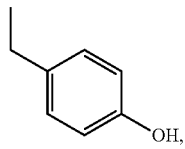

R2 is —CH$_2$CH$_2$COOH;
R1 is

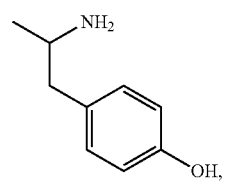

R2 is

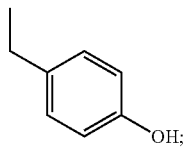

R1 is —CH$_2$NH$_2$, R2 is —(CH$_2$)$_4$NH$_2$;
R1 is —CHNH$_2$CHCH$_3$CH$_2$CH$_3$, R2 is —(CH$_2$)$_3$NHC-NHNH$_2$;
R1 is —CHNH$_2$(CH$_2$)$_4$NH$_2$, R2 is —CH$_2$CH$_2$COOH;
R1 is —CHNH$_2$CHCH$_3$CH$_2$CH$_3$, R2 is —CH$_2$CONH$_2$;
R1 is —CHNH$_2$CH$_2$CONH$_2$, R2 is —(CH$_2$)$_4$NH$_2$;
R1 is —CHNH$_2$CH(CH$_3$)$_2$, R2 is —CH$_2$CONH$_2$;
R1 is —CHNH$_2$CH$_2$CONH$_2$, R2 is —CH$_2$CONH$_2$;
R1 is —CHNH$_2$(CH$_2$)$_2$SCH$_3$, R2 is —CH$_2$CH$_2$COOH;
R1 is —CHNH$_2$(CH$_2$)$_4$NH$_2$, R2 is —CHCH$_3$OH;
R1 is —CH$_2$NH$_2$, R2 is —CH$_2$COOH;
R1 is —CHNH$_2$, CH(CH$_3$)$_2$, R2 is —CH$_2$OH;
R1 is —CHNH$_2$CH$_2$CONH$_2$, R2 is —CH$_2$COOH;
R1 is —CHNH$_2$CHCH$_3$CH$_2$CH$_3$, R2 is —CH$_2$COOH
R1 is —CHNH$_2$CH$_2$OH, R2 is —CH$_2$COOH
R1 is —C$_6$H$_6$C$_2$HN$_3$CHCOOHCHCH$_3$CH$_2$CH$_3$, R2 is —CH$_2$CH(CH$_3$)$_2$;
R1 is —C$_5$H$_3$NC$_2$HN$_3$CH$_2$COOH, R2 is —CH$_2$CH$_2$CONH$_2$; or
R1 is —C$_5$H$_3$N C$_2$HN$_3$CHCOOHCH$_2$CCONH$_2$, R2 is —CH$_2$CH$_2$CONH$_2$; and
R1' is —(CH$_2$)$_4$NH$_2$, R2' is —CHCH$_3$CH$_2$CH$_3$;
R1' is —(CH$_2$)$_4$NH$_2$, R2' is —H;
R1' is —CH$_2$CH$_2$COOH, R2' is —CHCH$_3$CH$_2$CH$_3$;
R1' is —CH$_2$CH$_2$OH, R2' is —H;
R1' is —CH$_2$CHCH$_3$OH, R2' is —H;
R1' is —CH$_2$CH$_2$OH, R2' is —CH(CH$_3$)$_2$;
R1' is —(CH$_2$)$_4$NH$_2$, R2' is —CHCH$_3$OH;
R1' is —CH$_2$CHCH$_3$OH, R2' is —(CH$_2$)$_4$NH$_2$;
R1' is —(CH$_2$)$_3$NHCNHNH$_2$, R2' is —CH$_3$;
R1' is —(CH$_2$)$_3$NHCNHNH$_2$, R2' is —CHCH$_3$CH$_2$CH$_3$;
R1' is —(CH$_2$)$_3$NHCNHNH$_2$, R2' is —H;
R1' is —CH$_2$CH$_2$COOH, R2' is —(CH$_2$)$_4$NH$_2$;
R1' is —CH$_2$CH$_2$COOH, R2' is —CH$_3$;
R1' is CH$_2$CH$_2$OH, R2' is

161

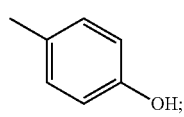

R1' is —(CH₂)₄CH₃, R2' is —(CH₂)₄NH₂;
R1'

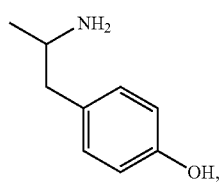

R2' is —CHCH₃CH₂CH₃;
R1' is —CHNH₂CH₂CH(CH₃)₂, R2' is —CHCH₃CH₂CH₃;
R1' is —CHNH₂CH₂CH(CH₃)₂, R2' is

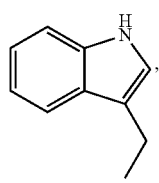

R1' is —CHNH₂CH₂CH(CH₃)₂, R2' is —(CH₂)₄NH₂;
R1' is —CHNH₂CH₂CH(CH₃)₂, R2' is —CH₂CH₂COOH;
R1' is —CHNH₂CH₂CH(CH₃)₂, R2' is

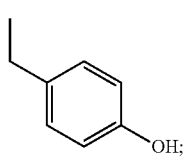

R1' is —CHNH₂CHCH₃CH₂CH₃, R2' is

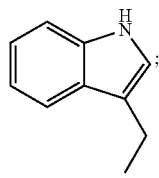

R1' is —CHNH₂CHCH₃CH₂CH₃, R2' is —(CH₂)₄NH₂;
R1' is —CHNH₂CHCH₃CH₂CH₃, R2' is —CH₂CH₂COOH;

162

R1' is —CHNH₂CHCH₃CH₂CH₃, R2' is

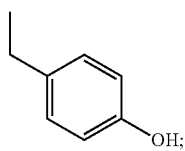

R1' is —CHNH₂CH₂OH, R2' is

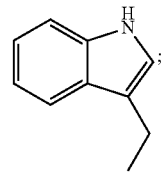

R1' is —CHNH₂CH₂OH, R2' is —(CH₂)₄NH₂;
R1' is —CHNH₂CH₂OH, R2' is —CH₂CH₂COOH;
R1' is —CHNH₂CH₂OH, R2' is —CHCH₃CH₂CH₃;
R1' is

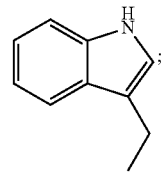

R2' is —CH₂CH₂COOH;
R1'

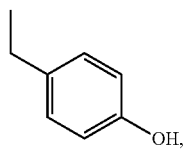

R2' is

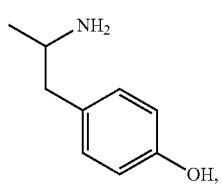

R1' is —CH₂NH₂, R2' is —(CH₂)₄NH₂;
R1' is —CHNH₂CHCH₃CH₂CH₃, R2' is —(CH₂)₃NHC-NHNH₂;
R1' is —CHNH₂(CH₂)₄NH₂, R2' is —CH₂CH₂COOH;
R1' is —CHNH₂CHCH₃CH₂CH₃, R2' is —CH₂CONH₂;
R1' is —CHNH₂CH₂CONH₂, R2' is —(CH₂)₄NH₂;
R1' is —CHNH₂CH(CH₃)₂, R2' is —CH₂CONH₂;
R1' is —CHNH₂CH₂CONH₂, R2' is —CH₂CONH₂;
R1' is —CHNH₂(CH₂)₂SCH₃, R2' is —CH₂CH₂COOH;
R1' is —CHNH₂(CH₂)₄NH₂, R2' is —CHCH₃OH;

R1' is —CH$_2$NH$_2$, R2' is —CH$_2$CH$_2$COOH;
R1' is —CHNH$_2$CH(CH$_3$)$_2$, R2' is —CH$_2$OH;
R1' is —CHNH$_2$CH$_2$CONH$_2$, R2' is —CH$_2$CH$_2$COOH;
R1' is —CHNH$_2$CHCH$_3$CH$_2$CH$_3$, R2' is —CH$_2$CH$_2$COOH; or
R1' is —CHNH$_2$CH$_2$OH, R2' is —CH$_2$COOH.

\* \* \* \* \*

UNITED STATES PATENT AND TRADEMARK OFFICE
CERTIFICATE OF CORRECTION

Page 1 of 2

PATENT NO.         : 9,562,023 B2
APPLICATION NO.    : 13/418917
DATED              : February 7, 2017
INVENTOR(S)        : Kevin Burgess It is certified that error appears in the above-identified patent and that said Letters Patent is hereby corrected as shown below:

In Column 1, Lines 18-20, delete the entire contents and insert --This invention was made with government support under grant numbers MH070040 and GM076261 awarded by The National Institutes of Health. The government has certain rights in the invention.-- therefor.

In Claim 4, Column 142, Line 67, insert --is-- after the term R1.

In Claim 4, Column 144, Line 58, delete "—$(CH_2)_2SCH_3$" and insert -- —$CHNH_2(CH_2)_2SCH_3$-- therefor.

In Claim 4, Column 144, Line 66, delete "z''" and insert --z'''-- therefor.

In Claim 5, Column 151, Lines 56-65, delete the entire contents and insert -- 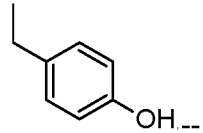-- therefor.

In Claim 6, Column 155, Lines 2-10, delete the entire contents and insert -- 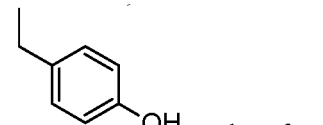 -- therefor.

In Claim 6, Column 156, Line 39, delete "α$CHNH_2CH_2CH(CH_3)_2$" and insert -- —$CHNH_2CH_2CH(CH_3)_2$-- therefor.

Signed and Sealed this
Thirtieth Day of May, 2017

Michelle K. Lee
*Director of the United States Patent and Trademark Office*

CERTIFICATE OF CORRECTION (continued)
U.S. Pat. No. 9,562,023 B2

In Claim 6, Column 157, Lines 26-35, delete the entire contents and insert -- 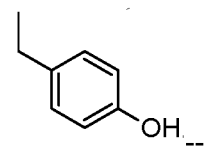 -- therefor.

In Claim 7, Column 159, Lines 55-63, delete the entire contents and insert -- 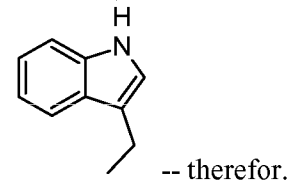 -- therefor.

In Claim 7, Column 160, Lines 25-31, delete the entire contents and insert -- 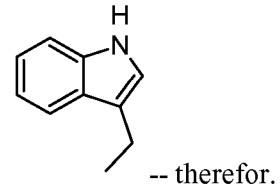 -- therefor.